(12) United States Patent
Moore et al.

(10) Patent No.: US 7,160,891 B2
(45) Date of Patent: Jan. 9, 2007

(54) QUINAZOLINE DERIVATIVES FOR THE TREATMENT OF T CELL MEDIATED DISEASES

(75) Inventors: Nelly Corine Moore, Macclesfield (GB); Keith Oldham, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/496,587

(22) PCT Filed: Nov. 20, 2002

(86) PCT No.: PCT/GB02/05222

§ 371 (c)(1),
(2), (4) Date: May 24, 2004

(87) PCT Pub. No.: WO03/045395

PCT Pub. Date: Jun. 5, 2003

(65) Prior Publication Data

US 2005/0038050 A1    Feb. 17, 2005

(30) Foreign Application Priority Data

Nov. 23, 2001   (GB) ................... 0128108.8

(51) Int. Cl.
*A61K 31/517*   (2006.01)
*C07D 43/02*    (2006.01)

(52) U.S. Cl. ............... 514/266.2; 514/266.4; 544/284; 544/293

(58) Field of Classification Search .......... 514/266.24, 514/266.2, 266.4; 544/284, 293
See application file for complete search history.

(56) References Cited

U.S. PATENT DOCUMENTS 7,049,438 B1 * 5/2006 Hennequin et al. ......... 544/283

FOREIGN PATENT DOCUMENTS

| WO | 96/39145 | * | 12/1996 |
| WO | 98/13354 | * | 4/1998 |
| WO | 01/04102 A | | 1/2001 |
| WO | 01/04102 A1 | | 1/2001 |
| WO | 01/94341 A | | 12/2001 |
| WO | 01/94341 A1 | | 12/2001 |

OTHER PUBLICATIONS

Myers, et al., Bioorganic & Medicinal Chemistry Letters, vol. 7, No. 4, Feb. 18, 1997, pp. 417-420.
Myers, et al., "The preapration ans SAR of 4-(anilino), 4-(phenoxy), and 4-(thiophenoxy)-quinazolines: Inhibitors of p56 and EGF-R tyrosine kinase activity", Bioorganic & Medicinal Chemistry Letters, vol. 7, No. 4, Feb. 18, 1997, pp. 417-420, XP004136037, ISSN: 0960-894X.

* cited by examiner

*Primary Examiner*—James O. Wilson
*Assistant Examiner*—Tamthom N. Truong
(74) *Attorney, Agent, or Firm*—Morgan Lewis & Bockius LLP

(57) ABSTRACT

The invention concerns the use of the quinazoline derivatives of Formula (I) wherein each of $Q_1$, Z, m, $R_1$, $R_2$, $R_3$ and $Q_2$ have any of the meanings defined in the description in the manufacture of a medicament for use in the prevention or treatment of T cell mediated diseases or medical conditions in a warm-blooded animal

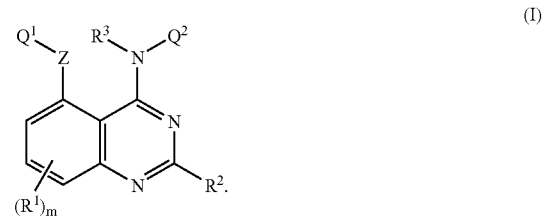

11 Claims, No Drawings

QUINAZOLINE DERIVATIVES FOR THE TREATMENT OF T CELL MEDIATED DISEASES

This invention concerns a new therapeutic use of certain quinazoline derivatives, or pharmaceutically-acceptable salts thereof. The compounds have been found to possess pharmacological properties of use in the treatment of autoimmune diseases or medical conditions, for example T cell mediated disease such as transplant rejection or rheumatoid arthritis.

A critical requirement of the immune system is the ability to differentiate between "self" and "non-self" (i.e. foreign) antigens. This discrimination is required to enable the immune system to mount a response to foreign proteins such as those on the surface of pathogens whilst maintaining tolerance to endogenous proteins and thereby preventing damage to normal tissues. An autoimmune disease results when self-tolerance breaks down and the immune system reacts against tissues such as the joints in rheumatoid arthritis or nerve fibres in multiple sclerosis. Stimulation of the human immune response is dependent on the recognition of protein antigens by T cells. However T cells do not become activated by and respond to antigen alone but are only triggered into action when the antigen is complexed with major histocompatibility complex (MHC) molecules on the surface of an antigen-presenting cell such as a B cell, macrophage or dendritic cell. Thus T cell activation requires the docking into the T cell receptor of the peptide/MHC complex expressed on an antigen-presenting cell. This interaction, which confers the antigen specificity to the T cell response, is essential for fall activation of T lymphocytes. Subsequent to this docking, some of the earliest signal transduction events leading to full T cell activation are mediated through the action of multiple tyrosine-specific protein kinases (E. Hsi et al., *J. Biol. Chem.* 1989, 264, 10836) including $p56^{lck}$ and ZAP-70. The tyrosine kinase $p56^{lck}$ is a lymphocyte specific member of the src family of non-receptor protein tyrosine kinases (J. D. Marth et al., *Cell,* 1985, 43, 393). The enzyme is associated with the inner surface of the plasma membrane where it binds to the T cell receptor associated glycoproteins CD4 (in helper T cells) and CD8 (in cytotoxic or killer T cells) (C. E. Rudd et al., *Proc. Natl. Acad. Sci. USA,* 1988, 85, 5190 and M. A. Campbell et al., *EMBO J.* 1990, 9, 2125).

It is believed that $p56^{lck}$ tyrosine kinase plays an essential role in T cell activation as, for example, the loss of $p56^{lck}$ expression in a human Jurkat T cell line prevents the normal T cell response to stimulation of the T cell receptor D. B. Straus et al., *Cell,* 1992, 70, 585) and a deficiency in $p56^{lck}$ expression causes severe immune deficiency in humans (F. D. Goldman et al., *J. Clin. Invest.,* 1998, 102, 421).

Certain autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes are believed to be associated with inappropriate T cell activation (see, for example, J. H. Hanke et al., *Inflamm. Res.,* 1995, 44, 357). In addition the acute rejection of transplanted organs can also be interpreted as a consequence of inappropriate T cell activation. Therefore, compounds which modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase, are expected to provide therapeutic agents for such pathological conditions.

Without wishing to imply that the compounds disclosed in the present invention possess pharmacological activity only by virtue of an effect on a single biological process, it is believed that the compounds modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase.

In particular, the quinazoline derivatives disclosed in the present invention are expected to be useful as immunoregulation or immunosuppressive agents for the prevention or treatment of organ rejection following transplant surgery.

Agents of this kind would offer therapy for transplant rejection and autoimmune diseases whilst avoiding toxicities associated with the commonly used, less selective immunosuppressants. The leading agent for the prevention or treatment of transplant rejection is cyclosporin A which, although effective, is often associated with side-effects such as renal damage and hypertension which results in kidney failure in a substantial number of patients. It is contemporary practice to treat rheumatoid arthritis initially with symptom relief agents such as NSAIDs, which do not have any beneficial effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

As stated above, the present invention is based, in particular, on the discovery that the quinazoline derivatives disclosed in the invention modulate T cell activation by way of inhibition of one or more of the multiple tyrosine-specific protein kinases which are involved in the early signal transduction steps which lead to fall T cell activation. Accordingly compounds disclosed in the present invention possess higher inhibitory potency against particular non-receptor tyrosine kinases such as $p56^{lck}$ tyrosine kinase than against other non-receptor tyrosine kinases or against receptor tyrosine kinases (RTKs) such as epidermal growth factor (EGF) RTK and/or VEGF RTK. In general, the quinazoline derivatives disclosed in the invention possess sufficient potency in inhibiting non-receptor tyrosine kinases such as $p56^{lck}$ tyrosine kinase that they may be used in an amount sufficient to inhibit, for example, $p56^{lck}$ tyrosine kinase whilst demonstrating reduced potency, preferably whilst demonstrating no significant activity, against RTKs such as EGF RTK or VEGF RTK. Thus the quinazoline derivatives disclosed in the invention can be used in the clinical management of those particular diseases which are sensitive to inhibition of such non-receptor tyrosine kinases, for example autoimmune diseases or medical conditions, for example T cell mediated disease such as transplant rejection or rheumatoid arthritis.

According to one aspect of the invention there is provided the use of a quinazoline derivative of the Formula I

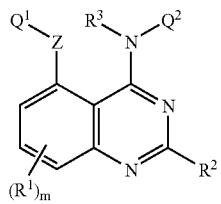

wherein m is 0, 1, 2 or 3;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$Q^3-X^1—$$

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^4-X^2—$$

wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$—X^3-Q^5$$

wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$—X^4—R^8$$

wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1-6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

$$—X^5-Q^6$$

wherein $X^5$ is a direct bond or is selected from O, CO and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl;

$R^3$ is hydrogen or (1–6C)alkyl;

Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;

$Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or, when Z is a direct bond or O, $Q^1$ may be (1–6C)alkyl, (2–8C)alkenyl, (2–8C)alkynyl, halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-

[(1–6C)alkyl]amino-(1–6C)alkyl, (1–6C)alkylthio-(1–6C)alkyl, (1–6C)alkylsulphinyl-(1–6C)alkyl or (1–6C)alkylsulphonyl-(1–6C)alkyl, and wherein adjacent carbon atoms in any (2–6C)alkylene chain within the $Q^1$-Z- group are optionally separated by the insertion into the chain of a group selected from O, S, SO, $SO_2$, $N(R^{12})$, CO, $CH(OR^{12})$, $CON(R^{12})$, $N(R^{12})CO$, $SO_2N(R^{12})$, $N(R^{12})SO_2$, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$=or HC≡ position a substituent selected from halogeno, carboxy, carbamoyl, (1–6C)alkoxycarbonyl, N-(1–6C)alkylcarbamoyl, di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is selected from CO and $N(R^{13})CO$, wherein $R^{13}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^7$-$Q^8$ wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $N(R^{14})C(R^{14})_2$, wherein $R^{14}$ is hydrogen or (1–6C)alkyl, and $Q^8$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^8$—$R^{15}$ wherein $X^8$ is a direct bond or is selected from O and $N(R^{16})$, wherein $R^{16}$ is hydrogen or (1–6C)alkyl, and $R^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^9$-$Q^9$ wherein $X^9$ is a direct bond or is selected from O, CO and $N(R^{17})$, wherein $R^{17}$ is hydrogen or (1–6C)alkyl, and $Q^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents; and $Q^2$ is an aryl group of formula Ia

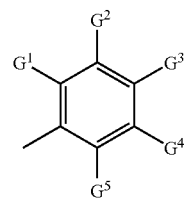

Ia wherein $G^1$ is selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^{10}$—$R^{18}$ wherein $X^{10}$ is a direct bond or is selected from O and $N(R^{19})$, wherein $R^{19}$ is hydrogen or (1–6C)alkyl, and $R^{18}$ is halogeno-(1–6C)alkyl, hydroxy-(1–6C)alkyl, (1–6C)alkoxy-(1-6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^{11}$-$Q^{10}$ wherein $X^{11}$ is a direct bond or is selected from O, S, SO, $SO_2$, $N(R^{20})$, CO, $CH(OR^{20})$, $CON(R^{20})$, $N(R^{20})CO$, $SO_2N(R^{20})$, $N(R^{20})SO_2$, $C(R^{20})_2O$, $C(R^{20})_2S$ and $N(R^{20})C(R^{20})_2$, wherein $R^{20}$ is hydrogen or (1–6C)alkyl, and $Q^{10}$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and any heterocyclyl group within $Q^{10}$ optionally bears 1 or 2 oxo or thioxo substituents, and each of $G^2$, $G^3$, $G^4$ and $G^5$, which may be the same or different, is selected from hydrogen, halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, or $G^1$ and $G^2$ together form a group of formula:— —CH=CH—CH=CH—, —N=CH—CH=CH—, —CH=N—CH=CH—, —CH=CH—N=CH—, —CH═CH—CH═N—, —N═CH—N═CH—, —CH═N—CH═N—, —N═CH—CH═N—, —N═N—CH═CH—, —CH═CH—N═N—, —CH═CH—O—, —O—CH═CH—, —CH═CH—S—, —S—CH═CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH═CH—NH—, —NH—CH═CH—, —CH₂—CH₂—NH—, —NH—CH₂—CH₂—, —N═CH—NH—, —NH—CH═N—, —NH—CH₂—NH—, —O—CH═N—, —N═CH—O—, —S—CH═N—, —N═CH—S—, —O—CH₂—NH—, —NH—CH₂—O—, —S—CH₂—NH—, —NH—CH₂—S—, —O—N═CH—, —CH═N—O—, —S—N═CH—, —CH═N—S—, —O—NH—CH₂—, —CH₂—NH—O—, —S—NH—CH₂—, —CH₂—NH—S—, —NH—N═CH—, —CH═N—NH—, —NH—NH—CH₂—, —CH₂—NH—NH—, —N═N—NH— or —NH—N═N—, or G¹ has any of the meanings defined hereinbefore and G² and G³ together or G³ and G⁴ together form a group of formula:— —CH═CH—CH═CH—, —N═CH—CH═CH—, —CH═N—CH═CH—, —CH═CH—N═CH—, —CH═CH—CH═N—, —N═CH—N═CH—, —CH═N—CH═N—, —N═CH—CH═N—, —N═N—CH═CH—, —CH═CH—N═N—, —CH═CH—O—, —O—CH═CH—, —CH═CH—S—, —S—CH═CH—, —CH₂—CH₂—O—, —O—CH₂—CH₂—, —CH₂—CH₂—S—, —S—CH₂—CH₂—, —O—CH₂—O—, —O—CH₂—CH₂—O—, —S—CH₂—S—, —S—CH₂—CH₂—S—, —CH═CH—NH—, —NH—CH═CH—, —CH₂—CH₂—NH—, —NH—CH₂—CH₂—, —N═CH—NH—, —NH—CH═N—, —NH—CH₂—NH—, —O—CH═N—, —N═CH—O—, —S—CH═N—, —N═CH—S—, —O—CH₂—NH—, —NH—CH₂—O—, —S—CH₂—NH—, —NH—CH₂—S—, —O—N═CH—, —CH═N—O—, —S—N═CH—, —CH═N—S—, —O—NH—CH₂—, —CH₂—NH—O—, —S—NH—CH₂—, —CH₂—NH—S—, —NH—N═CH—, —CH═N—NH—, —NH—NH—CH₂—, —CH₂—NH—NH—, —N═N—NH— or —NH—N═N—, and the 9- or 10-membered bicyclic heteroaryl or heterocyclic ring formed when G¹ and G² together, G² and G³ together or G³ and G⁴ together are linked optionally bears on the heteroaryl or heterocyclic portion of the bicyclic ring 1, 2 or 3 substituents, which may be the same or different, selected from halogeno, trifluoromethyl, cyano, nitro, hydroxy, amino, (1–6C)alkyl, (2–8C)alkenyl, (2–8C)alkynyl, (1–6C)alkoxy, (1–6C)alkylamino and di-[(1–6C)alkyl]amino, and any bicyclic heterocyclic ring so formed optionally bears 1 or 2 oxo or thioxo groups;

or a pharmaceutically-acceptable salt thereof;

in the manufacture of a medicament for use in the prevention or treatment of T cell mediated diseases or medical conditions in a warm-blooded animal such as man.

We have found that the compounds disclosed in the present invention are of use in the prevention or treatment of autoimmune diseases or medical conditions, for example T cell mediated disease such as transplant rejection, rheumatoid arthritis or multiple sclerosis. We have further found that these effects are believed to arise by virtue of inhibition of one or more of the multiple tyrosine-specific protein kinases which are involved in the early signal transduction steps which lead to full T cell activation, for example by way of inhibition of the enzyme $p56^{lck}$. Accordingly the compounds disclosed in the present invention are expected to be useful in the prevention or treatment of T cell mediated diseases or medical conditions. In particular the compounds disclosed in the present invention are expected to be useful in the prevention or treatment of those pathological conditions which are sensitive to inhibition of one or more of the multiple tyrosine-specific protein kinases which are involved in the early signal transduction steps which lead to T cell activation, for example by way of inhibition of $p56^{lck}$ tyrosine kinase. Further, the compounds disclosed in the present invention are expected to be useful in the prevention or treatment of those diseases or medical conditions which are mediated alone or in part by inhibition of the enzyme $p56^{lck}$, i.e. the compounds may be used to produce a $p56^{lck}$ enzyme inhibitory effect in a warm-blooded animal in need of such treatment. Specifically, the compounds disclosed in the present invention are expected to be useful in the prevention or treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds disclosed in the present invention are expected to be useful in the prevention or treatment of the acute rejection of transplanted tissue or organs.

According to a further feature of this aspect of the invention there is provided a method for the prevention or treatment of T cell mediated diseases or medical conditions in a warm-blooded animal, such as man, in need of such treatment which comprises administering to said animal an effective amount of a quinazoline derivative of the Formula I, or a pharmaceutically-acceptable salt thereof, as defined hereinbefore.

According to a further feature of the invention there is provided the use of a quinazoline derivative of the Formula I, or a pharmaceutically-acceptable salt thereof, as defined immediately hereinbefore in the manufacture of a medicament for use in the prevention or treatment of those pathological conditions which are sensitive to inhibition of one or more of the multiple tyrosine-specific protein kinases which are involved in the early signal transduction steps which lead to T cell activation.

According to a further feature of the invention there is provided a method for the prevention or treatment of those pathological conditions which are sensitive to inhibition of one or more of the multiple tyrosine-specific protein kinases which are involved in the early signal transduction steps which lead to T cell activation which comprises administering to said animal an effective amount of a quinazoline derivative of the Formula I, or a pharmaceutically-acceptable salt thereof, as defined immediately hereinbefore.

According to a further aspect of the invention there is provided the use as defined hereinbefore of a quinazoline derivative of the Formula I wherein each of m, $R^1$, $R^2$, $R^3$ and $Q^2$ has any of the meanings defined hereinbefore and Z is a direct bond or is selected from O, S, SO, $SO_2$, $N(R^{11})$, CO, $CH(OR^{11})$, $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl; and $Q^1$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N (R$^{12}$), N(R$^2$)SO$_2$, CH=CH and C≡C wherein R$^{12}$ is hydrogen or (1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl] amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

—X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N (R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl- (1–6C)alkyl, (3–7C)cycloalkenyl, (3–7C)cycloalkenyl- (1–6C)alkyl, heteroaryl, heteroaryl-(1–6C)alkyl, heterocyclyl or heterocyclyl-(1–6C)alkyl, and wherein any aryl, heteroaryl or heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C) alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di- [(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl] sulphamoyl, (1–6C)alkanesulphonylamino and N-(1–6C) alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C) alkylamino-(1–6C)alkyl or di-[(1–6C)alkyl]amino-(1–6C) alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z- group optionally bears 1 or 2 oxo or thioxo substituents.

According to a further aspect of the invention there is provided the use as defined hereinbefore of a quinazoline derivative of the Formula I wherein each of m, R$^1$, R$^2$, R$^3$ and Q$^2$ has any of the meanings defined hereinbefore and Z is selected from O, S, SO, SO$_2$, N(R$^{11}$), CO, CH(OR$^{11}$), CON(R$^{11}$), N(R$^{11}$)CO, SO$_2$N(R$^{11}$), N(R$^{11}$)SO$_2$, OC(R$^{11}$)$_2$, SC(R$_{11}$)$_2$ and N(R$^{11}$)C(R$^{11}$)$_2$, wherein R$^{11}$ is hydrogen or (1–6C)alkyl; and Q$^1$ is (3–7C)cycloalkyl, (3–7C)cycloalkyl-(1–6C)alkyl, (3–7C)cycloalkenyl, (3–7C)cycloalkenyl-(1–6C)alkyl, heterocyclyl or heterocyclyl-(1–6C)alkyl, and wherein adjacent carbon atoms in any (2–6C)alkylene chain within the Q$^1$-Z- group are optionally separated by the insertion into the chain of a group selected from O, S, SO, SO$_2$, N(R$^{12}$), CO, CH(OR$^{12}$), CON(R$^{12}$), N(R$^{12}$)CO, SO$_2$N (R$^{12}$), N(R$^{12}$)SO$_2$, CH=CH and C≡C wherein R$^{12}$ is hydrogen or (1–6C)alkyl, and wherein any CH$_2$ or CH$_3$ group within the Q$^1$-Z- group optionally bears on each said CH$_2$ or CH$_3$ group one or more halogeno or (1–6C)alkyl substituents or a substituent selected from hydroxy, cyano, amino, carboxy, carbamoyl, (1–6C)alkoxy, (1–6C)alkylthio, (1–6C)alkylsulphinyl, (1–6C)alkylsulphonyl, (1–6C)alkylamino, di-[(1–6C)alkyl] amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C) alkyl]sulphamoyl, (1–6C)alkanesulphonylamino and N-(1–6C)alkyl-(1–6C)alkanesulphonylamino, or from a group of the formula:

—X$^7$-Q$^8$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N (R$^{14}$), N(R$^{14}$)SO$_2$, C(R$^{14}$)$_2$O, C(R$^{14}$)$_2$S and N(R$^{14}$)C(R$^{14}$)$_2$, wherein R$^{14}$ is hydrogen or (1–6C)alkyl, and Q$^8$ is aryl, aryl-(1–6C)alkyl, (3–7C)cycloalkyl, (3–7C)cycloalkyl- (1–6C)alkyl, (3–7C)cycloalkenyl, (3–7C)cycloalkenyl- (1–6C)alkyl, heteroaryl, heteroaryl-(1–6C)alkyl, heterocyclyl or heterocyclyl-(1–6C)alkyl, and wherein any heterocyclyl group within the Q$^1$-Z- group optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy- (1–6C)alkyl, cyano-(1–6C)alkyl, amino-(1–6C)alkyl, (1–6C)alkylamino-(1–6C)alkyl or di-[(1–6C)alkyl]amino- (1–6C)alkyl, or from a group of the formula:

—X$^9$-Q$^9$ wherein X$^9$ is a direct bond or is selected from O, CO and N(R$^{17}$), wherein R$^{17}$ is hydrogen or (1–6C)alkyl, and Q$^9$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo or thioxo substituents.

In this specification the generic term "alkyl" includes both straight-chain and branched-chain alkyl groups such as propyl, isopropyl and tert-butyl, and (3–7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1–6C)alkoxy includes methoxy, ethoxy, cyclopropyloxy and cyclopentyloxy, (1–6C)alkylamino includes methylamino, ethylamino, cyclobutylamino and cyclohexylamino, and di-[(1–6Calkyl] amino includes dimethylamino, diethylamino, N-cyclobutyl-N-methylamino and N-cyclohexyl-N-ethylamino.

It is to be understood that, insofar as certain of the compounds of Formula I defined above may exist in optically active or racemic forms by virtue of one or more asymmetric carbon atoms, the invention includes in its compound definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Suitable values for the generic radicals referred to above include those set out below.

A suitable value for any one of the 'Q' groups ($Q^1$, $Q^3$ to $Q^{10}$) when it is aryl or for the aryl group within a 'Q' group is, for example, phenyl or naphthyl, preferably phenyl.

A suitable value for any one of the 'Q' groups ($Q^1$, $Q^3$ to $Q^8$) when it is (3–7C)cycloalkyl or for the (3–7C)cycloalkyl group within a 'Q' group is, for example, cyclopropyl, cyclobutyl, cyclopentyl, cyclohexyl, cycloheptyl or bicyclo [2.2.1]heptyl and a suitable value for any one of the 'Q' groups ($Q^1$, $Q^3$ to $Q^8$) when it is (3–7C)cycloalkenyl or for the (3–7C)cycloalkenyl group within a 'Q' group is, for example, cyclobutenyl, cyclopentenyl, cyclohexenyl or cycloheptenyl.

A suitable value for any one of the 'Q' groups ($Q^1$, $Q^3$ to $Q^{10}$) when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl.

A suitable value for any one of the 'Q' groups ($Q^1$, $Q^3$ to $Q^{10}$) when it is heterocyclyl or for the heterocyclyl group within a 'Q' group is, for example, a non-aromatic saturated or partially saturated 3 to 10 membered monocyclic or bicyclic ring with up to five heteroatoms selected from oxygen, nitrogen and sulphur, for example oxiranyl, oxetanyl, tetrahydrofuranyl, tetrahydropyranyl, oxepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, 1,1-dioxotetrahydro-4H-1, 4-thiazinyl, piperidinyl or piperazinyl, more preferably tetrahydrofuran-3-yl, tetrahydropyran-4-yl, pyrrolidin-3-yl, morpholino, 1,1-dioxotetrahydro-4H-1,4-thiazin-4-yl, piperidino, piperidin-4-yl or piperazin-1-yl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C)alkyl group is present.

Suitable values for any of the 'R' groups ($R^1$ to $R^{20}$), or for various groups within an $R^1$ substituent, or for $G^1$ or for various groups within $G^1$, or for any of the 'G' groups ($G^2$ to $G^5$) within $Q^2$, or for various groups within $Q^2$, or for $Q^1$ or for various groups within $Q^1$, or for various groups within the $Q^1$-Z- group include:— for halogeno fluoro, chloro, bromo and iodo;
for (1–6C)alkyl: methyl, ethyl, propyl, isopropyl and tert-butyl;
for (2–8C)alkenyl: vinyl, isopropenyl, allyl and but-2-enyl;
for (2–8C)alkynyl: ethynyl, 2-propynyl and but-2-ynyl;
for (1–6C)alkoxy: methoxy, ethoxy, propoxy, isopropoxy and butoxy;
for (2–6C)alkenyloxy: vinyloxy and allyloxy;
for (2–6C)alkynyloxy: ethynyloxy and 2-propynyloxy;
for (1–6C)alkylthio: methylthio, ethylthio and propylthio;
for (1–6C)alkylsulphinyl: methylsulphinyl and ethylsulphinyl;
for (1–6C)alkylsulphonyl: methylsulphonyl and ethylsulphonyl;
for (1–6C)alkylamino: methylamino, ethylamino, propylamino, isopropylamino and butylamino;
for di-[(1–6C)alkyl]amino: dimethylamino, diethylamino, N-ethyl-N-methylamino and diisopropylamino;
for (1–6C)alkoxycarbonyl: methoxycarbonyl, ethoxycarbonyl, propoxycarbonyl and tert-butoxycarbonyl;
for N-(1–6C)alkylcarbamoyl: N-methylcarbamoyl, N-ethylcarbamoyl and N-propylcarbamoyl;
for N,N-di-[(1–6C)alkyl]carbamoyl: N,N-dimethylcarbamoyl, N-ethyl-N-methylcarbamoyl and N,N-diethylcarbamoyl;
for (2–6C)alkanoyl: acetyl and propionyl;
for (2–6C)alkanoyloxy: acetoxy and propionyloxy;
for (2–6C)alkanoylamino: acetamido and propionamido;
for N-(1–6C)alkyl-(2–6C)alkanoylamino: N-methylacetamido and N,N-methylpropionamido;
for N-(1–6C)alkylsulphamoyl: N-methylsulphamoyl and N-ethylsulphamoyl;
for N,N-di-[(1–6C)alkyl]sulphamoyl: N,N-dimethylsulphamoyl;
for (1–6C)alkanesulphonylamino: methanesulphonylamino and ethanesulphonylamino;
for N-(1–6C)alkyl-(1–6C)alkanesulphonylamino: N-methylmethanesulphonylamino and N-methylethanesulphonylamino;

for (3–6C)alkenoylamino: acrylamido, methacrylamido and crotonamido;

for N-(1–6C)alkyl-(3–6C)alkenoylamino: N-methylacrylamido and N-methylcrotonamido;

for (3–6C)alkynoylamino: propiolamido;

for N-(1–6C)alkyl-(3–6C)alkynoylamino: N-methylpropiolamido;

for amino-(1–6C)alkyl: aminomethyl, 2-aminoethyl, 1-aminoethyl and 3-aminopropyl;

for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;

for halogeno-(1–6C)alkyl: chloromethyl, 2-chloroethyl, 1-chloroethyl and 3-chloropropyl;

for hydroxy-(1–6C)alkyl: hydroxymethyl, 2-hydroxyethyl, 1-hydroxyethyl and 3-hydroxypropyl;

for (1–6C)alkoxy-(1–6C)alkyl: methoxymethyl, ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for (1–6C)alkylthio-(1–6C)alkyl: methylthiomethyl, ethylthiomethyl, 2-methylthioethyl, 1-methylthioethyl and 3-methylthiopropyl;

for (1–6C)alkylsulphinyl-(1–6C)alkyl: methylsulphinylmethyl, ethylsulphinylmethyl, 2-methylsulphinylethyl, 1-methylsulphinylethyl and 3-methylsulphinylpropyl;

for (1–6C)alkylsulphonyl-(1–6C)alkyl: methylsulphonylmethyl, ethylsulphonylmethyl, 2-methylsulphonylethyl, 1-methylsulphonylethyl and 3-methylsulphonylpropyl;

for (2–6C)alkanoylamino-(1–6C)alkyl: acetamidomethyl, propionamidomethyl and 2-acetamidoethyl; and for (1–6C)alkoxycarbonylamino-(1–6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ when it is a (1–3C)alkylenedioxy group is, for example, methylenedioxy or ethylenedioxy and the oxygen atoms thereof occupy adjacent ring positions.

When, as defined hereinbefore, an $R^1$ group forms a group of the formula $Q^3$-$X^1$— and, for example, $X^1$ is a $OC(R^4)_2$ linking group, it is the carbon atom, not the oxygen atom, of the $OC(R^4)_2$ linking group which is attached to the quinazoline ring and the oxygen atom is attached to the $Q^3$ group. Similarly, when, for example a $CH_3$ group within a $R^1$ substituent bears a group of the formula —$X^3$-$Q^5$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^5$ group. A similar convention applies to the attachment of the groups of the formulae $Q^4$-$X^2$— and —$X^7$-$Q^7$.

As defined hereinbefore, adjacent carbon atoms in any (2–6C)alkylene chain within a $R^1$ substituent may be optionally separated by the insertion into the chain of a group such as O, $CON(R^5)$ or C≡C. For example, insertion of a C≡C group into the ethylene chain within a 2-morpholinoethoxy group gives rise to a 4-morpholinobut-2-ynyloxy group and, for example, insertion of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$-$X^2$— wherein $X^2$ is, for example, NHCO and $Q^4$ is a heterocyclyl-(1–6C)alkyl group, suitable $R^1$ substituents so formed include, for example, N-[heterocyclyl-(1–6C)alkyl]carbamoylvinyl groups such as N-(2-pyrrolidin-1-ylethyl)carbamoylvinyl or N-[heterocyclyl-(1–6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno or (1–6C)alkyl substituents, there are suitably 1 or 2 halogeno or (1–6C)alkyl substituents present on each said $CH_2$ group and there are suitably 1, 2 or 3 such substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl-(1–6C)alkoxy groups such as 2-hydroxy-3-piperidinopropoxy and 2-hydroxy-3-morpholinopropoxy, hydroxy-substituted amino-(2–6C)alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C)alkylamino-(2–6C)alkylamino groups such as 2-hydroxy-3-methylaminopropylamino, hydroxy-substituted di-[(1–6C)alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy, (1–6C)alkylsulphonyl-substituted (1–6C)alkoxy groups such as 2-methylsulphonylethoxy and heterocyclyl-substituted (1–6C)alkylamino-(1–6C)alkyl groups such as 2-morpholinoethylaminomethyl, 2-piperazin-1-ylethylaminomethyl and 3-morpholinopropylaminomethyl.

Similar considerations apply to the attachments and substitutions within the -Z-$Q^1$ group.

When, as defined hereinbefore, $G^1$ and $G^2$ together form, for example, a group of formula —O—CH═CH—, it is the oxygen atom, not the carbon atom, which is attached to the ortho-position of the phenyl ring of formula Ia and the carbon atom is attached to the adjacent meta-position of the phenyl ring of formula Ia. Similarly, when, for example, $G^2$ and $G^3$ together form, for example, a group of formula —CH═CH—CH═N—, it is the carbon atom, not the nitrogen atom, which is attached to the $G^2$ meta-position of the phenyl ring of formula Ia and the nitrogen atom is attached to the adjacent $G^3$ para-position of the phenyl ring of formula Ia. A similar convention applies to the attachment of the groups when, for example, $G^3$ and $G^4$ are joined.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular compounds defined in the invention include, for example, quinazoline derivatives of the Formula I, or pharmaceutically-acceptable salts thereof, wherein, unless otherwise stated, each of m, $R^1$, $R^2$, $R^3$, Z, $Q^1$ and $Q^2$ has any of the meanings defined hereinbefore or in paragraphs (a) to (cc) hereinafter:—

(a) m is 1 or 2, and each $R^1$ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

$Q^3$-$X^1$— wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^3$ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, and wherein any $CH_2$=CH— or HC≡C— group within a $R^1$ substituent optionally bears at the terminal $CH_2$=or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$-$X^2$— wherein $X^2$ is a direct bond or is CO or N($R^6$)CO, wherein $R^6$ is hydrogen or (1–6C)alkyl, and $Q^4$ is heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^3$-$Q^5$ wherein $X^3$ is a direct bond or is selected from O, N($R^7$), CON($R^7$), N($R^7$)CO and C($R^7$)$_2$O, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^4$—$R^8$ wherein $X^4$ is a direct bond or is selected from O and N($R^9$), wherein $R^9$ is hydrogen or (1–6C)alkyl, and $R^8$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and from a group of the formula:

—$X^5$-$Q^6$ wherein $X^5$ is a direct bond or is selected from O, CO and N($R^{10}$), wherein $R^{10}$ is hydrogen or (1–6C)alkyl, and $Q^6$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo substituents;

(b) m is 1 or 2, and each R group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propiolamido, or from a group of the formula:

$Q^3$-$X^1$— wherein $X^1$ is a direct bond or is selected from O, NH, CONH, NHCO and $OCH_2$ and $Q^3$ is phenyl, benzyl, cyclopropylmethyl, 2-thienyl, 1-imidazolyl, 1,2,3-triazol-1-yl, 2-, 3- or 4-pyridyl, 2-imidazol-1-ylethyl, 3-imidazol-1-ylpropyl, 2-(1,2,3-triazolyl)ethyl, 3-(1,2,3-triazolyl)propyl, 2-, 3- or 4-pyridylmethyl, 2-(2-, 3- or 4-pyridyl)ethyl, 3-(2-, 3- or 4-pyridyl)propyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-2-ylpropyl, pyrrolidin-2-ylmethyl, 2-pyrrolidin-2-ylethyl, 3-pyrrolidin-1-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any $CH_2$=CH— or HC≡C— group within a $R^1$ substituent optionally bears at the terminal $CH_2$=or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-dimethylaminopropyl or 4-dimethylaminobutyl, or from a group of the formula:

$Q^4$-$X^2$— wherein $X^2$ is a direct bond or is CO, NHCO or N(Me)CO and $Q^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, or from a group of the formula:

—$X^3$-$Q^5$ wherein $X^3$ is a direct bond or is selected from O, NH, CONH, NHCO and $CH_2O$ and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—$X^4$—$R^8$ wherein $X^4$ is a direct bond or is selected from O and NH and $R^8$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^5$-$Q^6$ wherein $X^5$ is a direct bond or is selected from O and NH and $Q^6$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(c) m is 1 or 2 and the $R^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, pyrid-2-ylmethoxy, pyrid-3-ylmethoxy, pyrid-4-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-dimethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$Q^4$-$X^2$— wherein $X^2$ is a direct bond or is NHCO or N(Me)CO and $Q^4$ is imidazolylmethyl, 2-imidazolylethyl, 3-imidazolylpropyl, pyridylmethyl, 2-pyridylethyl, 3-pyridylpropyl pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within a $R^1$ substituent is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within a substituent on $R^1$ optionally bears 1 or 2 oxo substituents;

(d) m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(e) m is 0;
(f) $R^2$ is hydrogen;
(g) $R^3$ is hydrogen;
(h) Z is a direct bond or is selected from O, S, SO, $SO_2$, $N(R^{11})$ and CO;
(i) Z is selected from $CON(R^{11})$, $N(R^{11})CO$, $SO_2N(R^{11})$, $N(R^{11})SO_2$, $OC(R^{11})_2$, $SC(R^{11})_2$ and $N(R^{11})C(R^{11})_2$, wherein $R^{11}$ is hydrogen or (1–6C)alkyl;
(j) the $Q^1$-Z- group is selected from (1–6C)alkyl, (2–8C)alkenyl, (2–8C)alkynyl, (1–6C)alkoxy, (2–8C)alkenyloxy, (2–8C)alkynyloxy, halogeno-(1–6C)allyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, halogeno-(1–6C)alkoxy, hydroxy-(1–6C)alkoxy, (1–6C)alkoxy-(1–6C)alkoxy, cyano-(1–6C)alkoxy, amino-(1–6C)alkoxy, (1–6C)alkylamino-(1–6C)alkoxy and di-[(1–6C)alkyl]amino-(1–6C)alkoxy, or Z is a direct bond or is selected from O, S, SO, $SO_2$, $N(R^{11})$ and CO wherein $R^{11}$ is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$=or HC≡ position a substituent selected from carbamoyl N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^7-X^6—$$

wherein $X^6$ is a direct bond or is CO or $N(R^{13})CO$, wherein $R^{13}$ is hydrogen or (1–6C)alkyl, and $Q^7$ is heteroaryl, heteroaryl-(1–6C)alkyl, heterocyclyl or heterocyclyl-(1–6C)alkyl, and wherein any $CH_2$ or $CH_3$ group within the $Q^1$-Z- group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

$$—X^7-Q^8$$

wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C)alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

$$—X^8—R^{15}$$

wherein $X^4$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

$$—X^9-Q^9$$

wherein $X^9$ is a direct bond or is selected from O, CO and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents;

(k) the $Q^1$-Z- group is selected from methoxy, ethoxy, propoxy, isopropoxy, 2-hydroxyethoxy, 3-hydroxypropoxy, 2-methoxyethoxy, 3-methoxypropoxy, 2-aminoethoxy, 3-aminopropoxy, 2-methylaminoethoxy, 3-methylaminopropoxy, 2-ethylaminoethoxy, 3-ethylaminopropoxy, 2-dimethylaminoethoxy, 3-dimethylaminopropoxy, cyclopropyloxy, cyclobutyloxy, cyclopentyloxy, cyclohexyloxy, cycloheptyloxy, cyclopropylmethoxy, cyclobutylmethoxy, cyclopentylmethoxy, cyclohexylmethoxy and cycloheptylmethoxy, or Z is a direct bond or is selected from O, S, SO, $SO_2$ and NH and $Q^1$ is phenyl, benzyl, 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazol-1-yl)ethyl, 2-(1,2,4-triazol-1-yl)ethyl, 3-(1,2,3-triazol-1-yl)propyl, 3-(1,2,4-triazol-1-yl)propyl, 2-, 3- or 4-pyridylmethyl, 2-(2-, 3- or 4-pyridyl)ethyl, 3-(2-, 3- or 4-pyridyl)propyl, oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the $Q^1$-Z- group are optionally separated by the insertion into the chain of a group selected from O, NH, CONH, NHCO, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, or from a group of the formula:

—$X^7$-$Q^8$ wherein $X^7$ is a direct bond or is selected from O, NH, CONH, NHCO and $CH_2O$ and $Q^8$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within the $Q^1$-Z- group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—$X^8$—$R^{15}$ wherein $X^8$ is a direct bond or is selected from O and NH and $R^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—$X^9$-$Q^9$ wherein $X^9$ is a direct bond or is selected from O and NH and $Q^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the $Q^1$-Z- group optionally bears 1 or 2 oxo substituents;

(l) the $Q^1$-Z- group is selected from methoxy, ethoxy, propoxy, isopropoxy, 2-hydroxyethoxy, 3-hydroxypropoxy, 2-methoxyethoxy, 3-methoxypropoxy, cyclobutyloxy, cyclopentyloxy, cyclohexyloxy, cycloheptyloxy, phenoxy, phenylthio, anilino, benzyloxy, cyclopropylmethoxy, tetrahydrofuran-3-yloxy, 3- or 4-tetrahydropyranyloxy, 2-imidazol-1-ylethoxy, 3-imidazol-1-ylpropoxy, 2-(1,2,3-triazol-1-yl)ethoxy, 2-(1,2,4-triazol-1-yl)ethoxy, 3-(1,2,3-triazol-1-yl)propoxy, 3-(1,2,4-triazol-1-yl)propoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3dimethylaminopropyl, 2-pyrrolidin-1-ylethyl, 3-pyrrolidin-1-ylpropyl 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within the $Q^1$-Z group optionally bears 1 or 2 oxo substituents;

(m) the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl) ethoxy, 3-(1,1-dioxotetrahydro-4H-1,4-thiazin-4-yl) propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

(n) Z is a direct bond or is selected from O, S, SO, $SO_2$, $N(R^{11})$ and CO wherein $R^{11}$ is hydrogen or (1–6C)alkyl, and $Q^1$ is aryl, aryl-(1–6C)alkyl, (3–7C)cycloalkyl, (3–7C)cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^2)CO$, CH=CH and C≡C wherein $R^{12}$ is hydrogen or (1–6C)alkyl, and wherein any $CH_2$=CH— or HC≡C— group within the $Q^1$-Z- group optionally bears at the terminal $CH_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^7$-$X^6$— wherein $X^6$ is a direct bond or is CO or $N(R^{13})CO$, wherein $R^{13}$ is hydrogen or (1–6C)alkyl, and $Q^7$ is heteroaryl, heteroaryl-(1–6C)alkyl, heterocyclyl or heterocyclyl-(1–6C) alkyl, and wherein any $CH_2$ or $CH_3$ group within the $Q^1$-Z- group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—$X^7$-$Q^8$ wherein $X^7$ is a direct bond or is selected from O, $N(R^{14})$, $CON(R^{14})$, $N(R^{14})CO$ and $C(R^{14})_2O$, wherein $R^{14}$ is hydrogen or (1–6C)alkyl, and $Q^8$ is heteroaryl, heteroaryl-(1–6C) alkyl, heterocyclyl or heterocyclyl-(1–6C)alkyl, and wherein any aryl, heteroaryl or heterocyclyl group within the $Q^1$-Z- group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl, or optionally bears 1 substituent selected from a group of the formula:

—$X^8$—$R^{15}$ wherein $X^4$ is a direct bond or is selected from O and $N(R^{16})$, wherein $R^{16}$ is hydrogen or (1–6C)alkyl, and $R^{15}$ is hydroxy-(1–6C)alkyl, (1–6C)alkoxy-(1–6C)alkyl, amino-(1-6C) alkyl, (1–6C)alkylamino-(1–6C)alkyl, di-[(1–6C)alkyl] amino-(1–6C)alkyl, (2–6C)alkanoylamino-(1–6C)alkyl or (1–6C)alkoxycarbonylamino-(1–6C)alkyl, and a group of the formula:

—$X^9$-$Q^9$ wherein $X^9$ is a direct bond or is selected from O and $N(R^{17})$, wherein $R^{17}$ is hydrogen or (1–6C)alkyl, and $Q^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the $Q^1$-Z- group optionally bears 1 or 2 oxo substituents;

(o) Z is a direct bond or is selected from O, S, SO, $SO_2$ and NH and $Q^1$ is phenyl, benzyl 2-thienyl, 1-imidazolyl, 1,2,3-triazol-1-yl, 1,2,4-triazol-1-yl, 2-, 3- or 4-pyridyl, 2-imidazol-1-ylethyl, 3-imidazol-1-ylpropyl, 2-(1,2,3-triazol-1-yl)ethyl, 2-(1,2,4-triazol-1-yl)ethyl, 3-(1,2,3-triazol-1-yl)propyl, 3-(1,2,4-triazol-1-yl)propyl, 2-, 3- or 4-pyridylmethyl, 2-(2-, 3- or 4-pyridyl)ethyl, 3-(2-, 3- or 4-pyridyl)propyl, oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazinyl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1, 1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the $Q^1$-Z- group are optionally separated by the insertion into the chain of a group selected from O, NH, CONH, NHCO, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, or from a group of the formula:

—$X^7$-$Q^8$ wherein $X^7$ is a direct bond or is selected from O, NH, CONH, NHCO and $CH_2O$ and $Q^8$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within the $Q^1$-Z- group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

wherein $X^8$ is a direct bond or is selected from O and NH and $R^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

wherein $X^9$ is a direct bond or is selected from O and NH and $Q^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the $Q^1$-Z- group optionally bears 1 or 2 oxo substituents;

(p) the $Q^1$-Z- group is selected from phenoxy, phenylthio, anilino, benzyloxy, cyclopropylmethoxy, tetrahydrofuran-3-yloxy, 3- or 4-tetrahydropyranyloxy, 2-imidazol-1-ylethoxy, 3-imidazol-1-ylpropoxy, 2-(1,2,3-triazol-1-yl)ethoxy, 2-(1,2,4-triazol-1-yl)ethoxy, 3-(1,2,3-triazol-1-yl)propoxy, 3-(1,2,4-triazol-1-yl)propoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl, 3-morpholinopropyl, 2-piperidinoethyl, 3-piperidinopropyl, 2-piperazin-1-ylethyl or 3-piperazin-1-ylpropyl, the last 8 of which substituents each optionally bears 1 or 2 substituents, which may be the same or different, selected from fluoro, chloro, methyl and methoxy, and wherein any heterocyclyl group within the $Q^1$-Z group optionally bears 1 or 2 oxo substituents;

(q) the $Q^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, ethylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

(r) Z is selected from O, S, SO, $SO_2$, $N(R^{11})$ and CO wherein $R^{11}$ is hydrogen or (1–6C)alkyl, and $Q^1$ is (3–7C)cycloalkyl, (3–7C)cycloalkyl-(1–6C)allyl, heterocyclyl or heterocyclyl-(1–6C)alkyl, and wherein adjacent carbon atoms in any (2–6C)alkylene chain within the $Q^1$-Z- group are optionally separated by the insertion into the chain of a group selected from O, $N(R^{12})$, $CON(R^{12})$, $N(R^{12})CO$, CH=CH and C≡C wherein $R^{12}$ is hydrogen or (1–6C)alkyl, and wherein any $CH_2$ or $CH_3$ group within the $Q^1$-Z- group optionally bears on each said $CH_2$ or $CH_3$ group a substituent selected from hydroxy, amino, (1–6C)alkoxy, (1–6C)alkylsulphonyl, (1–6C)alkylamino and di-[(1–6C)alkyl]amino, or from a group of the formula:

—X$^7$-Q$^8$ wherein X$^7$ is a direct bond or is selected from O, N(R$^{14}$), CON(R$^{14}$), N(R$^{14}$)CO and C(R$^{14}$)$_2$O, wherein R$^{14}$ is hydrogen or (1–6C)alkyl, and Q$^8$ is heteroaryl, heteroaryl-(1–6C)alkyl, heterocyclyl or heterocyclyl-(1–6C)alkyl, and wherein any heterocyclyl group within the Q$^1$-Z-group optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl and N,N-di-[(1–6C)alkyl]carbamoyl or optionally bears 1 substituent selected from a group of the formula:

—X$^8$—R$^{15}$ wherein X$^4$ is a direct bond or is selected from O and N(R$^{16}$), wherein R$^{16}$ is hydrogen or (1–6C)alkyl, and R$^{15}$ is hydroxy-(1–6C)alkyl, (1–6C)alkoxy-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, and a group of the formula:

—X$^9$-Q$^9$ wherein X$^9$ is a direct bond or is selected from O and N(R$^{17}$), wherein R$^{17}$ is hydrogen or (1–6C)alkyl, and Q$^9$ is heterocyclyl or heterocyclyl-(1–6C)alkyl which optionally bears 1 or 2 substituents, which may be the same or different, selected from halogeno, (1–6C)alkyl and (1–6C)alkoxy, and wherein any heterocyclyl group within the Q$^1$-Z-group optionally bears 1 or 2 oxo substituents;

(s) Z is selected from O, S, SO, SO$_2$ and NH and Q$^1$ is oxetan-3-yl, tetrahydrofuran-3-yl, 3- or 4-tetrahydropyranyl, 3- or 4-oxepanyl, 1-, 2- or 3-pyrrolidinyl, morpholino, 1,1-dioxotetrahydro-4H-1,4-thiazin-4-yl, piperidino, piperidin-3-yl, piperidin-4-yl, 1-, 3- or 4-homopiperidinyl, piperazin-1-yl, homopiperazin-1-yl, 1-, 2- or 3-pyrrolidinylmethyl, morpholinomethyl, piperidinomethyl, 3- or 4-piperidinylmethyl, 1-, 3- or 4-homopiperidinylmethyl, 2-pyrrolidin-1-ylethyl, 3-pyrrolidin-1-ylpropyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, 2-piperidin-3-ylethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within the Q$^1$-Z- group are optionally separated by the insertion into the chain of a group selected from O, NH, CONH, NHCO, CH=CH and C≡C, and wherein any CH$_2$ or CH$_3$ group within the Q$^1$-Z-group optionally bears on each said CH$_2$ or CH$_3$ group a substituent selected from hydroxy, amino, methoxy, methylsulphonyl, methylamino and dimethylamino, or from a group of the formula:

—X$^7$-Q$^8$ wherein X$^7$ is a direct bond or is selected from O, NH, CONH, NHCO and CH$_2$O and Q$^8$ is pyridyl pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any heterocyclyl group within the Q$^1$-Z-group optionally bears 1, 2 or 3 substituents, which may be the same or different, selected from fluoro, chloro, trifluoromethyl, hydroxy, amino, carbamoyl, methyl, ethyl and methoxy, or optionally bears 1 substituent selected from a group of the formula:

—X$^8$—R$^{15}$ wherein X$^8$ is a direct bond or is selected from O and NH and R$^{15}$ is 2-hydroxyethyl, 3-hydroxypropyl, 2-methoxyethyl, 3-methoxypropyl, aminomethyl, 2-aminoethyl, 3-aminopropyl, methylaminomethyl, 2-methylaminoethyl, 3-methylaminopropyl, 2-ethylaminoethyl, 3-ethylaminopropyl, dimethylaminomethyl, 2-dimethylaminoethyl, 3-dimethylaminopropyl, acetamidomethyl, methoxycarbonylaminomethyl, ethoxycarbonylaminomethyl or tert-butoxycarbonylaminomethyl, and from a group of the formula:

—X$^9$-Q$^9$ wherein X$^9$ is a direct bond or is selected from O and NH and Q$^9$ is pyrrolidin-1-ylmethyl, 2-pyrrolidin-1-ylethyl, 3-pyrrolidin-1-ylpropyl, morpholinomethyl, 2-morpholinoethyl, 3-morpholinopropyl, piperidinomethyl, 2-piperidinoethyl, 3-piperidinopropyl, piperazin-1-ylmethyl, 2-piperazin-1-ylethyl or 3-piperazin-1-ylpropyl, each of which optionally bears 1 or 2 substituents, which may be the same or different, selected from fluoro, chloro, methyl and methoxy, and wherein any heterocyclyl group within the Q$^1$-Z-group optionally bears 1 or 2 oxo substituents;

(t) the Q$^1$-Z- group is selected from cyclopropylmethoxy, tetrahydrofuran-3-yloxy, 3- or 4-tetrahydropyranyloxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, homopiperidin-3-yloxy, homopiperidin-4-yloxy, homopiperidin-3-ylmethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, homopiperidin-3-ylamino, homopiperidin-4-ylamino, homopiperidin-3-ylmethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within the $Q^1$-Z- group are optionally separated by the insertion into the chain of a group selected from O, NH, CH=CH and C≡C, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z group optionally bears 1 or 2 substituents, which may be the same or different, selected from fluoro, chloro, trifluoromethyl, hydroxy, amino, carbamoyl, methyl, ethyl and methoxy, and a piperidin-3-ylmethyl or piperidin-4-ylmethyl group within the $Q^1$-Z group is optionally N-substituted with 2-methoxyethyl, 3-methoxypropyl, 2-aminoethyl, 3-aminopropyl, 2-methylaminoethyl, 3-methylaminopropyl, 2-dimethylaminoethyl, 3-dimethylaminopropyl, 2-pyrrolidin-1-ylethyl, 3-pyrrolidin-1-ylpropyl, 2-morpholinoethyl 3-morpholinopropyl 2-piperidinoethyl, 3-piperidinopropyl, 2-piperazin-1-ylethyl or 3-piperazin-1-ylpropyl the last 8 of which substituents each optionally bears 1 or 2 substituents, which may be the same or different, selected from fluoro, chloro, methyl and methoxy, and wherein any heterocyclyl group within the $Q^1$-Z group optionally bears 1 or 2 oxo substituents;

(u) the $Q^1$-Z- group is selected from tetrahydrofuran-3-yloxy, tetrahydropyran-3-yloxy, tetrahydropyran-4-yloxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

(v) $Q^2$ is an aryl group of formula Ia

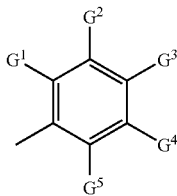

Ia wherein $G^1$ is selected from halogeno, trifluoromethyl, cyano, hydroxy, (1–6C)alkyl, (2–8C)alkenyl, (2–8C)alkynyl and (1–6C)alkoxy, and each of $G^2$, $G^3$, $G^4$ and $G^5$, which may be the same or different, is selected from hydrogen, halogeno, trifluoromethyl, cyano, hydroxy, (1–6C)alkyl, (2–8C)alkenyl, (2–8C)alkynyl and (1–6C)alkoxy, (w) $Q^2$ is an aryl group of formula Ia wherein $G^1$ and $G^2$ together form a group of formula:— —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—$CH_2$—O— or —O—$CH_2$—$CH_2$—O—, and the 9- or 10-membered bicyclic heteroaryl or heterocyclic ring formed when $G^1$ and $G^2$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^3$, $G^4$ and $G^5$, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

(x) $Q^2$ is an aryl group of formula Ia wherein $G^1$ is selected from halogeno, trifluoromethyl, cyano, hydroxy, (1–6C)alkyl, (2–8C)alkenyl, (2–8C)alkynyl and (1–6C)alkoxy, and $G^2$ and $G^3$ together or $G^3$ and $G^4$ together form a group of formula:— —CH=CH—CH=CH—, —N=CH—CH=CH—, —CH=N—CH=CH—, —CH=CH—N=CH—, —CH=CH—CH=N—, —CH=CH—O—, —O—CH=CH—, —CH=CH—S—, —S—CH=CH—, —O—$CH_2$—O— or —O—$CH_2$—$CH_2$—O—, and the 9- or 10-membered bicyclic heteroaryl or heterocyclic ring formed when $G^2$ and $G^3$ together or $G^3$ and $G^4$ together are linked optionally bears on the heteroaryl or heterocyclic portion of the bicyclic ring 1, 2 or 3 substituents, which may be the same or different, selected from halogeno, trifluoromethyl, cyano, hydroxy, (1–6C)alkyl, (2–8C)alkenyl, (2–8C)alkynyl and (1–6C)alkoxy, and any bicyclic heterocyclic ring so formed optionally bears 1 or 2 oxo or thioxo groups, and each of $G^4$ and $G^5$ or $G^2$ and $G^5$ as appropriate, which may be the same or different, is selected from hydrogen, halogeno, trifluoromethyl, cyano, hydroxy, (1–6C)alkyl, (2–8C)alkenyl, (2–8C)alkynyl and (1–6C)alkoxy;

(y) $Q^2$ is an aryl group of formula Ia wherein $G^1$ is selected from fluoro, chloro, bromo, iodo, trifluoromethyl, cyano, hydroxy, methyl, ethyl, vinyl, allyl, isopropenyl, ethynyl, 1-propynyl, 2-propynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, 1-propynyl, 2-propynyl, methoxy and ethoxy;

(z) $Q^2$ is an aryl group of formula Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, (aa) $Q^2$ is an aryl group of formula Ia wherein $G^1$ and $G^2$ together form a group of formula:— —CH=CH—CH=CH—, —O—CH=CH— or —O—CH$_2$O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

(bb) $Q^2$ is an aryl group of formula Ia wherein $G^1$ is selected from fluoro, chloro, bromo, iodo, trifluoromethyl, cyano, methyl ethyl, methoxy and ethoxy, and $G^2$ and $G^3$ together or $G^3$ and $G^4$ together form a group of formula:— —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^4$ and $G^5$ or $G^2$ and $G^5$ as appropriate, which may be the same or different, is selected from hydrogen, fluoro, chloro, bromo, trifluoromethyl, cyano, hydroxy, methyl, ethyl, methoxy and ethoxy; and (cc) $Q^2$ is an aryl group of formula Ia wherein $G^1$ and $G^2$ together form a group of formula:— —O—CH$_2$—O—, and the 9-membered bicyclic heterocyclic ring so formed optionally bears on the heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and the bicyclic heterocyclic ring so formed optionally bears 1 oxo or thioxo groups, each of $G^3$ and $G^4$, which may be the same or different, is selected from hydrogen, fluoro, chloro, bromo, trifluoromethyl, cyano, hydroxy, methyl, ethyl, methoxy and ethoxy, and $G^5$ is selected from hydrogen, fluoro, chloro or bromo.

As stated hereinbefore, certain compounds disclosed in the present invention, possess higher inhibitory potency against particular non-receptor tyrosine kinases such as p56$^{lck}$ tyrosine kinase than against other non-receptor tyrosine kinases or RTKs such as EGF RTK or VEGF RTK. Particular groups of compounds disclosed in the invention that possess such selectivity include, for example, quinazoline derivatives of the Formula I, or pharmaceutically-acceptable salts thereof, wherein each of m, $R^1$, $R^2$, $R^3$, Z and $Q^1$ has any of the meanings defined hereinbefore and:—

(a) $Q^2$ is an aryl group of formula Ia

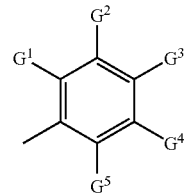

wherein $G^1$ is halogeno or trifluoromethyl,
each of $G^2$ and $G^5$ is hydrogen,
$G^3$ is selected from hydrogen, halogeno, trifluoromethyl, cyano, hydroxy, (1–6C)alkyl, (2–8C)alkenyl, (2–8C)alkynyl and (1–6C)alkoxy,
and $G^4$ is halogeno or (1–6C)alkoxy;

(b) $Q^2$ is an aryl group of formula Ia wherein $G^1$ is fluoro, chloro, bromo, iodo or trifluoromethyl,
each of $G^2$ and $G^5$ is hydrogen,
$G^3$ is selected from hydrogen, fluoro, chloro, bromo, trifluoromethyl, cyano, hydroxy, methyl, ethyl, vinyl, allyl, isopropenyl, ethynyl, methoxy and ethoxy, and $G^4$ is fluoro, chloro, bromo, methoxy or ethoxy;

(c) $Q^2$ is an aryl group of formula Ia wherein $G^1$ and $G^2$ together form a group of formula:— —O—CH$_2$—O—,
each of $G^3$ and $G^4$, which may be the same or different, is selected from hydrogen, halogeno, trifluoromethyl, cyano, hydroxy, (1–6C)alkyl and (1–6C)alkoxy, and $G^5$ is halogeno; or (d) $Q^2$ is an aryl group of formula Ia wherein $G^1$ and $G^2$ together form a group of formula:— —O—CH$_2$—O—,
each of $G^3$ and $G^4$, which may be the same or different, is selected from hydrogen, fluoro, chloro, bromo, trifluoromethyl, cyano, hydroxy, methyl, ethyl, methoxy and ethoxy,
and $G^5$ is selected from fluoro, chloro or bromo.

A preferred compound disclosed in the invention is a quinazoline derivative of the Formula I wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

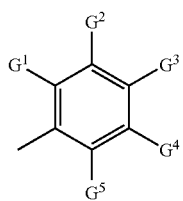

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula:— —CH═CH—CH═CH—, —O—CH═CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from propoxy, isopropoxy, 2-hydroxyethoxy, 3-hydroxypropoxy, 2-methoxyethoxy, 3-methoxypropoxy, cyclopentyloxy, cyclohexyloxy, tetrahydrofuran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazinyl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

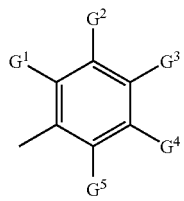

Ia wherein $G^1$ is selected from fluoro, chloro, bromo, iodo, trifluoromethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and each of $G^2$ and $G^5$ is hydrogen, or $G^1$ and $G^2$ together form a group of formula:— —CH═CH—CH═CH—, —O—CH═CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl)propoxy, 2-methoxyethoxy and 2-(2-methoxyethoxy)ethoxy;

the $Q^1$-Z- group is selected from isopropoxy, 2-methoxyethoxy, cyclohexyloxy, tetrahydrofuran-3-yloxy, tetrahydropyran-4-yloxy, 2-imidazol-1-ylethoxy, 2-(1,2,4-triazol-1-yl)ethoxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl)propoxy, each of $R^2$ and $R^3$ is hydrogen; and $Q^2$ is an aryl group of formula Ia

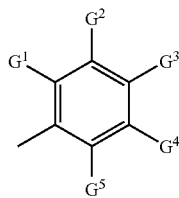

Ia wherein $G^1$ is selected from fluoro, chloro, bromo and iodo, each of $G^3$ and $G^4$, which may be the same or different, is selected from hydrogen, chloro and methoxy, and each of $G^2$ and $G^5$ is hydrogen, or $G^1$ and $G^2$ together form a group of formula:—
—CH=CH—CH=C(Cl)—, —O—CH=C(Cl)— or —O—CH$_2$—O—, and each of $G^3$, $G^4$ and $G^5$ is hydrogen;

or a pharmaceutically-acceptable acid-addition salt thereof.

A further preferred compound disclosed in the invention is a quinazoline derivative of the Formula I wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from phenoxy, benzyloxy, tetrahydrofuran-3-yloxy, tetrahydropyran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any CH$_2$ or CH$_3$ group within the $Q^1$-Z- group optionally bears on each said CH$_2$ or CH$_3$ group a substituent selected from hydroxy, amino, methoxy, methylsulphonyl, methylamino and dimethylamino, and wherein any phenyl or heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

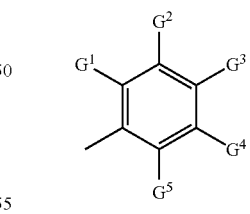

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula:—
—CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from tetrahydrofuran-3-yloxy, tetrahydropyran-4-yloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^1$ and $R^3$ is hydrogen; and $Q^2$ is an aryl group of formula Ia

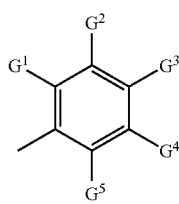

Ia wherein $G^1$ is selected from fluoro, chloro, bromo, iodo, trifluoromethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and each of $G^2$ and $G^5$ is hydrogen, or $G^1$ and $G^2$ together form a group of formula:— —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl)propoxy, 2-methoxyethoxy and 2-(2-methoxyethoxy)ethoxy;

the $Q^1$-Z- group is selected from tetrahydrofuran-3-yloxy, tetrahydropyran-4-yloxy, 2-imidazol-1-ylethoxy, 2-(1,2,4-triazol-1-yl)ethoxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl)propoxy, each of $R^2$ and $R^3$ is hydrogen; and $Q^2$ is an aryl group of formula Ia

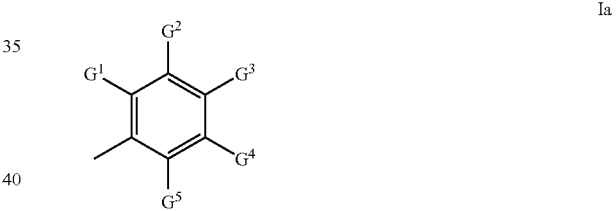

Ia wherein $G^1$ is selected from fluoro, chloro, bromo and iodo, each of $G^3$ and $G^4$, which may be the same or different, is selected from hydrogen, chloro and methoxy, and each of $G^2$ and $G^5$ is hydrogen, or $G^1$ and $G^2$ together form a group of formula:— —CH=CH—CH=C(Cl)—, —O—CH=C(Cl)— or —O—$CH_2$—O—, and each of $G^3$, $G^4$ and $G^5$ is hydrogen;

or a pharmaceutically-acceptable acid-addition salt thereof.

A further preferred compound disclosed in the invention is a quinazoline derivative of the Formula I wherein:

m is 0 or m is 1 and the $R^1$ group is located at the 6- or 7-position and is selected from hydroxy, amino, methyl, ethyl, propyl, methoxy, ethoxy, propoxy, methylamino, ethylamino, dimethylamino, diethylamino, acetamido, propionamido, benzyloxy, 2-imidazol-1-ylethoxy, 2-(1,2,4-triazol-1-yl)ethoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4- ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy and 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

the $Q^1$-Z- group is selected from tetrahydrofuran-3-yloxy, tetrahydropyran-3-yloxy, tetrahydropyran-4-yloxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, homopiperidin-3-yloxy, homopiperidin-4-yloxy, homopiperidin-3-ylmethoxy, 2-piperazin-1-ylethoxy, 3-piperazin-1-ylpropoxy, 2-homopiperazin-1-ylethoxy or 3-homopiperazin-1-ylpropoxy, and wherein any $CH_2$ or $CH_3$ group within the $Q^1$-Z- group optionally bears on each said $CH_2$ or $CH_3$ group a substituent selected from hydroxy, amino, methoxy, methylsulphonyl, methylamino and dimethylamino, and wherein any heterocyclyl group within the $Q^1$-Z- group optionally bears 1 or 2 substituents, which may be the same or different, selected from fluoro, chloro, trifluoromethyl, hydroxy, amino, methyl, ethyl and methoxy, and wherein any heterocyclyl group within the $Q^1$-Z- group optionally bears 1 or 2 oxo substituents;

each of $R^2$ and $R^3$ is hydrogen; and $Q^2$ is an aryl group of formula Ia

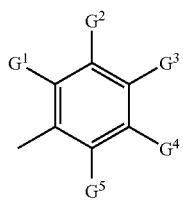

Ia wherein $G^1$ is selected from fluoro, chloro, bromo, iodo, trifluoromethyl, cyano, methyl, ethyl, vinyl, allyl, isopropenyl, ethynyl, methoxy and ethoxy, and each of $G^2$, $G^3$, $G^4$ and $G^5$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, or $G^1$ and $G^2$ together form a group of formula:— —CH=CH—CH=CH—, —O—CH=CH— or —O—$CH_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl, ethyl, methoxy and ethoxy, and any bicyclic heterocyclic ring so formed optionally bears 1 or 2 oxo or thioxo groups, and each of $G^3$, $G^4$ and $G^5$, which may be the same or different, is selected from hydrogen, fluoro, chloro, bromo, trifluoromethyl, cyano, hydroxy, methyl, ethyl, methoxy and ethoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-hydroxyethoxy, 3-hydroxypropoxy, 2-methoxyethoxy, 3-methoxypropoxy, 2-methylsulphonylethoxy, 3-methylsulphonylpropoxy and 2-(2-methoxyethoxy)ethoxy;

and wherein any $CH_2$ group within a $R^1$ substituent that is attached to two carbon atoms optionally bears a hydroxy group on said $CH_2$ group;

the $Q^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, N-methylpiperidin-3-yloxy, piperidin-4-yloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy and 3-(4-methylpiperazin-1-yl)propoxy, and wherein any $CH_2$ group within the $Q^1$-Z- group that is attached to two carbon atoms optionally bears a hydroxy group on said $CH_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

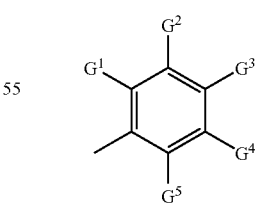

Ia wherein $G^1$ is selected from fluoro, chloro, bromo, iodo, trifluoromethyl, cyano, methyl, ethyl, vinyl, isopropenyl and ethynyl, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and each of $G^2$ and $G^5$ is hydrogen, or $G^1$ and $G^2$ together form a group of formula:— —CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, ethoxy, propoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, 2-(4-pyridyloxy)ethoxy, 2-pyridylmethoxy, 3-pyridylmethoxy and 4-pyridylmethoxy;

and wherein any CH$_2$ group within a $R^1$ substituent that is attached to two carbon atoms optionally bears a hydroxy group on said CH$_2$ group;

the $Q^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazinyl)ethoxy, 3-(1,1-dioxotetrahydro-4H-1,4-thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclobutyloxy, cyclopentyloxy and cyclohexyloxy, and wherein any CH$_2$ group within the $Q^1$-Z- group that is attached to two carbon atoms optionally bears a hydroxy group on said CH$_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

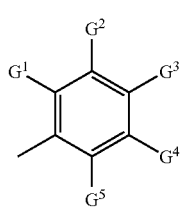

Ia wherein $G^1$ is selected from fluoro, chloro, bromo, iodo, trifluoromethyl, cyano, methyl, ethyl, vinyl, isopropenyl, ethynyl, methoxy and pyrrolidin-1yl, $G^2$ is hydrogen, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and $G^5$ is hydrogen or methoxy, or $G^1$ and $G^2$ together form a group of formula:— —CH=CH—CH=CH—, —O—CH=CH— or —O—CH$_2$—O—, and the 9- or 10membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, 2-piperidin-4-ylethoxy, 2-(N-methylpiperidin-4-yl)ethoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 2-tetrahydropyran-4-ylethoxy, 2-hydroxyethoxy, 3-hydroxypropoxy, 2-methoxyethoxy, 3-methoxypropoxy, 2-methylsulphonylethoxy, 3-methylsulphonylpropoxy, 2-(2-methoxyethoxy)ethoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 3-cyanopyrid-4-ylmethoxy, and wherein any CH$_2$ group within a $R^1$ substituent that is attached to two carbon atoms optionally bears a hydroxy group on said CH$_2$ group;

the $Q^1$-Z- group is selected from tetrahydrofuran-3-yloxy, tetrahydropyran-4-yloxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4thiazin-4-yl)propoxy, 2-piperidinoethoxy, 3-piperidinopropoxy, 3-piperidinyloxy, N-methylpiperidin-3-yloxy, 4-piperidinyloxy, N-methylpiperidin-4-yloxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, cyclobutyloxy, cyclopentyloxy and cyclohexyloxy, and wherein any CH$_2$ group within the $Q^1$-Z- group that is attached to two carbon atoms optionally bears a hydroxy group on said CH$_2$ group;

and wherein any heterocyclyl group within the $Q^1$-Z- group optionally bears 1 or 2 oxo substituents;

each of $R^2$ and $R^3$ is hydrogen; and $Q^2$ is an aryl group of formula Ia

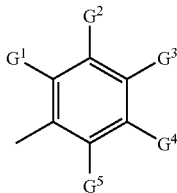

wherein $G^1$ is selected from fluoro, chloro, bromo, iodo, trifluoromethyl, cyano, methyl, ethyl, vinyl, isopropenyl, ethynyl, methoxy and pyrrolidin-1yl, $G^2$ is hydrogen, each of $G^3$ and $G^4$, which may be the same or different, is selected from hydrogen, fluoro, chloro, bromo, trifluoromethyl, cyano, hydroxy, methyl, ethyl, vinyl, allyl, isopropenyl, ethynyl, methoxy and ethoxy, and $G^5$ is hydrogen or methoxy, or $G^1$ and $G^2$ together form a group of formula:—
—CH=CH—CH=CH—, —O—CH=CH— or —O—CH$_2$—O—, and the 9- or 10-membered bicyclic heteroaryl or heterocyclic ring so formed optionally bears on the heteroaryl or heterocyclic portion of the bicyclic ring 1 or 2 substituents, which may be the same or different, selected from fluoro, chloro, bromo, trifluoromethyl, cyano, hydroxy, methyl and methoxy, and each of $G^3$, $G^4$ and $G^5$, which may be the same or different, is selected from hydrogen, fluoro, chloro, bromo, trifluoromethyl, cyano, hydroxy, methyl and methoxy;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from hydroxy, methoxy, benzyloxy, 3-morpholinopropoxy, 2-hydroxy-3-morpholinopropoxy, 3-(4-methylpiperazin-1-yl)propoxy, 2-hydroxy-3-(4-methylpiperazin-1-yl) propoxy, 2-methoxyethoxy and 2-(2-methoxyethoxy) ethoxy;

the $Q^1$-Z- group is selected from tetrahydrofuran-3-yloxy, tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, N-methylpiperidin-4-yloxy, piperidin-4-ylmethoxy, N-methylpiperidin-4-ylmethoxy and 3-(4-methylpiperazin-1-yl)propoxy, each of $R^2$ and $R^3$ is hydrogen; and
$Q^2$ is an aryl group of formula Ia

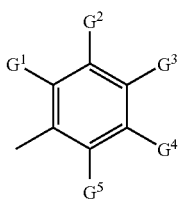

wherein $G^1$ is selected from fluoro, chloro, bromo and iodo, each of $G^3$ and $G^4$, which may be the same or different, is selected from hydrogen, chloro and methoxy, and each of ($G^2$ and $G^5$ is hydrogen, or $G^1$ and $G^2$ together form a group of formula:—
—CH=CH—CH=C(Cl)—, —O—CH=C(Cl)— or —O—CH$_2$—O—, and each of $G^3$, $G^4$ and $G^5$ is hydrogen;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the $Q^1$-Z- group is selected from tetrahydropyran-4-yloxy, 3-pyrrolidin-1-ylpropoxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of $R^2$ and $R^3$ is hydrogen; and
$Q^2$ is an aryl group of formula Ia

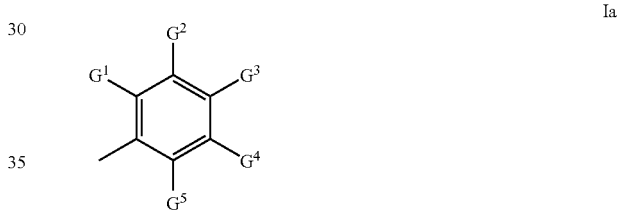

wherein $G^1$ is selected from chloro, bromo, trifluoromethyl, methyl, methoxy and pyrrolidin-1-yl, $G^2$ is hydrogen, $G^3$ is selected from hydrogen and chloro, $G^4$ is methoxy, and $G^5$ is hydrogen, or $G^1$ and $G^2$ together form a group of formula:—
—CH=CH—CH=C(Cl)—, —O—CH=C(Cl)— or —O—CH$_2$—O—, each of $G^3$ and $G^4$ is hydrogen, and $G^5$ is hydrogen or chloro;

or a pharmaceutically-acceptable acid-addition salt thereof.

A further preferred compound disclosed in the invention is a quinazoline derivative of the Formula I wherein:

m is 1 and the $R^1$ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 2-piperidin-4-ylethoxy, 2-(N-methylpiperidin-4-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-homopiperidin-1-ylethoxy, 3-homopiperidin-1-ylpropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy, 4-pyridylmethoxy and 2-cyanopyrid-4-ylmethoxy, and wherein any CH$_2$ group within a R$^1$ substituent that is attached to two carbon atoms optionally bears a hydroxy group on said CH$_2$ group;

the Q$^1$-Z- group is selected from tetrahydropyran-4-yloxy, 3-pyrrolidin-1-yloxy, N-methylpyrrolidin-3-yloxy, 3-morpholinopropoxy, 3-(1,1-dioxotetrahydro-4H-1,4-thiazin-4-yl)propoxy, 2-piperidinoethoxy, 4-piperidinyloxy, N-methylpiperidin-4-yloxy, piperidin-4-ylmethoxy, N-methylpiperidin-4-ylmethoxy, 3-(4-methylpiperazin-1-yl)propoxy, cyclopentyloxy and cyclohexyloxy;

each of R$^2$ and R$^3$ is hydrogen; and

Q$^2$ is an aryl group of formula Ia

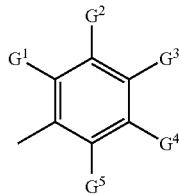

wherein G$^1$ is selected from chloro, bromo, trifluoromethyl, methyl, methoxy and pyrrolidin-1-yl, G$^2$ is hydrogen, G$^3$ is selected from hydrogen and chloro, G$^4$ is methoxy, and G$^5$ is hydrogen, or G$^1$ and G$^2$ together form a group of formula:—
—O—CH═CH—, —O—CH═C(Cl)— or —O—CH$_2$—O—, each of G$^3$ and G$^4$ is hydrogen, and G$^5$ is hydrogen or chloro;

or a pharmaceutically-acceptable acid-addition salt thereof.

A further preferred compound disclosed in the invention is a quinazoline derivative of the Formula I wherein:

m is 1 and the R$^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy, the Q$^1$-Z- group is selected from tetrahydropyran-4-yloxy, 4-piperidinyloxy, N-methylpiperidin-4-yloxy, cyclopentyloxy and cyclohexyloxy;

each of R$^2$ and R$^3$ is hydrogen; and

Q$^2$ is an aryl group of formula Ia

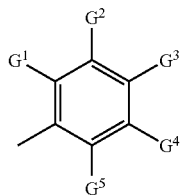

wherein G$^1$ and G$^2$ together form a group of formula:—
—O—CH$_2$—O—, each of G$^3$ and G$^4$ is hydrogen, and G$^5$ is chloro;

or a pharmaceutically-acceptable acid-addition salt thereof.

A further preferred compound disclosed in the invention is a quinazoline derivative of the Formula I wherein:

m is 1 and the R$^1$ group is located at the 7-position and is selected from methoxy, ethoxy, propoxy, isopropoxy, isobutoxy, 2-fluoroethoxy, 2,2,2-trifluoroethoxy, benzyloxy, 2-pyrrolidin-1-ylethoxy, 3-pyrrolidin-1-ylpropoxy, 2-piperidinoethoxy, 3-piperidinopropoxy, 3-(4-hydroxypiperidin-1-yl)propoxy, 2-piperidin-4-ylethoxy, 2-(N-methylpiperidin-4-yl)ethoxy, 2-morpholinoethoxy, 3-morpholinopropoxy, 2-piperazin-1-ylethoxy, 3-piperazin-1-ylpropoxy, 2-(4-methylpiperazin-1-yl)ethoxy, 3-(4-methylpiperazin-1-yl)propoxy, 3-(4-cyanomethylpiperazin-1-yl)propoxy, 2-[(2S)-2-carbamoylpyrrolidin-1-yl]ethoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, piperidin-4-ylmethoxy, N-methylpiperidin-4-ylmethoxy, 2-(4-pyridyloxy)ethoxy, 2-pyridylmethoxy, 3-pyridylmethoxy and 4-pyridylmethoxy;

the Q$^1$-Z- group is selected from tetrahydropyran-4-yloxy, 4-piperidinyloxy, N-methylpiperidin-4-yloxy, piperidin-4-ylmethoxy, N-methylpiperidin-4-ylmethoxy, cyclopentyloxy and cyclohexyloxy;

each of R$^2$ and R$^3$ is hydrogen; and

Q$^2$ is an aryl group of formula Ia

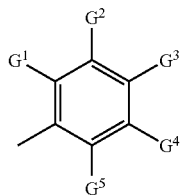

wherein G$^1$ and G$^2$ together form a group of formula:—
—O—CH$_2$—O—, each of G$^3$ and G$^4$ is hydrogen, and G$^5$ is chloro;

or a pharmaceutically-acceptable acid-addition salt thereof.

A particular preferred compound disclosed in the present invention is, for example, a quinazoline derivative of the Formula I selected from:—

4-(2-chloro-5-methoxyanilino)-5,7-di-(3-morpholinopropoxy)quinazoline, 4-(2-bromo-5-methoxyanilino)-7-methoxy-5-(N-methylpiperidin-4-yloxy)quinazoline, 4-(2-chloro-5-methoxyanilino)-7-methoxy-5-(N-methylpiperidin-4-yloxy)quinazoline, 4-(2-chloro-5-methoxyanilino)-7-[3-(4-methylpiperazin-1-yl)propoxy]-5-tetrahydropyran-4-yloxyquinazoline, 4-(2-chloro-5-methoxyanilino)-7-(3-morpholinopropoxy)-5-tetrahydropyran-4-yloxyquinazoline, 4-(2-chloro-5-methoxyanilino)-7-[2-hydroxy-3-(4-methylpiperazin-1-yl)propoxy]-5-tetrahydropyran-4-yloxyquinazoline, 4-(2-chloro-5-methoxyanilino)-7-(2-hydroxy-3-morpholinopropoxy)-5-tetrahydropyran-4-yloxyquinazoline, 4-(2-chloro-5-methoxyanilino)-7-[3-(4-methylpiperazin-1-yl)propoxy]-5-tetrahydrofuran-3-yloxyquinazoline, 4-(2-chloro-5-methoxyanilino)-7-(3-morpholinopropoxy)-5-tetrahydrofuran-3-yloxyquinazoline, 4-(5-chloronaphth-1-ylamino)-7-methoxy-5-(N-methylpiperidin-4-yloxy)quinazoline,
4-(3-chlorobenzofuran-7-ylamino)-7-methoxy-5-(N-methylpiperidin-4-yloxy)quinazoline,
7-benzyloxy-4-(2-bromo-5-methoxyanilino)-5-piperidin-4-yloxyquinazoline,
4-(2-bromo-5-methoxyanilino)-7-(3-methylsulphonylpropoxy)-5-piperidin-4-yloxyquinazoline,
4-(2-bromo-5-methoxyanilino)-7-methoxy-5-piperidin-4-ylmethoxyquinazoline,
4-(2,4-dichloro-5-methoxyanilino)-7-methoxy-5-(N-methylpiperidin-4-yloxy)quinazoline,
4-(2,5-methoxyanilino)-7-methoxy-5-(N-methylpiperidin-4-yloxy)quinazoline,
4-(2,4-dichloro-5-methoxyanilino)-7-(2-pyrrolidin-1-ylethoxy)-5-tetrahydropyran-4-yloxyquinazoline,
4-(2,4-dichloro-5-methoxyanilino)-7-(2-piperidinoethoxy)-5-tetrahydropyran-4-yloxyquinazoline,
4-(2,4-dichloro-5-methoxyanilino)-7-(2-morpholinoethoxy)-5-tetrahydropyran-4-yloxyquinazoline,
4-(2,4-dichloro-5-methoxyanilino)-7-[2-(4-methylpiperazin-1-yl)ethoxy]-5-tetrahydropyran-4-yloxyquinazoline,
4-(2-bromo-5-methoxyanilino)-7-(2-pyrrolidin-1-ylethoxy)-5-tetrahydropyran-4-yloxyquinazoline,
4-(2-bromo-5-methoxyanilino)-7-(2-piperidinoethoxy)-5-tetrahydropyran-4-yloxyquinazoline,
4-(2-bromo-5-methoxyanilino)-7-[2-(4-methylpiperazin-1-yl)ethoxy]-5-tetrahydropyran-4-yloxyquinazoline,
4-(2-bromo-5-methoxyanilino)-7-(4-pyridyloxyethoxy)-5-tetrahydropyran-4-yloxyquinazoline,
4-(2-bromo-5-methoxyanilino)-7-{2-[(2S)-2-(N,N-dimethylcarbamoyl)pyrrolidin-1-yl]ethoxy}-5-tetrahydropyran-4-yloxyquinazoline,
4-(2-bromo-5-methoxyanilino)-7-{2-[(2S)-2-(N-methylcarbamoyl)pyrrolidin-1-yl]ethoxy}-5-tetrahydropyran-4-yloxyquinazoline,
4-(2-bromo-5-methoxyanilino)-7-(4-pyridylmethoxy)-5-tetrahydropyran-4-yloxyquinazoline,
4-(5-methoxy-2-pyrrolidin-1-ylanilino)-7-[3-(4-methylpiperazin-1-yl)propoxy]-5-tetrahydropyran-4-yloxyquinazoline, and
4-(2-bromo-5-methoxyanilino)-5-cyclopentyloxy-7-(2-pyrrolidin-1-ylethoxy)quinazoline;

or a pharmaceutically-acceptable acid-addition salt thereof.
A further particular preferred compound disclosed in the present invention is, for example, a quinazoline derivative of the Formula I selected from:—
4-(2-chloro-5-methoxyanilino)-5-isopropoxy-7-(3-morpholinopropoxy)quinazoline and
4-(2-chloro-5-methoxyanilino)-5-isopropoxy-7-[3-(4-methylpiperazin-1-yl)propoxy]quinazoline, or a pharmaceutically-acceptable acid-addition salt thereof.
A further particular preferred compound disclosed in the present invention is, for example, a quinazoline derivative of the Formula I selected from:—
4-(6-chloro-2,3-methylenedioxyamino)-5-cyclopentyloxy-7-(2-pyrrolidin-1-ylethoxy)quinazoline,
4-(6-chloro-2,3-methylenedioxyanilino)-5-piperidin-4-yloxyquinazoline,
4-(6-chloro-2,3-methylenedioxyanilino)-7-methoxy-5-piperidin-4-yloxyquinazoline,
4-(6-chloro-2,3-methylenedioxyanilino)-7-methoxy-5-(N-methylpiperidin-4-yloxy)quinazoline,
4-(6-chloro-2,3-methylenedioxyanilino)-7-methoxy-5-piperidin-4-ylmethoxyquinazoline,
4-(6-chloro-2,3-methylenedioxyanilino)-7-(2-pyrrolidin-1-ylethoxy)-5-tetrahydropyran-4-yloxyquinazoline,
4-(6-chloro-2,3-methylenedioxyanilino)-7-(3-pyrrolidin-1-ylpropoxy)-5-tetrahydropyran-4-yloxyquinazoline,
4-(6-chloro-2,3-methylenedioxyamino)-7-[3-(4-methylpiperazin-1-yl)propoxy]-5-tetrahydropyran-4-yloxyquinazoline,
4-(6-chloro-2,3-methylenedioxyanilino)-7-[2-(4-methylpiperazin-1-yl)ethoxy]-5-tetrahydropyran-4-yloxyquinazoline,
4-(6-chloro-2,3-methylenedioxyanilino)-7-(2-piperidinoethoxy)-5-tetrahydropyran-4-yloxyquinazoline,
4-(6-chloro-2,3-methylenedioxyanilino)-7-[2-(4-pyridyloxy)ethoxy]-5-tetrahydropyran-4-yloxyquinazoline,
4-(6-chloro-2,3-methylenedioxyanilino)-7-piperidin-4-ylmethoxy-5-tetrahydropyran-4-yloxyquinazoline and
4-(6-chloro-2,3-methylenedioxyanilino)-7-(N-methylpiperidin-4-ylmethoxy)-5-tetrahydropyran-4-yloxyquinazoline;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are illustrated by the following representative process variants in which, unless otherwise stated, $Q^1$, Z, m, $R^1$, $R^2$, $R^3$ and $Q^2$ have any of the meanings defined hereinbefore. Necessary starting materials may be obtained by standard procedures of organic chemistry. The preparation of such stating materials is described in conjunction with the following representative process variants and within the accompanying Examples. Alternatively necessary starting materials are obtainable by analogous procedures to those illustrated which are within the ordinary skill of an organic chemist.

(a) The reaction, conveniently in the presence of a suitable base, of a quinazoline of the Formula II

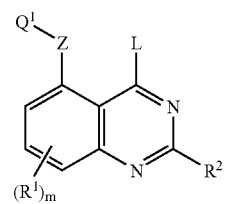

II wherein L is a displaceable group and $Q^1$, Z, m, $R^1$ and $R^2$ have any of the meanings defined hereinbefore except that any functional group is protected if necessary, with an aniline of the Formula $Q^2NHR^3$ wherein $Q^2$ and $R^3$ have any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide, or, for example, an alkali metal hydride, for example sodium hydride.

A suitable displaceable group L is, for example, a halogeno, alkoxy, aryloxy or sulphonyloxy group, for example a chloro, bromo, methoxy, phenoxy, pentafluorophenoxy, methanesulphonyloxy or toluene-4-sulphonyloxy group. The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxan, an aromatic solvent such as toluene, or a dipolar aprotic solvent such as N,N-dimethylformamide, N,N-dimethylacetamide, N-methylpyrrolidin-2-one or dimethylsulphoxide. The reaction is conveniently carried out at a temperature in the range, for example, 10 to 250° C., preferably in the range 40 to 80° C.

Typically, the quinazoline of the Formula II may be reacted with an aniline of the formula $Q^2NHR^3$ in the presence of a protic solvent such as isopropanol, conveniently in the presence of an acid, for example hydrogen chloride gas in diethyl ether, or hydrochloric acid, and at a temperature in the range, for example, 0 to 150° C., preferably at or near the reflux temperature of the reaction solvent.

The quinazoline derivative of the Formula I may be obtained from this process in the form of the free base or alternatively it may be obtained in the form of a salt with the acid of the formula H-L wherein L has the meaning defined hereinbefore. When it is desired to obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may in general be chosen from any of the groups described in the literature or known to the skilled chemist as appropriate for the protection of the group in is question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

Quinazoline starting materials of the Formula II may be obtained by conventional procedures. For example, a 3,4-dihydroquinazolin-4-one of Formula III

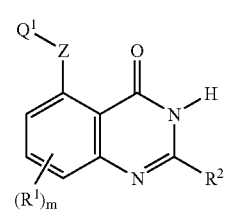

III wherein m, $R^1$, $Q^1$, Z and $R^2$ have any of the meanings defined hereinbefore except that any functional group is protected if necessary, may be reacted with a halogenating agent such as thionyl chloride, phosphoryl chloride or a mixture of carbon tetrachloride and triphenylphosphine whereafter any protecting group that is present is removed by conventional means.

The 4-chloroquinazoline so obtained may be converted, if required, into a 4-pentafluorophenoxyquinazoline by reaction with pentafluorophenol in the presence of a suitable base such as potassium carbonate and in the presence of a suitable solvent such as N,N-dimethylformamide.

(b) For the production of those compounds of the Formula I wherein Z is an oxygen atom, the coupling, conveniently in the presence of a suitable dehydrating agent, of an alcohol of the Formula

Q¹-OH wherein Q¹ has any of the meanings defined hereinbefore except that any functional group is protected if necessary with a quinazoline of the Formula IV

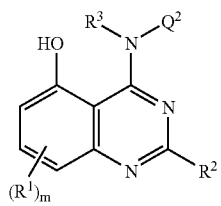

IV wherein m, R¹, R², R³ and Q² have any of the meanings defined hereinbefore except that any functional group is protected if necessary, whereafter any protecting group that is present is removed by conventional means.

A suitable dehydrating agent is, for example, a carbodiimide reagent such as dicyclohexylcarbodiimide or 1-(3-dimethylaminopropyl)-3-ethylcarbodiimide or a mixture of an azo compound such as diethyl or di-tert-butyl azodicarboxylate and a phosphine such as triphenylphosphine. The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

The quinazoline of the Formula IV may be obtained by conventional procedures. For example, a quinazoline of the Formula V

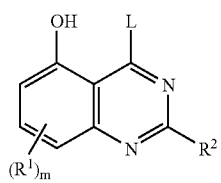

V wherein L is a displaceable group as defined hereinbefore and m, R¹ and R² have any of the meanings defined hereinbefore except that any functional group is protected if necessary, may be reacted with an aniline of the Formula

Q²NHR³ wherein Q² and R³ have any of the meanings defined hereinbefore except that any functional group is protected if necessary, whereafter any protecting group that is present is removed by conventional means.

(c) For the production of those compounds of the Formula I wherein m is 1 and R¹ is a group of the formula

Q³-X¹— wherein Q³ is an aryl-(1–6C)alkyl, (3–7C)cycloalkyl-(1–6C)alkyl, (3–7C)cycloalkenyl-(1–6C)alkyl, heteroaryl-(1–6C)alkyl or heterocyclyl-(1–6C)alkyl group and X¹ is an oxygen atom, the coupling, conveniently in the presence of a suitable dehydrating agent as defined hereinbefore, of a quinazoline of the Formula VI

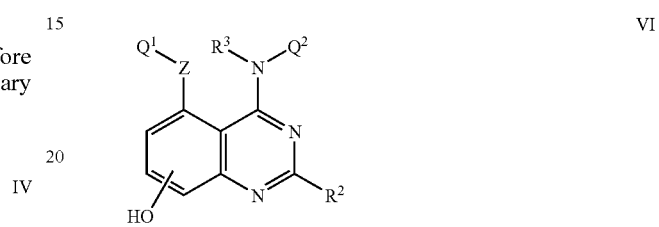

VI wherein Q¹, Z, R², R³ and Q² have any of the meanings defined hereinbefore except that any functional group is protected if necessary, with an appropriate alcohol wherein any functional group is protected if necessary, whereafter any protecting group that is present is removed by conventional means.

The reaction is conveniently carried out in the presence of a suitable inert solvent or diluent, for example a halogenated solvent such as methylene chloride, chloroform or carbon tetrachloride and at a temperature in the range, for example, 10 to 150° C., preferably at or near ambient temperature.

(d) For the production of those compounds of the Formula I wherein R¹ is a hydroxy group, the cleavage of a quinazoline derivative of the Formula I wherein R¹ is a (1–6C)alkoxy or arylmethoxy group.

The cleavage reaction may conveniently be carried out by any of the many procedures known for such a transformation. The cleavage reaction of a compound of the Formula I wherein R¹ is a (1–6C)alkoxy group may be carried out, for example, by treatment of the quinazoline derivative with an alkali metal (1–6C)alkylsulphide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide. The cleavage reaction of a compound of the Formula I wherein R¹ is a arylmethoxy group may be carried out, for example, by hydrogenation of the quinazoline derivative in the presence of a suitable metallic catalyst such as palladium or by reaction with an organic or inorganic acid, for example trifluoroacetic acid. Such reactions are preferably carried out in the presence of a suitable inert solvent or diluent as defined hereinbefore and at a temperature in the range, for example, 10 to 150° C., preferably at or near ambient temperature.

(e) For the production of those compounds of the Formula I wherein Q¹, R¹ or Q² contains a primary or secondary amino group, the cleavage of the corresponding compound of Formula I wherein Q¹, R¹ or Q² contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis, for example in the presence of trifluoroacetic acid.

(f) For the production of those compounds of the Formula I wherein $Q^1$, $R^1$ or $Q^2$ contains a (1–6C)alkoxy or substituted (1–6C)alkoxy group or a (1–6C)alkylamino or substituted (1–6C)alkylamino group, the alkylation, conveniently in the presence of a suitable base as defined hereinbefore, of a quinazoline derivative of the formula I wherein $Q^1$, $R^1$ or $Q^2$ contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1–6C)alkyl chloride, bromide or iodide or a substituted (1–6C)alkyl chloride, bromide or iodide, conveniently in the presence of a suitable base as defined hereinbefore, in a suitable inert solvent or diluent as defined hereinbefore and at a temperature in the range, for example, 10 to 140° C., conveniently at or near ambient temperature.

Conveniently for the production of those compounds of the Formula I wherein $Q^1$, $R^1$ or $Q^2$ contains a (1–6C)alkylamino or substituted (1–6C)alkylamino group, a reductive amination reaction may be employed. For example, for the production of those compounds of the Formula I wherein $Q^1$, $R^1$ or $Q^2$ contains a N-methyl group, the corresponding compound containing a N—H group may be reacted with formaldehyde in the presence of a suitable reducing agent. A suitable reducing agent is, for example, a hydride reducting agent, for example an alkali metal aluminium hydride such as lithium aluminium hydride or, preferably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. The reaction is performed at a temperature in the range, for example, 10 to 80° C., conveniently at or near ambient temperature.

(g) For the production of those compounds of the Formula I wherein $Q^1$, $R^1$ or $Q^2$ contains an amino-hydroxydisubstituted (1–6C)alkoxy group (such as 2-hydroxy-3-piperidinopropoxy, 2-hydroxy-3-methylaminopropoxy, 3-dimethylamino-2-hydroxypropoxy or 3-[N-(3-dimethylaminopropyl)-N-methylamino]-2-hydroxypropoxy), the reaction of a compound of the Formula I wherein $Q^1$, $R^1$ or $Q^2$ contains an epoxy-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

(h) The reaction, conveniently in the presence of a suitable base as defined hereinbefore, of a quinazoline of the Formula VII

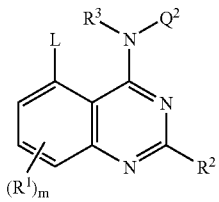

VII wherein L is a displaceable group as defined hereinbefore and m, $R^1$, $R^2$, $R^3$ and $Q^2$ have any of the meanings defined hereinbefore except that any functional group is protected if necessary, with a compound of the Formula $Q^1ZH$ wherein $Q^1$ and Z have any of the meanings defined hereinbefore except that any functional group is protected if necessary, whereafter any protecting group that is present is removed by conventional means.

The reaction is conveniently carried out in the presence of a suitable inert diluent or carrier as defined hereinbefore and at a temperature in the range 10 to 150° C., preferably at or near 50° C.

(i) For the production of those compounds of the Formula I wherein $Q^1$, $R^1$ or $Q^2$ contains an amino-substituted (1–6C)alkoxy group (such as 3-piperidinopropoxy, 3-methylaminopropoxy or 3-dimethylaminopropoxy), the reaction of a compound of the Formula I wherein $Q^1$, $R^1$ or $Q^2$ contains a halogeno-substituted (1–6C)alkoxy group with a heterocyclyl compound or an appropriate amine.

The reaction is conveniently carried out in the presence of a suitable inert diluent or carrier as defined hereinbefore and at a temperature in the range 10 to 150° C., preferably at or near ambient temperature.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

The following assays can be used to measure the effects of the compounds of the Formula I as $p56^{lck}$ inhibitors, as inhibitors of T cell activation, as inhibitors of cytokine production in mice and as inhibitors of transplant rejection.

(a) In Vitro Enzyme Assay

The ability of test compounds to inhibit phosphorylation by the enzyme $p56^{lck}$ of a tyrosine-containing polypeptide substrate was assessed using a conventional Elisa assay.

The following conventional procedure was used to obtain $p56^{lck}$ enzyme. An EcOR1/Not1 fragment containing the entire coding sequence of $p56^{lck}$ was generated by the technique of polymerase chain reaction (PCR) from Incyte clone No. 2829606. A 6-His tag was added to the sequence at the N-terminus during the PCR stage. Conventional sequence analysis identified a number of changes compared to the published sequence and these were found also to have been present in the original Incyte template. To achieve expression of the enzyme, the PCR fragment was inserted downstream of the polyhedrin promotor of pFASTBAC1 (Life Technologies Limited, Paisley, UK, Catalogue No. 10360-014). A recombinant Baculovirus was constructed using the Bac-to-Bac system (Life Technologies Limited). High Five insect cells (Invitrogen BV, PO Box 2312, 9704 CH Groningen, The Netherlands, Catalogue No. B855-02) were infected with the recombinant Baculovirus at a multiplicity of infection of 1 and incubated for 48 hours. The cells were harvested. Groups of $1.6 \times 10^9$ cells were lysed by incubation in 20 mM Hepes pH7.5 buffer containing 10% glycerol, 1% Triton-X-100, magnesium chloride (1.5 mM), ethylene glycol bis(2-aminoethyl ether N,N,N',N'-tetraacetic acid) (EGTA, 1 mM), sodium vanadate (1 mM), sodium fluoride (10 mM), imidazole (5 mM), sodium chloride (150 mM), phenylmethanesulphonyl fluoride (0.1 mM), pepstatin (1 mg/ml) and leupeptin (1 mg/ml). A soluble fraction was obtained by centrifugation and 6-His-p56$^{lck}$ was purified by column chromatography on a 1 ml Ni-NTA agarose column (Qiagen Limited, Crawley, West Sussex, UK). The protein was eluted using the above-mentioned buffer except that imidazole (100 mM) was also present. The p56$^{lck}$ enzyme so obtained was stored at −80° C.

Substrate solution [100 µl of a 2 µg/ml solution of the polyamino acid Poly(Glu, Ala, Tyr) 6:3:1 (Sigma Catalogue No. P3899) in phosphate buffered saline (PBS)] was added to each well of a Nunc 96-well immunoplate (Catalogue No. 439454) and the plate was sealed and stored at 4° C. for 16 hours. The excess of substrate solution was discarded, the substrate-coated wells were washed with Hepes pH7.4 buffer (50 mM, 300 µl) and blotted dry. Each test compound was dissolved in DMSO and diluted to give a series of dilutions (from 100 µM to 0.001 µM) of the compound in a 10:1 mixture of water and DMSO. Portions (25 µl) of each dilution of test compound were transferred to the 96-well assay plate. Aliquots (25 µl) of a 10:1 mixture of water and DMSO were added followed by aliquots (25 µl) of a mixture of adenosine triphosphate (ATP; 24 µl of a 1 mM aqueous solution) and manganese chloride (3 ml of a 40 mM aqueous solution).

p56$^{lck}$ enzyme (0.3 µl of a 0.5 mg/ml stock solution) was diluted in a mixture of Hepes pH 7.4 buffer (200 mM, 3 ml), sodium orthovanadate (2 mM, 0.6 ml), 1% Triton X-100 (0.6 ml), dithiothreitol (25 mM, 48 µl) and distilled water (1.8 ml). Aliquots (50 µl) of the resultant solution were transferred to each well in the assay plate and the plate was incubated at ambient temperature for 8 minutes. The wells were washed sequentially with two aliquots (300 µl) of phosphate-buffered saline (PBS) containing 0.1% Tween 20 (hereinafter PBS/T).

Aliquots (100 µl) were added to each well of a mixture of antiphosphotyrosine-4G10 monoclonal IgG2bk antibody (UBI Catalogue No. 05-321; 30 µl of a 50 µg/ml solution of the antibody in PBS/T), PBS/T (11 ml) and bovine serum albumin (BSA; Sigma Catalogue No. A6793; 55 mg) and the plate was incubated at ambient temperature for 1 hour. The wells were washed sequentially with two aliquots (300 µl) of PBS/T and blotted dry. Aliquots (100 µl) were added to each well of a mixture of sheep anti-mouse IgG-peroxidase antibody The extent of inhibition of the phosphorylation reaction at a range of concentrations of each test compound was determined and an IC$_{50}$ value was calculated.

(b) In Vitro T Cell Proliferation Assays

The ability of test compounds to inhibit T cell proliferation was assessed by using human peripheral blood mononuclear cells and stimulation of the T cells by way of the T cell receptor or other than by way of the T cell receptor.

Peripheral blood mononuclear cells (PBMC) were isolated from heparinised (10 units/ml heparin) human blood by density centrifugation (Lymphoprep™; Nycomed) spinning initially at 2000 rpm at ambient temperature for 20 minutes. Cells at the interphase were transferred to clean tubes, diluted 1:1 with RPMI 1640 medium (Gibco) and spun at 2000 rpm at ambient temperature for 10 minutes. The cell pellet was resuspended in RPMI 1640 medium and spun at 1400 rpm at ambient temperature for 10 minutes. The cell pellet was resuspended in RPMI 1640 medium and spun at 900 rpm at ambient temperature for 10 minutes to remove platelets. The prepared mononuclear cells were resuspended in an assay medium comprising RPMI 1640 culture medium supplemented with 50 units/ml penicillin, 50 µg/ml streptomycin, 1 mM glutamine and 10% heat-inactivated human AB serum.

Test compounds were solubilised in DMSO at a concentration of 10 mM and diluted 1:83.3 in assay medium. Aliquots (75 µl) were added to each well of a 96 well flat-bottomed tissue culture plate and subsequently serial 1 to 3 dilutions were made into assay medium giving final test concentrations in the range 0.1 to 30 µM. Control wells contained assay medium (50 µl) containing 1.2% DMSO. PBMCs (100 µl of a suspension of $2 \times 10^6$ cells/ml in assay medium) were added to each well and incubated for 1 hour at 37° C. in a humidified (5% $CO_2$/95% air) incubator.

The extent of inhibition of T cell proliferation at a range of concentrations of each test compound was determined and an IC$_{50}$ value was calculated.

(b)(i) T Cell Receptor Stimulation

Aliquots (50 µl) of the T cell receptor stimulatory anti-CD3 antibody (Pharmingen Catalogue No. 30100D; 40 ng/ml in assay medium) were added to each well and the cells were incubated for 24 hours at 37° C. in a humidified (5% $CO_2$/95% air) incubator. Tritiated thymidine (1 µCi per well) was added and the cells were incubated for up to a further 24 hours at 37° C. The cells were harvested onto a filter mat and radioactivity was counted using a Wallac 1450 Microbeta Plus liquid scintillation counter.

(b)(ii) Non T Cell Receptor Stimulation

Aliquots (50 µl) of a mixture of the cell stimulants PMA (phorbol-12-myristate-13-acetate, Sigma Catalogue No. P8139; 40 ng/ml) and Ionomycin (Sigma Catalogue No. I0684; 1.2 µM) were added to each well and the cells were incubated and analysed as described in paragraph (b)(i).

(c) In Vivo Skin Graft Rejection Test

The ability of test compounds to inhibit rodent skin allograft rejection was assessed using analogous procedures to those disclosed by J. Magae et al., *Cellular Immunology,* 1996, 173, 276–281 and R. Tsuji et al., *J. Antibiot.,* 1992, 45, 1295 to assess the effect of cyclosporin A on T cell properties in vivo.

(d) Test as Anti-arthritic Agent

Activity of a test compound as an anti-arthritic agent was assessed as follows. Acid soluble native type II collagen has been shown to be arthritogenic in rats causing polyarthritis when administered in Freunds incomplete adjuvant by (D. E. Trentham et al. *J. Exp. Med.,* 1977, 146, 857). This is now known as collagen-induced arthritis (CIA) and similar conditions can be induced in mice and primates. CIA in DBA/1 mice as described by R. O. Williams et al., *Proc Natl. Acad Sci.,* 1992, 89, 9784 and *Immunology,* 1995, 84, 433 is a tertiary model which can be used to demonstrate the anti-arthritic activity of a test compound.

Although the pharmacological properties of the compounds of the Formula I vary with structural change as expected, in general activity possessed by compounds of the Formula I may be demonstrated at the following concentrations or doses in one or more of the above tests (a), (b), (c) and (d):—

Test (a):—$IC_{50}$ in the range, for example, 0.001–5 µM;
Test (b)(i):—$IC_{50}$ in the range, for example, 0.01–10 µM;
Test (b)(ii):—$IC_{50}$ in the range, for example, 0.5->30 µM;
Test (c):—activity in the range, for example, 1–100 mg/kg;
Test (d):—activity in the range, for example, 1–100 mg/kg;

No physiologically-unacceptable toxicity was observed at the effective dose for those compounds of Formula I that were tested. Accordingly no untoward toxicological effects are expected when a compound of Formula I, or a pharmaceutically-acceptable salt thereof, as defined hereinbefore is administered at the dosage ranges defined hereinafter.

A pharmaceutical composition for the compounds of the Formula I comprises a quinazoline derivative of the Formula I, or a pharmaceutically-acceptable salt thereof, as defined hereinbefore in association with a pharmaceutically-acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose is received in the range, for example, 0.1 mg/kg to 75 mg/kg body weight, conveniently 0.1 mg/kg to 30 mg/kg body weight, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I as defined hereinbefore for use in the prevention or treatment of T cell mediated diseases or medical conditions in a warm-blooded animal such as man. According to a further aspect of the invention there is provided a quinazoline derivative of the Formula I as defined hereinbefore for use in the prevention or treatment of those pathological conditions which are sensitive to inhibition of one or more of the multiple tyrosine-specific protein kinases which are involved in the early signal transduction steps which lead to T cell activation.

The compounds disclosed in the present invention may be used in combination with other drugs and therapies used in the treatment of T cell mediated disease. For example, the compounds of the Formula I could be used in combination with drugs and therapies used in the treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the Formula I could be used in combination with drugs and therapies such as cyclosporin A used in the prevention or treatment of the acute rejection of transplanted organs.

For example, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of the Formula I may also be used with anti-inflammatory agents such as an inhibitor of the enzyme 5-lipoxygenase. The compounds of the Formula I may also be used with anti-inflammatory agents such as an inhibitor of the enzyme COX-2 such as celecoxib or rofecoxib.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds disclosed in the present invention may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

The compounds of the Formula I may be be used in the treatment of asthma in combination with antiasthmatic agents such as bronchodilators and leukotriene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of T cell activation. Thus, they are useful as pharmacological standards for use in the development of new biological tests and in the search for new pharmacological agents.

The compounds defined in the invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column;

(iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:—

| DMF | N,N-dimethylformamide |
|---|---|
| DMSO | dimethylsulphoxide |
| THF | tetrahydrofuran |
| NMP | N-methylpyrrolidin-2-one |

EXAMPLE 1

4-(2-chloro-5-ethoxyanilino)-5-(3-morpholinopropoxy)quinazoline

Di-tert-butyl azodicarboxylate (0.208 g) was added dropwise to a stirred mixture of 4-(2-chloro-5-methoxyanilino)-5-hydroxy-7-methoxyquinazoline (0.2 g), 4-(3-hydroxypropyl)morpholine (*Bull. Soc. Chim. Fr.,* 1962, 1117; 0.131 g), triphenylphosphine (0.237 g) and methylene chloride (3 ml). The reaction mixture was stirred at ambient temperature for 1 hour. The mixture was evaporated and the residue was purified by column chromatography on silica using a 99:1 mixture of methylene chloride and a saturated methanolic ammonia solution as eluent. The material so obtained was triturated under diethyl ether. The resultant solid was isolated, washed with diethyl ether and dried under vacuum to give the title compound (0.12 g); NMR Spectrum: (DMSOd$_6$ and CF$_3$COOD) 2.35 (m, 2H), 3.1 (t, 2H), 3.3 (t, 2H), 3.5 (d, 2H), 3.68 (t, 2), 3.8 (s, 3H), 4.0 (d, 2H), 4.02 (s, 3H), 4.6 (t, 2H), 6.93 (s, 1H), 7.05–7.15 (m, 2H), 7.5 (s, 1H), 7.57 (d, 1H), 8.87 (s, 1); Mass Spectrum: M+H$^+$ 459 and 461; Elemental Analysis: Found C, 60.0; H, 6.0; N, 12.1; C$_{23}$H$_{27}$ClN$_4$O$_4$ requires C, 60.19; H, 5.93; N, 12.2%.

The 4-(2-chloro-5-methoxyanilino)-5-hydroxy-7-methoxyquinazoline used as a starting material was prepared as follows:—

A mixture of 3,5-dimethoxyaniline hydrochloride (54.7 g), oxalyl chloride (54 ml) and methanol (500 ml) was stirred and heated to reflux for 1.5 hours. The mixture was cooled to ambient temperature. The precipitate was isolated, washed in turn with methanol and diethyl ether and dried under vacuum to give 4,6-dimethoxy-2,3-dioxoindoline (55 g); NMR Spectrum: (DMSOd$_6$) 3.85 (s, 3H), 3.9 (s, 3H), 6.0 (s, 1H), 6.2 (s, 1H), 10.9 (s, 1H); Mass Spectrum: M+Na$^+$ 230.

Hydrogen peroxide (30% solution in water, 30 ml) was added dropwise to a stirred solution of 4,6-dimethoxy-2,3-dioxoindoline (27 g) in a concentrated aqueous sodium hydroxide solution (33%, 220 ml). The resultant mixture was stirred at ambient temperature for 10 minutes. Ice was added and the basicity of the mixture was reduced to pH9 by the addition of concentrated aqueous hydrochloric acid and the mixture was then acidified to pH3.5 by the addition of glacial acetic acid. The resultant precipitate was isolated, washed with water and dried overnight under vacuum to give 2-amino-4,6-dimethoxybenzoic acid (15.9 g); NMR Spectrum: (DMSOd$_6$) 3.7 (s, 3H), 3.78 (s, 3H), 5.79 (s, 1H), 5.92 (s, 1H).

Using an analogous procedure to that described by Lombardi et al., *Chemistry & Industry,* 1990, 708, diazomethane was generated from a mixture of N-methyl-N-nitroso-4-toluenesulphonamide (31 g), ethanol (200 ml) and a saturated aqueous sodium hydroxide solution (35 ml) and bubbled though a solution of 2-amino-4,6-dimethoxybenzoic acid (15.9 g) in methylene chloride (280 ml) which had been cooled to 0° C. The resultant reaction mixture was evaporated and the residue was purified by column chromatography on silica using methylene chloride as eluent. There was thus obtained methyl 2-amino-4,6-dimethoxybenzoate (16.2 g); NMR Spectrum: (DMSOd$_6$) 3.65 (s, 3H), 3.7 (s, 6H), 5.75 (s, 1H), 5.9 (s, 1H), 6.2 (br s, 2H).

A mixture of methyl 2-amino-4,6-dimethoxybenzoate (16 g), formamidine acetate (24 g) and 2-methoxyethanol (330 ml) was stirred and heated to reflux until all of the starting material had reacted. The mixture was evaporated and the residue was triturated under water (100 ml). The resultant solid was isolated, washed with water and dried under vacuum to give 5,7-dimethoxy-3,4-dihydroquinazolin one (14.5 g); NMR Spectrum: (DMSOd$_6$) 3.82 (s, 3H), 3.86 (s, 3H), 6.5 (s, 1H), 6.7 (s, 1H), 7.9 (s, 1H), 11.7 (br s, 1H).

A mixture of a portion (0.35 g) of the material so obtained, phosphoryl chloride (0.95 ml) and acetonitrile (8 ml) was stirred and heated to reflux for 2 hours. The mixture was cooled to 0° C. and isopropanol (8 ml) and 2-chloro-5-methoxyaniline (0.321 g) were added in turn. The resultant mixture was heated to reflux for 1.5 hours. The mixture was cooled to ambient temperature and the resultant precipitate was filtered, washed with isopropanol and with diethyl ether and dried under vacuum. There was thus obtained 4-(2-chloro-5-methoxyanilino)-5,7-dimethoxyquinazoline hydrochloride (0.365 g); NMR Spectrum: (DMSOd$_6$) 3.8 (s, 3H), 4.0 (s, 3H), 4.2 (s, 3H), 7.0 (m, 3H), 7.6 (d, 1H), 7.62 (s, 1H), 8.8 (s, 1H), 10.9 (s, 1H); Mass Spectrum: M+H$^+$ 346 and 348.

A mixture of 4-(2-chloro-5-methoxyanilino)-5,7-dimethoxyquinazoline hydrochloride (2.5 g), pyridine hydrochloride (0.76 g) and pyridine (50 ml) was stirred and heated to reflux for 9 hours. The mixture was cooled to ambient temperature and evaporated. The residue was suspended in water and the mixture was basified to pH10 by the addition of aqueous sodium bicarbonate solution. The resultant solid precipitate was isolated, washed in turn with water, with methylene chloride and with diethyl ether and dried overnight under vacuum at 50° C. There was thus obtained 4-(2-chloro-5-methoxyanilino)-5-hydroxy-7-methoxyquinazoline (2.1 g); NMR Spectrum: (DMSOd$_6$) 3.8 (s, 3H), 3.85 (s, 3H), 6.3–6.5 (m, 2H), 6.8 (d, 1H), 7.4 (d, 1H), 8.1 (br s, 1H), 8.42 (br s, 1H).

EXAMPLE 2

Using an analogous procedure to that described in Example 1, the appropriate 5-hydroxyquinazoline was reacted with the appropriate alcohol to give the compounds described in Table I.

TABLE I

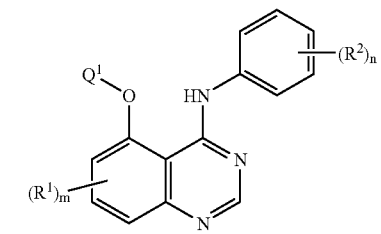

| No. & Note | $(R^1)_m$ | $Q^1$ | $(R^2)_n$ |
|---|---|---|---|
| [1] | 7-methoxy | 3-(4-methylpiperazin-1-yl)propyl | 2-chloro-5-methoxy |
| [2] | 7-methoxy | 2-piperidinoethyl | 2-chloro-5-methoxy |
| [3] | 7-methoxy | 3-pyrrolidin-1-ylpropyl | 2-chloro-5-methoxy |
| [4] | 7-methoxy | 2-(1,2,4-triazol-1-yl)ethyl | 2-chloro-5-methoxy |
| [5] | 7-benzyloxy | 3-morpholinopropyl | 2-chloro-5-methoxy |
| [6] | 7-benzyloxy | 3-pyrrolidin-1-ylpropyl | 2-chloro-5-methoxy |
| [7] | hydrogen | 3-morpholinopropyl | 2-bromo-5-methoxy |
| [8] | hydrogen | 3-(1,1-dioxotetrahydro-4H-1,4-thiazin-4-yl)propyl | 2-bromo-5-methoxy |
| [9] | hydrogen | 2-(4-methylpiperazin-1-yl)ethyl | 2-bromo-5-methoxy |
| [10] | hydrogen | 3-(4-methylpiperazin-1-yl)propyl | 2-chloro-5-methoxy |
| [11] | hydrogen | 2-imidazol-1-ylethyl | 2-chloro-5-methoxy |

TABLE I-continued

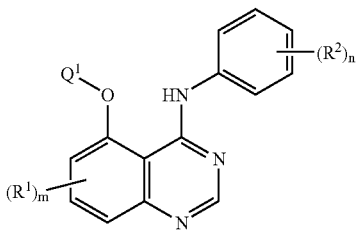

| No. & Note | $(R^1)_m$ | $Q^1$ | $(R^2)_n$ |
|---|---|---|---|
| [12] | 7-methoxy | N-methylpiperidin-4-yl | 2-chloro-5-methoxy |
| [13] | hydrogen | N-methylpiperidin-4-yl | 2-chloro-5-methoxy |
| [14] | hydrogen | N-methylpiperidin-4-yl | 2-bromo-5-methoxy |
| [15] | hydrogen | N-methylpiperidin-4-yl | 2,5-dichloro |
| [16] | hydrogen | N-(tert-butoxycarbonyl)-piperidin-4-ylmethyl | 2-chloro-5-methoxy |
| [17] | hydrogen | N-(tert-butoxycarbonyl)-piperidin-4-ylmethyl | 2-bromo-5-methoxy |
| [18] | 7-methoxy | 2-methoxyethyl | 2-chloro-5-methoxy |
| [19] | 7-methoxy | N-methylpyrrolidin-3-yl | 2-bromo-5-methoxy |
| [20] | 7-benzyloxy | 4-tetrahydropyranyl | 2-chloro-5-methoxy |
| [21] | hydrogen | 4-tetrahydropyranyl | 2-chloro-5-methoxy |
| [22] | 7-benzyloxy | 3-tetrahydrofuranyl | 2-chloro-5-methoxy |
| [23] | 7-(3-morpholinopropoxy) | 3-tetrahydrofuranyl | 2-chloro-5-methoxy |
| [24] | 7-[3-(4-methylpiperazin-1-yl)propoxy] | 3-tetrahydrofuranyl | 2-chloro-5-methoxy |
| [25] | 7-benzyloxy | isopropyl | 2-chloro-5-methoxy |
| [26] | 7-methoxy | 4-tetrahydropyranyl | 2-bromo-5-methoxy |
| [27] | 7-methoxy | 3-pyrrolidin-1-ylpropyl | 6-chloro-2,3-methylenedioxy |
| [28] | 7-methoxy | 3-(4-methylpiperazin-1-ylpropyl) | 6-chloro-2,3-methylenedioxy |

Notes

[1] The reaction product was triturated under a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$) 2.2–2.4 (m, 2H), 2.8 (br s, 3H), 3.2–3.7 (m, 10H), 3.8 (s, 3H), 4.0 (s, 3H), 4.6 (m, 2H), 6.95–7.0 (m, 2H), 7.08 (s, 1H), 7.55 (d, 1H), 7.6 (s, 1H), 8.8 (s, 1H), 10.6 (s, 1H); Mass Spectrum: M+H$^+$ 472 and 474.

The 1-(3-hydroxypropyl)-4-methylpiperazine used as a starting material was prepared as follows:—

A mixture of 3-bromopropanol (20 ml), N-methylpiperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil; NMR Spectrum: (CDCl$_3$) 1.72 (m, 2H), 2.3 (s, 3H), 2.2–2.8 (m, 8H), 2.6 (t, 2H), 3.8 (t, 2H), 5.3 (br s, 1H).

[2] The reaction product was dissolved in a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$COOD) 1.3–1.5 (m, 2H), 1.65–1.9 (m, 4H), 3.02 (t, 2H), 3.6 (d, 2H), 3.7 (br s, 2H), 3.8 (s, 3H), 4.02 (s, 3H), 4.9 (br s, 2H), 7.0 (s, 1H), 7.05 (m, 1H), 7.1 (s, 1H), 7.3 (s, 1H), 7.58 (d, 1H), 8.8 (s, 1H); Mass Spectrum: M+H$^+$ 443 and 445.

[3] The reaction product was dissolved in a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$COOD) 1.9 (m, 2H), 2.05 (m, 2H), 2.35 (m, 2H), 3.02 (m, 2H), 3.35 (t, 2H), 3.6 (m, 2H), 3.8 (s, 3H), 4.02 (s, 3H), 4.6 (t, 2H), 6.95 (d, 1H), 7.05 (m, 1H), 7.1 (s, 1H), 7.5 (d, 1H), 7.6 (d, 1H), 8.9 (s, 1H); Mass Spectrum: M+H$^+$ 443 and 445.

The N-(3-hydroxypropyl)pyrrolidine used as a starting material was prepared as follows:—

A mixture of 3-chloropropanol (66 g), pyrrolidine (50 g), potassium carbonate (145 g) and acetonitrile (1 L) was stirred and heated to reflux for 20 hours. The mixture was cooled to ambient temperature and filtered. The filtrate was evaporated and the residue was purified by distillation to give the required starting material as an oil (62 g); NMR Spectrum: (CDCl$_3$) 1.6–1.8 (m, 6H), 2.55 (br s, 4H), 2.75 (t, 2H), 3.85 (t, 2H), 5.5 (br s, 1H).

[4] The product was precipitated from the reaction mixture by the addition of further methylene chloride. The product was isolated, washed with diethyl ether and dried under vacuum. The product so obtained gave the following data: NMR Spectrum: (DMSOd$_6$ and CF$_3$COOD) 3.82 (s, 3H), 4.0 (s, 3H), 4.8 (m, 2H), 4.85 (m, 2H), 6.9 (s, 1H), 7.05 (s, 1H), 7.1 (m, 1H), 7.3 (d, 1H), 7.58 (d, 1H), 7.65 (s, 1H), 8.67 (s, 1H), 8.79 (s, 1H); Mass Spectrum: M+H$^+$ 427 and 429.

The N$^1$-(2-hydroxyethyl)-1,2,4-triazole used as a starting material was prepared according to the procedure disclosed in Ann. Pharm. Fr., 1977, 35, 503.

[5] The product gave the following data: NMR Spectrum: (DMSOd$_6$) 2.1 (m, 2H), 2.32 (br s, 4H), 2.45 (t, 2H), 3.52 (m, 4H), 3.8 (s, 3H), 4.5 (t, 2H), 5.3 (s, 2H), 6.8 (m, 1H), 6.95 (s, 1H), 6.92 (s, 1H), 7.3–7.6 (m, 6H), 8.35 (s, 1H), 8.55 (s, 1H), 10.12 (s, 1H); Mass Spectrum: M+H$^+$ 535 and 537.

The 7-benzyloxy-4-(2-chloro-5-methoxyanilino)-5-hydroxyquinazoline used as a starting material was prepared as follows:—

A mixture of 3,5-dibenzyloxyaniline hydrochloride (J. Org. Chem., 1975, 40, 1556; 10 g) and oxalyl chloride (15 ml) was heated to 170° C. for 3 hours. The mixture was cooled to ambient temperature, methanol (45 ml) was added and the mixture was heated to reflux for 1 hour. The mixture was cooled to ambient temperature and the precipitate was isolated, washed with methanol and dried under vacuum to give 4,6-dibenzyloxy-2,3-dioxoindoline (8.8 g); NMR Spectrum: (DMSOd$_6$) 5.22 (s, 2H), 5.28 (s, 2H), 6.12 (s, 1H), 6.42 (s, 1H), 7.3–7.55 (m, 10H), 10.97 (s, 1H).

Hydrogen peroxide (30% solution in water, 13 ml) was added dropwise to a stirred solution of 4,6-dibenzyloxy-2,3-dioxoindoline (14.3 g) in a concentrated aqueous sodium hydroxide solution (22.3 g in 90 ml of water) which had been heated to 70° C. The resultant mixture was stirred at 70° C. for 30 minutes and then cooled to ambient temperature. Ice was added and the basicity of the mixture was reduced to pH9 by the addition of 2N aqueous hydrochloric acid and the mixture was then acidified to pH3.7 by the addition of glacial acetic acid. The resultant precipitate was purified by column chromatography on silica using a 99:1 mixture of methylene chloride and methanol as eluent. There was thus obtained 2-amino-4,6-dibenzyloxybenzoic acid (8 g); NMR Spectrum: (DMSOd$_6$) 5.05 (s, 2H), 5.15 (s, 2H), 6.01 (s, 1H), 6.05 (s, 1H), 7.3–7.6 (m, 10H).

Using an analogous procedure to that described by Lombardi et al., Chemisty & Industry, 1990, 708, diazomethane was generated from a mixture of N-methyl-N-nitroso-4-toluenesulphonamide (11.5 g), ethanol (60 ml) and a saturated aqueous sodium hydroxide solution (30 ml) and bubbled though a solution of 2-amino-4,6-dibenzyloxybenzoic acid (8 g) in methylene chloride (170 ml) which had been cooled to 0° C. The resultant reaction mixture was evaporated and the residue was triturated under diethyl ether. There was thus obtained methyl 2-amino-4,6-dibenzyloxybenzoate (7.7 g); NMR Spectrum: (DMSOd$_6$) 3.74 (s, 3H), 5.07 (s, 2H), 5.11 (s, 2H), 6.0 (s, 1H), 6.04 (s, 1H), 6.25 (br s, 2H), 7.28–7.5 (m, 10H).

A mixture of methyl 2-amino-4,6-dibenzyloxybenzoate (7.7 g), formamidine acetate (7.2 g) and 2-methoxyethanol (100 ml) was stirred and heated to reflux until all of the starting material had reacted. The mixture was evaporated and the residue was triturated under water (60 ml). The resultant solid was isolated, washed with water and dried under vacuum to give 5,7-dibenzyloxy-3,4-dihydroquinazolin-4-one (6.8 g); NMR Spectrum: (DMSOd$_6$) 5.24 (s, 4H), 6.75 (s, 1H), 6.8 (s, 1H), 7.3–7.7 (m, 10H), 7.95 (s, 1H), 11.75 (br s, 1H).

A mixture of a portion (6 g) of the material so obtained, phosphoryl chloride (1.72 ml), diisopropylethylamine (7.3 ml) and 1,2-dichloroethane (60 ml) was stirred and heated to reflux for 2 hours. The mixture was evaporated and a mixture of the residue and isopropanol (80 ml) was cooled to 10° C. and 2-chloro-5-methoxyaniline (3.4 g) and diisopropylethylamine (1.45 ml) were added in turn. The resultant mixture was heated to reflux for 1.5 hours. The mixture was cooled to ambient temperature and the resultant precipitate was isolated, washed with isopropanol and with diethyl ether and dried under vacuum. There was thus obtained 4-(2-chloro-5-methoxyanilino)-5,7-dibenzyloxyquinazoline hydrochloride (6.35 g); NMR Spectrum: (DMSOd$_6$) 3.8 (s, 3H), 5.31 (s, 2H), 5.65 (s, 2H), 6.95 (m, 1H), 7.02 (s, 1H), 7.15 (s, 1H), 7.3–7.5 (m, 9H), 7.6 (d, 2H), 7.7 (s, 1H), 8.8 (s, 1H); Mass Spectrum: M+H$^+$ 498 and 500.

A mixture of 4-(2-chloro-5-methoxyanilino)-5,7-dibenzyloxyquinazoline hydrochloride (4.3 g), pyridine hydrochloride (0.94 g) and pyridine (90 ml) was stirred and heated to reflux for 9 hours. The mixture was cooled to ambient temperature and evaporated. The residue was triturated under water. The resultant solid precipitate was isolated, washed with water and dried overnight under vacuum. The material was then triturated under methanol. The resultant solid was isolated and dried under vacuum. There was thus obtained 7-benzyloxy-4-(2-chloro-5-methoxyanilino)-5-hydroxyquinazoline (3.1 g); NMR Spectrum: (DMSOd$_6$ and CF$_3$COOD) 3.85 (s, 3H), 5.3 (s, 2H), 6.85 (s, 2H), 7.0 (m, 1H), 7.3–7.6 (m, 6H), 7.8 (d, 1H), 8.85 (s, 1H).

[6] The product gave the following data: NMR Spectrum: (CDCl$_3$) 1.75 (br s, 4H), 2.2 (m, 2H), 2.5 (br s, 4H), 2.65 (t, 2H), 3.85 (s, 3H), 4.4 (t, 2H), 5.2 (s, 2H), 6.62 (d, 1H), 6.7 (s, 1H), 6.95 (s, 1H), 7.2–7.5 (m, 6H), 8.4 (s, 1H), 8.6 (s, 1H), 10.1 (s, 1H); Mass Spectrum: M+H$^+$ 519.

[7] The reaction product was triturated under diethyl ether, a 6.3M solution of hydrogen chloride in isopropanol was added and the mixture was stirred at ambient temperature for 1 hour. The resultant precipitate was isolated, washed with diethyl ether and dried under vacuum to give the product as a dihydrochloride salt which gave the following data: NMR Spectrum: (DMSOd$_6$ and CF$_3$COOD) 2.3–2.45 (m, 2H), 3.1 (t, 2H), 3.3 (t, 2H), 3.45 (d, 2H), 3.75 (t, 2H), 3.81 (s, 3H), 4.0 (d, 2H), 4.68 (t, 2H), 7.08 (m, 1H), 7.5–7.7 (m, 4H), 8.1 (m, 1H), 8.95 (s, 1H); Mass Spectrum: M+H$^+$ 473 and 475.

The 4-(2-bromo-5-methoxyanilino)-5-hydroxyquinazoline used as a starting material was prepared as follows:—

A mixture of 5-methoxy-3,4-dihydroquinazolin-4-one (International Patent Application WO 96/09294, pages 28 and 29; 2.1 g), phosphoryl chloride (1.23 ml), diisopropylethylamine (5.2 ml) and 1,2-dichloroethane (20 ml) was stirred and heated to 80° C. for 3 hours. The mixture was evaporated. The residue was dissolved in isopropanol (20 ml) and 2-bromo-5-methoxyaniline (*J. Amer. Chem. Soc.*, 1994, 116, 11797; 2.45 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2-bromo-5-methoxyanilino)-5-methoxyquinazoline hydrochloride (3.8 g); NMR Spectrum: (DMSOd$_6$ and CF$_3$COOD) 3.82 (s, 3H), 4.2 (s, 3H), 7.0 (m, 1H), 7.48 (d, 1H), 7.5 (d, 1H), 7.55 (d, 1H), 7.75 (d, 1H), 8.1 (m, 1H), 7.92 (s, 1H); Mass Spectrum: M+H$^+$ 360 and 362.

A mixture of 4-(2-bromo-5-methoxyanilino)-5-methoxyquinazoline hydrochloride (3.5 g), pyridine hydrochloride (2 g) and pyridine (30 ml) was stirred and heated to reflux for 18 hours. The mixture was cooled to ambient temperature and evaporated. The residue was suspended in water. the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2-bromo-5-methoxyanilino)-5-hydroxyquinazoline (2.15 g); NMR Spectrum: (DMSOd$_6$ and CF$_3$COOD) 3.8 (s, 3H), 6.95 (m, 1H), 7.25 (d, 1H), 7.3 (d, 1H), 7.7 (s, 1H), 7.75 (d, 1H), 7.9 (m, 1H), 8.9 (s, 1H); Mass Spectrum: M+H$^+$ 346 and 348.

[8] Using a similar work-up to that described in Note [7] above, the product was obtained as a dihydrochloride salt which gave the following data: NMR Spectrum: (DMSOd$_6$ and CF$_3$COOD) 2.4–2.5 (m, 2H), 3.5 (m, 2H), 3.7 (br s, 4H), 3.72–3.9 (br s, 4H), 3.8 (s, 3H), 4.7 (t, 2H), 7.0 (m, 1H), 7.4–7.6 (m, 3H), 7.75 (d, 1H), 8.1 (m, 1H), 9.02 (s, 1H); Mass Spectrum: M+H$^+$ 521 and 523.

The 3-(1,1-dioxotetrahydro-4H-1,4-thiazin-4-yl)propan-1-ol used as a starting material was prepared as follows:—

A mixture of 3-aminopropan-1-ol (0.650 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4-yl)propan-1-ol (0.8 g); NMR Spectrum: (CDCl$_3$) 1.7–1.8 (m, 2H), 2.73 (t, 2H), 3.06 (br s, 8H), 3.25 (s, 1H), 3.78 (t, 2H); Mass Spectrum: M+H$^+$ 194.

[9] Using a similar work-up to that described in Note [7] above, the product was obtained as a dihydrochloride salt which gave the following data: Mass Spectrum: M+H$^+$ 472 and 474.

The 1-(2-hydroxyethyl)-4-methylpiperazine used as a starting material was prepared as follows:—

A mixture of 2-bromoethanol (2.36 g), N-methylpiperazine (1.26 g), potassium carbonate (5.0 g) and ethanol (150 ml) was stirred and heated to reflux for 18 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18 (s, 3H), 2.3–2.7 (br m, 8H), 2.56 (t, 2H), 3.61 (t, 2H).

[10] Using a similar work-up to that described in Note [7] above, the product was obtained as a dihydrochloride salt which gave the following data: NMR Spectrum: (DMSOd$_6$ and CF$_3$COOD) 2.35–2.45 (m, 2H), 2.9 (s, 3H), 3.2–3.9 (m, 10H), 3.85 (s, 3H), 4.7 (t, 2H), 7.05 (m, 1H), 7.45–7.6 (m, 4H), 8.1 (m, 1H), 8.95 (s, 1H); Mass Spectrum: M+H$^+$ 442 and 444.

[11] Using a similar work-up to that described in Note [7] above, the product was obtained as a dihydrochloride salt which gave the following data: NMR Spectrum: (DMSOd$_6$ and CF$_3$COOD) 3.82 (s, 3H), 4.85 (t, 2H), 5.05 (t, 2H), 7.05 (m, 1H), 7.35 (d, 1H), 7.5–7.65 (m, 3H), 7.7 (s, 1H), 7.8 (s, 1H), 8.1 (m, 1H), 8.95 (s, 1H), 9.15 (s, 1H); Mass Spectrum: M+H$^+$ 396 and 398.

The N-(2-hydroxyethyl)imidazole used as a starting material was prepared according to the procedure disclosed in *J. Med. Chem.*, 1993, 2, 4052.

[12] The 4-hydroxy-1-methylpiperidine was added after the other reaction components had been stirred together at 0° C. for 1 hour. The resultant reaction mixture was stirred at ambient temperature for 3 hours. The reaction mixture was filtered and the filtrate was washed with a 1N aqueous sodium hydroxide solution. The organic solution was evaporated and the residue was purified by column chromatography on silica using a 98:2 mixture of methylene chloride and methanol as eluent. The material so obtained was triturated under a 6M solution of hydrogen chloride in diethyl ether. The resultant solid was isolated, washed with diethyl ether and dried under vacuum to give the product as a dihydrochloride salt which gave the following data: NMR Spectrum: (DMSOd$_6$ and CF$_3$COOD) 2.0–2.15 (m, 2H), 2.15–2.3 (m, 4H), 2.35 (s, 3H), 2.8–2.9 (m, 2H), 3.85 (s, 3H), 3.95 (s, 3H), 4.55 (m, 1H), 6.55 (s, 1H), 6.65 (m, 1m), 6.85 (s, 1H), 7.3 (d, 1H), 8.15 (d, 1H), 8.55 (s, 1H), 9.85 (br s, 1H); Mass Spectrum: M+H$^+$ 429 and 431.

[13] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.2–2.4 (m, 2H), 2.5 (d, 2H), 2.85 (s, 3H), 3.1–3.3 (m, 2H), 3.4–3.5 (m, 0.5H minor conformer), 3.55–3.7 (d, 1H major conformer and 0.5H minor conformer), 2.8 (s, 3H), 5.1–5.2 (m, 1H major conformer), 5.2–5.3 (m, 1H minor conformer), 7.05 (m, 1H major conformer), 7.1 (m, 1H minor conformer), 7.4–7.8 (m, 4H), 8.05–8.15 (m, 1H), 8.95 (s, 1H minor conformer), 9.0 (s, 1H major conformer); Mass Spectrum: M+H$^+$ 399 and 401.

[14] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.2–2.4 (m, 2H), 2.4–2.65 (m, 2H), 2.8

(s, 3H major conformer), 2.82 (s, 3H minor conformer), 3.1–3.3 (m, 2H), 3.45 (m, 0.5H minor conformer), 3.5–3.7 (m, 0.5H minor conformer), 3.8 (s, 3H), 5.1–5.2 (m, 1H major conformer), 5.25 (br s, 1H minor conformer), 7.0 (m, 1H major conformer), 7.05 (m, 1H minor conformer), 7.4–7.8 (m, 4H), 8.12 (m, 1H), 8.9 (s, 1H minor conformer), 9.0 (s, 1H); Mass Spectrum: M+H$^+$ 443 and 445.

[15] Using a similar work-up to that described in Note [7] above, the product was obtained as a dihydrochloride salt which gave the following data: NMR Spectrum: (DMSOd$_6$ and CF$_3$COOD) (two conformational isomers were noted in a ratio of about 3:2) 2.15–2.3 (m, 2H), 2.4–2.52 (m, 2H), 2.85 (s, 3H), 3.1–3.3 (m, 2H), 3.4–3.5 (m, 0.5H minor conformer), 3.6–3.7 (m, 1H minor conformer, 0.5H minor conformer), 5.1–5.2 (m, 1H), 5.2–5.3 (m, 1H minor conformer), 7.5–7.6 (m, 2H), 7.6–7.8 (m, 2H), 8.0–8.25 (m, 2H), 9.0 (s, 1H minor conformer), 9.1 (s, 1H major conformer); Mass Spectrum: M+H$^+$ 402 and 404.

The 4-(2,5-dichloroanilino)-5-hydroxyquinazoline used as a starting material was prepared as follows:—

A mixture of 5-methoxy-3,4-dihydroquinazolin-4-one (1.8 g), phosphoryl chloride (1.03 ml), diisopropylethylamine (4.4 ml) and 1,2-dichloroethane (20 ml) was stirred and heated to 80° C. for 3 hours. The mixture was evaporated. The residue was dissolved in isopropanol (20 ml) and 2,5-dichloroaniline (1.95 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2,5-dichloroanilino)-5-methoxyquinazoline hydrochloride (3.2 g); NMR Spectrum: (DMSOd$_6$) 4.19 (s, 3H), 7.45 (d, 1H), 7.5–7.6 (m, 2H), 7.75 (d, 1H), 8.05–8.15 (m, 2H), 8.95 (s, 1H).

A mixture of 4-(2,5-dichloroanilino)-5-methoxyquinazoline hydrochloride (3.2 g), pyridine hydrochloride (2.1 g) and pyridine (30 ml) was stirred and heated to reflux for 18 hours. The mixture was cooled to ambient temperature and evaporated. The residue was suspended in water, the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2,5-dichloroanilino)-5-hydroxyquinazoline (1.3 g); NMR Spectrum: (DMSOd$_6$ and CF$_3$COOD) 7.25 (d, 1H), 7.3 (d, 1H), 7.5 (m, 1H), 7.7 (d, 1H), 7.95 (m, 1H), 8.3 (s, 1H), 9.0 (s, 1H); Mass Spectrum: M+H$^+$ 306 and 308.

[16] The product gave the following data: NMR Spectrum: (CDCl$_3$) 1.2–1.4 (m, 2H), 1.5 (s, 9H), 1.9 (d, 2H), 2.3 (m, 1H), 2.8 (t, 2H), 3.9 (s, 3H), 4.1–4.2 (m, 2H), 4.2 (d, 2H), 6.66 (m, 1H), 6.93 (d, 1H), 7.7 (m, 1H), 8.45 (d, 1H), 8.7 (s, 1H); Mass Spectrum: M+H$^+$ 499 and 501.

The 4-(2-chloro-5-methoxyanilino)-5-hydroxyquinazoline used as a starting material was prepared as follows:—

A mixture of 5-methoxy-3,4-dihydroquinazolin-4-one (2.1 g), phosphoryl chloride (1.23 ml), diisopropylethylamine (5.2 ml) and 1,2-dichloroethane (20 ml) was stirred and heated to 80° C. for 3 hours. The mixture was evaporated. The residue was dissolved in isopropanol (20 ml) and 2-chloro-5-methoxyaniline (1.9 g) and a 6M solution of hydrogen chloride in isopropanol (0.33 ml) were added in turn. The resultant mixture was heated to 80° C. for 1.5 hours. The mixture was cooled to ambient temperature and the resultant precipitate was isolated, washed with isopropanol and with diethyl ether and dried under vacuum. There was thus obtained 4-(2-chloro-5-methoxyanilino)-5-methoxyquinazoline hydrochloride (3.4 g); NMR Spectrum: (DMSOd$_6$) 3.8 (s, 3H), 4.17 (s, 3H), 7.02 (m, 1H), 7.43 (d, 1H), 7.6 (m, 3H), 8.07 (m, 1H), 8.9 (s, 1H).

A mixture of the material so obtained, pyridine hydrochloride (1.1 g) and pyridine (30 ml) was stirred and heated to reflux for 18 hours. The mixture was cooled to ambient temperature and evaporated. The residue was suspended in water, the mixture was basified to pH11 by the addition of a concentrated ammonium hydroxide solution and stirred for 1 hour. The resultant precipitate was isolated, washed with water and with diethyl ether and dried under vacuum. There was thus obtained 4-(2-chloro-5-methoxyanilino)-5-hydroxyquinazoline (1.4 g); NMR Spectrum: (DMSOd$_6$ and CF$_3$COOD) 3.83 (s, 3H), 7.01 (m, 1H), 7.25 (d, 1H), 7.3 (d, 1H), 7.6 (d, 1H), 7.82 (d, 1H), 7.92 (m, 1H), 8.95 (s, 1H); Mass Spectrum: M+H$^+$ 302 and 304.

The N-(tert-butoxycarbonyl)piperidin-4-ylmethanol used as a starting material was prepared as follows:—

A solution of di-tert-butyl dicarbonate (41.7 g) in ethyl acetate (75 ml) was added dropwise to a stirred solution of ethyl piperidine-4-carboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-(tert-butoxycarbonyl)piperidine-4-carboxylate (48 g); NMR Spectrum: (CDCl$_3$) 1.25 (t, 3H), 1.45 (s, 9H), 1.55–1.7 (m, 2H), 1.8–2.0 (d, 2H), 2.35–2.5 (m, 1H), 2.7–2.95 (t, 2H), 3.9–4.1 (br s, 2H), 4.15 (q, 2H).

A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-(tert-butoxycarbonyl)piperidin-4-ylmethanol (36.3 g); NMR Spectrum: (CDCl$_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H).

[17] The product gave the following data: NMR Spectrum: (CDCl$_3$) 1.2–1.35 (m, 2H), 1.5 (s, 9H), 1.9 (d, 2H), 2.35 (m, 1H), 2.75 (t, 2H), 3.85 (s, 3H), 4.05–4.2 (m, 2H), 4.2 (d, 2H), 6.62 (m, 1H), 6.95 (d, 1H), 7.7 (m, 1H), 8.25 (d, 1H), 8.7 (s, 1H); Mass Spectrum: M+H$^+$ 543 and 545.

The 4-(2-bromo-5-methoxyanilino)-5-hydroxyquinazoline used as a starting material was prepared from 5-methoxy-3,4-dihydroquinazolin-4-one using analogous procedures to those described in the portion of Note [16] immediately above except that 2-bromo-5-methoxyaniline was used in place of 2-chloro-5-methoxyaniline.

[18] The product gave the following data: NMR Spectrum: (DMSOd$_6$) 3.25 (s, 3H), 3.79 (s, 3H), 3.83 (m, 2H), 3.98 (s, 3H), 4.58 (m, 2H), 6.95 (s, 1H), 7.0 (m, 1H), 7.07 (s, 1H), 7.55 (m, 2H), 8.8 (s, 1H), 10.64 (s, 1H); Mass Spectrum: M+H$^+$ 390 and 392.

[19] The reaction product was triturated under a mixture of isopropanol and diethyl ether and a 6M solution of hydrogen chloride in isopropanol was added. The resultant precipitate was isolated, washed with diethyl ether and dried under vacuum to give the product as the dihydrochloride salt; NMR Spectrum: (CDCl$_3$) 2.2–2.3 (m, 1H), 2.4 (s, 3H), 2.4–2.5 (m, 1H), 2.5–2.6 (m, 1H), 2.8–2.9 (m, 1H), 2.95–3.1 (m, 2H), 3.85 (s, 3H), 3.95 (s, 3H), 5.05 (m, 1H), 6.42 (s, 1H), 6.65 (m, 1), 6.88 (s, 1H), 7.5 (d, 1H), 7.9 (d, 1H), 8.55 (s, 1H), 9.7 (s, 1H); Mass Spectrum: M+H$^+$ 459 and 461.

The 4-(2-bromo-5-methoxyanilino)-5-hydroxy-7-methoxyquinazoline used as a starting material was prepared as follows:—

Using analogous procedures to those described in the second last paragraph of the portion of Example 1 that is concerned with the preparation of starting materials, 5,7-dimethoxy-3,4-dihydroquinazolin-4-one (3 g) was reacted with phosphoryl chloride (1.5 ml) and the resultant product was reacted with 2-bromo-5-methoxyaniline (3.53 g). There was thus obtained 4-(2-bromo-5-methoxyanilino)-5,7-dimethoxyquinazoline hydrochloride (5 g); NMR Spectrum: (DMSOd$_6$) 3.8 (s, 3H), 4.0 (s, 3H), 4.18 (s, 3H), 6.95 (m, 3H), 7.6 (br s, 1H), 7.7 (d, 1H), 7.8 (s, 1H), 10.85 (s, 1H); Mass Spectrum: M+H$^+$ 391 and 393.

A mixture of the material so obtained, pyridine hydrochloride (1.4 g) and pyridine (100 ml) was stirred and heated to reflux for 6 hours. A second portion (2.8 g) of pyridine hydrochloride was added portionwise and the mixture was heated to reflux for a further 18 hours. The mixture was cooled to ambient temperature and evaporated. The material so obtained was triturated under water. The precipitate was isolated and washed with methylene chloride (100 ml) for 1 hour. The solid was isolated and dried under vacuum. There was thus obtained 4-(2-bromo-5-methoxyanilino)-5-hydroxy-7-methoxyquinazoline (39 g); NMR Spectrum: (DMSOd$_6$ and CF$_3$COOD) 3.75 (s, 3H), 3.9 (s, 3H), 6.75 (s, 2D, 6.92 (m, 1H), 7.58–7.7 (m, 2H), 8.8 (s, 1H).

[20] 4-Hydroxytetrahydropyran was used as the appropriate alcohol. The product gave the following data: NMR Spectrum: (DMSOd$_6$) 1.75–1.9 (m, 2H), 2.15 (d, 2H), 3.5 (t, 2H), 3.8 (s, 3H), 3.9 (m, 2H), 5.05 (m, 1H), 5.3 (s, 2H), 5.8 (m, 1H), 6.95 (d, 1H), 7.05 (m, 2H), 7.3–7.6 (m, 6H), 8.1 (d, 1H), 8.5 (s, 1H), 9.85 (s, 1H); Mass Spectrum: M+H$^+$ 492 and 494.

[21] The reaction product was dissolved in diethyl ether and a 6M solution of hydrogen chloride in diethyl ether (0.1 ml) was added. The resultant precipitate was isolated, washed with diethyl ether and dried under vacuum to give the product as a hydrochloride salt which gave the following data: NMR Spectrum: (DMSOd$_6$ and CF$_3$CO$_2$D) 1.9–2.05 (m, 2H), 2.18 (d, 2H), 3.55 (t, 2H), 3.82 (s, 3H), 3.95 (m, 2H), 5.15 (m, 1H), 7.05 (m, 1H), 7.5 (d, 1H), 7.58 (d, 2H), 7.65 (d, 1H), 8.05 (m, 1H), 8.95 (s, 1H); Mass Spectrum: M+H$^+$ 1386 and 388.

[22] The product gave the following data: NMR Spectrum: (DMSOd$_6$ and CF$_3$CO$_2$D) 2.2–2.3 (m, 1H), 2.35–2.5 (m, 1H), 3.8 (s, 3H), 3.8–3.9 (m, 1H), 3.9–4.0 (m, 2H), 4.2 (d, 1H), 5.4 (s, 2H), 5.6 (br s, 1H), 7.01 (d, 1H), 7.05 (s, 1H), 7.18 (s, 1H), 7.42 (d, 1H), 7.45 (m, 2H), 7.52 (s, 1H), 7.55 (d, 2H), 7.6 (d, 1H), 8.9 (s, 1H); Mass Spectrum: M+H$^+$ 477 and 479.

[23] The product gave the following data: NMR Spectrum: (DMSOd$_6$) 1.9–2.0 (m, 2H), 2.15–2.25 (m, 1H), 2.3–2.5 (m, 5H), 2.5 (t, 2H), 3.6 (t, 4H), 3.8 (s, 3H), 3.9–4.0 (m, 3H), 4.1 (d, 1H), 4.2 (t, 2H), 5.45 (t, 1H), 6.75–6.8 (m, 2H), 6.85 (s, 1H), 7.45 (d, 1H), 8.1 (s, 1H), 8.5 (s, 1H), 9.72 (s, 1H); Mass Spectrum: M+H$^+$ 515 and 517.

[24] The product gave the following data: NMR Spectrum: (DMSOd$_6$) 1.9–2.0 (m, 2H), 2.14 (s, 3H), 2.15–2.35 (m, 2H), 2.2–2.6 (m, 10H), 3.8 (s, 3H), 3.85–4.0 (m, 3H), 4.12 (d, 1H), 4.2 (t, 2H), 5.45 (t, 1H), 7.75–7.8 (m, 2H), 7.85 (s, 1H), 7.45 (d, 1H), 8.1 (s, 1H), 8.5 (s, 1H), 9.72 (s, 1H); Mass Spectrum: M+H$^+$ 528 and 530.

[25] The product gave the following data: NMR Spectrum: (DMSOd$_6$ and CF$_3$CO$_2$D) 1.5 (d, 6H), 3.82 (s, 3H), 5.2 (m, 1H), 5.4 (s, 2H), 6.98 (s, 1H), 7.0 (m, 1H), 7.18 (s, 1H), 7.4 (d, 1H), 7.45 (m, 2H), 7.5–7.6 (m, 2H), 7.65 (d, 1H), 8.9 (s, 1H); Mass Spectrum: M+H$^+$ 449 and 451.

[26] The reaction product was dissolved in methylene chloride (2 ml) containing methanol (a few drops) and a 6M hydrogen chloride solution in diethyl ether (2 equivalents) was added. Diethyl ether (50 ml) was added and the resultant precipitate was isolated, washed with diethyl ether and dried under vacuum to give the product as a dihydrochloride salt (0.135 g); NMR Spectrum: (DMSOd$_6$ and CF$_3$CO$_2$D) 1.9–2.1 (m, 2H), 2.1–2.2 (m, 2H), 3.55 (m, 2H), 3.79 (s, 3H), 3.92 (m, 2H), 4.0 (s, 3H), 5.15 (m, 1H), 6.9 (s, 1H), 6.95 (m, 1H), 7.15 (d, 1H), 7.45 (d, 1H), 7.7 (d, 1H), 8.85 (s, 1H); Mass Spectrum: M+H$^+$ 460 and 462.

[27] The reaction product was triturated under a mixture of a 5M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$CO$_2$D) 1.9 (m, 2H), 2.05 (m, 2H), 2.35 (m, 2H), 3.05 (m, 2H), 3.3 (m, 2H), 3.6 (m, 2H), 4.05 (s, 3H), 4.65 (t, 2H), 6.15 (s, 2H), 6.95 (d, 1H), 7.1 (m, 2H), 7.15 (d, 1H), 8.85 (s, 1H); Mass Spectrum: M+H$^+$ 457 and 459.

The 4-(6-chloro-2,3-methylenedioxyanilino)-5-hydroxy-7-methoxyquinazoline used as a starting material was prepared as follows:—

Phosphoryl chloride (2.7 ml) was added dropwise to a mixture of 5,7-dimethoxy-3,4-dihydroquinazolin-4-one (1 g), diisopropylethylamine (2.27 ml) and 1,2-dichloroethane (20 ml) and the resultant mixture was stirred and heated to 80° C. for 3 hours. The mixture was evaporated. There was thus obtained 4-chloro-5,7-dimethoxyquinazoline which was used without further purification. The material so obtained was suspended in isopropanol (14 ml) and 6-chloro-2,3-methylenedioxyaniline (Example 17, Note [30]; 0.915 g) and a 5N solution of hydrogen chloride in isopropanol (0.97 ml) were added in turn. The reaction mixture was stirred and heated to 90° C. for 1.5 hours. The mixture was cooled to ambient temperature and the precipitate was isolated, washed with isopropanol and with diethyl ether and dried under vacuum. The material so obtained was dissolved in a mixture of methylene chloride and methanol and a saturated methanolic ammonia solution was added. The resultant mixture was filtered and the filtrate was evaporated. There was thus obtained 4-(6-chloro-2,3-methylenedioxyanilino)-5,7-dimethoxyquinazoline (1.36 g); NMR Spectrum: (DMSOd$_6$) 3.95 (s, 3H), 4.1 (s, 3H), 6.1 (s, 2H), 6.85 (d, 1H), 6.9 (d, 1H), 7.05 (d, 1H), 7.1 (d, 1H), 8.65 (s, 1H).

Pyridine (0.54 ml) was dissolved in methylene chloride (5 ml) and a 5N solution of hydrogen chloride in isopropanol (1.34 ml) was added. After a few minutes the mixture was evaporated. Pyridine (24 ml) was added followed by 4-(6-chloro-2,3-methylenedioxyanilino)-5,7-dimethoxyquinazoline (1.2 g) and the reaction mixture was heated to 125° C. for 6 hours. The resultant mixture was evaporated and the residue was triturated under water. The resultant solid was isolated, washed with water and dried under vacuum. The material so obtained was purified by column chromatography on silica using a 7:3 mixture of methylene chloride and acetonitrile as eluent. There was thus obtained 4-(6-chloro-2,3-methylenedioxyanilino)-5-hydroxy-7-methoxyquinazoline (0.72 g); NMR Spectrum: (DMSOd$_6$ and CF$_3$CO$_2$D) 3.9 (s, 3H), 6.15 (s, 2H), 6.75 (m, 2H), 7.05 (d, 1H), 7.1 (d, 1H), 8.75 (s, 1H).

[28]The reaction product was triturated under a mixture of a 5M solution of hydrogen chloride in isopropanol was added. The resultant precipitate was isolated, washed with diethyl ether and dried under vacuum to give the product as the dihydrochloride salt; NMR Spectrum: (DMSOd$_6$ and CF$_3$CO$_2$D) 2.35 (m, 2H), 2.9 (s, 3H), 3.2–4.0 (m, 10H), 4.05 (s, 3H), 4.65 (t, 2H), 6.15 (s, 2H), 6.95 (d, 1H), 7.1 (m, 3H), 8.85 (s, 1H); Mass Spectrum: M+H$^+$ 486 and 488.

EXAMPLE 3

4-(2-bromo-5-methoxyanilino)-7-methoxy-5-(N-methylpiperidin-4-yloxy)quinazoline

A mixture of 4-chloro-7-methoxy-5-(N-methylpiperidin-4-yloxy)quinazoline (0.11 g), 2-bromo-5-methoxyaniline hydrochloride (0.099 g) and isopropanol (8 ml) was stirred and heated to 80° C. for 30 minutes. The mixture was evaporated and the residue was triturated under the minimum volume of isopropanol. The resultant solid was isolated, washed with isopropanol and with diethyl ether and dried under vacuum. There was thus obtained the title compound as a dihydrochloride salt (0.06 g). A sample of the material was treated with a saturated methanolic ammonia solution. The mixture was filtered and the filtrate was evaporated to give the title compound in free base form; NMR Spectrum (CDCl$_3$): 2.15–2.25 (m, 6H), 2.35 (s, 3H), 2.9 (m, 2H), 3.84 (s, 3H), 3.93 (s, 3H), 4.6 (br s, 1H), 6.62 (s, 1H), 6.6 (m, 1H), 6.85 (s, 1H), 7.5 (d, 1H), 7.9 (s, 1H), 8.55 (s, 1H), 9.64 (br s, 1H); Mass Spectrum: M+H$^+$ 473 and 475.

The 4-chloro-7-methoxy-5-(N-methylpiperidin-4-yloxy)quinazoline used as a starting material was prepared as follows:—

Pyridine (40 ml) was added dropwise to magnesium bromide (3.6 g) which had been cooled to 0° C. 5,7-Dimethoxy-3,4-dihydroquinazolin-4-one (4 g) was added and the mixture was heated to reflux for 15 minutes. The mixture was evaporated and the residue was stirred under a mixture of glacial acetic acid (12 ml) and water (80 ml) for 10 minutes The resultant solid was isolated, washed with water and dried under vacuum at 50° C. There was thus obtained 5-hydroxy-7-methoxy-3,4-dihydroquinazolin one (3.75 g); NMR Spectrum: (DMSOd$_6$) 3.95 (s, 3H), 6.45 (s, 1H), 6.62 (s, 1H), 8.1 (s, 1H).

A portion (1.8 g) of the material so obtained was added to a stirred suspension of sodium hydride (0.79 g of a 60% dispersion in mineral oil which was washed with THF) in DMF (18 ml). The mixture was stirred at ambient temperature for 1 hour. The mixture was cooled to 0° C. and chloromethyl pivalate (1.62 ml) was added dropwise. The mixture was stirred at ambient temperature for 1 hour, poured into a mixture of glacial acetic acid (50 ml) and water (200 ml) and stirred at ambient temperature for 5 minutes. The resultant precipitate was isolated, washed with water and dried overnight under vacuum. The solid was triturated under pentane, isolated and dried under vacuum. There was thus obtained 5-hydroxy-7-methoxy-3-pivaloyloxymethyl-3,4-dihydroquinazolin-4-one (2.5 g); NMR Spectrum: (CDCl$_3$) 1.2 (s, 9H), 3.9 (s, 3H), 5.88 (s, 2H), 6.5 (s, 1H), 6.68 (s, 1H), 8.15 (s, 1H), 11.36 (s, 1H).

A solution of di-tert-butyl azodicarboxylate (1.7 g) in methylene chloride (5 ml) was added to a stirred mixture of 5-hydroxy-7-methoxy-3-pivaloyloxymethyl-3,4-dihydroquinazolin-4-one (1.5 g), triphenylphosphine (1.9 g), 4-hydroxy-1-methylpiperidine (0.675 g) and methylene chloride (20 ml) which had been cooled to 5° C. The mixture was stirred at ambient temperature for 1 hour. The mixture was evaporated and the residue was purified by column chromatography on silica using a 9:10:1 mixture of methylene chloride, ethyl acetate and a saturated methanolic ammonia solution as eluent. The material so obtained was triturated under diethyl ether. The resultant solid was washed with diethyl ether and dried under vacuum to give 7-methoxy-5-(N-methylpiperidin-4-yloxy)-3-pivaloyloxymethyl-3,4-dihydroquinazolin-4-one (1.75 g); NMR Spectrum: (CDCl$_3$): 1.2 (s, 9H), 2.05 (br s, 4H), 2.3 (s, 3H), 2.3–2.42 (m, 2H), 2.7–2.8 (m, 2H), 3.9 (s, 3H), 4.48 (m, 1H), 5.9 (s, 2H), 6.5 (d, 1H), 6.71 (d, 1H), 8.18 (s, 1H).

A mixture of the material so obtained and a saturated methanolic ammonia solution (100 ml) was stirred at ambient temperature for 15 hours. The mixture was evaporated and the residue was triturated under diethyl ether. The resultant precipitate was isolated, washed with diethyl ether and dried under vacuum. There was thus obtained 7-methoxy-5-(N-methylpiperidin-4-yloxy)-3,4-dihydroquinazolin-4-one (0.855 g); NMR Spectrum: (DMSOd$_6$) 1.7 (m, 2H), 1.9 (m, 2H), 2.15 (s, 3H), 1.15–1.25 (m, 2H), 2.55–2.7 (m, 2H), 3.85 (s, 3H), 4.5 (m, 1H), 6.55 (d, 1H), 6.65 (d, 1H), 7.89 (s, 1H), 11.62 (br s, 1H).

A mixture of 7-methoxy-5-(N-methylpiperidin-4-yloxy)-3,4-dihydroquinazolin-4-one (0.65 g), triphenylphosphine (1.18 g), carbon tetrachloride (0.45 ml) and methylene chloride (25 ml) was stirred and heated to reflux for 2 hours. The mixture was evaporated and the residue was purified by column chromatography on silica using a 10:9:1 mixture of ethyl acetate, methylene chloride and a saturated methanolic ammonia solution as eluent. The material so obtained was triturated under pentane and the resultant solid was isolated and dried under vacuum. There was thus obtained 4-chloro-7-methoxy-5-(N-methylpiperidin-4-yloxy)quinazoline (0.5 g); NMR Spectrum: (CDCl$_3$) 1.95–2.15 (m, 4H), 2.3 (s, 3H), 2.3–2.45 (m, 2H), 2.6–2.8 (m, 2H), 3.92 (s, 3H), 4.55 (br s, 1H), 6.56 (s, 1H), 6.9 (s, 1H), 8.77 (s, 1H).

EXAMPLE 4

Using an analogous procedure to that described in Example 3, the appropriate 4-chloroquinazoline was reacted with the appropriate aniline to give the compound described in Table II.

TABLE II

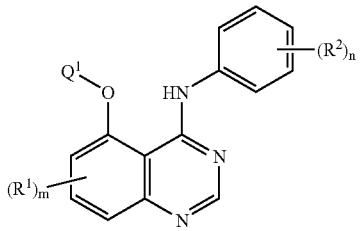

| No. and Note | $(R^1)_m$ | $Q^1$ | $(R^2)_n$ |
|---|---|---|---|
| [1] | 7-methoxy | N-methylpiperidin-4-yl | 2,4-dichloro-5-methoxy |
| [2] | 7-methoxy | N-methylpiperidin-4-yl | 2-fluoro-4-chloro-5-methoxy |
| [3] | 7-(2-pyrrolidin-1-ylethoxy) | 4-tetrahydropyranyl | 2,5-dimethoxy |
| [4] | 7-methoxy | N-methylpiperidin-4-yl | 6-chloro-2,3-methylenedioxy |
| [5] | 7-fluoro | 4-tetrahydropyranyl | 6-chloro-2,3-methylenedioxy |
| [6] | 7-(2-pyrrolidin-1-ylethoxy) | 4-tetrahydropyranyl | 2,3-ethylenedioxy |
| [7] | 7-methoxy | N-methylpiperidin-4-yl | 2,3-ethylenedioxy |
| [8] | 7-methoxy | piperidin-4-yl | 2,3-ethylenedioxy |

Notes

[1] The reaction product was obtained as the dihydrochloride salt from which the free base was isolated using an analogous procedure to that described in Example 3. The free base gave the following data: NMR Spectrum: (CDCl$_3$) 2.0–2.15 (m, 2H), 2.15–2.3 (m, 4H), 2.32 (s, 3H), 2.85 (m, 2H), 3.92 (s, 3H), 3.95 (s, 3H), 4.55 (m, 1H), 6.56 (d, 1H), 6.86 (d, 1H), 7.42 (s, 1H), 8.31 (s, 1H), 8.56 (s, 1H), 9.87 (s, 1H); Mass Spectrum: M+H$^+$ 463 and 465.

[2] The reaction product was obtained as the dihydrochloride salt; NMR Spectrum: (DMSOd$_6$ and NaOD) 1.9–2.1 (m, 2H), 2.2–2.35 (m, 2H), 2.6 (s, 3H), 2.6 (m, 2H), 3.1–3.2 (m, 2H), 3.92 (s, 3H), 3.95 (s, 3H), 4.95 (m, 1H), 6.92 (s, 1H), 6.95 (s, 1H), 7.6 (d, 1H), 8.6 (s, 1H), 8.7 (br s, 1H); Mass Spectrum: M+H$^+$ 447 and 449.

The 4-chloro-2-fluoro-5-methoxyaniline used as starting material was prepared as follows:—

A 6N aqueous sodium hydroxide solution (17 ml) was added dropwise to a stirred solution of 4-chloro-2-fluoro-5-methoxycarbonyloxy-1-nitrobenzene (J. Med. Chem., 1999, 42, 5369; 25 g) in methanol (200 ml) which was cooled to 5° C. The reaction mixture was stirred at ambient temperature for 30 minutes. A 12N aqueous hydrochloric acid solution (8.5 ml) was added and the mixture was evaporated. The residue was partitioned between methylene chloride and water. The organic layer was washed with brine, dried over magnesium sulphate and evaporated to give 4-chloro-2-fluoro-5-hydroxy-1-nitrobenzene (18.5 g); NMR Spectrum: (CDCl$_3$) 5.8 (br s, 1H), 7.35 (d, 1H), 7.75 (d, 1H).

Dimethyl sulphate (10.5 ml) was added to a stirred mixture of 4-chloro-2-fluoro-5-hydroxy-1-nitrobenzene (14 g), potassium carbonate (13 g) and DMF (70 ml) and the reaction mixture was stirred at ambient temperature for 16 hours. The mixture was poured into water (500 ml) and the resultant precipitate was isolated and dried under vacuum. The solid so obtained was partitioned between methylene chloride and water. The organic layer was washed with brine, dried over magnesium sulphate and evaporated to give 4-chloro-2-fluoro-5-methoxy-1-nitrobenzene (14.1 g); NMR Spectrum: (CDCl$_3$) 3.94 (s, 3H), 7.4 (d, 1H), 7.6 (d, 1H).

A mixture of the material so obtained, platinum oxide (0.5 g) and ethanol (250 ml) was stirred under 1.2 atmosphere pressure of hydrogen for 2 hours. The mixture was filtered and the filtrate was evaporated. The residue was purified by column chromatography on silica using methylene chloride as eluent. There was thus obtained 4-chloro-2-fluoro-5-methoxyaniline (8.5 g); NMR Spectrum: (CDCl$_3$) 3.7 (br s, 2H), 3.81 (s, 3H), 6.38 (d, 1H), 7.02 (d, 1H), 7.28 (s, 1H).

[3] The reaction product was obtained as the dihydrochloride salt; NMR Spectrum: (DMSOd$_6$ and CF$_3$CO$_2$D) 1.85–2.0 (m, 4H), 2.0–2.15 (m, 2H), 2.2–2.3 (m, 2H), 3.15–3.25 (m, 2H), 3.58 (t, 2H), 3.65–3.75 (m, 4H), 3.78 (s, 3H), 3.95 (s, 3H), 4.02 (m, 2H), 4.6 (m, 2H), 5.2 (m, 1H), 6.9 (m, 1H), 7.02 (d, 1H), 7.16 (d, 1H), 7.23 (d, 1H), 8.16 (d, 1H), 8.98 (s, 1H); Mass Spectrum: M+H$^+$ 495.

The 4-chloro-7-(2-pyrrolidin-1-ylethoxy)-5-tetrahydropyran-4-yloxyquinazoline used as a starting material is described in Example 19, Note [6].

[4] The reaction product was obtained as the dihydrochloride salt from which the free base was isolated using an analogous procedure to that described in Example 3. The free base gave the following data: NMR Spectrum: (CDCl$_3$) 2.0–2.15 (m, 2H), 2.15–2.3 (m, 2H), 2.3 (s, 3H), 2.3–2.5 (m, 2H), 2.75 (m, 2H), 3.92 (s, 3H), 4.6 (m, 1H), 6.05 (s, 2H), 6.50 (d, 1H), 6.72 (d, 1H), 6.84 (d, 1H), 6.97 (d, 1H), 8.52 (s, 1H), 9.26 (s, 1H); Mass Spectrum: M+H$^+$ 443 and 445.

[5] The reaction product was obtained as the dihydrochloride salt from which the free base was isolated using an analogous procedure to that described in Example 3. The free base gave the following data: NMR Spectrum: (CDCl$_3$) 1.92–2.1 (m, 2H), 2.2–2.3 (m, 2H), 3.6–3.7 (m, 2H), 4.0–4.1 (m, 2H), 4.8 (m, 1H), 6.1 (s, 2H), 6.7 (m, 1H), 6.75 (d, 1H), 6.98 (d, 1H), 7.15 (m, 1H), 8.6 (s, 1H), 9.32 (s, 1H); Mass Spectrum: M+H$^+$ 418 and 420.

The 4-chloro-7-fluoro-5-tetrahydropyran-4-yloxyquinazoline used as a starting material was prepared as follows:—

A solution of 3,5-difluoroaniline (10.8 g) in a mixture of 12N aqueous hydrochloric acid solution (7.5 ml) and water (90 ml) was added to a stirred mixture of chloral hydrate (9.2 ml), sodium sulphate decahydrate (240 g) and water (210 ml). A solution of hydroxylamine hydrochloride (18.6 g) in water (90 ml) was then added and the mixture was heated to 120° C. for 45 minutes. The mixture was cooled to ambient temperature and the precipitate was isolated and dried under vacuum. The material so obtained was added to concentrated sulphuric acid (60 ml) and the mixture was stirred and heated to 80–90° C. for 10 minutes. The mixture was cooled to ambient temperature and poured onto a 1:1 mixture of ice and water (600 ml). The precipitate was isolated, washed with water and dried under vacuum at 50° C. to give 4,6-difluoro-2,3-dioxoindoline (14 g); NMR Spectrum: (DMSOd$_6$) 6.61 (m, 1H), 6.9 (m, 1H).

Hydrogen peroxide (35% solution in water, 23 ml) was added dropwise to a stirred solution of 4,6-difluoro-2,3-dioxoindoline (14 g) in a concentrated aqueous sodium hydroxide solution (33%, 115 ml) that was heated to 70° C. The mixture was heated to 70° C. for 15 minutes. The resultant mixture was cooled to 0° C. and the the mixture was acidified to pH4 by the addition of concentrated aqueous hydrochloric acid. The mixture was extracted with ethyl acetate. The organic layer was separated, washed with brine, dried over magnesium sulphate and evaporated to give 2-amino-4,6-difluorobenzoic acid (12 g); NMR Spectrum: (DMSOd$_6$) 6.25 (m, 1H), 6.38 (m, 1H).

Diethyl azodicarboxylate (26.7 ml) was added dropwise to a stirred mixture of 2-amino-4,6-difluorobenzoic acid (26.6 g), triphenylphosphine (45 g), methanol (9 ml) and methylene chloride (350 ml) that had been cooled to 5° C. The mixture was allowed to warm to ambient temperature and was stirred for 2 hours. The reaction mixture was poured onto a chromatography column loaded with silica and eluted with methylene chloride. There was thus obtained methyl 2-amino-4,6-difluorobenzoate (25.2 g); NMR Spectrum: (DMSOd$_6$) 3.8 (s, 3H), 6.3 (m, 1H), 6.4 (m, 1H), 7.0 (br s, 2H); Mass Spectrum: M+H$^+$ 188.

A mixture of methyl 2-amino-4,6-difluorobenzoate (47 g), formamidine acetate (79 g) and 2-methoxyethanol (750 ml) was stirred and heated to reflux for 10 hours. A second portion (26 g) of formamidine acetate was added and the mixture was heated to reflux for a further 2.5 hours. The mixture was cooled to ambient temperature and evaporated. The residue was washed with diethyl ether and with water and dried under vacuum over phosphorus pentoxide. The filtrate was evaporated to dryness and the residue was triturated under diethyl ether. The resultant solid was isolated and dried under vacuum. The two batches of solid were combined and purified by column chromatography on silica using a 19:1 mixture of methylene chloride and methanol as eluent. There was thus obtained 5,7-difluoro-3,4-dihydroquinazolin-4-one (33.7 g); NMR Spectrum: (DMSOd$_6$) 7.3–7.4 (m, 2H), 8.12 (s, 1H); Mass Spectrum: M+H$^+$ 183.

Sodium hydride (60% dispersion in mineral oil; 0.6 g) was added portionwise to a solution of 4-hydroxytetrahydropyran (0.78 g) in DMF (10 ml) that had been cooled to 5° C. The mixture was allowed to warm to ambient temperature and was stirred for 15 minutes. 5,7-Difluoro-3,4-dihydroquinazolin-4-one (0.9 g) was added and the mixture was stirred at ambient temperature for 30 minutes. The mixture was poured into water (100 ml) and, with vigorous stirring, glacial acetic acid was added to acidify the mixture to pH5. The resultant solid was isolated, washed with water and with diethyl ether and dried under vacuum. There was thus obtained 7-fluoro-5-tetrahydropyran-4-yloxy-3,4-dihydroquinazolin-4-one (1.1 g); NMR Spectrum: (DMSOd$_6$) 1.6–1.75 (m, 2H), 1.9–2.0 (m, 2H), 3.5–3.6 (m, 2H), 3.85–3.95 (m, 2H), 4.8 (m, 1H), 6.9 (m, 1H), 7.05 (m, 1H), 8.0 (s, 1H); Mass Spectrum: M+H$^+$ 265.

A mixture of 7-fluoro-5-tetrahydropyran-4-yloxy-3,4-dihydroquinazolin-4-one (1 g), phosphoryl chloride (4 ml), diisopropylethylamine (1.5 ml) and 1,2-dichloroethane (15 ml) was stirred and heated to 80° C. for 3 hours. The mixture was evaporated to give 4-chloro-7-fluoro-5-tetrahydropyran-4-yloxyquinazoline which was used without further purification.

[6] 2,3-Ethylenedioxyaniline (*J. Med. Chem.*, 1995, 38, 4044) was used as a starting material. The reaction product was obtained as the dihydrochloride salt; NMR Spectrum: (DMSOd$_6$ and CF$_3$CO$_2$D) 1.8–2.0 (m, 4H), 2.0–2.1 (m, 2H), 2.15–2.25 (m, 2H), 3.1–3.25 (m, 2H), 3.55 (m, 2H), 3.6–3.75 (m, 4H), 4.0 (m, 2H), 4.32 (m, 2H), 4.42 (m, 2H), 4.58 (t, 2H), 5.2 (m, 1H), 6.85 (d, 1H), 6.95 (m, 1H), 6.99 (d, 1H), 7.2 (d, 1H), 8.0 (d, 1H), 8.94 (s, 1H); Mass Spectrum: M+H$^+$ 493.

[7] The reaction product was obtained as the dihydrochloride salt from which the free base was isolated using an analogous procedure to that described in Example 3. The free base gave the following data: NMR Spectrum: (CDCl$_3$) 1.95–2.1 (m, 2H), 2.15–2.3 (m, 4H), 2.3 (s, 3H), 2.9 (m, 2H), 3.9 (s, 3H), 4.32 (m, 2H), 4.4 (m, 2H), 4.52 (m, 1H), 6.5 (d, 1H), 6.65 (m, 1H), 6.8 (d, 1H), 6.92 (m, 1H), 8.3 (d, 1H), 8.6 (s, 1H), 10.05 (s, 1H); Mass Spectrum: M+H$^+$ 423.

[8] The reactants were 5-(1-tert-butoxycarbonylpiperidin-4-yloxy)-4-chloro-7-methoxyquinazoline and 2,3-ethylenedioxyaniline. The precipitate from the reaction mixture was isolated, washed in turn with isopropanol, ethyl acetate and diethyl ether and dried under vacuum. The material so obtained was dissolved in a 2M solution of hydrogen chloride in diethyl ether and the mixture was stirred at ambient temperature for 2 hours. The resultant solid was isolated, washed with diethyl ether and dried under vacuum. The reaction product so obtained was obtained a dihydrochloride salt; NMR Spectrum: (DMSOd$_6$ and CF$_3$CO$_2$D) 2.0–2.15 (m, 2H), 2.35–2.55 (m, 2H), 3.2 (m, 2H), 3.45 (m, 2H), 4.02 (s, 3H), 4.4 (m, 2H), 4.52 (m, 2H), 5.2 (m, 1H), 6.85 (d, 1H), 6.98 (m, 2H), 7.2 (d, 1H), 8.05 (d, 1H), 8.98 (s, 1H); Mass Spectrum: M+H$^+$ 409.

The 5-(1-tert-butoxycarbonylpiperidin-4-yloxy)-4-chloro-7-methoxyquinazoline used as a starting material is described in Example 33.

EXAMPLE 5

4-(5-chloronaphth-1-ylamino)-7-methoxy-5-(N-methylpiperidin-4-yloxy)quinazoline dihydrochloride A mixture of 4-chloro-7-methoxy-5-(N-methylpiperidin-4-yloxy)quinazoline (0.08 g), 5-chloro-1-naphthylamine (0.055 g), 6.2M hydrogen chloride in isopropanol (0.044 ml) and isopropanol (3 ml) was stirred and heated to reflux for 2 hours. The mixture was cooled to ambient temperature and the precipitate was isolated, washed with diethyl ether and dried under vacuum. There was thus obtained the title compound (0.129 g), a portion of which was treated with a saturated methanolic ammonia solution. The mixture was filtered and the filtrate was evaporated to give the free base; NMR Spectrum: (CDCl$_3$) 1.9–2.1 (m, 4H), 2.22 (s, 3H), 2.25–2.4 (m, 2H), 2.6–2.7 (m, 2H), 3.94 (s, 3H), 4.7 (br s, 1H), 6.6 (s, 1H), 6.9 (s, 1H), 7.4 (m, 1H), 7.62 (d, 1H), 7.7 (m, 1H), 8.0 (m, 2H), 8.25 (d, 1H), 8.46 (s, 1H), 9.9 (br s, 1H); Mass Spectrum: M+H$^+$ 449 and 451.

EXAMPLE 6

4-(3-chlorobenzofuran-7-ylamino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 7-amino-3-chlorobenzofuran to give the title compound, a portion of which was treated with a saturated methanolic ammonia solution. The mixture was filtered and the filtrate was evaporated to give the free base; NMR Spectrum: (CDCl$_3$) 2.0–2.4 (m, 6H), 2.33 (s, 3), 2.9 (m, 2H), 3.93 (s, 3H), 4.6 (m, 1H), 6.56 (s, 1H), 6.9 (s, 1H), 7.3–7.4 (m, 2H), 7.7 (br s, 1H), 8.64 (s, 1H), 8.7 (d, 1H), 10.3 (br s, 1H); Mass Spectrum: M+H⁺ 439 and 441.

The 7-amino-3-chlorobenzofuran used as a starting material was prepared as follows:—

For a 30 minute period, chlorine gas was bubbled through a solution of 7-nitrobenzofuran (1.2 g) in glacial acetic acid (12 ml) which had been cooled at 18° C. The resultant mixture was evaporated and the residue was partitioned between diethyl ether and water. The organic layer was washed in turn with a saturated aqueous sodium bicarbonate solution, water and a saturated aqueous sodium chloride solution, dried (MgSO₄) and evaporated. The residue was purified by column chromatography on silica to give a mixture of cis and trans 2,3-dichloro-7-nitro-2,3-dihydrobenzofuran. The material so obtained was dissolved in ethanol (2 ml) and a solution of 0.8M potassium hydroxide in ethanol (2.7 ml) was added. The mixture was stirred at ambient temperature for 75 minutes. The mixture was evaporated to remove the ethanol. The residue was diluted with water and the mixture was acidified to pH2 by the addition of concentrated hydrochloric acid. The mixture was extracted with diethyl ether. The organic extract was washed with water and with a saturated aqueous sodium chloride solution, dried (MgSO₄) and evaporated. There was thus obtained 3-chloro-7-nitrobenzofuran (0.7 g); NMR Spectrum: DMSOd₆) 7.63 (m, 1H), 8.12 (d, 1H), 8.3 (d, 1H), 8.65 (s, 1H); Mass Spectrum: M+H⁺ 197 and 199.

A suspension of hydrazine hydrate (0.049 ml) and Raney nickel (0.01 g) in methanol (2 ml) was heated to 60° C. and added dropwise to a mixture of 3-chloro-7-nitrobenzofuran (0.04 g) and methanol (4 ml). The resultant mixture was heated to reflux for 10 minutes, filtered and evaporated. The residue was partitioned between methylene chloride and water. The organic layer was washed with water, dried (MgSO₄) and evaporated. The residue was purified by column chromatography on silica using a 1:1 mixture of methylene chloride and petroleum ether as eluent. There was thus obtained 3-chloro-7-aminobenzofuran (0.021 g); NMR Spectrum: (DMSOd₆ and CF₃COOD) 6.65 (d, 1H), 6.75 (d, 1H), 7.05 (m, 1H), 8.2 (s, 1H); Mass Spectrum: M+H⁺ 167.

EXAMPLE 7

4-(2,3-methylenedioxyanilino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 2,3-methylenedioxyaniline (*J. Med. Chem.*, 1979, 22, 1354) to give the title compound, a portion of which was treated with a saturated methanolic ammonia solution. The mixture was filtered and the filtrate was evaporated to give the free base; NMR Spectrum: (CDCl₃) 2.0–2.1 (m, 2H), 2.15–2.3 (m, 4H), 2.31 (s, 3H), 2.85 (m, 2H), 3.91 (s, 3H), 6.01 (s, 2H), 6.5 (d, 1H), 6.68 (d, 1H), 6.82 (d, 1H), 6.91 (m, 1H), 8.0 (d, 1H), 8.6 (s, 1H), 9.72 (s, 1H); Mass Spectrum: M+H⁺ 409.

EXAMPLE 8

4-(2-chloro-5-methoxyanilino)-5-(N-methylpiperidin-4-ylmethoxy)quinazoline

A mixture of 5-[N-(tert-butoxycarbonyl)piperidin-4-ylmethoxy]-4-(2-chloro-5-methoxyanilino)quinazoline (0.2 g), a concentrated aqueous formaldehyde solution (37%, 0.4 ml) and formic acid (4 ml) was stirred and heated to 100° C. for 2.5 hours. The mixture was cooled to ambient temperature and evaporated. The residue was triturated under diethyl ether and the resultant solid was isolated and dried under vacuum. There was thus obtained 4-(2-chloro-5-methoxyanilino)-5-(N-methylpiperidin-4-ylmethoxy)quinazoline, as a formic acid salt (0.09 g); NMR Spectrum: (CDCl₃) 1.8–2.0 (m, 2H), 2.05–2.15 (m, 2H), 2.35 (m, 1H), 2.6 (t, 2H), 3.55 (d, 2H), 3.93 (s, 3H), 4.21 (d, 2H), 6.68 (m, 1H), 6.95 (d, 1H), 7.31 (d, 1H), 7.54 (d, 1H), 7.7 (m, 1H), 8.35 (br s, 1H), 8.39 (d, 1H), 8.7 (s, 1H); Mass Spectrum: M+H⁺ 413.

EXAMPLE 9

4-(2-bromo-5-methoxyanilino)-5-(1-methylpiperidin-4-ylmethoxy)quinazoline

Using an analogous procedure to that described in Example 8, 4-(2-bromo-5-methoxyanilino)-5-[N-(tert-butoxycarbonyl)piperidin-4-ylmethoxy]quinazoline (0.22 g) was reacted with concentrated aqueous formaldehyde solution (0.4 ml) to give the title compound, as a formic acid salt (0.183 g); NMR Spectrum: (CDCl₃) 1.7–1.9 (m, 2H), 2.06 (d, 2H), 2.2 (m, 1H), 2.58 (t, 2H), 2.68 (s, 3H), 3.51 (d, 2H), 3.8 (s, 3H), 4.24 (d, 2H), 6.64 (m, 1H), 6.94 (d, 1H), 7.48 (d, 1H), 7.54 (d, 1H), 7.69 (m, 1H), 8.2 (d, 1H), 8.3 (br s, 1H), 8.69 (s, 1H), 9.94 (s, 1H); Mass Spectrum: M+H⁺ 457 and 459.

EXAMPLE 10

4-(2-bromo-5-methoxyanilino)-5-piperidin-4-ylmethoxyquinazoline

A mixture of 4-(2-bromo-5-methoxyanilino)-5-[N-(tert-butoxycarbonyl)piperidin-4-ylmethoxy]quinazoline (0.108 g), trifluoroacetic acid (1 ml) and methylene chloride (1 ml) was stirred at ambient temperature for 1.5 hours. The mixture was evaporated and the residue was triturated under diethyl ether. The resultant solid was isolated and dried under vacuum. The solid was dissolved in methylene chloride and few drops of a saturated methanolic ammonia solution was added. The solution was poured onto a chromatography column filled with silica and eluted with a 97:3 mixture of methylene chloride and a saturated methanolic ammonia solution. There was thus obtained the title compound (0.082 g); NMR Spectrum: (CDCl₃) 1.2–1.4 (m, 2H), 1.9 (d, 2H), 2.3 (m, 1H), 2.65 (t, 2H), 3.12 (d, 2H), 3.84 (s, 3H), 4.2 (d, 2H), 6.61 (m, 1H), 6.93 (d, 1H), 7.5 (d, 2H), 7.68 (m, 1H), 8.22 (d, 1H), 8.68 (s, 1H); Mass Spectrum: M+H⁺ 443 and 445.

EXAMPLE 11

4-(2-chloro-5-methoxyanilino)-7-hydroxy-5-(3-morpholinopropoxy)quinazoline

A mixture of 7-benzyloxy-4-(2-chloro-5-methoxyanilino)-5-(3-morpholinopropoxy)quinazoline (0.185 g), 10% palladium on charcoal catalyst (0.018 g), ethanol (2.5 ml), THF (2.5 ml) and DMF (1 ml) was stirred under an atmosphere pressure of hydrogen for 16 hours. The mixture was filtered and the filtrate was evaporated. The residue was purified by column chromatography on silica using a 9:1 mixture of methylene chloride and a saturated methanolic ammonia solution as eluent. There was thus obtained the title compound (0.045 g); NMR Spectrum: (DMSOd$_6$) 2.05 (m, 2H), 2.35 (br s, 4H), 2.45 (t, 2H), 3.55 (t, 4H), 3.8 (s, 3H), 4.42 (t, 2H), 6.7 (d, 2H), 7.45 (d, 1H), 8.3 (s, 1H), 8.45 (s, 1H), 10.05 (s, 1H); Mass Spectrum: M+H$^+$ 445.

EXAMPLE 12

4-(2-chloro-5-methoxyanilino)-5,7-di-(3-morpholinopropoxy)quinazoline

Di-tert-butyl azodicarboxylate (0.035 g) was added dropwise to a stirred mixture of 4-(2-chloro-5-methoxyanilino)-7-hydroxy-5-(3-morpholinopropoxy)quinazoline (0.045 g), 4-(3-hydroxypropyl)morpholine (0.016 g), triphenylphosphine (0.04 g) and methylene chloride (1 ml). The reaction mixture was stirred at ambient temperature for 10 minutes. The mixture was evaporated and the residue was purified by column chromatography on silica using a 9:10:1 mixture of methylene chloride, ethyl acetate and a saturated methanolic ammonia solution as eluent. The material so obtained was triturated under diethyl ether. The resultant solid was isolated, washed with diethyl ether and dried under vacuum to give the title compound (0.018 g); NMR Spectrum: DMSOd$_6$ and CF$_3$COOD) 2.2–2.4 (m, 4H), 3.15 (m, 4H), 3.35 (m, 4H), 3.5 (m, 4H), 3.7 (m, 4H), 3.8 (s, 3H), 4.02 (t, 4H), 4.35 (t, 2H), 4.6 (t, 2H), 6.95 (s, 1H), 7.03 (s, 1H), 7.05 (m, 1H), 7.5 (s, 1H), 7.6 (d, 1H), 8.88 (s, 1H); Mass Spectrum: M+H$^+$ 572 and 574.

EXAMPLE 13

4-(2-chloro-5-methoxyanilino)-7-hydroxy-5-(3-pyrrolidin-1-ylpropoxy)quinazoline

A mixture of 7-benzyloxy-4-(2-chloro-5-methoxyanilino)-5-(3-pyrrolidin-1-ylpropoxy)quinazoline (0.68 g), 10% palladium on charcoal catalyst (0.16 g), ethanol (13 ml) and THF (13 ml) was stirred under 5 atmospheres pressure of hydrogen for 16 hours. The mixture was filtered and the filtrate was evaporated. The residue was triturated under methanol. The resultant solid was isolated, washed with diethyl ether and dried under vacuum. There was thus obtained the title compound (0.405 g); NMR Spectrum: (DMSOd$_6$) 1.65 (br s, 4H), 2.1 (m, 2H), 2.4 (br s, 4H), 2.55 (t, 2H), 3.8 (s, 3H), 4.4 (t, 2H), 6.7 (m, 2H), 6.75 (m, 1H), 7.48 (d, 1H), 8.3 (d, 1H), 8.4 (s, 1H), 10.05 (s, 1H).

EXAMPLE 14

Using an analogous procedure to that described in Example 12, the appropriate 7-hydroxy-substituted quinazoline was reacted with the appropriate alcohol to give the compounds described in Table III.

TABLE III

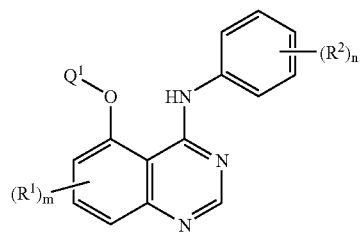

| No. & Note | $(R^1)_m$ | $Q^1$ | $(R^2)_n$ |
|---|---|---|---|
| [1] | 7-(3-morpholinopropoxy) | 3-pyrrolidin-1-ylpropyl | 2-chloro-5-methoxy |
| [2] | 7-[3-(4-methylpiperazin-1-yl)propoxy] | 3-pyrrolidin-1-ylpropyl | 2-chloro-5-methoxy |
| [3] | 7-(2-methoxyethoxy) | 3-pyrrolidin-1-ylpropyl | 2-chloro-5-methoxy |
| [4] | 7-[2-(2-methoxyethoxy)ethoxy] | 3-pyrrolidin-1-ylpropyl | 2-chloro-5-methoxy |
| [5] | 7-isopropoxy | 4-piperidinyl | 2-bromo-5-methoxy |
| [6] | 7-(3-methylsulphonyl)propoxy | 4-piperidinyl | 2-bromo-5-methoxy |
| [7] | 7-(2-pyridylmethoxy) | N-(2-pyridylmethyl)-piperidin-4-yl | 2-bromo-5-methoxy |
| [8] | 7-[3-(4-methylpiperazin-1-yl)propoxy] | 4-tetrahydropyranyl | 2-chloro-5-methoxy |
| [9] | 7-(3-morpholinopropoxy) | 4-tetrahydropyranyl | 2-chloro-5-methoxy |
| [10] | 7-(N-methylpiperidin-4-yloxy) | 4-tetrahydropyranyl | 2-bromo-5-methoxy |
| [11] | 7-(2-pyrrolidin-1-ylethoxy) | 4-tetrahydropyranyl | 2-bromo-5-methoxy |
| [12] | 7-(3-pyrrolidin-1-ylpropoxy) | 4-tetrahydropyranyl | 2-bromo-5-methoxy |
| [13] | 7-(2-piperidinoethoxy) | 4-tetrahydropyranyl | 2-bromo-5-methoxy |
| [14] | 7-[2-(4-methylpiperazin-1-yl)ethoxy] | 4-tetrahydropyranyl | 2-bromo-5-methoxy |
| [15] | 7-[3-(4-methylpiperazin-1-yl)propoxy] | 4-tetrahydropyranyl | 2-bromo-5-methoxy |
| [16] | 7-[2-(2-morpholinomethyl-5-methylimidazol-1-yl)ethoxy] | 4-tetrahydropyranyl | 2-bromo-5-methoxy |
| [17] | 7-{2-[2-(N,N-dimethylcarbamoyl)-pyrrolidin-1-yl]ethoxy} | 4-tetrahydropyranyl | 2-bromo-5-methoxy |
| [18] | 7-{3-[2-(N,N-dimethylcarbamoyl)-pyrrolidin-1-yl]propoxy} | 4-tetrahydropyranyl | 2-bromo-5-methoxy |
| [19] | 7-[2-(2,5-dimethoxymethyl-pyrrolidin-1-yl)ethoxy] | 4-tetrahydropyranyl | 2-bromo-5-methoxy |
| [20] | 7-[2-(4-pyridyloxy)ethoxy] | 4-tetrahydropyranyl | 2-bromo-5-methoxy |
| [21] | 7-(3-morpholinopropoxy) | cyclohexyl | 2-chloro-5-methoxy |
| [22] | 7-(2-pyrrolidin-1-ylethoxy) | cyclopentyl | 2,4-dichloro-5-methoxy |
| [23] | 7-(3-morpholinopropoxy) | isopropyl | 2-chloro-5-methoxy |
| [24] | 7-[3-(4-methylpiperazin-1-yl)propoxy] | isopropyl | 2-chloro-5-methoxy |
| [25] | 7-(2-pyrrolidin-1-ylethoxy) | 4-tetrahydropyranyl | 2,3-methylenedioxy |
| [26] | 7-(3-pyrrolidin-1-ylpropoxy) | 4-tetrahydropyranyl | 2,3-methylenedioxy |
| [27] | 7-(3-pyridylmethoxy) | 4-piperidinyl | 2-bromo-5-methoxy |
| [28] | 7-(2-pyrrolidin-1-ylethoxy) | 4-tetrahydropyranyl | 2,4-dichloro-5-methoxy |

TABLE III-continued

| No. & Note | $(R^1)_m$ | $Q^1$ | $(R^2)_n$ |
|---|---|---|---|
| [29] | 7-(3-pyrrolidin-1-ylpropoxy) | 4-tetrahydropyranyl | 2,4-dichloro-5-methoxy |
| [30] | 7-(2-piperidinoethoxy) | 4-tetrahydropyranyl | 2,4-dichloro-5-methoxy |
| [31] | 7-[2-(4-methylpiperazin-1-yl)ethoxy] | 4-tetrahydropyranyl | 2,4-dichloro-5-methoxy |
| [32] | 7-(2-morpholinoethoxy) | 4-tetrahydropyranyl | 2,4-dichloro-5-methoxy |
| [33] | 7-{2-[2-(N-methylcarbamoyl)-pyrrolidin-1-yl]ethoxy} | 4-tetrahydropyranyl | 2,4-dichloro-5-methoxy |
| [34] | 7-[2-(2-carbamoylpyrrolidin-1-yl)ethoxy] | 4-tetrahydropyranyl | 2,4-dichloro-5-methoxy |
| [35] | 7-[2-(2-morpholinocarbonyl-pyrrolidin-1-yl)ethoxy] | 4-tetrahydropyranyl | 2,4-dichloro-5-methoxy |
| [36] | 7-{2-[2-(4-methylpiperazin-1-ylcarbonyl)pyrrolidin-1-yl]ethoxy} | 4-tetrahydropyranyl | 2,4-dichloro-5-methoxy |
| [37] | 7-{2-[2-(pyrrolidin-1-ylcarbonyl)-pyrrolidin-1-yl]ethoxy} | 4-tetrahydropyranyl | 2,4-dichloro-5-methoxy |
| [38] | 7-[2-(2-piperidinocarbonyl-pyrrolidin-1-yl)ethoxy] | 4-tetrahydropyranyl | 2,4-dichloro-5-methoxy |
| [39] | 7-[2-(2-methylpyrrolidin-1-yl)ethoxy] | 4-tetrahydropyranyl | 2,4-dichloro-5-methoxy |
| [40] | 7-[2-(2-methoxymethylpyrrolidin-1-yl)ethoxy] | 4-tetrahydropyranyl | 2,4-dichloro-5-methoxy |
| [41] | 7-[2-(4-pyridyloxy)ethoxy] | 4-tetrahydropyranyl | 2,4-dichloro-5-methoxy |
| [42] | 7-(3-pyridylmethoxy) | 4-tetrahydropyranyl | 2,4-dichloro-5-methoxy |
| [43] | 7-(4-pyridylmethoxy) | 4-tetrahydropyranyl | 2,4-dichloro-5-methoxy |
| [44] | 7-(N-methylpiperidin-4-yloxy) | 4-tetrahydropyranyl | 2,4-dichloro-5-methoxy |
| [45] | 7-{2-[2-(N-methylcarbamoyl)-pyrrolidin-1-yl]ethoxy} | 4-tetrahydropyranyl | 2-bromo-5-methoxy |
| [46] | 7-[2-(2-morpholinocarbonyl-pyrrolidin-1-yl)ethoxy] | 4-tetrahydropyranyl | 2-bromo-5-methoxy |
| [47] | 7-{2-[2-(4-methylpiperazin-1-ylcarbonyl)pyrrolidin-1-yl]ethoxy} | 4-tetrahydropyranyl | 2-bromo-5-methoxy |
| [48] | 7-{2-[2-(pyrrolidin-1-ylcarbonyl)-pyrrolidin-1-yl]ethoxy} | 4-tetrahydropyranyl | 2-bromo-5-methoxy |
| [49] | 7-[2-(2-piperidinocarbonyl-pyrrolidin-1-yl)ethoxy] | 4-tetrahydropyranyl | 2-bromo-5-methoxy |
| [50] | 7-[2-(2-carbamoylpyrrolidin-1-yl)ethoxy] | 4-tetrahydropyranyl | 2-bromo-5-methoxy |
| [51] | 7-[2-(2-methylpyrrolidin-1-yl)ethoxy] | 4-tetrahydropyranyl | 2-bromo-5-methoxy |
| [52] | 7-[2-(2-methoxymethylpyrrolidin-1-yl)ethoxy] | 4-tetrahydropyranyl | 2-bromo-5-methoxy |
| [53] | 7-(3-pyridylmethoxy) | 4-tetrahydropyranyl | 2-bromo-5-methoxy |
| [54] | 7-(4-pyridylmethoxy) | 4-tetrahydropyranyl | 2-bromo-5-methoxy |
| [55] | 7-isopropoxy | 4-piperidinyl | 6-chloro-2,3-methylenedioxy |
| [56] | 7-ethoxy | 4-piperidinyl | 6-chloro-2,3-methylenedioxy |
| [57] | 7-isobutoxy | 4-piperidinyl | 6-chloro-2,3-methylenedioxy |
| [58] | 7-(2-fluoroethoxy) | 4-piperidinyl | 6-chloro-2,3-methylenedioxy |
| [59] | 7-[2-(2,5-dimethoxymethyl-pyrrolidin-1-yl)ethoxy] | 4-tetrahydropyranyl | 2,3-methylenedioxy |
| [60] | 7-[2-(4-pyridyloxy)ethoxy] | 4-tetrahydropyranyl | 2,3-methylenedioxy |
| [61] | 7-(3-pyridylmethoxy) | 4-tetrahydropyranyl | 2,3-methylenedioxy |
| [62] | 7-(4-pyridylmethoxy) | 4-tetrahydropyranyl | 2,3-methylenedioxy |
| [63] | 7-{2-[2-(N-methylcarbamoyl)-pyrrolidin-1-yl]ethoxy} | 4-tetrahydropyranyl | 2,3-methylenedioxy |
| [64] | 7-[2-(2-morpholinocarbonyl-pyrrolidin-1-yl)ethoxy] | 4-tetrahydropyranyl | 2,3-methylenedioxy |
| [65] | 7-{2-[2-(4-methylpiperazin-1-ylcarbonyl)pyrrolidin-1-yl]ethoxy} | 4-tetrahydropyranyl | 2,3-methylenedioxy |
| [66] | 7-{2-[2-(pyrrolidin-1-ylcarbonyl)-pyrrolidin-1-yl]ethoxy} | 4-tetrahydropyranyl | 2,3-methylenedioxy |
| [67] | 7-[2-(2-piperidinocarbonyl-pyrrolidin-1-yl)ethoxy] | 4-tetrahydropyranyl | 2,3-methylenedioxy |
| [68] | 7-[2-(2-carbamoylpyrrolidin-1-yl)ethoxy] | 4-tetrahydropyranyl | 2,3-methylenedioxy |
| [69] | 7-[2-(2-methylpyrrolidin-1-yl)ethoxy] | 4-tetrahydropyranyl | 2,3-methylenedioxy |

TABLE III-continued

| No. & Note | (R¹)ₘ | Q¹ | (R²)ₙ |
|---|---|---|---|
| [70] | 7-[2-(2-methoxymethylpyrrolidin-1-yl)ethoxy] | 4-tetrahydropyranyl | 2,3-methylenedioxy |
| [71] | 7-(3-piperazin-1-ylpropoxy) | 4-tetrahydropyranyl | 6-chloro-2,3-methylenedioxy |
| [72] | 7-[3-(4-methylpiperazin-1-yl)propoxy] | 4-tetrahydropyranyl | 6-chloro-2,3-methylenedioxy |
| [73] | 7-[2-(4-methylpiperazin-1-yl)ethoxy] | 4-tetrahydropyranyl | 6-chloro-2,3-methylenedioxy |
| [74] | 7-(2-piperidinoethoxy) | 4-tetrahydropyranyl | 6-chloro-2,3-methylenedioxy |
| [75] | 7-(2-piperidin-4-ylethoxy) | 4-tetrahydropyranyl | 6-chloro-2,3-methylenedioxy |
| [76] | 7-[2-(4-pyridyloxy)ethoxy] | 4-tetrahydropyranyl | 6-chloro-2,3-methylenedioxy |
| [77] | 7-[N-(tert-butoxycarbonyl)piperidin-4-ylmethoxy] | 4-tetrahydropyranyl | 6-chloro-2,3-methylenedioxy |
| [78] | 7-(3-pyrrolidin-1-ylpropoxy) | cyclopentyl | 2,3-methylenedioxy |
| [79] | 7-[3-(4-methylpiperazin-1-yl)propoxy] | cyclopentyl | 2,3-methylenedioxy |
| [80] | 7-[2-(4-methylpiperazin-1-yl)ethoxy] | cyclopentyl | 2,3-methylenedioxy |
| [81] | 7-(2-piperidinoethoxy) | cyclopentyl | 2,3-methylenedioxy |
| [82] | 7-{2-[2-(4-methylpiperazin-1-ylcarbonyl)pyrrolidin-1-yl]ethoxy} | cyclopentyl | 2,3-methylenedioxy |
| [83] | 7-piperidin-4-ylmethoxy) | cyclopentyl | 2,3-methylenedioxy |
| [84] | 7-(3-piperazin-1-ylpropoxy) | cyclopentyl | 2,3-methylenedioxy |

Notes

[1] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the trihydrochloride salt; NMR Spectrum: (DMSOd₆ and CF₃COOD) 1.8–2.1 (m, 4H), 2.35 (m, 4H), 3.05 (m, 2H), 3.15 (t, 2H), 3.35 (m, 4H), 3.55 (m, 4H), 3.8 (s, 3H), 3.85 (t, 2H), 4.05 (d, 2H), 4.4 (t, 2H), 4.7 (t, 2H), 7.0–7.15 (m, 3H), 7.52 (d, 1H), 7.56 (d, 1H), 8.86 (s, 1H); Mass Spectrum: M+H⁺ 556 and 558.

[2] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the trihydrochloride salt; NMR Spectrum: (DMSOd₆ and CF₃COOD) 1.8–2.05 (m, 4H), 2.4 (m, 4H), 2.95 (s, 3H), 3.02 (m, 2H), 3.2–3.65 (m, 12H), 3.8 (t, 2H), 3.85 (s, 3H), 4.4 (t, 2H), 4.7 (t, 2H), 7.02 (s, 1H), 7.05 (m, 1H), 7.1 (s, 1H), 7.5 (s, 1H), 7.6 (d, 1H), 7.95 (s, 1H).

[3] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the dihydrochloride salt; NMR Spectrum: (DMSOd₆ and CF₃COOD) 1.85–2.1 (m, 4H), 2.38 (m, 2H), 3.05 (m, 2H), 3.35 (t, 2H), 3.4 (s, 3H), 3.6 (m, 2H), 3.8 (s, 3H), 3.85 (m, 2H), 4.4 (t, 2H), 4.65 (t, 2H), 7.0 (s, 1H), 7.05 (m, 1H), 7.12 (s, 1H), 7.52 (d, 1H), 7.6 (d, 1H), 8.87 (s, 1H); Mass Spectrum: M+H⁺ 487 and 489.

[4] The reaction product was treated with a 6M solution of hydrogen chloride in diethyl ether (5 ml) at ambient temperature for 30 minutes. The resultant solid was isolated, washed with isopropanol and with diethyl ether and dried under vacuum to give the product as the dihydrochloride salt; NMR Spectrum: (DMSOd₆ and CF₃COOD) 1.8–2.05 (m, 4H), 2.35 (m, 2H), 3.0 (m, 2H), 3.25 (s, 3H), 3.35 (t, 2H), 3.5 (t, 2H), 3.55 (m, 2H), 3.65 (t, 2H), 3.8 (s, 3H), 3.85 (m, 2H), 4.35 (m, 2H), 4.65 (t, 2H), 7.0 (s, 1H), 7.05 (m, 1H), 7.12 (s, 1H), 7.45 (s, 1H), 7.57 (d, 1H), 8.85 (s, 1H); Mass Spectrum: M+H⁺ 531 and 533.

[5] The reaction mixture was stirred at ambient temperature for 2 hours. The reaction product was treated with 6M hydrogen chloride in isopropanol to give 4-(2-bromo-5-methoxyanilino)-7-isopropoxy-5-piperidin-4-yloxyquinazoline dihydrochloride, a portion of which was converted to the free base using an analogous procedure to that described in Example 3. The free base gave the following data: NMR Spectrum: (CDCl₃) 1.45 (d, 6H), 1.8–2.0 (m, 2H), 2.25 (d, 2H), 2.75 (m, 2H), 3.2 (m, 2H), 3.82 (s, 3H), 4.65 (m, 1H), 4.75 (m, 1H), 6.52 (d, 1H), 6.65 (m, 1H), 6.85 (d, 1H), 7.5 (d, 1H), 7.92 (d, 1H), 8.52 (s, 1H), 9.72 (s, 1H); Mass Spectrum: M+H⁺ 487 and 489.

The 4-(2-bromo-5-methoxyanilino)-7-hydroxy-5-piperidin-4-yloxyquinazoline used as a starting material is described in Example 20 hereinafter.

[6] The reaction mixture was stirred at ambient temperature for 1 hour whereafter a second portion of each of di-tert-butyl azodicarboxylate and triphenylphosphine were added and the reaction mixture was stirred at ambient temperature for 30 minutes. The reaction product was dissolved in methanol containing potassium carbonate and heated to reflux for 15 minutes. The mixture was filtered and the filtrate was evaporated to give the required product; NMR Spectrum: (CDCl$_3$) 1.85–2.0 (m, 2H), 2.25 (d, 2H), 2.42 (m, 2H), 2.8 (m, 2H), 3.0 (s, 3H), 3.21 (m, 2H), 3.3 (m, 2H), 3.82 (s, 3H), 4.25 (m, 2H), 4.65 (m, 1H), 6.55 (d, 1H), 6.62 (m, 1H), 6.82 (d, 1H), 7.5 (d, 1H), 7.9 (d, 1H), 8.52 (s, 1H), 9.75 (s, 1H); Mass Spectrum: M+H$^+$ 565 and 567.

[7] The reactants were 4-(2-bromo-5-methoxyanilino)-7-hydroxy-5-piperidin-4-yloxyquinazoline and 2-pyridyl-methanol. The reaction mixture was stirred at ambient temperature for 1 hour whereafter a second portion of each of di-tert-butyl azodicarboxylate and triphenylphosphine were added and the reaction mixture was stirred at ambient temperature for 30 minutes. The reaction product was dissolved in methanol containing potassium carbonate and heated to reflux for 15 minutes. The mixture was filtered and the filtrate was evaporated to give the required product; NMR Spectrum: (CDCl$_3$) 2.05–2.2 (m, 2H), 2.2–2.3 (m, 2H), 2.35 (m, 2H), 2.92 (d, 2H), 3.68 (s, 3H), 3.82 (s, 3H), 4.6 (m, 1H), 5.32 (s, 2H), 6.62 (m, 1H), 6.7 (d, 1H), 6.92 (d, 1H), 7.2 (m, 1H), 7.4 (d, 1H), 7.5 (m, 2H), 7.65 (m, 1H), 7.75 (m, 1H), 7.88 (d, 1H), 8.52 (s, 1H), 8.55 (m, 2H), 8.65 (d, 1H), 9.72 (s, 1H); Mass Spectrum: M+H$^+$ 627 and 629.

[8] The reaction mixture was stirred at ambient temperature for 2 hours. The reaction product, obtained as the free base, gave the following data: NMR Spectrum: (CDCl$_3$) 2.0–2.15 (m, 6H), 2.3 (s, 3H), 2.35–2.7 (m, 10H), 3.6 (t, 2H), 3.85 (s, 3H), 4.0–4.2 (m, 4H), 4.75 (m, 1H), 6.6 (s, 1H), 6.7 (m, 1H), 6.9 (s, 1H), 7.32 (d, 1H), 8.2 (s, 1H), 8.58 (s, 1H), 9.85 (s, 1H); Mass Spectrum: M+H$^+$ 542 and 544.

The 4-(2-chloro-5-methoxyanilino)-7-hydroxy-5-tetrahydropyran-4-yloxyquinazoline, used as a starting material, is described in Example 21.

[9] The reaction mixture was stirred at ambient temperature for 2 hours. The reaction product, obtained as the free base, gave the following data: NMR Spectrum: (DMSOd$_6$ and CF$_3$CO$_2$D) 1.85–2.0 (s, 2H), 2.18 (d, 2H), 2.2–2.3 (m, 2H), 3.15 (m, 2H), 3.3–3.4 (m, 2H), 3.5 (d, 2H), 3.7 (t, 2H), 3.8 (s, 3H), 3.95. (m, 2H), 4.05 (d, 2H), 4.3 (t, 2H), 5.15 (m, 1H), 6.9 (s, 1H), 7.02 (m, 1H), 7.1 (s, 1H), 7.6 (m, 2H), 8.9 (s, 1H); Mass Spectrum: M+H$^+$ 529 and 531.

[10] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.8–2.0 (m, 2H), 2.0–2.2 (m, 4H), 2.2–2.3 (m, 4H), 2.33 (s, 3H), 2.78 (m, 2H), 3.6 (m, 2H), 3.84 (s, 3H), 4.08 (m, 2H), 4.45 (m, 1H), 4.75 (m, 1H), 6.55 (s, 1H), 6.65 (m, 1H), 6.85 (d, 1H), 7.5 (d, 1H), 7.92 (d, 1H), 8.52 (s, 1H), 9.7 (s, 1H); Mass Spectrum: M+H$^+$ 543 and 545.

The 4-(2-bromo-5-methoxyanilino)-7-hydroxy-5-tetrahydropyran-4-yloxyquinazoline, used as a starting material, is described in Example 24.

[11] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.85 (m, 4H), 2.1 (m, 2H), 2.22 (d, 2H), 2.65 (m, 4H), 2.98 (t, 2H), 3.58 (t, 2H), 3.85 (s, 3H), 4.05 (m, 2H), 4.22 (t, 2H), 4.75 (m, 1H), 6.65 (m, 2H), 6.87 (s, 1H), 7.5 (d, 1H), 7.95 (s, 1H), 8.55 (s, 1H), 9.7 (s, 1H); Mass Spectrum: M+H$^+$ 543 and 545.

[12] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.8 (m, 4H), 2.0–2.2 (m, 4H), 2.22 (d, 2H), 2.45–2.6 (m, 4H), 2.68 (m, 2H), 3.6 (m, 2H), 3.85 (s, 3H), 4.05 (m, 2H), 4.15 (m, 2H), 4.78 (m, 1H), 6.55 (d, 1H), 6.65 (m, 1H), 6.85 (d, 1H), 7.5 (d, 1H), 7.95 (d, 1H), 8.55 (s, 1H), 9.7 (s, 1H); Mass Spectrum: M+H$^+$ 557 and 559.

[13] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.63 (br s, 6H), 2.0–2.2 (m, 2H), 2.25 (d, 2H), 2.55 (br s, 4H), 2.85 (t, 2H), 3.6 (m, 2H), 384 (s, 3H), 4.05 (m, 2H), 4.25 (m, 2H), 4.75 (m, 1H), 6.62 (m, 2H), 6.85 (d, 1H), 7.5 (d, 1H), 7.95 (d, 1H), 8.55 (s, 1H), 9.7 (s, 1H); Mass Spectrum: M+H$^+$ 557 and 559.

[14] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.0–2.18 (m, 2H), 2.25 (d, 2H), 2.31 (s, 3H), 2.5 (br s, 4H), 2.65 (br s, 4H), 2.9 (t, 2H), 3.6 (m, 2H), 3.84 (s, 3H), 4.05 (m, 2H), 4.25 (t, 2H), 4.75 (m, 1H), 6.62 (m, 2H), 6.85 (d, 1H), 7.5 (d, 1H), 7.95 (d, 1H), 8.55 (s, 1H), 9.7 (s, 1H); Mass Spectrum: M+H$^+$ 572 and 574.

[15] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.02–2.2 (m, 4H), 2.25 (d, 2H), 2.29 (s, 3H), 2.35–2.7 (m, 10H), 3.6 (m, 2H), 3.84 (s, 3H), 4.1 (m, 2H), 4.15 (t, 2H), 4.75 (m, 1H), 6.55 (s, 1H), 6.65 (m, 1H), 6.85 (d, 1H), 7.5 (d, 1H), 7.95 (d, 1H), 8.55 (s, 1H), 9.7 (s, 1H); Mass Spectrum: M+H$^+$ 586 and 588.

[16] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 2.0–2.2 (m, 2H), 2.22 (d, 2H), 2.3 (s, 3H), 2.45 (br s, 4H), 3.6 (t, 2H), 3.65 (br s, 6H), 3.85 (s, 3H), 4.05 (m, 2H), 4.42 (m, 2H), 4.45 (m, 2H), 4.75 (m, 1H), 6.48 (s, 1H), 6.65 (m, 1H), 6.7 (s, 1H), 6.82 (d, 1H), 7.5 (d, 1H), 7.92 (d, 1H), 8.55 (s, 1H), 9.68 (s, 1H); Mass Spectrum: M+H$^+$ 653 and 655.

The 1-(2-hydroxyethyl)-5-methyl-2-morpholinomethylimidazole used as a starting material was prepared as follows:—

A mixture of 4-methyl-1-tritylimidazole (*J. Heterocyclic Chem.*, 1982, 19, 253; 32.5 g), methyl bromoacetate (11.4 ml) and acetone (500 ml) was heated to reflux for 2 hours. The solvent was removed by evaporation and the residue was dissolved in methanol (100 ml) and heated to reflux for 45 minutes. The mixture was evaporated and the residue was triturated under diethyl ether. The resultant precipitate was isolated and stirred at ambient temperature for 1 hour in a mixture of diethyl ether (200 ml) and a saturated methanolic ammonia solution (20 ml). The mixture was filtered and the filtrate was evaporated. The residue was purified by column chromatography on silica using a 49:1 mixture of methylene chloride and methanol as eluent. There was thus obtained methyl 2-(5-methylimidazol-1-yl)acetate (6 g); NMR Spectrum: (CDCl$_3$) 2.16 (s, 3H), 3.78 (s, 3H), 4.61 (s, 3H), 6.8 (s, 1H), 7.42 (s, 1H).

A solution of a portion (1.7 g) of the material so obtained in diethyl ether (20 ml) was added dropwise to a stirred suspension of lithium aluminium hydride (0.76 g) in diethyl ether (70 ml) which was cooled to 0° C. The resultant mixture was stirred at ambient temperature for 1 hour. The mixture was cooled to 0° C. and a 6N aqueous sodium hydroxide solution (0.8 ml) and water (2.4 ml) were added dropwise in turn. The mixture was stirred at ambient temperature for 30 minutes and then evaporated. The residue was dissolved in methylene chloride, dried over magnesium sulphate and evaporated to give 1-(2-hydroxyethyl)-5-methylimidazole (1.1 g); NMR Spectrum: (CDCl$_3$) 2.17 (s, 3H), 3.81 (t, 2H), 3.92 (t, 2H), 6.6 (s, 1H), 7.24 (s, 1H).

Tert-butyldimethylsilyl chloride (9.05 g) was added to a stirred mixture of 1-(2-hydroxyethyl)-5-methylimidazole (6.4 g), imidazole (7.5 g) and methylene chloride (30 ml) which was cooled to 0° C. The reaction mixture was stirred at ambient temperature for 4 hours. The mixture was poured into water. The organic layer was washed with brine, dried over magnesium sulphate and evaporated to give 1-(2-tert-butyldimethylsilyloxyethyl)-5-methylimidazole (11.7 g); NMR Spectrum: (CDCl$_3$) −0.04 (s, 6H), 0.85 (s, 6H), 2.2 (s, 3H), 3.8 (m, 2H), 3.94 (m, 2H), 6.75 (s, 1H), 7.43 (s, 1H).

The material so obtained was dissolved in THF (400 ml) and the solution was cooled at −60° C. n-Butyllithium (2.5M in hexane, 40 ml) was added dropwise and the mixture was stirred at −50° C. for 1 hour. The mixture was cooled to −60° C. and DMF (12.5 ml) was added dropwise. The resultant mixture was allowed to warm to ambient temperature and was stirred for 2 hours. Diethyl ether (500 ml) was added and the reaction mixture was poured into a saturated aqueous ammonium chloride solution. The organic layer was separated, washed with brine, dried over magnesium sulphate and evaporated. The material so obtained was purified by column chromatography on silica using increasingly polar mixtures of methylene chloride and a saturated methanolic ammonia solution as eluent. There was thus obtained 1-(2-tert-butyldimethylsilyloxyethyl)-2-formyl-5-methylimidazole (11 g); NMR Spectrum: (CDCl$_3$) −0.1 (s, 6H), 0.79 (s, 9H), 2.32 (s, 3H), 3.91 (t, 2H), 4.4 (t, 2H), 7.07 (s, 1H), 9.71 (s, 1H).

A portion (0.79 g) of the material so obtained was dissolved in methylene chloride (24 ml) and morpholine (0.263 ml) and acetic acid (0.175 ml) were added. Sodium borohydride triacetate (0.8 g) was added portionwise and the mixture was stirred at ambient temperature for 16 hours. The mixture was evaporated and the residue was purified by column chromatography on silica using a 49:1 mixture of methylene chloride and a saturated methanolic ammonia solution as eluent. There was thus obtained 1-(2-tert-butyldimethylsilyloxyethyl)-5-methyl-2-morpholinomethylimidazole (0.5 g); NMR Spectrum: (CDCl$_3$) 0 (s, 6H), 0.82 (s, 9H), 2.25 (s, 3H), 2.45 (m, 4H), 3.6 (s, 2H), 3.68 (m, 4H), 3.85 (t, 2H), 4.1 (t, 2H), 6.7 (s, 1H).

A mixture of the material so obtained, 12N aqueous hydrochloric acid (0.26 ml) and methanol (10 ml) was stirred at ambient temperature for 5 hours. The mixture was evaporated and the residue was triturated under pentane. The resultant solid was isolated and dried under vacuum. The solid was stirred at ambient temperature for 1 hour in a mixture of methylene chloride and a saturated methanolic ammonia solution. The mixture was filtered and the filtrate was evaporated. The residue was purified by column chromatography on silica using a 19:1 mixture of methylene chloride and a saturated methanolic ammonia solution as eluent. There was thus obtained 1-(2-hydroxyethyl)-5-methyl-2-morpholinomethylimidazole (0.25 g); NMR Spectrum: (CDCl$_3$) 2.2 (s, 3H), 2.6 (br s, 4H), 3.58 (s, 2H), 3.7 (m, 4H), 3.85 (t, 2H), 4.1 (t, 2H), 6.5–6.9 (br s, 1H), 6.65 (s, 1H).

[17] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.75–2.3 (m, 8H), 2.5 (m, 1H), 2.8–2.9 (m, 1H), 2.9 (s, 3H), 3.1 (s, 3H), 3.18 (m, 1H), 3.35 (m, 1H), 3.48 (m, 1H), 3.58 (m, 2H), 3.82 (s, 3H), 4.05 (m, 2H), 4.2 (m, 2H), 4.72 (m, 1H), 6.6 (m, 2H), 6.8 (s, 1H), 7.5 (d, 1H), 7.92 (d, 1H), 8.5 (s, 1H), 9.68 (s, 1H); Mass Spectrum: M+H$^+$ 614 and 616.

The (2S)-1-(2-hydroxyethyl)-N,N-dimethylpyrrolidine-2-carboxamide used as a starting material was prepared as follows:—

A mixture of 1-(tert-butoxycarbonyl)-L-proline (10.75 g), 1-(3-dimethylaminopropyl)-3-ethylcarbodiimide hydrochloride (10.6 g), dimethylamine hydrochloride (5.33 g), 4-dimethylaminopyridine (6.1 g) and methylene chloride (200 ml) was stirred at ambient temperature for 4 hours. The mixture was poured into water. The organic layer was separated, washed in turn with a 1N aqueous potassium hydrogen sulphate solution, with a 5% aqueous sodium bicarbonate solution and brine, dried over magnesium sulphate and evaporated to give 1-(tert-butoxycarbonyl)-N,N-dimethyl-L-prolinamide (11.2 g); NMR Spectrum: (CDCl$_3$) 1.4 and 1.5 (2 s, 9H), 1.8–1.9 (m, 2H), 1.95–2.2 (m, 2H), 3.0 and 3.1 (2 d, 6H), 3.35–3.6 (m, 2H), 4.55 and 4.7 (2 m, 1H).

A mixture of a portion (0.24 g) of the material so obtained and trifluoroacetic acid (3 ml) was stirred at ambient temperature for 2 hours. The mixture was evaporated and the residue was triturated under diethyl ether. A slight excess of a 2M solution of hydrogen chloride in diethyl ether was added and the precipitate was isolated and dried under vacuum to give N,N-dimethyl-L-prolinamide hydrochloride salt (0.25 g); NMR Spectrum: (DMSOd$_6$ and CF$_3$CO$_2$D) 1.7–2.0 (m, 3H), 2.3–2.5 (m, 1H), 2.95 (s, 3H), 3.05 (s, 3H), 3.1–3.4 (m, 2H), 4.6 (m, 1H).

A mixture of N,N-dimethyl-L-prolinamide hydrochloride salt (6.3 g), 2-bromoethanol (3.8 ml), potassium carbonate (14 g) and acetonitrile (70 ml) was stirred and heated to reflux for 16 hours. The mixture was filtered and the filtrate was evaporated. The residue was purified by column chromatography on silica using a 24:1 mixture of methylene chloride and a saturated methanolic ammonia solution as eluent. There was thus obtained (2S)-1-(2-hydroxyethyl)-N,N-dimethylpyrrolidine-2-carboxamide (3.4 g); NMR Spectrum: (CDCl$_3$) 1.6 (m, 1H), 1.6–2.0 (m, 4H), 2.1–2.3 (m, 2H), 2.4 (m, 1H), 2.9 (m, 1H), 3.0 (s, 3H), 3.05 (s, 3H), 3.25–3.4 (m, 2H), 3.75 (m, 1H), 3.9 (m, 1H), 5.1 (br s, 1H); Mass Spectrum: M+H$^+$ 187.

[18] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.7–2.5 (m, 12H), 2.95 (s, 3H), 3.1 (s, 3H), 2.8–3.0 (m, 1H), 3.2–3.4 (m, 2H), 3.58 (t, 2H), 3.82 (s, 3H), 4.05 (m, 2H), 4.1 (t, 2H), 4.75 (m, 1H), 6.55 (d, 1H), 6.6 (m, 1H), 6.8 (d, 1H), 7.48 (d, 1H), 7.92 (d, 1H), 8.5 (s, 1H), 9.65 (s, 1H); Mass Spectrum: M+H$^+$ 628 and 630.

The (2S)-1-(3-hydroxypropyl)-N,N-dimethylpyrrolidine-2-carboxamide used as a starting material was prepared as follows using an analogous procedure to that described in International Patent Application WO 98/13354 (Example 76 thereof):—

Using an analogous procedure to that described in the last paragraph of the portion of Note [17] immediately above that is concerned with the preparation of starting materials, 3-bromopropanol was reacted with N,N-dimethyl-L-prolinamide hydrochloride salt.

[19] The reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.6–1.8 (m, 2H), 1.9–2.0 (m, 2H), 2.05–2.15 (m, 2H), 2.25 (d, 2H), 3.21 (m, 2H), 3.25–3.5 (m, 6H), 3.33 (s, 3H), 3.34 (s, 3H), 3.58 (m, 2H), 3.84 (s, 3H), 4.05 (m, 2H), 4.25 (m, 2H), 4.75 (m, 1H), 6.6 (d, 1H), 6.65 (m, 1H), 6.9 (d, 1H), 7.5 (d, 1H), 7.95 (d, 1H), 8.55 (s, 1H), 9.7 (s, 1H); Mass Spectrum: M+H$^+$ 631 and 633.

The (2R,5R)-1-(2-hydroxyethyl)-2,5-dimethoxymethylpyrrolidine used as a starting material was prepared as follows:—

A mixture of (2R,5R)-2,5-dimethoxymethylpyrrolidine (0.25 g), 2-bromoethanol (1.1 ml), potassium carbonate (2.8 g) and acetonitrile (10 ml) was stirred and heated to reflux for 18 hours. The mixture was filtered and the filtrate was poured on a column of silica and eluted by a 49:1 mixture of methylene chloride and a saturated methanolic ammonia solution. There was thus obtained (2R,5R)-1-(2-hydroxyethyl)-2,5-dimethoxymethylpyrrolidine (0.23 g); Mass Spectrum: M$^+$H$^+$ 204.

[20] 4-(2-Hydroxyethoxy)pyridine (*J. Chem. Soc. Perkin II*, 1987, 1867) was used as a starting material. The product gave the following data: NMR Spectrum: (DMSOd$_6$) 1.65–1.9 (m, 2H), 2.25 (d, 2H), 3.55 (m, 2H), 3.78 (s, 3H), 3.9 (m, 2H), 4.4–4.55 (m, 4H), 5.1 (m, 1H), 6.78 (m, 1H), 6.85 (d, 1H), 7.0 (d, 1H), 7.05 (d, 2H), 7.6 (d, 1H), 7.84 (d, 1H), 8.4 (d, 2H), 8.45 (s, 1H), 9.69 (s, 1H); Mass Spectrum: M+H$^+$ 567 and 569.

[21] The reaction mixture was stirred at ambient temperature for 2 hours. The reaction product, obtained as the free base, gave the following data: NMR Spectrum: (DMSOd$_6$ and CF$_3$CO$_2$D) 1.2–1.35 (m, 1H), 1.4–1.5 (m, 2H), 1.6 (m, 1H), 1.7–1.8 (m, 4H), 2.1–2.15 (m, 2H), 2.2–2.3 (m, 2H), 3.1–3.2 (t, 2H), 3.35 (t, 2H), 3.55 (d, 2H), 3.7 (t, 2H), 3.8 (s, 3H), 4.05 (d, 2H), 4.3 (t, 2H), 4.92 (m, 1H), 6.9 (s, 1H), 7.02 (d, 1H), 7.05 (s, 1H), 7.58 (d, 1H), 7.58 (s, 1H), 7.9 (s, 1H); Mass Spectrum: M+H$^+$ 527 and 529.

The 4-(2-chloro-5-methoxyanlino)-5-cyclohexyloxy-7-hydroxyquinazoline used as a starting material was prepared as follows:—

Using an analogous procedure to that described in Example 1, 7-benzyloxy-4-(2-chloro-5-methoxyanilino)-5-hydroxyquinazoline (0.53 g) was reacted with cyclohexanol to give 7-benzyloxy-4-(2-chloro-5-methoxyanilino)-5-cyclohexyloxyquinazoline (0.25 g); NMR Spectrum: (DMSOd$_6$ and CF$_3$CO$_2$D) 1.3–1.4 (m, 1H), 1.4–1.55 (m, 2H), 1.55–1.65 (m, 1H), 1.7–1.85 (m, 4H), 2.15 (m, 2H), 3.82 (s, 3H), 4.95 (m, 1H), 5.4 (s, 2H), 7.0 (d, 1H), 7.05 (m, 1H), 7.2 (s, 1H), 7.4–7.65 (m, 7H), 8.9 (s, 1H); Mass Spectrum: M+H$^+$ 490 and 492.

Using an analogous procedure to that described in Example 20, 7-benzyloxy-4-(2-chloro-5-methoxyanilino)-5-cyclohexyloxyquinazoline was reacted with trifluoroacetic acid to give 4-(2-chloro-5-methoxyanilino)-5-cyclohexyloxy-7-hydroxyquinazoline; NMR Spectrum: (DMSOd$_6$ and CF$_3$CO$_2$D) 1.2–1.35 (m, 1H), 1.4–1.55 (m, 2H), 1.55–1.65 (m, 1H), 1.7–1.85 (m, 4H), 2.15 (m, 2H), 3.82 (s, 3H), 4.85 (m, 1H), 6.8 (s, 1H), 7.0 (s, 1H), 7.05 (m, 1H), 7.55 (d, 1H), 7.6 (d, 1H), 8.82 (s, 1H); Mass Spectrum: M+H$^+$ 400 and 402.

[22] The reaction mixture was stirred at ambient temperature for 2 hours. The reaction product, obtained as the free base, gave the following data: NMR Spectrum: (CDCl$_3$) 1.65–1.75 (m, 2H), 1.75–1.8 (m, 2H), 1.8–1.9 (m, 4H), 2.05–2.18 (m, 4H), 2.65 (m, 4H), 2.98 (m, 2H), 3.95 (s, 3H), 4.22 (m, 2H), 5.02 (m, 1H), 6.62 (d, 1H), 6.85 (d, 1H), 7.4 (s, 1H), 8.38 (s, 1H), 8.55 (s, 1H), 9.8 (s, 1H); Mass Spectrum: M+H$^+$ 517 and 519.

The 5-cyclopentyloxy-4-(2,4-dichloro-5-methoxyanilino)-7-hydroxyquinazoline used as a starting material was prepared as follows:—

Di-tert-butyl azodicarboxylate (1.1 g) was added portionwise to a stirred mixture 5-hydroxy-7-methoxy-3,4-dihydroquinazolin-4-one (1 g), cyclopentanol (0.385 ml), triphenylphosphine (1.28 g) and methylene chloride (16 ml) which was maintained at ambient temperature using a water bath. The mixture was stirred at ambient temperature for 1 hour. A 6M solution of hydrogen chloride in diethyl ether (4 ml) was added and the mixture was stirred at ambient temperature for 10 minutes. The resultant precipitate was isolated, washed with methylene chloride and with ethyl acetate and dried under vacuum. The product so obtained was stirred in methanol (16 ml) containing sodium hydroxide (0.28 g) at ambient temperature for 1 hour. The mixture was evaporated and the solid was triturated under water (20 ml) containing acetic acid (1 ml). The resultant precipitate was isolated, washed in turn with water, ethyl acetate and diethyl ether. There was thus obtained 5-cyclopentyloxy-7-methoxy-3,4-dihydroquinazoline-4-one (0.52 g); NMR Spectrum: (CDCl$_3$) 1.55 (br s, 2H), 1.75 (m, 4H), 1.9 (m, 2H), 3.85 (s, 3H), 4.9 (br s, 1H), 6.5 (s, 1H), 6.62 (s, 1H), 7.9 (s, 1H), 11.62 (br s, 1H); Mass Spectrum: M+H$^+$ 261.5.

The material so obtained was mixed with potassium carbonate (0.414 g) and N-methylpyrrolidin-2-one (10 ml) and thiophenol (0.306 ml) was added. The resultant mixture was stirred and heated to 175° C. for 30 minutes. The mixture was evaporated and the residue was poured into water (20 ml) containing acetic acid (1 ml). The resultant precipitate was isolated, washed with ethyl acetate and dried under vacuum to give 5-cyclopentyloxy-7-hydroxy-3,4-dihydroquinazolin-4-one (0.4 g); NMR Spectrum: (DMSOd$_6$) 1.6 (m, 2H), 1.8 (m, 4H), 1.9 (m, 2H), 4.8 (br s, 1H), 6.38 (s, 1H), 6.5 (s, 1H), 7.8 (s, 1H), 10.35 (s, 1H), 11.5 (br s, 1H); Mass Spectrum: M+H$^+$ 247.5.

A mixture of 5-cyclopentyloxy-7-hydroxy-3,4-dihydroquinazolin-4-one (13 g), acetic anhydride (25 ml) and pyridine (21 ml) was stirred and heated to 100° C. for 1 hour. The mixture was evaporated and the residue was dissolved in a mixture of water (70 ml) and methanol (70 ml) and stirred at 15° C. for 30 minutes. The methanol was evaporated and the resultant precipitate was isolated, washed with water and dried under vacuum to give 7-acetoxy-5-cyclopentyloxy-3,4-dihydroquinazolin-4-one (12.2 g); NMR Spectrum: DMSOd$_6$) 1.6 (br s, 2H), 1.8 (m, 4H), 1.92 (m, 2H), 2.3 (s, 3H), 4.9 (m, 1H), 6.8 (s, 1H), 6.9 (s, 1H), 7.95 (s, 1H), 11.9 (br s, 1H); Mass Spectrum: M+H$^+$ 289.6.

Using an analogous procedure to that described in the last paragraph of Note [9] in Example 15, 7-acetoxy-5-cyclopentyloxy-3,4-dihydroquinazolin-4-one (5 g) was reacted with carbon tetrachloride and triphenylphosphine to give 7-acetoxy-4-chloro-5-cyclopentyloxyquinazoline (5.3 g); NMR Spectrum: (CDCl$_3$) 1.65–1.8 (m, 2H), 1.8–2.05 (m, 4H), 2.1 (m, 2H), 2.4 (s, 3H), 4.95 (m, 1H), 6.78 (d, 1H), 7.35 (d, 1H), 8.9 (s, 1H); Mass Spectrum: M+H$^+$ 307 and 309.

A mixture of a portion (1 g) of the material so obtained, 2,4-dichloro-5-methoxyaniline hydrochloride (0.82 g), triethylamine (0.408 ml) and isopropanol (6 ml) was stirred and heated to 80° C. for 1.5 hours. The precipitate was isolated, washed in turn with isopropanol, ethyl acetate and diethyl ether and dried under vacuum to give 7-acetoxy-5-cyclopentyloxy-4-(2,4-dichloro-5-methoxyanilino)quinazoline (1.2 g); NMR Spectrum: (DMSOd$_6$) 1.6–1.8 (m, 4H), 1.95–2.2 (m, 4H), 2.4 (s, 3H), 3.9 (s, 3H), 5.25 (br s, 1H), 7.3 (s, 2H), 7.82 (s, 1H), 7.9 (s, 1H), 8.82 (s, 1H), 10.32 (s, 1H); Mass Spectrum: M+H$^+$ 462 and 464.

A mixture of the material so obtained and a saturated methanolic ammonia solution (20 ml) was stirred at ambient temperature for 4 hours. The mixture was evaporated and the residue was triturated under water. The resultant solid was isolated and dried under vacuum to give 5-cyclopentyloxy-4-(2,4-dichloro-5-methoxyanilino)-7-hydroxyquinazoline (1 g); NMR Spectrum: (DMSOd$_6$) 1.6–1.8 (m, 4H), 1.95 (m, 2H), 2.0–2.15 (m, 2H), 3.9 (s, 3H), 5.15 (m, 1H), 6.7 (s, 2H), 7.7 (s, 1H), 8.3 (s, 1H), 8.4 (s, 1H), 9.7 (s, 1H), 10.5–10.7 (br s, 1H); Mass Spectrum: M+H$^+$ 420 and 422.

[23] The free base product gave the following data: NMR Spectrum: (DMSOd$_6$ and CF$_3$CO$_2$D) 1.5 (d, 6H), 2.2–2.3 (m, 2H), 3.15 (t, 2H), 3.3–3.4 (m, 2H), 3.52 (d, 2H), 3.7 (m, 2H), 3.8 (s, 3H), 4.02 (d, 2H), 4.3 (t, 2H), 5.1–5.2 (m, 1H), 6.9 (s, 1H), 7.0 (m, 2H), 7.55 (d, 1H), 7.65 (s, 1H), 8.9 (s, 1H); Mass Spectrum: M+H$^+$ 487 and 489.

[24] The free base product gave the following data: NMR Spectrum: (DMSOd$_6$) 1.5 (d, 6H), 1.95 (m, 2H), 2.18 (s, 3H), 2.2–2.6 (m, 10H), 3.8 (s, 3H), 4.2 (t, 2H), 5.1 (m, 1H), 6.75–6.85 (m, 3H), 7.48 (d, 1H), 8.2 (s, 1H), 8.5 (s, 1H), 10.0 (s, 1H); Mass Spectrum: M+H$^+$ 500 and 502.

[25] The reaction mixture was stirred at ambient temperature for 2 hours. The free base product gave the following data: NMR Spectrum: (DMSOd$_6$) 1.7 (br s, 4H), 1.8–1.95 (m, 2H), 2.15 (d, 2H), 2.55 (br s, 4H), 2.85 (m, 2H), 3.55 (m, 2H), 3.95 (m, 2H), 4.22 (m, 2H), 5.05 (m, 1H), 6.15 (s, 2H), 6.75 (d, 1H), 6.85 (d, 1H), 6.9–7.0 (m, 2H), 8.1 (d, 1H), 8.5 (s, 1H), 9.85 (s, 1H); Mass Spectrum: M+H$^+$ 479.

The 4-(2,3-methylenedioxyanilino)-7-hydroxy-5-tetrahydropyran-4-yloxyquinazoline used as a starting material was prepared as follows:—

A mixture of 7-acetoxy-5-tetrahydropyran-4-yloxy-3,4-dihydroquinazolin-4-one (3.04 g), diisopropylethylamine (4.34 ml), phosphoryl chloride (1.02 ml) and 1,2-dichloroethane (60 ml) was stirred and heated to 80° C. for 2 hours. The mixture was evaporated to give 7-acetoxy-4-chloro-5-tetrahydropyran-4-yloxyquinazoline which was used without further purification.

A mixture of the material so obtained, 2,3-methylenedioxyaniline (1.5 g) and isopropanol (20 ml) was stirred and heated to 80° C. for 1 hour. The mixture was cooled to ambient temperature and the resultant solid was isolated, washed in turn with isopropanol and diethyl ether and dried under vacuum. There was thus obtained 7-acetoxy-4-(2,3-methylenedioxyanilino)-5-tetrahydropyran-4-yloxyquinazoline hydrochloride (3.6 g); NMR Spectrum: (DMSOd$_6$) 1.9–2.05 (m, 2H), 2.1–2.25 (m, 2H), 2.4 (s, 3H), 3.55 (m, 2H), 3.98 (m, 2H), 5.1 (m, 1H), 6.2 (s, 2H), 6.95–7.05 (m, 2H), 7.32 (s, 1H), 7.5 (s, 1H), 7.62. (m, 1H), 9.0 (s, 1H); Mass Spectrum: M+H$^+$ 424.

Using an analogous procedure to that described in the last paragraph of Note [22] immediately above, 7-acetoxy-4-(2, 3-methylenedioxyanilino)-5-tetrahydropyran-4-yloxyquinazoline was reacted with a saturated methanolic ammonia solution to give 4-(2,3-methylenedioxyanilino)-7-hydroxy-5-tetrahydropyran-4-yloxyquinazoline; NMR Spectrum: (DMSOd$_6$) 1.8–1.95 (m, 2H), 2.1–2.2 (m, 2H), 3.52 (m, 2H), 3.8 (s, 3H), 3.9 (m, 2H), 4.95 (m, 1H), 6.7 (s, 1H), 6.75 (d, 1H), 6.85 (s, 1H), 7.6 (d, 1H), 7.88 (s, 1H), 8.4 (s, 1H), 9.65 (s, 1H), 10.6 (br s, 1H); Mass Spectrum: M+H$^+$ 382.

[26] The reaction mixture was stirred at ambient temperature for 2 hours. The free base product gave the following data: NMR Spectrum: (DMSOd$_6$) 1.7 (br s, 4H), 1.75–1.9 (m, 2H), 1.9–2.0 (m, 2H), 2.15 (d, 2H), 2.5 (br s, 4H), 2.6 (m, 2H), 3.55 (m, 2H), 3.9 (m, 2H), 4.18 (m, 2H), 5.0 (m, 1H), 6.1 (s, 2H), 6.72 (d, 1H), 6.8 (s, 1H), 6.9 (m, 2H), 8.08 (d, 1H), 8.5 (s, 1H), 8.82 (s, 1H); Mass Spectrum: M+H$^+$ 493.

[27] The reaction mixture was stirred at ambient temperature for 2 hours. The reaction product was treated with 6M hydrogen chloride in isopropanol to give 4-(2-bromo-5-methoxyanilino)-5-piperidin-4-yloxy-7-(3-pyridylmethoxy) quinazoline dihydrochloride, a portion of which was converted to the free base using an analogous procedure to that described in Example 3. The free base gave the following data: NMR Spectrum: (CDCl$_3$) 1.85–2.0 (m, 2H), 2.25 (d, 2H), 2.78 (m, 2H), 3.2 (m, 2H), 3.85 (s, 3H), 4.65 (m, 1H), 5.2 (s, 2H), 6.62 (s, 1H), 6.65 (m, 1H), 6.92 (d, 1H), 7.38 (m, 1H), 7.5 (d, 1H), 7.82 (d, 1H), 7.92 (d, 1H), 8.55 (s, 1H), 8.65 (d, 1H), 8.75 (s, 1H), 9.72 (s, 1H); Mass Spectrum: M+H$^+$ 536 and 538.

[28] The reaction mixture was stirred at ambient temperature for 2 hours. The reaction product gave the following data: NMR Spectrum: (CDCl$_3$) 1.8–1.9 (m, 4H), 1.95–2.1 (m, 2H), 2.12 (d, 2H), 2.68 (br s, 4H), 3.0 (t, 2H), 3.58 (t, 2H), 3.98 (s, 3H), 4.08 (m, 2H), 4.25 (t, 2H), 4.72 (m, 1H), 6.8 (d, 1H), 6.9 (d, 1H), 7.42 (s, 1H), 8.4 (s, 1H), 8.6 (s, 1H), 9.9 (s, 1H); Mass Spectrum: M+H$^+$ 533 and 535.

The 4-(2,4-dichloro-5-methoxyanilino)-7-hydroxy-5-tetrahydropyran-4-yloxyquinazoline used as a starting material was prepared as follows:—

A mixture of 7-acetoxy-4-chloro-5-tetrahydropyran-4-yloxyquinazoline prepared from 7-acetoxy-5-tetrahydropyran-4-yloxy-3,4-dihydroquinazolin-4-one (3.04 g) and phosphoryl chloride), 2,4-dichloro-5-methoxyaniline (2.1 g) and isopropanol (20 ml) was stirred and heated to 80° C. for 1 hour. The mixture was cooled to ambient temperature and the resultant solid was isolated, washed in turn with isopropanol and diethyl ether and dried under vacuum. There was thus obtained 7-acetoxy-4-(2,4-dichloro-5-methoxyanilino)-5-tetrahydropyran-4-yloxyquinazoline hydrochloride (3.5 g); NMR Spectrum: (DMSOd$_6$ and CF$_3$CO$_2$D) 1.9–2.1 (m, 2H), 2.15 (d, 2H), 2.4 (s, 3H), 3.52 (t, 2H), 3.9 (s, 3H), 3.95 (m, 2H), 5.1 (m, 1H), 7.4 (d, 1H), 7.55 (d, 1H), 7.78 (s, 1H), 7.95 (s, 1H), 8.95 (s, 1H); Mass Spectrum: M+H$^+$ 478 and 480.

Using an analogous procedure to that described in the last paragraph of Note [22] immediately above, 7-acetoxy-4-(2,4-dichloro-5-methoxyanilino)-5-tetrahydropyran-4-yloxyquinazoline was reacted with a saturated methanolic ammonia solution to give 4-(2,4-dichloro-5-methoxyanilino)-7-hydroxy-5-tetrahydropyran-4-yloxyquinazoline; NMR Spectrum: (DMSOd$_6$) 1.75–1.9 (m, 2H), 2.18 (d, 2H), 3.52 (t, 2H), 3.9 (s, 3H), 3.95 (m, 2H), 4.95 (m, 1H), 6.7 (d, 1H), 6.82 (d, 1H), 7.7 (s, 1H), 8.35 (s, 1H), 8.42 (s, 1H), 9.85 (s, 1H), 10.5–10.7 (br s, 1H); Mass Spectrum: M+H$^+$ 436 and 438.

[29] The reaction mixture was stirred at ambient temperature for 2 hours. The reaction product gave the following data: NMR Spectrum: (CDCl$_3$) 1.85 (br s, 4H), 2.0–2.15 (m, 4H), 2.25 (d, 2H), 2.6 (br s, 4H), 2.68 (t, 2H), 3.6 (t, 2H), 3.96 (s, 3H), 4.08 (m, 2H), 4.18 (t, 2H), 4.75 (m, 1H), 6.6 (d, 1H), 6.88 (d, 1H), 7.45 (s, 1H), 8.4 (s, 1H), 8.6 (s, 1H); Mass Spectrum: M+H$^+$ 547 and 549.

[30] The reaction mixture was stirred at ambient temperature for 2 hours. The reaction product gave the following data: NMR Spectrum: (CDCl$_3$) 1.4–1.5 (m, 2H), 1.5–1.75 (m, 6H), 2.0–2.1 (m, 2H), 2.25 (d, 2H), 2.52 (br s, 4H), 2.85 (t, 2H), 3.58 (m, 2H), 3.96 (s, 3H), 4.08 (m, 2H), 4.25 (t, 2H), 4.75 (m, 1H), 6.65 (d, 1H), 6.68 (d, 1H), 7.25 (s, 1H), 8.4 (s, 1H), 8.58 (s, 1H), 9.85 (s, 1H); Mass Spectrum: M+H$^+$ 547 and 549.

[31] The reaction mixture was stirred at ambient temperature for 2 hours. The reaction product gave the following data: NMR Spectrum: (CDCl$_3$) 1.98–2.12 (m, 4H), 2.22 (d, 2H), 2.32 (s, 3H), 2.5 (br s, 2H), 2.65 (br s, 2H), 2.9 (t, 2H), 3.6 (m, 2H), 3.96 (s, 3H), 4.08 (m, 2H), 4.25 (t, 2H), 4.75 (m, 1H), 6.61 (d, 1H), 6.86 (d, 1H), 7.42 (s, 1H), 8.4 (s, 1H), 8.6 (s, 1H), 9.85 (d, 1H); Mass Spectrum: M+H$^+$ 562 and 564.

[32] The reaction mixture was stirred at ambient temperature for 2 hours. The reaction product gave the following data: NMR Spectrum: (CDCl$_3$) 2.0–2.1 (m, 2H), 2.22 (d, 2H), 2.6 (m, 4H), 2.9 (t, 2H), 3.6 (m, 2H), 3.8 (m, 4H), 3.98 (s, 3H), 4.08. (m, 2H), 4.25 (t, 2H), 4.75 (m, 1H), 6.62 (d, 1H), 6.88 (d, 1H), 7.42 (s, 1H), 8.4 (s, 1H), 8.6 (s, 1H), 9.9 (s, 1H); Mass Spectrum: M+H$^+$ 549 and 551.

[33] The reaction mixture was stirred at ambient temperature for 3 hours. The reaction product gave the following data: Mass Spectrum: M+H$^+$ 590 and 592.

The (2S)-1-(2-hydroxyethyl)-N-methylprolinamide used as a starting material was obtained as follows:—

A mixture of 1-tert-butoxycarbonyl-L-proline (5.4 g), 1-(3-dimethylaminopropyl)-3-ethylcarbodiimide (5.3 g), methylamine hydrochloride (2.2 g), 4-dimethylaminopyridine (3 g) and methylene chloride (50 ml) was stirred at ambient temperature for 16 hours. The resultant mixture was poured in water and the organic layer was separated, washed in turn with a 1M aqueous potassium hydrogen sulphate solution, a saturated aqueous sodium bicarbonate solution and brine, dried over magnesium sulphate and evaporated. There was thus obtained 1-(tert-butoxycarbonyl)-N-methyl-L-prolinamide (5.6 g); Mass Spectrum: M+H$^+$ 229.

A mixture of a portion (4.4 g) of the material so obtained and trifluoroacetic acid (10 ml) was stirred at ambient temperature for 2 hours. The mixture was evaporated and the residue was triturated under diethyl ether. The resultant solid was isolated, washed with diethyl ether and dried under vacuum. There was thus obtained to give N-methyl-L-prolinamide trifluoroacetic acid salt (3.7 g); NMR Spectrum: (DMSOd$_6$ and CF$_3$CO$_2$D) 1.85–2.05 (m, 3H), 2.2–2.3 (m, 1H), 2.73 (s, 3H), 3.2–3.4 (m, 2H), 4.2 (m, 1H).

A mixture of a portion (2.5 g) of the material so obtained, 2-bromoethanol (2.15 ml), potassium carbonate (5.5 g) and acetonitrile (20 ml) was stirred and heated to reflux for 18 hours. The mixture was cooled to ambient temperature, filtered and evaporated and the residue was purified by column chromatography on silica using a 49:1 mixture of methylene chloride and a saturated methanolic ammonia solution as eluent. There was thus obtained (2S)-1-(2-hydroxyethyl)-N-methylprolinamide (0.5 g); NMR Spectrum: (CDCl$_3$) 1.6–2.0 (m, 4H), 2.1–2.3 (m, 1H), 2.3–2.45 (m, 1H), 2.6–2.7 (m, 1H), 2.85 (d, 3H), 2.8–2.9 (m, 1H), 3.1–3.2 (m, 1H), 3.2–3.3 (m, 1H), 3.6–3.8 (m, 2H); Mass Spectrum: M+H$^+$ 173.

[34] The reaction mixture was stirred at ambient temperature for 3 hours. The reaction product gave the following data: Mass Spectrum: M+H$^+$ 576 and 578.

The (2S)-1-(2-hydroxyethyl)prolinamide used as a starting material was prepared by the reaction of L-prolinamide and 2-bromoethanol using an analogous procedure to that described in Note [33] immediately above. There was thus obtained the required starting material; NMR Spectrum: (CDCl$_3$) 1.6–2.0 (m, 4H), 2.1–2.25 (m, 1H), 2.35–2.45 (m, 1H), 2.6–2.7 (m, 1H), 2.8–3.0 (m, 1H); 3.1 (m, 1H), 3.2–3.3 (m, 1H), 3.6–3.8 (m, 2H), 5.6 (br s, 1H), 7.4 (br s, 1H); Mass Spectrum: M+H$^+$ 159.

[35] The reaction mixture was stirred at ambient temperature for 3 hours. The reaction product gave the following data: Mass Spectrum: M+H$^+$ 646 and 648.

The (2S)-1-(2-hydroxyethyl)-2-morpholinocarbonylpyrrolidine used as a starting material was prepared as follows:—

Using analogous procedures to those described in Note [33] immediately above, 1-tert-butoxycarbonyl-L-proline was reacted with morpholine to give (2S)-1-(tert-butoxycarbonyl)-2-morpholinocarbonylpyrrolidine which was deprotected and reacted with 2-bromoethanol. There was thus obtained the required starting material; NMR Spectrum: (CDCl$_3$) 1.7–2.0 (m, 4H), 2.1–2.2 (m, 1H), 2.4–2.5 (m, 1H), 2.6–2.7 (m, 1H), 2.8–2.9 (m, 1H), 3.3–3.4 (m, 2H), 3.4–3.8 (m, 10H); Mass Spectrum: M+H$^+$ 229.

[36] The reaction mixture was stirred at ambient temperature for 3 hours. The reaction product gave the following data: Mass Spectrum: M+H⁺ 659 and 661.

The (2S)-1-(2-hydroxyethyl)-2-(4-methylpiperazin-1-yl-carbonyl)pyrrolidine used as a starting material was prepared as follows:—

Using analogous procedures to those described in Note [33] immediately above, 1-tert-butoxycarbonyl-L-proline was reacted with 1-methylpiperazine to give (2S)-1-tert-butoxycarbonyl-2-(4-methylpiperazin-1-ylcarbonyl)pyrrolidine which was deprotected and reacted with 2-bromoethanol. There was thus obtained the required starting material; NMR Spectrum: (CDCl₃) 1.7–2.05 (m, 4H), 2.1–2.25 (m, 1H), 2.32 (s, 3H), 2.35–2.5 (m, 4H), 2.6–2.7 (m, 1H), 2.8–2.9 (m, 1H), 3.3–3.7 (m, 8H), 4.15 (br s, 1H); Mass Spectrum: M+H⁺ 242.

[37] The reaction mixture was stirred at ambient temperature for 3 hours. The reaction product gave the following data: Mass Spectrum: M+H⁺ 630 and 632.

The (2S)-1-(2-hydroxyethyl)-2-(pyrrolidin-1-ylcarbonyl)pyrrolidine used as a starting material was prepared as follows:—

Using analogous procedures to those described in Note [33] immediately above, 1-tert-butoxycarbonyl-L-proline was reacted with pyrrolidine to give (2S)-1-(tert-butoxycarbonyl)-2-(pyrrolidin-1-ylcarbonyl)pyrrolidine which was deprotected and reacted with 2-bromoethanol. There was thus obtained the required starting material; NMR Spectrum: (CDCl₃) 1.7–2.05 (m, 8H), 2.1–2.3 (m, 1H), 2.4–2.5 (m, 1H), 2.55–2.7 (m, 1H), 2.8–2.9 (m, 1H), 3.2–3.3 (m, 2H), 3.4–3.7 (m, 5H), 4.1 (br s, 1H); Mass Spectrum: M+H⁺ 213.

[38] The reaction mixture was stirred at ambient temperature for 3 hours. The reaction product gave the following data: Mass Spectrum: M+H⁺ 644 and 646.

The (2S)-1-(2-hydroxyethyl)-2-piperidinocarbonylpyrrolidine used as a starting material was prepared as follows:—

Using analogous procedures to those described in Note [33] immediately above, 1-tert-butoxycarbonyl-L-proline was reacted with piperidine to give (2S)-1-tert-butoxycarbonyl-2-piperidinocarbonylpyrrolidine which was deprotected and reacted with 2-bromoethanol. There was thus obtained the required starting material; NMR Spectrum: (CDCl₃) 1.5–1.9 (m, 10H), 1.9–2.0 (m, 1H), 2.1–2.2 (m, 1H), 2.4–2.5 (m, 1H), 2.55–2.65 (m, 1H), 2.8–2.9 (m, 1H), 3.3–3.7 (m, 6H), 4.3 (br s, 1H); Mass Spectrum: M+H⁺ 227.

[39] The reaction mixture was stirred at ambient temperature for 3 hours. The reaction product gave the following data: Mass Spectrum: M+H⁺ 547 and 549.

The (2R)-1-(2-hydroxyethyl)-2-methylpyrrolidine used as a starting material was obtained as follows:—

A mixture of (2R)-2-methylpyrrolidine (0.853 g), 2-bromoethanol (1.1 ml), potassium carbonate (2.8 g) and acetonitrile (10 ml) was stirred and heated to reflux for 18 hours. The mixture was filtered and the filtrate was evaporated. The resultant residue was purified by column chromatography on silica using a 49:1 mixture of methylene chloride and a saturated methanolic ammonia solution as eluent. There was thus obtained (2R)-1-(2-hydroxyethyl)-2-methylpyrrolidine (0.35 g); NMR Spectrum: (CDCl₃) 1.1 (d, 3H), 1.3–1.5 (m, 1H), 1.6–1.8 (m, 3H), 1.95 (m, 1H), 2.15 (m, 1H), 2.28 (m, 1H), 2.4–2.5 (m, 1H), 2.95–3.05 (m, 1H), 3.2 (m, 1H), 3.5–3.8 (m, 2H); Mass Spectrum: M+H⁺ 130.

[40] The reaction mixture was stirred at ambient temperature for 3 hours. The reaction product gave the following data: Mass Spectrum: M+H⁺ 577 and 579.

The (2S)-1-(2-hydroxyethyl)-2-methoxymethylpyrrolidine used as a starting material was obtained as follows:—

Using an analogous procedure to those described in Note [39] immediately above, (2S)-2-methoxymethylpyrrolidine was reacted with 2-bromoethanol to give (2S)-1-(2-hydroxyethyl)-2-methoxymethylpyrrolidine; NMR Spectrum: (CDCl₃) 1.5–1.65 (m, 1H), 1.65–1.8 (m, 2H), 1.8–2.0 (m, 2H), 2.3 (m, 1H), 2.6 (m, 1H), 2.8 (m, 1H), 2.95–3.05 (m, 1H), 3.17 (m, 1H), 3.3 (t, 1H), 3.35 (t, 1H), 3.37 (s, 3H), 3.5–3.7 (m, 2H).

[41] The reaction mixture was stirred at ambient temperature for 3 hours. The reaction product gave the following data: Mass Spectrum: M+H⁺ 557 and 559.

[42] The reaction mixture was stirred at ambient temperature for 3 hours. The reaction product gave the following data: Mass Spectrum: M+H⁺ 527 and 529.

[43] The reaction mixture was stirred at ambient temperature for 3 hours. The reaction product gave the following data: Mass Spectrum: M+H⁺ 527 and 529.

[44] The reaction mixture was stirred at ambient temperature for 3 hours. The reaction product gave the following data: Mass Spectrum: M+H⁺ 533 and 535.

[45] (2S)-1-(2-Hydroxyethyl)-N-methylprolinamide was used as a starting material and the reaction mixture was stirred at ambient temperature for 3 hours. The reaction product gave the following data: Mass Spectrum: M+H⁺ 600 and 602.

[46] (2S)-1-(2-Hydroxyethyl)-2-morpholinocarbonylpyrrolidine was used as a starting material and the reaction mixture was stirred at ambient temperature for 3 hours. The reaction product gave the following data: Mass Spectrum: M+H⁺ 658 and 660.

[47] (2S)-1-(2-Hydroxyethyl)-2-(4-methylpiperazin-1-yl-carbonyl)pyrrolidine was used as a starting material and the reaction mixture was stirred at ambient temperature for 3 hours. The reaction product gave the following data: Mass Spectrum: M+H⁺ 671 and 673.

[48] (2S)-1-(2-Hydroxyethyl)-2-(pyrrolidin-1-ylcarbonyl)pyrrolidine was used as a starting material and the reaction mixture was stirred at ambient temperature for 3 hours. The reaction, product gave the following data: Mass Spectrum: M+H⁺ 642 and 644.

[49] (2S)-1-(2-Hydroxyethyl)-2-piperidinocarbonylpyrrolidine was used as a starting material and the reaction mixture was stirred at ambient temperature for 3 hours. The reaction product gave the following data: Mass Spectrum: M+H⁺ 656 and 658.

[50] (2S)-1-(2-Hydroxyethyl)prolinamide was used as a starting material and the reaction mixture was stirred at ambient temperature for 3 hours. The reaction product gave the following data: Mass Spectrum: M+H⁺ 588 and 590.

[51] (2R)-1-(2-Hydroxyethyl)-2-methylpyrrolidine was used as a starting material and the reaction mixture was stirred at ambient temperature for 3 hours. The reaction product gave the following data: Mass Spectrum: M+H⁺ 557 and 559.

[52] (2S)-1-(2-Hydroxyethyl)-2-methoxymethylpyrrolidine was used as a starting material and the reaction mixture was stirred at ambient temperature for 3 hours; The reaction product gave the following data: Mass Spectrum: M+H⁺ 587 and 589.

[53] The reaction mixture was stirred at ambient temperature for 3 hours. The reaction product gave the following data: Mass Spectrum: M+H⁺ 537 and 539.

[54] The reaction mixture was stirred at ambient temperature for 3 hours. The reaction product gave the following data: Mass Spectrum: M+H⁺ 537 and 539.

[55] The reactants were 5-[N-(tert-butoxycarbonyl)piperidin-4-yloxy]-4-(6-chloro-2,3-methylenedioxyanilino)-7-hydroxyquinazoline and isopropanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-isopropoxy-5-piperidin-4-yloxyquinazoline; NMR Spectrum: (CDCl$_3$) 1.4 (d, 6H), 1.8–1.9 (m, 2H), 2.25 (m, 2H), 1.75–1.85 (m, 2H), 3.1–3.2 (m, 2H), 4.7 (m, 1H), 4.72 (m, 1H), 6.05 (s, 2H), 6.5 (d, 1H), 6.7 (d, 1H), 6.82 (d, 1H), 6.98 (d, 1H), 8.5 (s, 1H), 9.32 (s, 1H); Mass Spectrum: M+H⁺ 457 and 459.

The 5-[N-(tert-butoxycarbonyl)piperidin-4-yloxy]-4-(6-chloro-2,3-methylenedioxyanilino)-7-hydroxyquinazoline used as a starting material is described in Example 35 hereinafter.

[56] The reactants were 5-[N-(tert-butoxycarbonyl)piperidin-4-yloxy]-4-(6-chloro-2,3-methylenedioxyanilino)-7-hydroxyquinazoline and ethanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-ethoxy-5-piperidin-4-yloxyquinazoline; NMR Spectrum: (CDCl$_3$) 1.45 (t, 3H), 1.7–1.9 (m, 2H), 2.1–2.25 (m, 2H), 2.7–2.8 (m, 2H), 3.05–3.2 (m, 2H), 4.12 (q, 2H), 4.6 (m, 1H), 6.02 (s, 2H), 6.48 (d, 1H), 6.7 (d, 1H), 6.8 (d, 1H), 6.92 (d, 1H), 8.5 (s, 1H), 9.3 (s, 1H); Mass Spectrum: M+H⁺ 443 and 445.

[57] The reactants were 5-[N-(tert-butoxycarbonyl)piperidin-4-yloxy]-4-(6-chloro-2,3-methylenedioxyanilino)-7-hydroxyquinazoline and isobutanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-isobutoxy-5-piperidin-4-yloxyquinazoline; NMR Spectrum: (CDCl$_3$) 1.05 (d, 6H), 1.8–1.9 (m, 2H), 2.12 (m, 1H), 2.2–2.3 (m, 2H), 2.75–2.9 (m, 2H), 3.1–3.2 (m, 2H), 4.85 (d, 2H), 4.65 (m, 1H), 6.05 (s, 2H), 6.5 (d, 1H), 6.7 (d, 1H), 6.8 (d, 1H), 6.95 (d, 1H), 8.5 (s, 1H), 9.32 (s, 1H); Mass Spectrum: M+H⁺ 471 and 473.

[58] The reactants were 5-[N-(tert-butoxycarbonyl)piperidin-4-yloxy]4-(6-chloro-2,3-methylenedioxyanilino)-7-hydroxyquinazoline and 2-fluoroethanol. The reaction mixture was stirred at ambient temperature for 1 hour. Thereafter, a 6M solution of hydrogen chloride in diethyl ether was added and the reaction mixture was stirred at ambient temperature for 1 hour. The resultant precipitate was isolated, washed with ethyl acetate and diethyl ether and dried. There was thus obtained the required product, 4-(6-chloro-2,3-methylenedioxyanilino)-7-(2-fluoroethoxy)-5-piperidin-4-yloxyquinazoline; NMR Spectrum: (CDCl$_3$) 1.8–2.0 (m, 2H), 2.2–2.3 (m, 2H), 2.8–2.9 (m, 2H), 3.1–3.3 (m, 2H), 4.3 (m, 1H), 4.4 (m, 1H), 4.7 (m, 1H), 4.8 (m, 1H), 4.9 (m, 1H), 6.08 (s, 2H), 6.6 (d, 1H), 6.75 (d, 1H), 6.82 (d, 1H), 7.0 (d, 1H), 8.55 (s, 1H), 9.35 (s, 1H); Mass Spectrum: M+H⁺ 461 and 463.

[59] (2R,5R)-1-(2-Hydroxyethyl)-2,5-dimethoxymethylpyrrolidine was used as a starting material and the reaction mixture was stirred at ambient temperature for 2 hours. The reaction product was treated with 6M hydrogen chloride in diethyl ether to give the dihydrochloride salt. A portion thereof was treated with a saturated methanolic ammonia solution, the mixture was filtered and the filtrate evaporated to give the free base which gave the following data: NMR Spectrum: (CDCl$_3$) 1.6–1.7 (m, 4H), 1.9–2.1 (m, 2H), 2.22 (m, 2H), 3.15–3.5 (m, 8H), 3.33 (s, 6H), 3.6 (m, 2H), 4.08 (m, 2H), 4.12 (m, 2H), 4.75 (m, 1H), 6.05 (s, 2H), 6.58 (d, 1H), 6.7 (d, 1H), 6.9 (d, 1H), 6.95 (m, 1H), 8.1 (d, 1H), 8.6 (s, 1H), 9.75 (s, 1H); Mass Spectrum: M+H⁺ 567.

[60] The reaction mixture was stirred at ambient temperature for 3 hours. The reaction product was purified by column chromatography on silica using a 24:1 mixture of methylene chloride and a saturated methanolic ammonia solution as eluent. The resultant product gave the following data: Mass Spectrum: M+H⁺ 503.

[61] The reaction mixture was stirred at ambient temperature for 3 hours. The reaction product was purified by column chromatography on silica using increasingly polar mixtures of methylene chloride and a saturated methanolic ammonia solution as eluent. The resultant product gave the following data: Mass Spectrum: M+H⁺ 473.

[62] The reaction mixture was stirred at ambient temperature for 3 hours. The reaction product was purified by column chromatography on silica using increasingly polar mixtures of methylene chloride and a saturated methanolic ammonia solution as eluent. The resultant product gave the following data: Mass Spectrum: M+H⁺ 473.

[63] (2S)-1-(2-Hydroxyethyl)-N-methylprolinamide was used as a starting material and the reaction mixture was stirred at ambient temperature for 3 hours. The reaction product gave the following data: Mass Spectrum: M+H⁺ 536.

[64] (2S)-1-(2-Hydroxyethyl)-2-morpholinocarbonylpyrrolidine was used as a starting material and the reaction mixture was stirred at ambient temperature for 3 hours. The reaction product gave the following data: Mass Spectrum: M+H⁺ 592.

[65] (2S)-1-(2-Hydroxyethyl)-2-(4-methylpiperazin-1-ylcarbonyl)pyrrolidine was used as a starting material and the reaction mixture was stirred at ambient temperature for 3 hours. The reaction product gave the following data: Mass Spectrum: M+H⁺ 605.

[66] (2S)-1-(2-Hydroxyethyl)-2-(pyrrolidin-1-ylcarbonyl)pyrrolidine was used as a starting material and the reaction mixture was stirred at ambient temperature for 3 hours. The reaction product gave the following data: Mass Spectrum: M+H⁺ 576.

[67] (2S)-1-(2-Hydroxyethyl)-2-piperidinocarbonylpyrrolidine was used as a starting material and the reaction mixture was stirred at ambient temperature for 3 hours. The reaction product gave the following data: Mass Spectrum: M+H$^+$ 590.

[68] (2S)-1-(2-Hydroxyethyl)prolinamide was used as a starting material and the reaction mixture was stirred at ambient temperature for 3 hours. The reaction product gave the following data: Mass Spectrum: M+H$^+$ 522.

[69] (2R)-1-(2-Hydroxyethyl)-2-methylpyrrolidine was used as a starting material and the reaction mixture was stirred at ambient temperature for 3 hours. The reaction product gave the following data: Mass Spectrum: M+H$^+$ 493.

[70] (2S)-1-(2-Hydroxyethyl)-2-methoxymethylpyrrolidine was used as a starting material and the reaction mixture was stirred at ambient temperature for 3 hours. The reaction product gave the following data: Mass Spectrum: M+H$^+$ 523.

[71] The reactants were 4-(6-chloro-2,3-methylenedioxyanilino)-7-hydroxy-5-tetrahydropyran-4-yloxyquinazoline and 1-(tert-butoxycarbonyl)-4-(3-hydroxypropyl)piperazine and the reaction mixture was stirred at ambient temperature for 2 hours. Thereafter, trifluoroacetic acid (1 ml) was added and the mixture was stirred at ambient temperature for 16 hours. The mixture was evaporated and the residue was triturated under a saturated methanolic ammonia solution (1 ml). Methylene chloride was added and the mixture was filtered. The filtrate was evaporated and the residue was purified by column chromatography on silica using a 97:3 mixture of methylene chloride and a saturated methanolic ammonia solution as eluent. The material so obtained was treated with a 6M solution of hydrogen chloride in diethyl ether. The precipitate was isolated, washed with diethyl ether and dried under vacuum to give the dihydrochloride salt (0.11 g) of the required product, a portion of which was converted to the free base using an analogous procedure to that described in Example 3. The free base gave the following data: NMR Spectrum: (CDCl$_3$) 1.9–2.1 (m, 4H), 2.2–2.3 (m, 2H), 2.3–2.5 (m, 4H), 2.55 (m, 2H), 2.91 (m, 4H), 3.65 (m, 2H), 4.05 (m, 2H), 4.15 (m, 2H), 4.8 (m, 1H), 6.06 (s, 2H), 6.5 (d, 1H), 6.72 (d, 1H), 6.84 (d, 1H), 6.97 (d, 1H), 8.5 (s, 1H), 9.26 (s, 1H); Mass Spectrum: M+H$^+$ 542 and 544.

The 4-(6-chloro-2,3-methylenedioxyanilino)-7-hydroxy-5-tetrahydropyran-4-yloxyquinazoline used as a starting material was prepared as follows:—

A mixture of 7-benzyloxy-4-(6-chloro-2,3-methylenedioxyanilino)-5-tetrahydropyran-4-yloxyquinazoline (Example 17[34], 0.2 g) and trifluoroacetic acid (2 ml) was stirred and heated to 80° C. for 6 hours. The mixture was evaporated and the residue was triturated under a 6M solution of hydrogen chloride in diethyl ether. The resultant solid was isolated, washed with diethyl ether and dried under vacuum. The solid was treated with a saturated methanolic ammonia solution. The mixture was filtered, the filtrate was evaporated and the residue was triturated under methylene chloride. The solid so obtained was washed with methylene chloride and dried under vacuum. There was thus obtained 4-(6-chloro-2,3-methylenedioxyanilino)-7-hydroxy-5-tetrahydropyran-4-yloxyquinazoline (0.17 g); NMR Spectrum: (DMSOd$_6$) 1.8–1.9 (m, 2H), 2.05–2.2 (m, 2H), 3.5–3.6 (m, 2H), 3.8–3.9 (m, 2H), 4.95 (m, 1H), 6.08 (s, 2H), 6.7 (d, 1H), 6.8 (d, 1H), 6.95 (d, 1H), 7.05 (d, 1H), 8.35 (s, 2H), 9.32 (s, 1H), 10.8 (br s, 1H); Mass Spectrum: M−H$^-$ 414 and 416.

The 1-tert-butoxycarbonyl-4-(3-hydroxypropyl)piperazine used as a starting material was prepared using an analogous procedure to that described in European Patent Application No. 0388309:—

A mixture of 3-bromopropanol (25 ml), 1-tert-butoxycarbonyl)piperazine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil.

[72] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.1 (m, 4H), 2.15–2.3 (m, 2H), 2.28 (s, 3H), 2.4–2.7 (m, 10H), 3.6–3.7 (m, 2H), 4.0–4.1 (m, 2H), 4.15 (m, 2H), 4.75 (m, 1H), 6.05 (s, 2H), 6.5 (d, 1H), 6.72 (d, 1H), 6.83 (d, 1H), 6.97 (d, 1H), 8.52 (s, 1H), 9.26 (s, 1H); Mass Spectrum: M+H$^+$ 556 and 558.

[73] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.05 (m, 2H), 2.2–2.3 (m, 2H), 2.31 (s, 3H), 2.4–2.7 (m, 8H), 2.87 (m, 2H), 2.55–2.7 (m, 2H), 3.95–4.05 (m, 2H), 4.25 (m, 2H), 4.75 (m, 1H), 6.05 (s, 2H), 6.55 (d, 1H), 6.72 (d, 1H), 6.83 (d, 1H), 6.97 (d, 1H), 8.52 (s, 1H), 9.26 (s, 1H); Mass Spectrum: M+H$^+$ 542 and 544.

[74] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.4–1.5 (m, 2H), 1.6–1.7 (m, 4H), 1.9–2.05 (m, 2H), 2.2–2.3 (m, 2H), 2.5 (br s, 4H), 2.82 (m, 2H), 3.62 (m, 2H), 4.05 (m, 2H), 4.22 (m, 2H), 4.75 (m, 1H), 6.05 (s, 2H), 6.55 (d, 1H), 6.71 (d, 1H), 6.83 (d, 1H), 6.97 (d, 1H), 8.52 (s, 1H), 9.27 (s, 1H); Mass Spectrum: M+H$^+$ 527 and 529.

[75] The reactants were 4-(6-chloro-2,3-methylenedioxyanilino)-7-hydroxy-5-tetrahydropyran-4-yloxyquinazoline and N-(tert-butoxycarbonyl)-4-(2-hydroxyethyl)piperidine (J. Med. Chem., 1994, 3, 2721) and the reaction mixture was stirred at ambient temperature for 2 hours. Thereafter, trifluoroacetic acid (1 ml) was added and the mixture was stirred at ambient temperature for 16 hours. The mixture was evaporated and the residue was triturated under a saturated methanolic ammonia solution (1 ml). Methylene chloride was added and the mixture was filtered. The filtrate was evaporated and the residue was purified by column chromatography on silica using a 97:3 mixture of methylene chloride and a saturated methanolic ammonia solution as eluent. The material so obtained was treated with a 6M solution of hydrogen chloride in diethyl ether. The precipitate was isolated, washed with diethyl ether and dried under vacuum to give the required product; NMR Spectrum: (DMSOd$_6$ and CF$_3$CO$_2$D) 1.35–1.5 (m, 2H), 1.75–1.95 (m, 5H), 2.0–2.15

(m, 4H), 2.8–2.95 (m, 2H), 3.3 (d, 2H), 3.55 (m, 2H), 3.92 (m, 2H), 4.25 (m, 2H), 5.15 (m, 1H), 6.14 (s, 2H), 6.94 (d, 1H), 7.04 (d, 1H), 7.13 (d, 1H), 7.15 (s, 1H), 8.84 (s, 1H); Mass Spectrum: M+H$^+$ 527 and 529.

[76] The reaction mixture was stirred at ambient temperature for 2 hours. The reaction product was treated with 6M hydrogen chloride in diethyl ether to give the dihydrochloride salt of the product, a portion of which was converted to the free base using an analogous procedure to that described in Example 3. The free base gave the following data: NMR Spectrum: (CDCl$_3$) 1.9–2.1 (m, 2H), 2.2–2.3 (m, 2H), 3.6–3.7 (m, 2H), 4.0–4.1 (m, 2H), 4.42 (m, 2H), 4.5 (m, 2H), 4.8 (m, 1H), 6.06 (s, 2H), 6.56 (d, 1H), 6.73 (d, 1H), 6.9 (m, 3H), 7.0 (d, 1H), 8.47 (d, 2H), 8.54 (s, 1H), 9.28 (s, 1H); Mass Spectrum: M+H$^+$ 537 and 539.

[77] The reaction mixture was stirred at ambient temperature for 2 hours. The product gave the following data: NMR Spectrum: (CDCl$_3$) 1.25–1.4 (m, 2H), 1.5 (s, 9H), 1.75–1.9 (m, 2H), 1.9–2.1 (m, 3H), 2.2–2.3 (m, 2H), 2.7–2.8 (m, 2H), 3.6–3.7 (m, 2H), 3.95 (d, 2H), 4.0–4.1 (m, 2H), 4.1–4.3 (m, 2H), 4.78 (m, 1H), 6.08 (s, 2H), 6.5 (d, 1H), 6.75 (d, 1H), 6.82 (d, 1H), 6.97 (d, 1H), 8.52 (s, 1H), 9.28 (s, 1H); Mass Spectrum: M+H$^+$ 613 and 615.

[78] The reaction mixture was stirred at ambient temperature for 1 hour. The reaction product gave the following data: NMR Spectrum: (CDCl$_3$) 1.6–1.75 (m, 4H), 1.75–1.9 (m, 6H), 2.0–2.2 (m, 4H), 2.55 (m, 4H), 2.65 (m, 2H), 4.15 (m, 2H), 5.0 (m, 1H), 6.02 (s, 2H), 6.5 (d, 1H), 6.65 (d, 1H), 6.8 (d, 1H), 6.9 (m, 1H), 8.12 (d, 1H), 8.58 (s, 1H), 8.8 (s, 1H); Mass Spectrum: M+H$^+$ 477.

[79] The reaction mixture was stirred at ambient temperature for 1 hour. The reaction product gave the following data: NMR Spectrum: (CDCl$_3$) 1.65–1.8 (m, 4H), 1.9 (m, 2H), 2.0–2.2 (m, 8H), 2.3 (s, 3H), 2.3–2.7 (m, 6H), 4.15 (t, 2H), 5.0 (m, 1H), 6.02 (s, 2H), 6.5 (s, 1H), 6.65 (d, 1H), 6.8 (d, 1H), 6.92 (m, 1H), 8.15 (d, 1H), 8.6 (s, 1H), 9.8 (s, 1H); Mass Spectrum: M+H$^+$ 506.

[80] The reaction mixture was stirred at ambient temperature for 1 hour. The reaction product gave the following data: NMR Spectrum: (CDCl$_3$) 1.65–1.8 (m, 2H), 1.8–1.95 (m, 2H), 1.95–2.2 (m, 4H), 2.3 (s, 3H), 2.4–2.6 (m, 4H), 2.6–2.8 (m, 4H), 2.9 (m, 2H), 4.2 (m, 2H), 5.0 (m, 1H), 6.0 (s, 2H), 6.52 (d, 1H), 6.65 (d, 1H), 6.8 (d, 1H), 6.9 (m, 1H), 8.15 (d, 1H), 8.6 (s, 1H), 9.8 (s, 1H); Mass Spectrum: M+H$^+$ 492.

[81] The reaction mixture was stirred at ambient temperature for 1 hour. The reaction product gave the following data: NMR Spectrum: (CDCl$_3$) 1.6–1.7 (m, 6H), 1.7–1.8 (m, 2H), 1.8–1.95 (m, 2H), 2.0–2.2 (m, 4H), 2.55 (br s, 4H), 2.82 (m, 2H), 4.22 (m, 2H), 5.0 (m, 1H), 6.02 (s, 2H), 6.52 (s, 1H), 6.65 (d, 1H), 6.8 (d, 1H), 6.9 (m, 1H), 8.15 (d, 1H), 8.6 (s, 1H), 9.8 (s, 1H); Mass Spectrum: M+H$^+$ 477.

[82] (2S)-1-(2-Hydroxyethyl)-2-(4-methylpiperazin-1-ylcarbonyl)pyrrolidine was used as a starting material and the reaction mixture was stirred at ambient temperature for 1 hour. The reaction product gave the following data: Mass Spectrum: M+H$^+$ 589.

[83] N-(tert-Butoxycarbonyl)piperidin-4-ylmethanol was used as a reactant. The reaction mixture was stirred at ambient temperature for 1 hour. Thereafter, a 6M solution of hydrogen chloride in diethyl ether (2 ml) was added and the reaction mixture was stirred at ambient temperature for 16 hours. The mixture was diluted with methylene chloride (10 ml) and a saturated methanolic ammonia solution (3 ml) was added. The mixture was filtered and the filtrate was evaporated to dryness. The residue was purified by column chromatography on silica using a 50:47:3 mixture of methylene chloride, ethyl acetate and a saturated methanolic ammonia solution as eluent. The reaction product gave the following data: NMR Spectrum: (CDCl$_3$) 1.25–1.42 (m, 2H), 1.6–1.7 (m, 4H), 1.8–2.0 (m, 3H), 2.0–2.2 (m, 4H), 2.7 (m, 2H), 3.15 (d, 2H), 3.95 (d, 2H), 5.05 (m, 1H), 6.02 (s, 2H), 6.5 (d, 1H), 6.65 (d, 1H), 6.8 (d, 1H), 6.9 (m, 1H), 8.15 (d, 1H), 8.6 (s, 1H), 8.8 (s, 1H); Mass Spectrum: M+H$^+$ 463.

[84] 1-(tert-Butoxycarbonyl)-4-(3-hydroxypropyl)piperazine was used as a reactant. The reaction mixture was stirred at ambient temperature for 1 hour. Thereafter, a 6M solution of hydrogen chloride in diethyl ether (2 ml) was added and the reaction mixture was stirred at ambient temperature for 16 hours. The mixture was diluted with methylene chloride (10 ml) and a saturated methanolic ammonia solution (3 ml) was added. The mixture was filtered and the filtrate was evaporated to dryness. The residue was purified by column chromatography on silica using a 50:47:3 mixture of methylene chloride, ethyl acetate and a saturated methanolic ammonia solution as eluent. The reaction product gave the following data: NMR Spectrum: (CDCl$_3$) 1.9–2.1 (m, 2H), 1.8–1.95 (m, 2H), 1.95–2.2 (m, 6H), 1.9 (br s, 4H), 1.95 (m, 2H), 2.9 (m, 4H), 4.15 (m, 2H), 5.0 (m, 1H), 6.02 (s, 2H), 6.5 (d, 1H), 6.65 (d, 1H), 6.8 (d, 1H), 6.9 (m, 1H), 8.12 (d, 1H), 8.6 (s, 1H), 8.8 (s, 1H); Mass Spectrum: M+H$^+$ 492.

EXAMPLE 15

Using an analogous procedure to that described in Example 5, the appropriate 4-chloroquinazoline was reacted with the appropriate aniline in the presence of hydrogen chloride to give the dihydrochloride salts of the compounds described in Table IV, a portion of each of which was converted to the free base.

TABLE IV

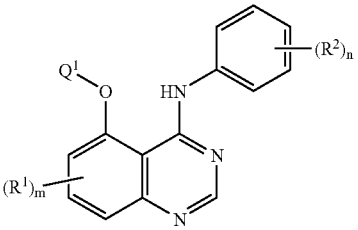

| No. and Note | $(R^1)_m$ | $Q^1$ | $(R^2)_n$ |
|---|---|---|---|
| [1] | 7-methoxy | piperidin-4-ylmethyl | 2-bromo-5-methoxy |
| [2] | 7-methoxy | piperidin-4-ylmethyl | 2-chloro-5-methoxy |
| [3] | 7-methoxy | piperidin-4-ylmethyl | 2,5-dimethoxy |
| [4] | 7-methoxy | piperidin-4-ylmethyl | 2,5-dichloro |
| [5] | 7-methoxy | piperidin-4-ylmethyl | 2,3-methylenedioxy |
| [6] | 7-methoxy | N-methylpiperidin-4-yl | 2,5-dichloro |
| [7] | 7-methoxy | N-methylpiperidin-4-yl | 2-bromo-5-chloro |
| [8] | 7-benzyloxy | piperidin-4-yl | 2-bromo-5-methoxy |
| [9] | 6-methoxy | N-methylpiperidin-4-yl | 2-chloro-5-methoxy |
| [10] | 7-[3-(4-methyl-piperazin-1-yl)propoxy] | 4-tetrahydropyranyl | 2,4-dichloro-5-methoxy |
| [11] | 6-[3-(4-methyl-piperazin-1-yl)propoxy] | 4-tetrahydropyranyl | 2-chloro-5-methoxy |
| [12] | 6-[3-(4-methyl-piperazin-1-yl)propoxy] | 4-tetrahydropyranyl | 2,5-dichloro |

TABLE IV-continued

[structure: quinazoline with (R¹)ₘ substituent, Q¹-O- at position 5, and 4-HN-phenyl-(R²)ₙ]

| No. and Note | (R¹)ₘ | Q¹ | (R²)ₙ |
|---|---|---|---|
| [13] | 6-[3-(4-methyl-piperazin-1-yl)propoxy] | 4-tetrahydropyranyl | 2-bromo-5-methoxy |
| [14] | 7-[3-(4-methyl-piperazin-1-yl)propoxy] | 4-tetrahydropyranyl | 4-chloro-2-fluoro-5-methoxy |
| [15] | 7-[3-(4-methyl-piperazin-1-yl)propoxy] | 4-tetrahydropyranyl | 4-bromo-2-fluoro |
| [16] | 7-[3-(4-methyl-piperazin-1-yl)propoxy] | 4-tetrahydropyranyl | 2-pyrrolidin-1-yl-5-methoxy |
| [17] | 7-[3-(4-methyl-piperazin-1-yl)propoxy] | 4-tetrahydropyranyl | 2,3-methylenedioxy |
| [18] | 7-benzyloxy | N-tert-butoxycarbonyl-piperidin-4-yl | 6-chloro-2,3-methylenedioxy |
| [19] | 7-hydroxy | cyclopentyl | 2,3-methylenedioxy |

Notes

[1] The reactants were 5-[N-(tert-butoxycarbonyl)piperidin-4-ylmethoxy]-4-chloro-7-methoxyquinazoline and 2-bromo-5-methoxyaniline hydrochloride and the reaction mixture was heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl₃) 1.3 (m, 2H), 1.9 (d, 2H), 2.3 (m, 1H), 2.68 (m, 2H), 3.12 (d, 2H), 3.85 (s, 3H), 3.95 (s, 3H), 4.15 (d, 2H), 6.52 (d, 1H), 6.62 (m, 1H), 6.88 (s, 1H), 7.5 (d, 1H), 8.22 (d, 1H), 8.6 (s, 1H), 8.9 (s, 1H); Mass Spectrum: M+H⁺ 473 and 475.

The 5-[N-(tert-butoxycarbonyl)piperidin-4-ylmethoxy]-4-chloro-7-methoxyquinazoline used as a starting material was prepared as follows:—

Diethyl azodicarboxylate (3.85 ml) was added dropwise to a stirred mixture of 5-hydroxy-7-methoxy-3-pivaloyloxymethyl-3,4-dihydroquinazolin-4-one (5 g), N-(tert-butoxycarbonyl)piperidin-4-ylmethanol (4.2 g), triphenylphosphine (6.4 g) and methylene chloride (50 ml) which had been cooled to 10° C. The mixture was stirred at ambient temperature for 1 hour. The resultant mixture was poured onto a column of silica and eluted with increasingly polar mixtures of methylene chloride and ethyl acetate. The product so obtained was dissolved in a saturated methanolic ammonia solution (250 ml) and solid sodium hydroxide (0.65 g) was added. The resultant mixture was stirred at ambient temperature for 30 minutes. The mixture was evaporated and the residue was purified by column chromatography on silica using increasingly polar mixtures of methylene chloride and ethyl acetate and then methylene chloride, ethyl acetate and methanol as eluent. The product so obtained was triturated under diethyl ether. The resultant solid was isolated, washed with diethyl ether and dried under vacuum. There was thus obtained 5-[N-(tert-butoxycarbonyl)piperidin-4-ylmethoxy]-7-methoxy-3,4-dihydroquinazolin-4-one (3.4 g); NMR Spectrum: (CDCl₃) 1.3–1.4 (m, 2H), 1.46 (s, 9H), 1.95 (d, 2H), 2.15 (m, 1H), 2.35 (t, 2H), 3.9 (s, 3H), 3.9 (m, 2H), 4.15 (br s, 2H), 6.45 (d, 1H), 6.75 (d, 1H), 7.93 (s, 1H), 11.0 (br s, 1H); Mass Spectrum: M+H⁺ 390.

A mixture of a portion (2.9 g) of the material so obtained, triphenyl phosphine (5.3 g), carbon tetrachloride (3 ml) and 1,2-dichloroethane (50 ml) was stirred and heated to 70° C. for 2.5 hours. The mixture was poured onto silica and eluted with increasingly polar mixtures of methylene chloride and ethyl acetate. The material so obtained was triturated under diethyl ether. The resultant precipitate was isolated, washed with diethyl ether and dried. There was thus obtained 5-[N-(tert-butoxycarbonyl)piperidin-4-ylmethoxy]-4-chloro-7-methoxyquinazoline (1.9 g); NMR Spectrum: (CDCl₃) 1.35–1.5 (m, 2H), 1.45 (s, 9H), 1.92 (d, 2H), 2.15 (m, 1H), 2.8 (t, 2H), 3.95 (d, 2H), 3.97 (s, 3H), 4.2 (br s, 2H), 6.6 (d, 1H), 6.98 (d, 1H), 8.82 (s, 1H).

[2] The reactants were 5-[N-(tert-butoxycarbonyl)piperidin-4-ylmethoxy]-4-chloro-7-methoxyquinazoline and 2-chloro-5-methoxyaniline and the reaction mixture was heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl₃) 1.3–1.4 (m, 2H), 1.92 (d, 2H), 2.3 (m, 1H), 2.7 (t, 2H), 3.2 (d, 2H), 3.85 (s, 3H), 3.95 (s, 3H), 4.15 (d, 2H), 6.52 (s, 1H), 6.65 (m, 1H), 6.9 (s, 1H), 7.32 (d, 1H), 8.4 (s, 1H), 8.62 (s, 1H), 10.2 (s, 1H); Mass Spectrum: M+H⁺ 429 and 431.

[3] The reactants were 5-[N-(tert-butoxycarbonyl)piperidin-4-ylmethoxy]4-chloro-7-methoxyquinazoline and 2,5-dimethoxyaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution The organic layer was washed with brine, dried over magnesium sulphate and evaporated. The residue was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl₃) 1.3–1.5 (m, 2H), 1.95 (d, 2H), 2.25 (m, 1H), 2.7 (m, 2H), 3.2 (d, 2H), 3.84 (s, 3H), 3.92 (s, 3H), 3.93 (s, 3H), 4.1 (d, 2H), 6.5 (s, 1H), 6.6 (m, 1H), 6.9 (m, 2H), 8.52 (d, 1H), 8.6 (s, 1H), 10.15 (s, 1H); Mass Spectrum: M+H⁺ 425.

[4] The reactants were 5-[N-(tert-butoxycarbonyl)piperidin-4-ylmethoxy]-4-chloro-7-methoxyquinazoline and 2,5-dichloroaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution. The organic layer was washed with brine, dried over magnesium sulphate and evaporated. The residue was purified by column chromatography on silica using a 9:10:1 mixture of methylene chloride, ethyl acetate and methanol as eluent. The material so obtained was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl$_3$) 1.25–1.4 (m, 2H), 1.9 (d, 2H), 2.25 (m, 1H), 2.65 (m, 2H), 3.15 (d, 2H), 3.95 (s, 3H), 4.12 (d, 2H), 6.55 (d, 1H), 6.9 (d, 1H), 7.05 (m, 1H), 7.35 (d, 1H), 8.6 (s, 1H), 8.87 (d, 1H), 10.09 (br s, 1H); Mass Spectrum: M+H$^+$ 433 and 435.

[5] The reactants were 5-[N-(tert-butoxycarbonyl)piperidin-4-ylmethoxy]-4-chloro-7-methoxyquinazoline and 2,3-methylenedioxyaniline and the reaction mixture was heated to 80° C. for 2 hours. The reaction mixture was evaporated and the residue was dissolved in methylene chloride (1 ml). Trifluoroacetic acid (1 ml) was added and the mixture was stirred at ambient temperature for 15 minutes. The resultant mixture was evaporated and the residue was partitioned between ethyl acetate and 1N aqueous sodium hydroxide solution. The organic layer was washed with brine, dried over magnesium sulphate and evaporated. The residue was dissolved in isopropanol (1 ml) and 6M hydrogen chloride in isopropanol (0.1 ml) was added. The resultant precipitate was isolated, washed with isopropanol and with diethyl ether and dried under vacuum. There was thus obtained the required product as the dihydrochloride salt, a portion of which was converted to the free base which gave the following data: NMR Spectrum: (CDCl$_3$) 1.25–1.4 (m, 2H), 1.85 (d, 2H), 2.2 (m, 1H), 2.65 m, 2H), 3.2 (d, 2H), 3.9 (s, 3H), 4.02 (d, 2H), 6.0 (s, 2H), 6.48 (d, 1H), 6.62 (d, 1H), 6.85 (d, 1H), 6.9 (m, 1H), 8.07 (d, 1H), 8.58 (s, 1H), 9.6 (s, 1H); Mass Spectrum: M+H$^+$ 409.

[6] The free base gave the following data: NMR Spectrum: (CDCl$_3$) 1.95–2.1 (m, 2H), 2.15–2.35 (m, 4H), 2.3 (s, 3H), 2.85 (m, 2H), 3.92 (s, 3H), 4.5 (m, 1H), 6.55 (d, 1H), 6.85 (d, 1H), 7.03 (m, 1H), 7.3 (d, 1H), 8.6 (s, 1H), 8.85 (s, 1H); Mass Spectrum: M+H$^+$ 433 and 435.

[7] The free base gave the following data: NMR Spectrum: (CDCl$_3$) 2.0–2.15 (m, 2H), 2.15–2.3 (m, 4H), 2.28 (s, 3H), 2.85 (m, 2H), 3.92 (s, 3H), 4.5 (m, 1H), 6.5 (s, 1H), 6.85 (s, 1H), 7.0 (m, 1H), 7.5 (d, 1H), 8.35 (s, 1H), 8.55 (s, 1H), 9.7 (s, 1H); Mass Spectrum: M+H$^+$ 477, 479 and 481.

[8] The reactants were 7-benzyloxy-5-[N-(tert-butoxycarbonyl)piperidin-4-yloxy]-4-chloroquinazoline and 2-bromo-5-methoxyaniline hydrochloride and the reaction mixture as heated to 80° C. for 2 hours. A second portion of 6M hydrogen chloride in isopropanol (0.06 ml) was added and the reaction mixture was heated to 80° C. for a further 4 hours. The reaction product was obtained as the dihydrochloride salt, a portion of which was converted to the free base which gave the following data: NMR Spectrum: (CDCl$_3$) 1.95–2.1 (m, 2H), 2.25 (d, 2H), 2.8 (m, 2H), 3.22 (m, 2H), 3.78 (s, 3H), 4.6 (m, 1H), 5.12 (s, 3H), 6.58 (m, 2H), 6.9 (d, 1H), 7.25–7.5 (m, 5H), 7.89 (d, 1H), 8.5 (s, 1H), 9.6 (s, 1H); Mass Spectrum: M+H$^+$ 535 and 537.

The 7-benzyloxy-5-[N-(tert-butoxycarbonyl)piperidin-4-yloxy]-4-chloroquinazoline used as a starting material was prepared as follows:—

A mixture of 5,7-dibenzyloxy-3,4-dihydroquinazolin-4-one (2 g), magnesium bromide (1 g) and pyridine (10 ml) was stirred and heated to 120° C. for 20 minutes. The mixture was evaporated and the residue was dissolved in a mixture of water (20 ml) and glacial acetic acid (4 ml) and stirred for 10 minutes. The resultant precipitate was isolated, washed with water and dried under vacuum over phosphorus pentoxide at 50° C. There was thus obtained 7-benzyloxy-5-hydroxy-3,4-dihydroquinazolin-4-one (1.5 g); NMR Spectrum: (DMSOd$_6$) 5.22 (s, 2H), 6.5 (d, 1H), 6.7 (d, 1H), 7.3–7.5 (m, 5H), 8.05 (s, 1H); Mass Spectrum: M+H$^+$ 269.5.

The material so obtained was added portionwise to a stirred suspension of sodium hydride (60% dispersion in mineral oil, 0.46 g; washed with pentane) in DMF (15 ml) which was cooled to 0° C. The mixture was stirred at ambient temperature for 30 minutes. The resultant mixture was cooled at 0° C., chloromethyl pivalate (1.2 ml) was added and the mixture was stirred at ambient temperature for 1 hour. The mixture was poured into water (70 ml) containing acetic acid (4 ml) and the resultant precipitate was isolated and dried under vacuum. The material so obtained was dissolved in methylene chloride and the organic solution was dried over magnesium sulphate and evaporated. The residue was triturated under pentane and the resultant solid was isolated and dried under vacuum. There was thus obtained 7-benzyloxy-5-hydroxy-3-pivaloyloxymethyl-3,4-dihydroquinazolin-4-one (1.95 g); NMR Spectrum: (CDCl$_3$) 1.2 (s, 9H), 5.12 (s, 2H), 5.88 (s, 2H), 6.58 (d, 1H), 6.72 (d, 1H), 7.3–7.5 (m, 5H), 8.15 (s, 1H), 11.32 (s, 1H); Mass Spectrum: M+H$^+$ 383.

The material so obtained was reacted with N-(tert-butoxycarbonyl)-4-hydroxypiperidine using an analogous procedure to that described in the first paragraph of the portion of Note [1] immediately above that is concerned with the preparation of starting materials. There was thus obtained 7-benzyloxy-5-[N-(tert-butoxycarbonyl)piperidin-4-yloxy]-3,4-dihydroquinazolin-4-one (1.4 g); NMR Spectrum: (CDCl$_3$) 1.5 (s, 9H), 1.82 (m, 4H), 3.52 (m, 2H), 3.7 (m, 2H), 4.65 (m, 1H), 5.2 (s, 2H), 6.6 (d, 1H), 6.9 (d, 1H), 7.3–7.5 (m, 5H), 7.92 (s, 1H), 10.56 (br s, 1H); Mass Spectrum: M+H$^+$ 452.6.

A mixture of the material so obtained, triphenylphosphine (1.66 g), carbon tetrachloride (0.92 ml) and 1,2-dichloroethane (40 ml) was stirred and heated to 70° C. for 1.5 hours. The mixture was evaporated and the residue was purified by column chromatography on silica using a 9:1 mixture of methylene chloride and ethyl acetate as eluent. There was thus obtained 7-benzyloxy-5-[N-(tert-butoxycarbonyl)piperidin-4-yloxy]-4-chloroquinazoline (1.1 g); NMR Spectrum: (CDCl$_3$) 1.5 (s, 9H), 1.98 (m, 4H), 3.5–3.7 (m, 4H), 4.75 (m, 1H), 5.2 (s, 2H), 6.7 (d, 1H), 7.08 (d, 1H), 7.32–7.52 (m, 5H), 8.82 (s, 1H); Mass Spectrum: M+H$^+$ 470.

[9] The free base gave the following data: NMR Spectrum: (CDCl$_3$) 1.95–2.15 (m, 6H), 2.25 (s, 3H), 2.85 (br s, 2H), 3.87 (s, 3H), 4.02 (s, 3H), 4.45 (m, 1H), 6.65 (m, 1H), 7.35 (d, 1H), 7.55 (d, 1H), 7.7 (d, 1H), 8.5 (d, 1H), 8.6 (s, 1H), 10.45 (br s, 1H); Mass Spectrum: M+H$^+$ 429 and 431.

The 4-chloro-6-methoxy-5-(N-methylpiperidin-4-yloxy)quinazoline used as a starting material was prepared as follows:—

A solution of ferrous sulphate heptahydrate (99 g) in water (410 ml) that had been heated to 70° C. was added to a mixture of 2-benzyloxy-3-methoxy-6-nitrobenzoic acid (*Bull. Soc. Chim. France,* 1965, 1417; 15.5 g) and concentrated aqueous ammonium hydroxide (370 ml) which was heated to 70° C. The resultant mixture was heated to reflux for 30 minutes. The mixture was filtered and the basicity of the filtrate was adjusted to pH8 by the addition of 2N aqueous hydrochloric acid and then the filtrate was acidified to pH4 by the addition of 1M aqueous citric acid solution. The mixture was partitioned between ethyl acetate and water. The organic layer was washed with water and with brine, dried over magnesium sulphate and evaporated to give 6-amino-2-benzyloxy-3-methoxybenzoic acid (12.15 g); NMR Spectrum: ($CDCl_3$) 3.9 (s, 3H), 5.22 (s, 2H), 6.5 (d, 1H), 7.05 (d, 1H), 7.35–7.55 (m, 5H): Mass Spectrum: $M+H^+$ 274.

A mixture of the material so obtained, triazine (3.6 g), piperidine (3 ml) and ethanol (275 ml) was stirred and heated to reflux for 16 hours. The mixture was cooled to ambient temperature. The precipitate was isolated, washed with ethanol and with diethyl ether and dried under vacuum to give 5-benzyloxy-6-methoxy-3,4-dihydroquinazolinone (10.3 g); NMR Spectrum: ($CDCl_3$) 3.9 (s, 3H), 5.15 (s, 2H), 7.2–7.45 (m, 4H), 7.5 (d, 1H), 7.62 (d, 2H), 7.8 (s, 1H), 11.1 (br s, 1H); Mass Spectrum: $M+H^+$ 283.

A solution of a portion (5 g) of the material so obtained in trifluoroacetic acid (50 ml) was stirred at ambient temperature for 30 minutes. The mixture was evaporated and the residue was dissolved in water. The solution was basified to pH8.5 by the portionwise addition of sodium bicarbonate. The resultant precipitate was isolated, washed with water and dried under vacuum at 50° C. over phosphorus pentoxide. There was thus obtained 5-hydroxy-6-methoxy-3,4-dihydroquinazolin-4-one (3.4 g); NMR Spectrum: ($DMSOd_6$) 3.85 (s, 3H), 7.12 (d, 1H), 7.52 (d, 1H), 7.98 (s, 1H), 11.89 (s, 1H); Mass Spectrum: $M+H^+$ 193.

The material so obtained was added to a stirred suspension of sodium hydride (1.59 g of a 60% dispersion in mineral oil which was washed with pentane) in DMF (18 ml) which was cooled to 0° C. The mixture was stirred at ambient temperature for 30 minutes. The mixture was cooled to 0° C. and chloromethyl pivalate (4.1 ml) was added dropwise. The mixture was stirred at ambient temperature for 1.5 hours. The resultant precipitate was isolated, washed with water and dried overnight under vacuum. The solid was dissolved in methylene chloride and the solution was dried over magnesium sulphate. The solution was evaporated and the residue was triturated under pentane. The resultant solid was isolated and dried under vacuum. There was thus obtained 5-hydroxy-6-methoxy-3-pivaloyloxymethyl-3,4-dihydroquinazolin-4-one (4.6 g); NMR Spectrum: ($CDCl_3$) 1.25 (s, 9H), 4.0 (s, 3H), 5.9 (s, 2H), 7.2 (d, 1H), 7.38 (d, 1H), 8.08 (s, 1H), 11.5 (s, 1H); Mass Spectrum: $M+H^+$ 307.

A solution of di-tert-butyl azodicarboxylate (1.75 g) in methylene chloride (3 ml) was added to a stirred mixture of 5-hydroxy-6-methoxy-3-pivaloyloxymethyl-3,4-dihydroquinazolin-4-one (1.55 g), triphenylphosphine (1.99 g), 4-hydroxy-1-methylpiperidine (0.75 g) and methylene chloride (12 ml) which had been cooled to 5° C. The mixture was stirred at ambient temperature for 1 hour. The mixture was evaporated and the residue was purified by column chromatography on silica using a 9:10:1 mixture of methylene chloride, ethyl acetate and a saturated methanolic ammonia solution as eluent. The material so obtained was stirred in a saturated methanolic ammonia solution for 48 hours. The mixture was evaporated and the residue was triturated under diethyl ether. The resultant solid was washed with diethyl ether and dried under vacuum to give 6-methoxy-5-(N-methylpiperidin-4-yloxy)-3,4-dihydroquinazolin-4-one (0.92 g); NMR Spectrum: ($DMSOd_6$) 1.7–1.9 (m, 4H), 1.95 (t, 2H), 2.15 (s, 3H), 2.7 (m, 2H), 3.85 (s, 3H), 4.08 (m, 1H), 7.4 (d, 1H), 7.6 (d, 1H), 7.85 (s, 1H), 11.8 (br s, 1H); Mass Spectrum: $M+H^+$ 290.

A mixture of a portion (0.3 g) of the material so obtained, triphenylphosphine (0.54 g), carbon tetrachloride (0.3 ml) and 1,2-dichloroethane (13 ml) was stirred and heated to 70° C. for 2.5 hours. The mixture was evaporated and the residue was purified by column chromatography on silica using a 10:9:1 mixture of ethyl acetate, methylene chloride and a saturated methanolic ammonia solution as eluent. There was thus obtained 4-chloro-6-methoxy-5-(N-methylpiperidin-4-yloxy)quinazoline (0.22 g); NMR Spectrum: ($CDCl_3$) 1.82–2.1 (m, 6H), 2.25 (s, 3H), 2.85 (m, 2H), 4.0 (s, 3H), 4.4 (m, 1H), 7.7 (d, 1H), 7.8 (d, 1H), 8.82 (s, 1H).

[10] The free base gave the following data: NMR Spectrum: ($CDCl_3$) 2.02 (m, 4H), 2.2 (d, 2H), 2.4 (s, 3H), 2.5–2.8 (m, 10H), 3.55 (t, 2H), 3.95 (s, 3H), 4.05 (m, 2H), 4.1 (t, 2H), 4.7 (m, 1H), 6.55 (d, 1H), 6.82 (d, 1H), 7.4 (s, 1H), 8.35 (s, 1H), 8.55 (s, 1H), 9.82 (s, 1H); Mass Spectrum: $M+H^+$ 576 and 578.

The 4-chloro-7-[3-(4-methylpiperazin-1-yl)propoxy]-5-tetrahydropyran-4-yloxyquinazoline used as a starting material was prepared as follows:—

5-Hydroxy-7-methoxy-3-pivaloyloxymethyl-3,4-dihydroquinazolin-4-one (0.61 g) was reacted with 4-hydroxytetrahydropyran (0.23 ml) using an analogous procedure to that described in the first paragraph of the portion of Note [1] immediately above that is concerned with the preparation of starting materials. There was thus obtained 7-methoxy-5-tetrahydropyran-4-yloxy-3,4-dihydroquinazolin-4-one (0.3 g); NMR Spectrum: ($DMSOd_6$) 1.6–1.75 (m, 2H), 1.9–2.0 (m, 2H), 3.52 (m, 2H), 3.85 (s, 3H), 3.95 (m, 2H), 4.75 (m, 1H), 6.65 (d, 1H), 6.7 (m, 1H), 7.92 (s, 1H).

A mixture of 7-methoxy-5-tetrahydropyran-4-yloxy-3,4-dihydroquinazolin-4-one (4 g), thiophenol (2.2 ml), potassium carbonate (3 g) and N-methylpyrrolidin-2-one (40 ml) was stirred and heated to 200° C. for 25 minutes. The mixture was evaporated and the residue was acidified by the addition of 12N aqueous hydrochloric acid (2 ml). Methylene chloride (5 ml) was added. The resultant precipitate was isolated, washed in turn with water and diethyl ether and dried under vacuum to give 7-hydroxy-5-tetrahydropyran-4-yloxy-3,4-dihydroquinazolin-4-one (3.4 g); NMR Spectrum: ($DMSOd_6$) 1.6–1.75 (m, 2H), 1.9–2.0 (m, 2H), 3.45–3.6 (m, 2H), 3.8 (m, 3H), 4.65 (m, 1H), 6.5 (d, 1H), 6.65 (m, 1H), 7.92 (s, 1H), 10.4 (s, 1H), 11.5 (s, 1H); Mass Spectrum: $M+H^+$ 263.

A mixture of 7-hydroxy-5-tetrahydropyran-4-yloxy-3,4-dihydroquiazolin-4-one (3.2 g), pyridine (3.2 ml) and acetic anhydride (20 ml) was stirred and heated to 100° C. for 2 hours. The mixture was evaporated. The residue was dissolved in a mixture of methanol and water and stirred at ambient temperature for 2 hours. The mixture was evaporated to remove the methanol and the residual aqueous layer was freeze-dried. The residue was purified by column chromatography on silica using a 19:1 mixture of methylene chloride and methanol as eluent. There was thus obtained 7-acetoxy-5-tetrahydropyran-4-yloxy-3,4-dihydroquinazolin-4-one (3.1 g); NMR Spectrum: ($DMSOd_6$) 1.7 (m, 2H), 1.92 (m, 2H), 2.3 (s, 3H), 3.5 (m, 2H), 3.9 (m, 2H), 4.72 (m, 1H), 6.95 (d, 2H), 7.98 (s, 1H), 10.9 (br s, 1H); Mass Spectrum: $M+H^+$ 305.

A mixture of a portion (1.2 g) of the material so obtained, phosphoryl chloride (0.41 ml), di-isopropylethylamine (1.74 ml) and 1,2-dichloroethane (30 ml) was stirred and heated to 80° C. for 2.5 hours. The mixture was evaporated. The material so obtained was dissolved in a saturated methanolic ammonia solution and stirred for 2.5 hours. The mixture was evaporated and the residue was purified by column chromatography on silica using a 97:3 mixture of methylene chloride and methanol as eluent. There was thus obtained 4-chloro-7-hydroxy-5-tetrahydropyran-4-yloxyquinazoline (0.5 g); NMR Spectrum: (DMSOd$_6$) 1.8 (m, 2H), 2.08 (m, 2H), 3.6 (m, 2H), 3.9 (m, 2H), 4.9 (m, 1H), 6.9 (d, 2H), 8.76 (s, 1H); Mass Spectrum: M+H$^+$ 281 and 283.

Di-tert-butyl azodicarboxylate (0.65 g) was added to a stirred mixture of 4-chloro-7-hydroxy-5-tetrahydropyran-4-yloxyquinazoline (0.5 g), triphenylphosphine (0.75 g), 1-(3-hydroxypropyl)-4-methylpiperazine (0.34 g) and methylene chloride (20 ml) and the mixture was stirred at ambient temperature for 1.5 hours. The mixture was poured onto a column of silica and eluted initially with a 49:1 mixture of methylene chloride and methanol followed by a 97:3 mixture of methylene chloride and a saturated methanolic ammonia solution. There was thus obtained 4-chloro-7-[3-(4-methylpiperazin-4-yl)propoxy]-5-tetrahydropyran-4-yloxyquinazoline (0.54 g); NMR Spectrum: (CDCl$_3$) 1.9–2.2 (m, 6H), 2.25 (s, 3H), 2.32–2.68 (m, 10H), 3.68 (m, 2H), 4.05 (m, 2H), 4.15 (t, 2H), 4.72 (m, 1H), 6.58 (d, 1H), 6.92 (d, 1H), 8.8 (s, 1H); Mass Spectrum: M+H$^+$ 421 and 423.

[11] The free base gave the following data: NMR Spectrum: (CDCl$_3$) 1.95–2.2 (m, 6H), 2.5 (s, 3H), 2.6–2.9 (m, 10H), 3.35 (m, 2H), 3.9 (s, 3H), 4.02 (m, 2H), 4.25 (t, 2H), 4.6 (m, 1H), 6.65 (m, 1H), 7.35 (d, 1H), 7.55 (d, 1H), 7.68 (d, 1H), 8.55 (s, 1H), 8.65 (s, 1H), 10.45 (s, 1H); Mass Spectrum: M+H$^+$ 542 and 544.

The 4-chloro-6-[3-(4-methylpiperazin-1-yl)propoxy]-5-tetrahydropyran-4-yloxyquinazoline used as a starting material was prepared as follows:—

Di-tert-butyl azodicarboxylate (3.6 g) was added portionwise to a stirred mixture of 5-hydroxy-6-methoxy-3-pivaloyloxymethyl-3,4-dihydroquinazolin-4-one (3 g), triphenylphosphine (4.1 g), 4-hydroxytetrahydropyran (1.2 ml) and methylene chloride (50 ml) and the mixture was stirred at ambient temperature for 30 minutes. The mixture was evaporated and the residue was stirred in a saturated methanolic ammonia solution for 7 hours. The mixture was evaporated and the residue was purified by column chromatography on silica using a 9:10:1 mixture of methylene chloride, ethyl acetate and a saturated methanolic ammonia solution as eluent. There was thus obtained 6-methoxy-5-tetrahydropyran-4-yloxy-3,4-dihydroquinazolin-4-one (2.3 g); NMR Spectrum: DMSOd$_6$) 1.65–1.8 (m, 2H), 1.8–1.9 (m, 2H), 3.35 (m, 2H), 3.9 (s, 3H), 3.92 (m, 2H), 4.3 (m, 1H), 7.42 (d, 1H), 7.6 (d, 1H), 7.9 (s, 1H), 11.8 (br s, 1H); Mass Spectrum: M+H$^+$ 277.

A mixture of a portion (1.9 g) of the material so obtained, thiophenol (1 ml), potassium carbonate (1.4 g) and N-methylpyrrolid-2-one (20 ml) was stirred and heated to 200° C. for 30 minutes. The mixture was evaporated. The residue was dissolved in a mixture of methylene chloride (25 ml), methanol (1 ml) and acetic acid (2 ml) and the solution was poured onto a column of silica and was eluted with a 9:10:1 mixture of methylene chloride, ethyl acetate and methanol. The material so obtained was triturated under diethyl ether and the resultant solid was washed with diethyl ether and dried under vacuum. There was thus obtained 6-hydroxy-5-tetrahydropyran-4-yloxy-3,4-dihydroquinazolin-4one (1.65 g); NMR Spectrum: (DMSOd$_6$) 1.7–1.9 (m, 4H), 3.2–3.4 (m, 2H), 3.92 (m, 2H), 4.3 (m, 1H), 7.3 (d, 1H), 7.35 (d, 1H), 7.85 (s, 1H), 9.55 (br s, 1H), 11.75 (br s, 1H); Mass Spectrum: M+H$^+$ 263.

A mixture of a portion (0.7 g) of the material so obtained, piperidine (0.7 ml) and acetic anhydride (10 ml) was heated to reflux for 1 hour. The mixture was evaporated. The residue was dissolved in a 1:1 mixture of methanol and water (18 ml) and stirred at ambient temperature for 1 hour. The resultant precipitate was isolated, washed with water and dried under vacuum to give 6-acetoxy-5-tetrahydropyran-4-yloxy-3,4-dihydroquinazolin-4-one (0.54 g); NMR Spectrum: (CDCl$_3$) 1.8–2.0 (m, 2H), 2.0–2.1 (m, 2H), 2.4 (s, 3H), 3.45 (m, 2H), 4.02 (m, 2H), 4.4 (m, 1H), 7.5–7.6 (m, 2H), 8.0 (s, 1H), 10.5 (br s, 1H); Mass Spectrum: M+H$^+$ 305.

A mixture of the material so obtained, triphenylphosphine (0.93 g), carbon tetrachloride (0.515 ml) and 1,2-dichloroethane (24 ml) was stirred and heated to 70° C. for 2.5 hours. The mixture was evaporated and the residue was dissolved in a saturated methanolic ammonia solution (20 ml) and stirred at ambient temperature for 1 hour. The mixture was filtered and the filtrate was poured onto a column of silica and eluted in turn with methylene chloride, a 1:1 mixture of methylene chloride and ethyl acetate and a 24:25:1 mixture of methylene chloride, ethyl acetate and methanol. There was thus obtained 4-chloro-6-hydroxy-5-tetrahydropyran-4-yloxyquinazoline.

Using an analogous procedure to that described in the last paragraph of the portion of Note [10] immediately above that is concerned with the preparation of starting materials, 4-chloro-6-hydroxy-5-tetrahydropyran-4-yloxyquinazoline (1.12 g) was reacted with 1-(3-hydroxypropyl)-4-methylpiperazine to give 4-chloro-6-[3-(4-methylpiperazin-1-yl)propoxy]-5-tetrahydropyran-4-yloxyquinazoline (0.56 g); NMR Spectrum: (CDCl$_3$) 1.85–2.2 (m, 6H), 2.32 (s, 3H), 2.35–2.7 (m, 10H), 3.42 (m, 2H), 4.05 (m, 2H), 4.25 (m, 2H), 4.65 (m, 1H), 7.75 (d, 1H), 7.85 (d, 1H), 8.9 (s, 1H); Mass Spectrum: M+H$^+$ 421 and 423.

[12] The free base gave the following data: NMR Spectrum: (CDCl$_3$) 1.82–2.18 (m, 6H), 2.35 (s, 3H), 2.4–2.7 (m, 10H), 3.35 (m, 2H), 4.02 (d, 2H), 4.25 (t, 2H), 4.65 (m, 1H), 7.08 (m, 1H), 7.4 (d, 1H), 7.6 (d, 1H), 7.7 (d, 1H), 8.68 (s, 1H), 9.0 (s, 1H), 10.5 (s, 1H); Mass Spectrum: M+H$^+$ 546 and 548.

[13] The free base gave the following data: NMR Spectrum: (CDCl$_3$) 1.9–2.15 (m, 6H), 2.35 (s, 3H), 2.4–2.75 (m, 10H), 3.35 (m, 2H), 3.89 (s, 3H), 4.02 (m, 2H), 4.25 (t, 2H), 4.65 (m, 1H), 6.65 (m, 1H), 7.5 (d, 1H), 7.55 (d, 1H), 7.65 (d, 1H), 8.35 (d, 1H), 8.6 (s, 1H), 10.28 (s, 1H); Mass Spectrum: M+H$^+$ 586 and 588.

[14] 4-Chloro-2-fluoro-5-methoxyaniline is disclosed in International Patent Application WO 86/02642. The free base of the product gave the following data: NMR Spectrum: (CDCl$_3$) 1.9–2.1 (m, 4H), 2.22 (d, 2H), 2.27 (s, 3H), 2.32–2.62 (m, 10H), 3.55 (m, 2H), 3.94 (s, 3H), 4.08 (m, 2H), 4.15 (t, 2H), 4.7 (m, 1H), 6.52 (s, 1H), 6.82 (s, 1H), 7.15 (d, 1H), 8.6 (s, 1H), 8.8 (d, 1H), 10.1 (s, 1H); Mass Spectrum: M+H$^+$ 560 and 562.

[15] The free base gave the following data: NMR Spectrum: (CDCl$_3$) 1.9–2.1 (m, 4H), 2.22 (d, 2H), 2.28 (s, 3H), 2.35–2.7 (m, 10H), 3.6 (m, 2H), 4.08 (m, 2H), 4.12 (t, 2H), 4.7 (m, 1H), 6.5 (d, 1H), 6.82 (d, 1H), 7.25–7.35 (m, 2H), 8.57 (s, 1H), 8.77 (m, 1H), 10.02 (s, 1H); Mass Spectrum: M+H$^+$ 574 and 576.

[16] 2-Pyrrolidin-1-yl-5-methoxyaniline is disclosed in International Patent Application WO 85/01939. The free base of the product gave the following data: NMR Spectrum: (CDCl$_3$) 1.8–2.0 (m, 8H), 2.2 (d, 2H), 2.29 (s, 3H), 2.4–2.7 (m, 12H), 3.1 (t, 2H), 3.6 (m, 2H), 3.82 (s, 3H), 4.02 (m, 2H), 4.15 (t, 2H), 4.7 (m, 1H), 6.5 (d, 1H), 6.65 (m, 1H), 6.85 (d, 1H), 7.05 (d, 1H), 7.9 (d, 1H), 8.55 (s, 1H), 9.82 (s, 1H); Mass Spectrum: M+H$^+$ 577.

[17] The free base gave the following data: NMR Spectrum: (CDCl$_3$) 1.95 (m, 4H), 2.18 (d, 2H), 2.25 (s, 3H), 2.3–2.6 (m, 10H), 3.55 (t, 2H), 4.02 (m, 2H), 4.1 (t, 2H), 4.68 (m, 1H), 5.95 (s, 2H), 6.45 (s, 1H), 6.6 (d, 1H), 6.78 (s, 1H), 6.85 (m, 1H), 8.02 (d, 1H), 8.5 (s, 1H), 9.68 (s, 1H); Mass Spectrum: M+H$^+$ 522.

[18] The reactants were 7-benzyloxy-5-[-N-(tert-butoxycarbonyl)piperidin-4-yloxy]-4-chloroquinazoline (1.92 g) and 6-chloro-2,3-methylenedioxyaniline (0.771 g) and the reaction mixture was heated to reflux for 1.5 hours. The reaction mixture was cooled to ambient temperature and the precipitate was isolated, washed in turn with isopropanol, ethyl acetate and diethyl ether and dried under vacuum. The material so obtained was dissolved in a 2M solution of hydrogen chloride in diethyl ether and stirred at ambient temperature for 2 hours. The resultant solid was isolated, washed with diethyl ether and dried under vacuum. There was thus obtained the required compound as a dihydrochloride salt (2.4 g) which gave the following data: NMR Spectrum: (DMSOd$_6$) 1.4 (s, 9H), 1.8–1.95 (m, 2H), 2.0–2.1 (m, 2H), 2.9–3.1 (m, 2H), 3.4 (m, 2H), 5.08 (m, 1H), 5.35 (s, 2H), 6.12 (s, 2H), 7.0–7.05 (m, 2H), 7.12 (d, 1H), 7.22 (d, 1H), 7.3–7.6 (m, 5H), 8.75 (s, 1H), 10.1 (s, 1H); Mass Spectrum: M+H$^+$ 605 and 607.

[19] The reactants were 7-acetoxy-4-chloro-5-cyclopentyloxyquinazoline and 2,3-methylenedioxyaniline. The precipitate from the reaction mixture was isolated, dissolved in a saturated methanolic ammonia solution (20 ml) and stirred at ambient temperature for 2 hours. The mixture was evaporated and the residue was triturated under water. The solid so obtained was washed with water and dried overnight under vacuum. The product gave the following data: NMR Spectrum: (DMSOd$_6$) 1.6–1.7 (m, 2H), 1.7–1.9 (m, 2H), 1.9–2.15 (m, 4H), 5.1 (br s, 1H), 6.12 (s, 2H), 6.63 (s, 1H), 6.65 (s, 1H), 6.72 (d, 1H), 6.9 (m, 1H), 8.15 (d, 1H), 8.42 (s, 1H), 9.8 (s, 1H), 10.58 (s, 1H); Mass Spectrum: M+H$^+$ 366.

EXAMPLE 16

4-(2-iodoanilino)-7-methoxy-5-(N-methylpiperidin-4-yloxy)quinazoline dihydrochloride A mixture of 4-chloro-7-methoxy-5-(N-methylpiperidin-4-yloxy)quinazoline (0.08 g), 2-iodoaniline (0.068 g), 6M hydrogen chloride in isopropanol (0.05 ml) and isopropanol (3 ml) was stirred and heated to 80° C. for 2 hours. The mixture was cooled to 0° C. and diethyl ether was added. The resultant precipitate was isolated, washed with diethyl ether and dried under vacuum. The solid so obtained was dissolved in methylene chloride and the solution was washed with a saturated aqueous sodium bicarbonate solution. The organic solution was poured onto a column of silica and eluted with a 9:10:1 mixture of methylene chloride, ethyl acetate and methanol followed by a 9:10:1 mixture of methylene chloride, ethyl acetate and a saturated methanolic ammonia solution. The material so obtained was dissolved in diethyl ether and 6M hydrogen chloride in diethyl ether (0.1 ml) was added. The resultant precipitate was isolated, washed with diethyl ether and dried under vacuum. There was thus obtained the title compound (0.081 g), as the dihydrochloride salt, a portion of which was converted to the free base using an analogous procedure to that described in Example 3. The free base gave the following data: NMR Spectrum: (CDCl$_3$) 2.1–2.4 (m, 6H), 2.3 (s, 3H), 2.8 (m, 2H), 3.92 (s, 3H), 4.6 (m, 1H), 6.55 (s, 1H), 6.85 (s, 1H), 6.95 (t, 1H), 7.42 (t, 1H), 7.9 (d, 2H), 8.5 (s, 1H), 9.5 (s, 1H); Mass Spectrum: M+H$^+$ 491.

EXAMPLE 17

Using an analogous procedure to that described in Example 16, the appropriate 4-chloroquinazoline was reacted with the appropriate aniline in the presence of hydrogen chloride to give the dihydrochloride salt of each of the compounds described in Table V, a portion of each of which was converted to the free base using an analogous procedure to that described in Example 3.

TABLE V

| No. and Note | (R$^1$)$_m$ | Q$^1$ | (R$^2$)$_n$ |
|---|---|---|---|
| [1] | 7-methoxy | N-methylpiperidin-4-yl | 2,4-dichloro |
| [2] | 7-methoxy | N-methylpiperidin-4-yl | 4-bromo-2-chloro |
| [3] | 7-methoxy | N-methylpiperidin-4-yl | 2-chloro-4-cyano |
| [4] | 7-methoxy | N-methylpiperidin-4-yl | 2-bromo-4-fluoro |
| [5] | 7-methoxy | N-methylpiperidin-4-yl | 2-bromo-4-chloro |
| [6] | 7-methoxy | N-methylpiperidin-4-yl | 2,4-dibromo |
| [7] | 7-methoxy | N-methylpiperidin-4-yl | 2-bromo |
| [8] | 7-methoxy | N-methylpiperidin-4-yl | 2-bromo-4-methyl |
| [9] | 7-methoxy | N-methylpiperidin-4-yl | 2-fluoro-4-chloro |
| [10] | 7-methoxy | N-methylpiperidin-4-yl | 2-fluoro-4-bromo |
| [11] | 7-methoxy | N-methylpiperidin-4-yl | 2-fluoro-3-chloro |
| [12] | 7-methoxy | N-methylpiperidin-4-yl | 2,4-dimethoxy |
| [13] | 7-methoxy | N-methylpiperidin-4-yl | 2,3-dimethoxy |
| [14] | 7-methoxy | N-methylpiperidin-4-yl | 2-methoxy-5-methyl |
| [15] | 7-methoxy | N-methylpiperidin-4-yl | 2-methoxy-5-chloro |
| [16] | 7-methoxy | N-methylpiperidin-4-yl | 2-methoxy |
| [17] | 7-methoxy | N-methylpiperidin-4-yl | 2-ethoxy |
| [18] | 7-methoxy | N-methylpiperidin-4-yl | 2-methylthio |
| [19] | 7-methoxy | N-methylpiperidin-4-yl | 2-acetyl-4-chloro |
| [20] | 7-methoxy | N-methylpiperidin-4-yl | 2-methyl-5-chloro |
| [21] | 7-methoxy | N-methylpiperidin-4-yl | 2-methyl-3-chloro |
| [22] | 7-methoxy | N-methylpiperidin-4-yl | 2-methyl-4-chloro |
| [23] | 7-methoxy | N-methylpiperidin-4-yl | 2-methyl-5-methoxy |
| [24] | 7-methoxy | N-methylpiperidin-4-yl | 2-isopropenyl |
| [25] | 7-methoxy | N-methylpiperidin-4-yl | 2-(1-pyrrolyl) |
| [26] | 7-methoxy | N-methylpiperidin-4-yl | 2-piperidino |
| [27] | 7-(2-pyrrolidin-1-ylethoxy) | cyclopentyl | 2-bromo-5-methoxy |
| [28] | 7-(2-pyrrolidin-1-ylethoxy) | cyclopentyl | 5-methoxy-2-pyrrolidin-1-yl |
| [29] | 7-(2-pyrrolidin-1-ylethoxy) | cyclopentyl | 5-methoxy-2-morpholinomethyl |
| [30] | 7-(2-pyrrolidin-1-ylethoxy) | cyclopentyl | 6-chloro-2,3-methylenedioxy |
| [31] | 7-methoxy | piperidin-4-ylmethyl | 6-chloro-2,3-methylenedioxy |
| [32] | 7-(2-pyrrolidin-1-ylethoxy) | 4-tetrahydropyranyl | 6-chloro-2,3-methylenedioxy |
| [33] | 7-(3-pyrrolidin-1-ylpropoxy) | 4-tetrahydropyranyl | 6-chloro-2,3-methylenedioxy |
| [34] | 7-benzyloxy | 4-tetrahydropyranyl | 6-chloro-2,3-methylenedioxy |

Notes

[1] The free base gave the following data: NMR Spectrum: (CDCl$_3$) 2.0–2.1 (m, 2H), 2.15–2.4 (m, 4H), 2.3 (s, 3H), 2.75–2.9 (m, 2H), 3.89 (s, 3H), 4.55 (m, 1H), 6.5 (s, 1H), 6.82 (s, 1H), 7.28 (m, 1H), 7.42 (d, 1H), 8.35 (d, 1H), 8.5 (s, 1H), 9.8 (s, 1H); Mass Spectrum: M+H$^+$ 433 and 435.

[2] The free base gave the following data: NMR Spectrum: (CDCl$_3$) 1.95–2.1 (m, 2H), 2.15–2.35 (m, 4H), 2.3 (s, 3H), 2.7–2.9 (m, 2H), 3.9 (s, 3H), 4.42–4.6 (m, 1H), 6.55 (d, 1H), 6.82 (d, 1H), 7.4 (m, 1H), 7.55 (d, 1H), 8.3 (d, 1H), 8.51 (s, 1H), 9.8 (s, 1H); Mass Spectrum: M+H$^+$ 477 and 479.

[3] The free base gave the following data: NMR Spectrum: (CDCl$_3$) 1.95–2.1 (m, 2H), 2.1–2.25 (m, 4H), 2.28 (s, 3H), 2.85 (br d, 2H), 3.9 (s, 3H), 4.5 (m, 1H), 6.55 (d, 1H), 6.85 (d, 1H), 7.58 (m, 1H), 7.7 (s, 1H), 8.6 (s, 1H), 8.82 (d, 1H); Mass Spectrum: M+H$^+$ 424 and 426.

[4] The free base gave the following data: NMR Spectrum: (CDCl$_3$) 2.0–2.1 (m, 2H), 2.15–2.4 (m, 4H), 2.28 (s, 3H), 2.8 (m, 2H), 3.9 (s, 3H), 4.55 (m, 1H), 6.5 (s, 1H), 6.8 (s, 1H), 7.1 (m, 1H), 7.35 (m, 1H), 8.05 (m, 1H), 8.48 (s, 1H), 9.55 (br s, 1H); Mass Spectrum: M+H$^+$ 461 and 463.

[5] The free base gave the following data: NMR Spectrum: (CDCl$_3$) 2.0–2.15 (m, 2H), 2.2–2.4 (m, 4H), 2.3 (s, 3H), 2.8 (m, 2H), 3.9 (s, 3H), 4.5–4.6 (m, 1H), 6.5. (d, 1H), 6.8 (d, 1H), 7.3 (m, 1H), 7.6 (d, 1H), 8.15 (d, 1H), 8.5 (s, 1H), 9.6 (br s, 1H); Mass Spectrum: M+H$^+$ 477 and 479.

[6] The free base gave the following data: NMR Spectrum: (CDCl$_3$) 2.0–2.2 (m, 2H), 2.2–2.35 (m, 4H), 2.25 (s, 3H), 2.7–2.9 (m, 2H), 3.9 (s, 3H), 4.5–4.6 (m, 2H), 6.55 (s, 1H), 6.85 (s, 1H), 7.15 (m, 1H), 7.45 (d, 1H), 8.45 (s, 1H), 8.55 (s, 1H), 9.68 (br s, 1H); Mass Spectrum: +H$^+$ 521, 523 and 525.

[7] The free base gave the following data: NMR Spectrum: (CDCl$_3$) 2.0–2.15 (m, 2H), 2.15–2.38 (m, 4H), 2.3 (s, 3H), 2.8 (m, 2H), 3.9 (s, 3H), 4.55 (m, 1H), 6.5 (d, 1H), 6.82 (d, 1H), 7.02 (m, 1H), 7.35 (m, 1H), 7.36 (d, 1H), 8.15 (d, 1H), 8.5 (s, 1H), 9.65 (s, 1H); Mass Spectrum: M+H$^+$ 443 and 445.

[8] The free base gave the following data: NMR Spectrum: (CDCl$_3$) 2.0–2.15 (m, 2H), 2.2–2.4 (m, 4H), 2.28 (s, 3H), 2.31 (s, 3H), 2.8 (m, 2H), 3.89 (s, 3H), 4.55 (m, 1H), 6.5 (s, 1H), 6.8 (s, 1H), 7.15 (m, 1H), 7.42 (s, 1H), 7.95 (d, 1H), 8.48 (s, 1H), 9.55 (s, 1H); Mass Spectrum: M+H$^+$ 457 and 449.

[9] The free base gave the following data: NMR Spectrum: (CDCl$_3$) 1.95–2.1 (m, 2H), 2.15–2.3 (m, 4H), 2.3 (s, 3H), 2.85 (d, 1H), 3.9 (s, 3H), 4.5 (m, 1H), 6.5 (d, 1H), 6.82 (d, 1H), 7.1–7.2 (m, 2H), 8.58 (s, 1H), 8.75 (m, 1H); Mass Spectrum: M+H$^+$ 417 and 419.

[10] The free base gave the following data: NMR Spectrum: (CDCl$_3$) 1.95–2.1 (m, 2H), 2.15–2.35 (m, 4H), 2.32 (s, 3H), 2.9 (m, 2H), 3.89 (s, 3H), 4.55 (m, 1H), 6.5 (s, 1H), 6.85 (d, 1H), 7.25–7.35 (m, 2H), 8.58 (s, 1H), 8.75 (m, 1H); Mass Spectrum: M+H$^+$ 461 and 463.

[11] The free base gave the following data: NMR Spectrum: (CDCl$_3$) 1.95–2.1 (m, 2H), 2.12–2.28 (m, 4H), 2.28 (s, 3H), 2.85 (m, 2H), 3.86 (s, 3H), 4.5 (m, 1H), 6.5 (s, 1H), 6.8 (s, 1H), 7.0–7.1 (m, 2H), 8.55 (s, 1H), 8.68 (m, 1H); Mass Spectrum: M+H$^+$ 417 and 419.

[12] The free base gave the following data: NMR Spectrum: (CDCl$_3$) 1.95–2.1 (m, 2H), 2.1–2.22 (m, 4H), 2.25 (s, 3H), 2.82 (m, 2H), 3.77 (s, 3H), 3.83 (s, 3H), 3.85 (s, 3H), 4.48 (m, 1H), 6.45 (d, 1H), 6.52 (m, 1H), 6.8 (m, 2H), 8.45 (d, 1H), 8.52 (s, 1H); Mass Spectrum: M+H$^+$ 425.

[13] The free base gave the following data: NMR Spectrum: (CDCl$_3$) 1.9–2.1 (m, 2H), 2.1–2.25 (m, 4H), 2.28 (s, 3H), 2.7–2.9 (m, 2H), 3.8 (s, 3H), 3.85 (s, 3H), 3.9 (s, 3H), 4.5 (m, 1H), 6.45 (d, 1H), 6.5–6.6 (m, 2H), 6.8 (d, 1H), 8.4 (d, 1H), 8.5 (s, 1H), 9.85 (s, 1H); Mass Spectrum: M+H$^+$ 425.

[14] The free base gave the following data: NMR Spectrum: (CDCl$_3$) 1.95–2.1 (m, 2H), 2.15–2.3 (m, 4H), 2.27 (s, 3H), 2.3 (s, 3H), 2.85 (m, 2H), 3.87 (s, 3H), 3.89 (s, 3H), 4.5 (m, 1H), 6.5 (s, 1H), 6.8–6.9 (m, 3H), 8.45 (s, 1H), 8.55 (s, 1H); Mass Spectrum: M+H$^+$ 409.

[15] The free base gave the following data: NMR Spectrum: (CDCl$_3$) 1.95–2.1 (m, 2H), 2.15–2.3 (m, 4H), 2.3 (s, 3H), 2.85 (d, 2H), 3.89 (s, 3H), 3.9 (s, 3H), 4.5 (m, 1H), 6.5 (d, 1H), 6.8 (m, 2H), 7.0 (m, 1H), 8.6 (s, 1H), 8.85 (d, 1H); Mass Spectrum: M+H$^+$ 429 and 431.

[16] The free base gave the following data: NMR Spectrum: (CDCl$_3$) 2.0–2.1 (m, 2H), 2.15–2.3 (m, 4H), 2.29 (s, 3H), 2.85 (m, 2H), 3.88 (s, 3H), 3.9 (s, 3H), 4.52 (m, 1H), 6.5 (s, 1H), 6.8 (s, 1H), 6.95 (m, 1H), 7.02 (m, 2H), 8.55 (s, 1H), 8.65 (m, 1H); Mass Spectrum: M+H$^+$ 395.

[17] The free base gave the following data: NMR Spectrum: (CDCl$_3$) 1.4 (t, 3H), 1.9–2.1 (m, 2H), 2.1–2.3 (m, 4H), 2.24 (s, 3H), 2.7–2.9 (m, 2H), 3.9 (s, 3H), 4.2 (q, 2H), 4.4–4.55 (m, 1H), 6.5 (d, 1H), 6.8 (d, 1H), 6.9 (m, 1H), 6.95–7.1 (m, 2H), 8.38 (m, 1H), 8.5 (s, 1H), 9.85 (br s, 1H); Mass Spectrum: M+H$^+$ 409.

[18] The free base gave the following data: NMR Spectrum: (CDCl$_3$) 2.05–2.35 (m, 6H), 2.27 (s, 3H), 2.38 (s, 3H), 2.7–2.9. (m, 2H), 3.9 (s, 3H), 4.5–4.6 (m, 1H), 6.5 (d, 1H), 6.8 (d, 1H), 7.15 (m, 1H), 7.26 (m, 1H), 7.38 (m, 1H), 7.98 (d, 1H), 8.5 (s, 1H), 9.7 (br s, 1H); Mass Spectrum: M+H$^+$ 411.

[19] The free base gave the following data: NMR Spectrum: (CDCl$_3$) 2.15–2.35 (m, 6H), 2.27 (s, 3H), 2.57 (s, 3H), 2.82 (m, 2H), 3.89 (s, 3H), 4.55 (m, 1H), 6.52 (s, 1H), 6.8 (s, 1H), 7.48 (m, 1H), 7.75 (d, 1H), 8.3 (d, 1H), 8.5 (s, 1H); Mass Spectrum: M+H$^+$ 441and 443.

[20] The free base gave the following data: NMR Spectrum: (CDCl$_3$) 1.9–2.0 (m, 2H), 2.15–2.4 (m, 4H), 2.26 (s, 3H), 2.28 (s, 3H), 2.75 (br s, 2H), 3.9 (s, 3H), 4.55 (br s, 1H), 6.5 (d, 1H), 6.82 (s, 1H), 7.1 (m, 1H), 7.18 (d, 1H), 7.8 (s, 1H), 8.48 (s, 1H), 9.1 (s, 1H); Mass Spectrum: M+H$^+$ 413 and 415.

[21] The free base gave the following data: NMR Spectrum: (CDCl$_3$) 1.9–2.0 (m, 2H), 2.15–2.25 (m, 2H), 2.28 (s, 3H), 2.25–2.38 (m, 2H), 2.35 (s, 3H), 2.7 (br s, 2H), 3.9 (s, 3H), 4.6 (m, 1H), 6.5 (d, 1H), 6.8 (d, 1H), 7.18 (m, 1H), 7.28 (m, 1H), 7.5 (d, 1H), 8.45 (s, 1H), 9.35 (s, 1H); Mass Spectrum: M+H$^+$ 413 and 415.

[22] The free base gave the following data: NMR Spectrum: (CDCl$_3$) 1.9–2.0 (m, 2H), 2.2–2.4 (m, 4H), 2.27 (s, 3H), 2.65–2.8 (m, 2H), 3.89 (s, 3H), 4.55 (m, 1H), 6.5 (d, 1H), 6.8 (d, 1H), 7.15–7.25 (m, 2H), 7.6 (d, 1H), 8.45 (s, 1H), 9.25 (s, 1H); Mass Spectrum: M+H$^+$ 413 and 415.

[23] The free base gave the following data: NMR Spectrum: (CDCl$_3$) 1.9–2.0 (m, 2H), 2.15–2.22 (m, 4H), 2.17 (s, 3H), 2.22 (s, 3H), 2.72 (m, 2H), 3.78 (s, 3H), 3.89 (s, 3H), 4.55

(m, 1H), 6.5 (d, 1H), 6.7 (m, 1H), 6.8 (d, 1H), 7.15 (d, 1H), 7.3 (d, 1H), 8.45 (s, 1H), 9.3 (s, 1H); Mass Spectrum: M+H+ 409.

[24] The free base gave the following data: NMR Spectrum: (CDCl₃) 1.85–2.0 (m, 2H), 2.05 (s, 3H), 2.1–2.3 (m, 4H), 2.28 (s, 3H), 2.72 (m, 2H), 3.92 (s, 3H), 4.5 (m, 1H), 5.1 (s, 1H), 5.25 (s, 1H), 6.5 (s, 1H), 6.82 (s, 1H), 7.2 (t, 1H), 7.3 (d, 1H), 7.35 (t, 1H), 7.85 (d, 1H), 8.5 (s, 1H), 9.35 (s, 1H).

[25] The free base gave the following data: NMR Spectrum: (CDCl₃) 1.45–1.6 (m, 2H), 1.8–1.95 (m, 2H), 2.05–2.2 (m, 2H), 2.2 (s, 3H), 2.4–2.55 (br s, 2H), 3.95 (s, 3H), 4.25–4.35 (m, 2H), 6.25 (d, 2H), 6.4 (s, 1H), 6.8 (s, 1H), 6.85 (d, 2H), 7.2 (m, 1H), 7.3 (m, 1H), 7.35 (m, 1H), 8.05 (d, 1H), 8.5 (s, 1H), 9.25 (br s, 1H); Mass Spectrum: M+H+ 430.

[26] The free base gave the following data: NMR Spectrum: (CDCl₃) 1.6 (m, 2H), 1.7 (m, 4H), 2.1 (m, 2H), 2.2 (s, 3H), 2.2 (m, 2H), 2.3 (m, 2H), 2.7 (m, 2H), 2.9 (m, 4H), 3.95 (s, 3H), 4.6 (m, 1H), 6.1 (d, 1H), 6.9 (d, 1H), 7.1–7.2 (m, 3H), 8.02 (m, 1H), 8.52 (s, 1H), 9.72 (s, 1H); Mass Spectrum: M+H+ 448.

[27] The free base gave the following data: NMR Spectrum: (CDCl₃) 1.6–1.78 (m, 4H), 1.85 (m, 4H), 2.1 (m, 4H), 2.65 (m, 4H), 2.98 (m, 2H), 3.82 (s, 3H), 4.25 (m, 2H), 5.02 (m, 1H), 6.4 (d, 1H), 6.45 (m, 1H), 6.82 (d, 1H), 7.5 (d, 1H), 7.85 (d, 1H), 8.52 (s, 1H), 9.62 (s, 1H); Mass Spectrum: M+H+ 527 and 529.

The 4-chloro-5-cyclopentyloxy-7-(2-pyrrolidin-1-ylethoxy)quinazoline used as a starting material was prepared as follows:—

A mixture of 7-acetoxy-4-chloro-5-cyclopentyloxyquinazoline (1 g), a saturated methanolic ammonia solution (10 ml) and methanol (10 ml) was stirred at ambient temperature for 30 minutes. The mixture was evaporated and the residue was triturated under water. The resultant solid was isolated, washed with water and dried under vacuum to give 4-chloro-5-cyclopentyloxy-7-hydroxyquinazoline (0.67 g); NMR Spectrum: (DMSOd₆) 1.6–1.75 (m, 2H), 1.75–1.85 (m, 2H), 1.85–2.05 (m, 4H), 5.0 (m, 1H), 6.72 (d, 1H), 6.8. (d, 1H), 8.7 (s, 1H); Mass Spectrum: M+H+ 265.

Using an analogous procedure to that described in Example 1, 4-chloro-5-cyclopentyloxy-7-hydroquinazoline (0.84 g) was reacted with 2-pyrrolidin-1-ylethanol (0.448 ml). There was thus obtained 4-chloro-5-cyclopentyloxy-7-(2-pyrrolidin-1-ylethoxy)quinazoline (0.82 g); NMR Spectrum: (CDCl₃) 1.65–2.12 (m, 12H), 2.65 (m, 4H), 2.97 (m, 2H), 4.25 (m, 2H), 4.9 (m, 1H), 6.65 (d, 1H), 6.92 (d, 1H), 8.8 (s, 1H); Mass Spectrum: M+H+ 362 and 364.

[28] The reaction product was purified by column chromatography on reversed phase silica using decreasingly polar mixtures of water, acetonitrile and a saturated methanolic ammonia solution as eluent. The free base gave the following data: NMR Spectrum: (CDCl₃) 1.6–1.75 (m, 2H), 1.8 (m, 2H), 1.8–1.95 (m, 8H), 2.05 (m, 4H), 2.65 (br s, 1H), 2.95 (m, 2H), 3.05 (br s, 4H), 3.8 (s, 3H), 4.25 (m, 2H), 4.95 (m, 1H), 6.55 (s, 1H), 6.65 (m, 1H), 6.8 (s, 1H), 7.1 (d, 1H), 7.75 (d, 1H), 8.5 (s, 1H), 9.7 (s, 1H); Mass Spectrum: M+H+ 518.

[29] The free base gave the following data: NMR Spectrum: (CDCl₃) 1.65–1.9 (m, 8H), 1.9–2.15 (m, 4H), 2.35 (m, 4H), 2.65 (m, 4H), 2.98 (m, 2H), 3.42 (s, 2H), 3.55 (m, 4H), 3.82 (s, 3H), 4.25 (m, 2H), 5.0 (m, 1H), 6.6 (s, 1H), 6.8 (m, 2H), 7.1 (s, 1H), 7.38 (d, 1H), 8.42 (s, 1H), 9.3 (s, 1H); Mass Spectrum: M+H+ 548.

The 2-morpholinomethyl-5-methoxyaniline used as a starting material was prepared as follows:—

A mixture of 4-methoxy-2-nitrotoluene (20 g), N-bromosuccinimide (23 g), a catalytic amount of benzoyl peroxide and carbon tetrachloride (100 ml) was heated to reflux for 8 hours. The mixture was diluted with methylene chloride (200 ml) and washed in turn with a 2N aqueous sodium hydroxide solution and brine. The organic layer was dried over magnesium sulphate and evaporated. There was thus obtained 4-methoxy-2-nitrobenzyl bromide (29 g) which was used without further purification.

Morpholine (2.8 ml) was added to a stirred solution of 4-methoxy-2-nitrobenzyl bromide (4 g) in diethyl ether (150 ml) which was cooled to 0° C. The resultant mixture was stirred at ambient temperature for 16 hours. The mixture was filtered and the filtrate was evaporated. There was thus obtained 2-morpholinomethyl-5-methoxy-1-nitrobenzene (4 g); NMR Spectrum: (CDCl₃) 2.4 (m, 4H), 3.68 (m, 4H), 3.7 (s, 2H), 3.88 (s, 3H), 7.1 (m, 1H), 7.35 (d, 1H), 7.45 (d, 1H).

A mixture of the material so obtained, 10% palladium on charcoal catalyst (0.2 g) and methanol (100 ml) was stirred under an atmosphere pressure of hydrogen for 1 hour. The mixture was filtered and the filtrate was evaporated. The residue was purified by column chromatography on silica using a 49:1 mixture of methylene chloride and methanol as eluent. There was thus obtained 2-morpholinomethyl-5-methoxyaniline (1.9 g); NMR Spectrum: (CDCl₃) 2.4 (br s, 4H), 3.48 (s, 2H), 3.7 (m, 4H), 3.78 (s, 3H), 4.75 (br s, 2H), 6.2 (s, 1H), 6.25 (d, 1H), 6.9 (d, 1H).

[30] The free base gave the following data: NMR Spectrum: (CDCl₃) 1.7–1.8 (m, 2H), 1.9 (br s, 4H), 2.1 (m, 2H), 2.65 (br s, 4H), 3.0 (br s, 2H), 4.25 (m, 2H), 5.0 (m, 1H), 6.05 (s, 1H), 6.55 (d, 1H), 6.7 (d, 1H), 6.8 (d, 1H), 6.98 (d, 1H), 8.5 (s, 1H), 9.3 (s, 1H); Mass Spectrum: M+H+ 497 and 499.

The 6-chloro-2,3-methylenedioxyaniline used as a starting material was prepared as follows:—

Sulphuryl chloride (72.5 ml) was added dropwise during 1.7 hours to a stirred mixture of benzodioxole (100 g), aluminium trichloride (0.43 g) and diphenyl sulphide (0.55 ml). Once the reaction started with the evolution of sulphur dioxide, the reaction mixture was cooled in a water bath to a temperature of approximately 22° C. After completion of the addition. the reaction mixture was stirred at ambient temperature for 45 minutes. The reaction mixture was degassed under vacuum and filtered and the filtrate was distilled at atmospheric pressure using a Vigreux distillation column. There was thus obtained 5-chloro-1,3-benzodioxole; b.p. 185–187° C.; NMR Spectrum: (CDCl₃) 6.0 (s, 2H); 6.7 (d, 1H); 6.75–6.9 (m, 2H).

A mixture of diisopropylamine (4.92 ml) and THF (100 ml) was cooled to −78° C. and n-butyllithium (2.5 M in hexane, 14 ml) was added dropwise. The mixture was stirred at −78° C. for 15 minutes. 5-Chloro-1,3-benzodioxole (3.73 ml) was added dropwise and the reaction mixture was stirred at −78° C. for 30 minutes. Dry carbon dioxide gas was bubbled into the reaction mixture for 30 minutes. The resultant reaction mixture was allowed to warm to ambient temperature and was stirred for a further hour. Water was added and the organic solvent was evaporated. The residue was acidified to pH2 by the addition of 2N aqueous hydrochloric acid solution. The resultant solid was isolated and washed in turn with water and diethyl ether. There was thus obtained 5-chloro-1,3-benzodioxole-4-carboxylic acid (5.4 g); NMR Spectrum: (DMSOd₆) 6.15 (s, 2H), 7.0 (m, 2H), 13.7 (br s, 1H).

A portion (1 g) of the material so obtained was dissolved in 1,4-dioxane (15 ml) and anhydrous tert-butanol (4 ml), diphenylphosphoryl azide (1.12 ml) and triethylamine (0.73 ml) were added in turn. The resultant mixture was stirred and heated to 100° C. for 4 hours. The mixture was evaporated and the residue was partitioned between ethyl acetate and a 5% aqueous citric acid solution. The organic phase was washed in turn with water, a saturated aqueous sodium bicarbonate solution and brine, dried over magnesium sulphate and evaporated. The residue was purified by column chromatography on silica using a 9:1 mixture of petroleum ether (b.p. 40–60° C.) and ethyl acetate as eluent. There was thus obtained tert-butyl 5-chloro-1,3-benzodioxol-4-ylcarbamate (1.1 g); NMR Spectrum: (DMSOd$_6$) 1.45 (s, 9H), 6.1 (s, 2H), 6.85 (d, 1H), 6.95 (d, 1H), 8.75 (s, 1H).

A mixture of the material so obtained (1.1 g), trifluoroacetic acid (6 ml) and methylene chloride (20 ml) was stirred at ambient temperature for 3 hours. The solvent was evaporated and the residue was partitioned between ethyl acetate and a saturated aqueous sodium bicarbonate solution. The organic phase was washed with brine, dried over magnesium sulphate and evaporated. There was thus obtained 6-chloro-2,3-methylenedioxyaniline (0.642 g); NMR Spectrum: (DMSOd$_6$) 5.15 (s, 2H), 6.0 (s, 2H), 6.25 (d, 1H), 6.75 (d, 1H).

[31] The reactants were 5-[N-(tert-butoxycarbonyl)piperidin-1-ylmethoxy]-4-chloro-7-methoxyquinazoline (0.4 g) and 6-chloro-(2,3-methylenedioxy)aniline (0.089 g). After basification and purification by column chromatography, the reaction product was suspended in a 2M solution of hydrogen chloride in diethyl ether (15 ml) and stirred at ambient temperature for 3 hours. The resultant solid was isolated, washed with diethyl ether and dried under vacuum. The dihydrochloride salt so obtained gave the following data: NMR Spectrum: (DMSOd$_6$) 1.4–1.6 (m, 2H), 1.95 (d, 2H), 2.3–2.4 (m, 1H), 2.8–2.9 (m, 2H), 3.3 (m, 2H), 3.97 (s, 3H), 4.4 (d, 2H), 6.12 (s, 2H), 6.95 (d, 1H), 7.03 (d, 1H), 7.07 (d, 1H), 7.11 (d, 1H), 8.74 (s, 1H), 8.8–9.0 (m, 2H), 10.25 (br s, 1H); Mass Spectrum: M+H$^+$ 443 and 445.

[32] The free base gave the following data: NMR Spectrum: (CDCl$_3$) 1.8–1.9 (m, 4H), 1.9–2.05 (m, 2H), 2.2–2.3 (m, 2H), 2.6–2.7 (m, 4H), 2.95 (m, 2H), 3.6–3.7 (m, 2H), 4.05 (m, 2H), 4.25 (m, 2H), 4.75 (m, 1H), 6.05 (s, 2H), 6.6 (d, 1H), 6.71 (d, 1H), 6.84 (d, 1H), 6.97 (d, 1H), 8.5 (s, 1H), 9.3 (s, 1H); Mass Spectrum: M+H$^+$ 513 and 515.

The 4-chloro-7-(2-pyrrolidin-1-ylethoxy)-5-tetrahydropyran-4-yloxyquinazoline used as a starting material is described in Note [6] in Example 19.

[33] The free base gave the following data: NMR Spectrum: (CDCl$_3$) 1.75–1.9 (m, 4H), 1.9–2.15 (m, 4H), 2.2–2.3 (m, 2H), 2.55 (br s, 4H), 2.65 (m, 2H), 3.65 (m, 2H), 4.02 (m, 2H), 4.15 (m, 2H), 4.8 (m, 1H), 6.05 (s, 2H), 6.52 (d, 1H), 6.72 (d, 1H), 6.82 (d, 1H), 6.97 (d, 1H), 8.5 (s, 1H), 9.26 (s, 1H); Mass Spectrum: M+H$^+$ 527 and 529.

The 4-chloro-7-(3-pyrrolidin-1-ylpropoxy)-5-tetrahydropyran-4-yloxyquinazoline used as a starting material was prepared as follows:—

Using an analogous procedure to that described in Note [6] below Example 19, 4-chloro-7-hydroxy-5-tetrahydropyran-4-yloxyquinazoline (0.112 g) was reacted with 1-(3-hydroxypropyl)pyrrolidine (0.062 g) to give 4-chloro-7-(3-pyrrolidin-1-ylpropoxy)-5-tetrahydropyran-4-yloxyquinazoline (0.125 g); NMR Spectrum: (CDCl$_3$) 1.7–1.9 (m, 4H), 1.95–2.2 (m, 6H), 2.55 (br s, 4H), 2.65 (m, 2H), 3.65–3.75 (m, 2H), 4.0–4.1 (m, 2H), 4.2 (m, 2H), 4.75 (m, 1H), 6.6 (d, 1H), 6.95 (d, 1H), 8.8 (s, 1H); Mass Spectrum: M+H$^+$ 392 and 394.

[34] The free base gave the following data: NMR Spectrum: (CDCl$_3$) 2.1–2.2 (m, 2H), 2.15–2.3 (m, 2H), 3.52–3.65 (m, 2H), 3.95–4.08 (m, 2H), 4.75 (m, 1H), 5.18 (s, 2H), 6.05 (s, 2H), 6.6 (d, 1H), 6.75 (d, 1H), 6.9–7.0 (m, 2H), 7.3–7.5 (m, 5H), 8.55 (s, 1H), 9.34 (s, 1H); Mass Spectrum: M+H$^+$ 506 and 508.

The 7-benzyloxy-4-chloro-5-tetrahydropyran-4-yloxyquinazoline used as a starting material was prepared as follows:—

Di-tert-butyl azodicarboxylate (16.3 g) was added portionwise to a stirred mixture of 7-benzyloxy-5-hydroxy-3-pivaloyloxymethyl-3,4-dihydroquinazolin-4-one (17 g), 4-hydroxytetrahydropyran (5.4 g) and methylene chloride (200 ml) that had been cooled to 5° C. The mixture was allowed to warm to ambient temperature and was stirred for 2 hours. The mixture was evaporated and the residue was dissolved in a saturated methanolic ammonia solution. The resultant mixture was stirred at ambient temperature for 16 hours. The mixture was evaporated and the residue was triturated under diethyl ether. The solid so obtained was dried under vacuum to give 7-benzyloxy-5-tetrahydropyran-4-yloxy-3,4-dihydroquinazolin-4-one (12.5 g); NMR Spectrum: (DMSOd$_6$) 1.6–1.7 (m, 2H), 1.85–1.95 (m, 2H), 3.5 (m, 2H), 3.9 (m, 2H), 4.75 (m, 1H), 5.22 (s, 2H), 6.7 (d, 1H), 6.8 (d, 1H), 7.3–7.5 (m, 5H), 7.9 (s, 1H); Mass Spectrum: M+H$^+$ 353.

A mixture of 7-benzyloxy-5-tetrahydropyran-4-yloxy-3,4-dihydroquinazolin-4-one (9 g), phosphoryl chloride (2.8 ml), di-isopropylethylamine (11.4 ml) and 1,2-dichloroethane (130 ml) was stirred and heated to 80° C. for 3 hours. The mixture was evaporated to give 7-benzyloxy-4-chloro-5-tetrahydropyran-4-yloxyquinazoline which was used without further purification.

EXAMPLE 18

4-(2,6-dichloroanilino)-7-methoxy-5-(N-methylpiperidin-4-yloxy)quinazoline dihydrochloride Sodium hexamethyldisilazane (1M solution in THF; 0.65 ml) was added to a solution of 2,6-dichloroaniline (0.105 g) in DMF (3 ml) and the mixture was stirred at ambient temperature for 5 minutes. A solution of 4-chloro-7-methoxy-5-(N-methylpiperidin-4-yloxy)quinazoline (0.1 g) in DMF (8 ml) was added and the mixture was stirred at ambient temperature for 1 hour. A saturated aqueous ammonium chloride solution was added and the mixture was extracted with ethyl acetate. The organic layer was evaporated and the residue was purified by column chromatography on silica using as eluent a 9:10:1 mixture of methylene chloride, ethyl acetate and methanol followed by a 9:10:1 mixture of methylene chloride, ethyl acetate and a saturated methanolic ammonia solution. The material so obtained was triturated under diethyl ether. The solid was isolated and dried under vacuum. The material so obtained was dissolved in a mixture of isopropanol (2 ml) and diethyl ether (2 ml) and 6M hydrogen chloride in isopropanol (0.11 ml) was added. The mixture was evaporated and the residual solid was dried under vacuum. There was thus obtained the title compound as a dihydrochloride salt (0.06 g), a portion of which was converted into the free base using an analogous procedure to that described in Example 3. The free base gave the following characterising data: NMR Spectrum: (CDCl$_3$) 2.0–2.1 (m, 2H), 2.15–2.25 (m, 2H), 2.3 (s, 3H), 2.4 (m, 2H), 2.68 (m, 2H), 3.95 (s, 3H), 4.65 (m, 1H), 6.55 (d, 1H), 6.85 (d, 1H), 7.22 (m, 1H), 7.45 (d, 2H), 8.5 (s, 1, 9.3 (s, 1H); Mass Spectrum: M+H$^+$ 433 and 435.

EXAMPLE 19

Using an analogous procedure to that described in Example 18, the appropriate 4-chloroquinazoline was reacted with the appropriate aniline in the presence of sodium hexamethyldisilazane to give the compounds described in Table VI. Each product was purified by way of its dihydrochloride salt and, unless otherwise stated, a portion of each compound was converted to the free base using an analogous procedure to that described in Example 3.

TABLE VI

| No. & Note | (R$^1$)$_m$ | Q$^1$ | (R$^2$)$_m$ |
|---|---|---|---|
| [1] | 7-methoxy | N-methyl-piperidin-4-yl | 2-bromo-4-chloro-6-fluoro |
| [2] | 7-methoxy | N-methyl-piperidin-4-yl | 4-chloro-2-trifluoromethyl |
| [3] | 7-methoxy | N-methyl-piperidin-4-yl | 4-cyano-2-trifluoromethyl |
| [4] | 7-(2-pyrrolidin-1-ylethoxy) | cyclopentyl | 2-bromo-4-chloro-6-fluoro |
| [5] | 7-(2-pyrrolidin-1-ylethoxy) | cyclopentyl | 4-chloro-2-trifluoromethyl |
| [6] | 7-(2-pyrrolidin-1-ylethoxy) | 4-tetrahydropyranyl | 4-chloro-2-trifluoromethyl |
| [7] | 7-(2-pyrrolidin-1-ylethoxy) | 4-tetrahydropyranyl | 2-bromo-4-chloro-6-fluoro |

Notes

[1] The free base gave the following data: NMR Spectrum: (CDCl$_3$) 1.98–2.1 (m, 2H), 2.22 (m, 2H), 2.31 (s, 3H), 2.4 (m, 2H), 2.7 (br s, 2H), 3.95 (s, 3H), 4.65 (m, 1H), 6.55 (d, 1H), 6.85 (d, 1H), 7.25 (m, 1H), 7.52 (d, 1H), 8.48 (s, 1H), 9.15 (s, 1H); Mass Spectrum: M+H$^+$ 495, 497 and 499.

[2] The free base gave the following data: NMR Spectrum: (CDCl$_3$) 1.82–2.05 (m, 2H), 2.1–2.3 (m, 4H), 2.25 (s, 3H), 2.75 (m, 2H), 3.9 (s, 3H), 4.5 (m, 1H), 6.5 (d, 1H), 6.8 (d, 1H), 7.55 (m, 1H), 7.65 (d, 1H), 7.82 (d, 1H), 8.4 (s, 1H), 9.5 (s, 1H); Mass Spectrum: M+H$^+$ 467 and 469.

[3] The free base gave the following data: NMR Spectrum: (CDCl$_3$) 1.9–2.0 (m, 2H), 2.15–2.25 (m, 4H), 2.3 (s, 3H), 2.85 (br s, 2H), 3.85 (s, 3H), 4.55 (m, 1H), 6.6 (d, 1H), 6.9 (d, 1H), 7.88 (m, 1H), 8.0 (s, 1H), 8.3 (d, 1H), 8.52 (s, 1H), 9.78 (s, 1H); Mass Spectrum: M+H$^+$ 458.

[4] The free base gave the following data: NMR Spectrum: (CDCl$_3$) 1.7–1.95 (m, 8H), 2.05 (br s, 4H), 2.65 (br s, 4H), 2.95 (m, 2H), 4.25 (m, 2H), 5.02 (m, 1H), 6.6 (s, 1H), 6.85 (s, 1H), 7.2 (m, 1H), 7.5 (s, 1H), 8.45 (s, 1H), 9.1 (s, 1H); Mass Spectrum: M+H$^+$ 549 and 551.

[5] The free base gave the following data: NMR Spectrum: (CDCl$_3$) 1.5–1.75 (m, 2H), 1.75–1.9 (m, 6H), 1.9–2.05 (m, 2H), 2.05–2.15 (m, 2H), 2.62 (br s, 4H), 2.98 (m, 2H), 4.25 (m, 2H), 4.98 (m, 1H), 6.6 (s, 1H), 6.85 (s, 1H), 7.55 (m, 1H), 7.65 (d, 1H), 7.85 (d, 1H), 8.45 (s, 1H), 9.45 (s, 1H); Mass Spectrum: M+H$^+$ 521 and 523.

[6] The dihydrochloride salt gave the following data: NMR Spectrum: (DMSOd$_6$ and CF$_3$CO$_2$D) 1.8–2.2 (m, 8H), 3.1–3.3 (m, 2H), 3.5 (t, 2H), 3.6–3.75 (m, 4H), 3.95 (d, 2H), 4.6 (t, 2H), 5.1 (m, 1H), 7.0 (d, 1H), 7.2 (d, 1H), 7.75 (d, 1H), 7.95 (m, 1H), 8.0 (d, 1H), 8.8 (s, 1H); Mass Spectrum: M+H$^+$ 537 and 539.

The 4-chloro-7-(2-pyrrolidin-1-ylethoxy)-5-tetrahydropyran-4-yloxyquinazoline used as a starting material was prepared as follows:—

Di-tert-butyl azodicarboxylate (0.99 g) was added to a stirred mixture of 4-chloro-7-hydroxy-5-tetrahydropyran-4-yloxyquinazoline (0.75 g), triphenylphosphine (1.14 g), 1-(2-hydroxyethyl)pyrrolidine (0.372 g) and methylene chloride (20 ml) and the mixture was stirred at ambient temperature for 0.5 hours. The mixture was poured onto a column of silica and eluted initially with a 49:1 mixture of methylene chloride and methanol followed by a 97:3 mixture of methylene chloride and a saturated methanolic ammonia solution. There was thus obtained 4-chloro-7-(2-pyrrolidin-1-ylethoxy)-5-tetrahydropyran-4-yloxyquinazoline (0.9 g); NMR Spectrum: (CDCl$_3$) 1.8–1.9 (m, 4H), 1.9–2.05 (m, 2H), 2.1–2.2 (m, 2H), 2.6–2.7 (m, 4H), 2.97 (m, 2H), 3.65–3.75 (m, 2H), 4.0–4.1 (m, 2H), 4.25 (m, 2H), 4.75 (m, 1H), 6.7 (d, 1H), 6.96 (d, 1H), 9.81 (s, 1H); Mass Spectrum: M+H$^+$ 378 and 380.

[7] The dihydrochloride salt gave the following data: NMR Spectrum: (DMSOd$_6$ and CF$_3$CO$_2$D) 1.85–2.2 (m, 8H), 3.15–3.25 (m, 2H), 3.5–3.65 (m, 2H), 3.65–3.75 (m, 4H), 4.0 (m, 2H), 4.6 (t, 2H), 5.15 (m, 1H), 7.0 (d, 1H), 7.22 (d, 1H), 7.73 (m, 1H), 7.87 (d, 1H), 8.88 (s, 1H); Mass Spectrum: M+H$^+$ 565 and 567.

EXAMPLE 20

4-(2-bromo-5-methoxyanilino)-7-hydroxy-5-piperidin-4-yloxyquinazoline

A mixture of 7-benzyloxy-4-(2-bromo-5-methoxyanilino)-5-piperidin-4-yloxyquinazoline (0.35 g) and trifluoroacetic acid (6 ml) was stirred and heated to 80° C. for 5 hours. The mixture was evaporated and the residue was dissolved in water (12 ml). The solution was basified to pH8 by the addition of sodium bicarbonate. The resultant precipitate was isolated, washed with water and with ethyl acetate and dried under vacuum. There was thus obtained the title compound (0.26 g); NMR Spectrum: (DMSOd$_6$) 1.95–2.15 (m, 2H), 2.32 (d, 2H), 3.05 (t, 2H), 3.3–3.4 (m, 2H), 3.8 (s, 3H), 5.0 (r, 1H), 6.75 (m, 2H), 6.85 (s, 1H), 7.6 (d, 1H), 7.98 (s, 1H), 8.4 (s, H), 9.58 (s, 1H); Mass Spectrum: M+H$^+$ 445 and 447.

EXAMPLE 21

4-(2-chloro-5-methoxyanilino)-7-hydroxy-5-tetrahydropyran-4-yloxyquinazoline

Using an analogous procedure to that described in Example 20, 7-benzyloxy-4-(2-chloro-5-methoxyanilino)-5-tetrahydropyran-4-yloxyquinazoline (0.78 g) was, reacted with trifluoroacetic acid (5 ml). The reaction mixture was evaporated and the residue was triturated under diethyl ether. The precipitate was isolated and the solid was dissolved in a mixture of methylene chloride and a saturated methanolic ammonia solution. The mixture was evaporated and the residue was purified by column chromatography on silica using a 97:3 mixture of methylene chloride and methanol as eluent. There was thus obtained the title compound (0.47 g); NMR Spectrum: (DMSOd$_6$) 1.8–1.9 (m, 2H), 2.2 (d, 2H), 3.52 (t, 2H), 3.8 (s, 3H), 3.92 (m, 2H), 4.95 (m, 1H), 6.7 (s, 1H), 6.75–6.85 (m, 2H), 7.5 (d, 1H), 8.12 (d, 1H), 8.4 (s, 1H), 9.85 (s, 1H); Mass Spectrum: M+H$^+$ 402 and 404.

EXAMPLE 22

4-(2-chloro-5-methoxyanilino)-7-[(2R)-2-hydroxy-3-morpholinopropoxy]-5-tetrahydropyran-4-yloxyquinazoline A mixture of 4-(2-chloro-5-methoxyanilino)-7-[(2R)-2,3-epoxypropoxy]-5-tetrahydropyran-4-yloxyquinazoline (0.08 g), morpholine (0.044 ml), ethanol (1 ml) and chloroform (1 ml) was stirred and heated to 45° C. for 16 hours. The mixture was cooled to ambient temperature and evaporated. The residue was triturated under pentane. The resultant solid was isolated, washed with diethyl ether and dried under vacuum to give the title compound (0.08 g); NMR Spectrum: (DMSOd$_6$ and CF$_3$CO$_2$D) 1.9–2.05 (m, 2H), 2.15 (d, 2H), 3.1–3.45 (m, 5H), 3.45–3.6 (m, 3H), 3.7–3.9 (m, 2H), 3.8 (s, 3H), 3.9–4.1 (m, 2H), 4.22 m, 1H), 4.45 (m, 1H), 5.15 (m, 1H), 6.95 (s, 1H), 7.02 (m, 1H), 7.15 (s, 1H), 7.5–7.6 (m, 2H), 8.9 (s, 1H); Mass Spectrum: M+H$^+$ 545 and 547.

The 4-(2-chloro-5-methoxyanilino)-7-[(2R)-2,3-epoxypropoxy]-5-tetrahydropyran-4-yloxyquinazoline used as a starting material was prepared as follows:—

Caesium fluoride (0.213 g) and (2R)-(–)-glycidyl tosylate (0.119 g) were added in turn to a solution of 4-(2-chloro-5-methoxyanilino)-7-hydroxy-5-tetrahydropyran-4-yloxyquinazoline (0.19 g) in DMA (2 ml) and the reaction mixture was stirred and heated to 50° C. for 4.5 hours. The mixture was evaporated and the residue was partitioned between ethyl acetate and a saturated aqueous sodium bicarbonate solution. The organic layer was washed with water and with brine, dried over magnesium sulphate and evaporated. The residue was purified by column chromatography on silica using a 49:1 mixture of methylene chloride and methanol as eluent. There was thus obtained 4-(2-chloro-5-methoxyanilino)-7-[(2R)-2,3-epoxypropoxy]-5-tetrahydropyran-4-yloxyquinazoline (0.155 g); NMR Spectrum: (CDCl$_3$) 2.0–2.1 (m, 2H), 2.25 (d, 2H), 2.8 (m, 1H), 2.98 (m, 1H), 3.45 (br s, 1H), 3.6 (t, 2H), 3.85 (s, 3H), 3.95–4.1 (m, 3H), 4.45 (m, 1H), 4.75 (m, 1H), 6.6–6.7 (m, 2H), 6.85 (s, 1H), 7.32 (d, 1H), 8.2 (d, 1H), 8.6 (s, 1H), 9.85 (s, 1H); Mass Spectrum: M+H$^+$ 458 and 460.

EXAMPLE 23

4-(2-chloro-5-methoxyanilino)-7-[(2R)-2-hydroxy-3-(4-methylpiperazin-1-yl)propoxy]-5-tetrahydropyran-4-yloxyquinazoline Using an analogous procedure to that described in Example 22, 4-(2-chloro-5-methoxyanilino)-7-[(2R)-2,3-epoxypropoxy]-5-tetrahydropyran-4-yloxyquinazoline (0.07 g) was reacted with 1-methylpiperazine (0.05 ml) to give the title compound (0.04 g); NMR Spectrum: (DMSOd$_6$) 1.8–1.9 (m, 2H), 2.2 (s, 3H), 2.2 (d, 2H), 2.25–2.6 (m, 10H), 3.55 (t, 2H), 3.8 (s, 3H), 3.92 (m, 2H), 4.05 (m, 2H), 4.2 (m, 1H), 4.9 (d, 1H), 5.1 (m, 1H), 6.8 (m, 1H), 6.85 (d, 1H), 6.95 (d, 1H), 7.5 (d, 1H), 8.12 (d, 1H), 8.5 (s, 1H), 9.9 (s, 1H); Mass Spectrum: M+H$^+$ 558 and 560.

EXAMPLE 24

4-(2-bromo-5-methoxyanilino)-7-hydroxy-5-tetrahydropyran-4-yloxyquinazoline

A mixture of 7-acetoxy-4-chloro-5-tetrahydropyran-4-yloxyquinazoline (1.7 g), 2-bromo-5-methoxy aniline (1.1 g) and isopropanol (10 ml) was stirred and heated to 80° C. for 1 hour. The resultant precipitate was isolated, washed with isopropanol and dried under vacuum to give 7-acetoxy-4-(2-bromo-5-methoxyanilino)-5-tetrahydropyran-4-yloxyquinazoline hydrochloride (2 g); NMR Spectrum: (DMSOd$_6$ and CF$_3$CO$_2$D) 1.9–2.1 (m, 2H), 2.17 (d, 2H), 2.38 (s, 3H), 3.5 (t, 2H), 3.8 (s, 3H), 3.95 (m, 2H), 5.1 (m, 1H), 7.0 (m, 1H), 7.32 (s, 1H), 7.42 (d, 1H), 7.5 (s, 1H), 7.7 (d, 1H), 8.9 (s, 1H); Mass Spectrum: M+H$^+$ 488 and 490.

A mixture of a portion (0.15 g) of the material so obtained and a saturated methanolic ammonia solution (5 ml) was stirred at ambient temperature for 16 hours. The mixture was evaporated and the residue was triturated under water. The resultant solid was isolated and dried under vacuum to give the title compound (0.091 g); NMR Spectrum: (DMSOd$_6$) 1.8–2.0 (m, 2H), 2.15 (d, 2H), 3.52 (t, 2H), 3.8 (s, 3H), 3.9 (m, 2H), 4.95 (m, 1H), 6.7 (s, 1H), 6.75 (m, 1H), 6.8 (d, 1H), 7.6 (d, 1H), 7.85 (d, 1H), 8.35 (s, 1H), 9.65 (s, 1H), 10.58 (s, 1H); Mass Spectrum: M+H$^+$ 446 and 448.

The 7-acetoxy-4-chloro-5-tetrahydropyran-4-yloxyquinazoline used as a starting material was prepared as follows:—

A solution of 7-acetoxy-5-tetrahydropyran-4-yloxy-3,4-dihydroquinazolin-4-one (1.52 g) in 1,2-dichloroethane (30 ml) containing phosphorus oxychloride (0.51 ml) and diisopropylethylamine (2.17 ml) was stirred and heated to 80° C. for 2 hours. The mixture was evaporated to give the required material which was used without further purification.

EXAMPLE 25

4-(2-chloro-5-methoxyanilino)-7-hydroxy-5-tetrahydrofuran-3-yloxyquinazoline

Using an analogous procedure to that described in Example 20, 7-benzyloxy-4-(2-chloro-5-methoxyanilino)-5-tetrahydrofuran-3-yloxyquinazoline (0.39 g) was reacted with trifluoroacetic acid (2.5 ml). The reaction mixture was evaporated and the residue was triturated under diethyl ether. The precipitate was isolated and the solid was dissolved in a mixture of methylene chloride and a saturated methanolic ammonia solution. The mixture was evaporated and the residue was purified by column chromatography on silica using a 97:3 mixture of methylene chloride and methanol as eluent. There was thus obtained the title compound (0.47 g); NMR Spectrum: (DMSOd$_6$ and CF$_3$CO$_2$D) 2.2–2.3 (m, 1H), 2.3–2.5 (m, 1H), 3.8 (s, 3H), 3.75–3.9 (m, 1H), 3.9–4.0 (m, 2H), 4.2 (d, 1H), 5.5 (m, 1H), 6.8 (s, 1H), 6.92 (s, 1H), 7.02 (m, 1H), 7.55 (d, 1H), 7.6 (d, 1H), 8.85 (s, 1H); Mass Spectrum: M+H$^+$ 388 and 390.

EXAMPLE 26

4-(2-chloro-5-methoxyanilino)-7-hydroxy-5-isopropoxyquinazoline

Using an analogous procedure to that described in Example 20, 7-benzyloxy-4-(2-chloro-5-methoxyanilino)-5-isopropoxyquinazoline (0.33 g) was reacted with trifluoroacetic acid. There was thus obtained the title compound (0.17 g); NMR Spectrum: (DMSOd$_6$ and CF$_3$CO$_2$D) 1.55 (d, 6H), 3.85 (s, 3H), 5.1 (m, 1H), 6.8 (s, 1H), 6.92 (s, 1H), 7.0 (m, 1H), 7.58 (d, 1H), 7.65 (d, 1H), 8.85 (s, 1H); Mass Spectrum: M+H$^+$ 360 and 362.

EXAMPLE 27

4-(benzofuran-7-ylamino)-7-methoxy-5-(N-methylpiperidin-4-yloxy)quinazoline dihydrochloride Using an analogous procedure to that described in Example 5, 4-chloro-7-methoxy-5-(N-methylpiperidin-4-yloxy)quinazoline was reacted with 7-aminobenzofuran to give the title compound, a portion of which was treated with a saturated methanolic ammonia solution. The mixture was filtered and the filtrate was evaporated to give the free base; NMR Spectrum: (CDCl$_3$) 2.15–2.35 (m, 6H), 2.32 (s, 3H), 2.92 (m, 2H), 3.9 (s, 3H), 4.6 (m, 1H), 6.5 (d, 1H), 6.8 (d, 1H), 6.85 (d, 1H), 7.25–7.4 (m, 2H), 7.68 (d, 1H), 8.58 (d, 1H), 8.6 (s, 1H), 10.25 (br s, 1H); Mass Spectrum: M+H$^+$ 405.

The 7-aminobenzofuran used as a starting material was prepared as follows:—

Hydrazine hydrate (0.45 ml) was added dropwise to a stirred mixture of 7-nitrobenzofuran (*J. Med. Chem.*, 1988, 31, 1934; 0.5 g), Raney nickel (0.02 g) and methanol (9 ml) that had been warmed to 55° C. The resultant mixture was heated to reflux for 30 minutes. The catalyst was removed by filtration and the filtrate was evaporated. The residue was partitioned between methylene chloride and water. The organic phase was dried over magnesium sulphate and evaporated to give 7-aminobenzofuran (0.4 g) as an oil; NMR Spectrum: (DMSOd$_6$) 5.25 (br s, 2H), 6.55 (d, 1H), 6.8 (m, 2H), 6.9 (t, 1H), 7.85 (d, 1H).

EXAMPLE 28

4-(3-chlorobenzofuran-7-ylamino)-7-[3-(4-methylpiperazin-1-yl)propoxy]-5-tetrahydropyran-4-yloxyquinazoline dihydrochloride Using an analogous procedure to that described in Example 5, 4-chloro-7-[3-(4-methylpiperazin-1-yl)propoxy]-5-tetrahydropyran-4-yloxyquinazoline was reacted with 7-amino-3-chlorobenzofuran to give the title compound, a portion of which was treated with a saturated methanolic ammonia solution. The mixture was filtered and the filtrate was evaporated to give the free base; NMR Spectrum: (CDCl$_3$) 2.07 (m, 2H), 2.1 (m, 2H), 2.25 (m, 2H), 2.27 (s, 3H), 2.35–2.68 (m, 10H), 3.6 (t, 2H), 4.0–4.2 (m, 4H), 4.75 (m, 1H), 6.52 (s, 1H), 6.85 (s, 1H), 7.35 (m, 2H), 7.65 (s, 1H), 8.6 (s, 1H), 8.7 (d, 1H), 10.3 (s, 1H); Mass Spectrum: M+H$^+$ 522 and 524.

EXAMPLE 29

4-(2,4-dichloro-5-methoxyanilino)-7-(3-piperazin-1-ylpropoxy)-5-tetrahydropyran-4-yloxyquinazoline dihydrochloride A mixture of 4-(2,4-dichloro-5-methoxyanilino)-7-[3-(4-tert-butoxycarbonylpiperazin-1-yl)propoxy]-5-tetrahydropyran-4-yloxyquinazoline (0.12 g) and trifluoroacetic acid (2 ml) was stirred at ambient temperature for 2 hours. The mixture was evaporated and the residue was triturated under diethyl ether. The resultant solid was isolated and dried under vacuum. The solid was dissolved in diethyl ether and 6M hydrogen chloride gas in diethyl ether (0.5 ml) was added. The resultant solid was isolated, washed with diethyl ether and dried under vacuum. There was thus obtained the title compound (0.112 g); NMR Spectrum: (DMSOd$_6$ and CF$_3$CO$_2$H) 1.9–2.1 (m, 2H), 2.15 (d, 2H), 2.28–2.4 (m, 2H), 3.4 (m, 2H), 3.4–3.9 (m, 10H), 3.92 (s, 3H), 3.95 (m, 2H), 4.39 (t, 2H), 5.2 (m, 1H), 7.0 (d, 1H), 7.2 (d, 1H), 7.78 (s, 1H), 7.82 (s, 1H), 8.9 (s, 1H); Mass Spectrum: M+H$^+$ 562 and 564.

The 4-(2,4-dichloro-5-methoxyanilino)-7-[3-(4-tert-butoxycarbonylpiperazin-1-yl)propoxy]-5-tetrahydropyran-4-yloxyquinazoline used as a starting material was prepared as follows:—

Using an analogous procedure to that described in Example 12, 4-(2,4-dichloro-5-methoxyanilino)-7-hydroxy-5-tetrahydropyran-4-yloxyquinazoline (0.109 g) was reacted with 1-tert-butoxycarbonyl-4-(3-hydroxypropyl)piperazine (0.074 g) to give 4-(2,4-dichloro-5-methoxyanilino)-7-[3-(4-tert-butoxycarbonylpiperazin-1-yl)propoxy]-5-tetrahydropyran-4-yloxyquinazoline (0.12 g).

EXAMPLE 30

4-(2,4-dichloro-5-methoxyanilino)-7-piperidin-4-ylmethoxy-5-tetrahydropyran-4-yloxyquinazoline A mixture of 4-(2,4-dichloro-5-methoxyanilino)-7-(1-tert-butoxycarbonylpiperidin-4-ylmethoxy)-5-tetrahydropyran-4-yloxyquinazoline (0.11 g) and trifluoroacetic acid (2 ml) was stirred at ambient temperature for 2 hours. The mixture was evaporated and the residue was triturated under diethyl ether. The resultant solid was isolated and dried under vacuum. The solid was dissolved in diethyl ether and 6M hydrogen chloride gas in diethyl ether (0.5 ml) was added. The resultant solid was isolated, washed with diethyl ether and dried under vacuum. There was thus obtained the dihydrochloride salt of the title compound. The solid was dissolved in methylene chloride and few drops of a saturated methanolic ammonia solution was added. The solution was poured onto a chromatography column filled with silica and eluted with a 24:1 mixture of methylene chloride and a saturated methanolic ammonia solution. There was thus obtained the title compound (0.08 g); NMR Spectrum: (CDCl$_3$) 1.9–2.1 (m, 2H), 1.95 (d, 2H), 1.9–2.15 (m, 3H), 2.52 (d, 2H), 2.7 (m, 2H), 3.2 (d, 2H), 3.6 (m, 2H), 3.9–4.0 (m, 2H), 4.05 (s, 3H), 4.1 (td, 2H), 4.75 (m, 1H), 6.6 (d, 1H), 6.85 (m, 1H), 7.45 (s, 1H), 8.4 (s, 1H), 8.6 (s, 1H); Mass Spectrum: M+H$^+$ 533 and 535.

The 4-(2,4-dichloro-5-methoxyanilino)-7-(1-tert-butoxycarbonylpiperidin-4-ylmethoxy)-5-tetrahydropyran-4-yloxyquinazoline used as a starting material was prepared as follows:—

Using an analogous procedure to that described in Example 12, 4-(2,4-dichloro-5-methoxyanilino)-7-hydroxy- 5-tetrahydropyran-4-yloxyquinazoline (0.109 g) was reacted with 1-tert-butoxycarbonylpiperidin-4-ylmethanol (0.065 g) to give 4-(2,4-dichloro-5-methoxyanilino)-7-(1-tert-butoxycarbonylpiperidin-4-ylmethoxy)-5-tetrahydropyran-4-yloxyquinazoline (0.11 g).

EXAMPLE 31

4-(6-chloro-2,3-methylenedioxyanilino)-7-fluoro-5-piperidin-4-yloxyquinazoline dihydrochloride A mixture of 5-(1-tert-butoxycarbonylpiperidin-4-yloxy)-4-(6-chloro-2,3-methylenedioxyanilino)-7-fluoroquinazoline dihydrochloride (0.12 g) and a 2M solution of hydrogen chloride in diethyl ether (5 ml) was stirred at ambient temperature for 1 hour. The resultant precipitate was isolated, washed with diethyl ether and dried under vacuum. There was thus obtained the title compound (0.086 g); NMR Spectrum: (DMSOd$_6$) 2.1–2.3 (m, 4H), 3.0–3.15 (m, 2H), 3.3 (m, 2H), 5.1 (m, 1H), 6.12 (s, 2H), 7.01 (d, 1H), 7.1 (d, 1H), 7.3 (d, 1H), 7.53 (d, 1H), 8.75 (s, 1H), 9.05 (br s, 1H), 9.3 (br s, 1H), 9.95 (br s, 1H); Mass Spectrum: M+H$^+$ 417 and 419.

The 5-(1-tert-butoxycarbonylpiperidin-4-yloxy)-4-(6-chloro-2,3-methylenedioxyanilino)-7-fluoroquinazoline dihydrochloride used as a starting material was prepared as follows:—

Sodium hydride (60% dispersion in mineral oil; 0.55 g) was added portionwise to a solution of tert-butyl 4-hydroxypiperidine-1-carboxylate (1.65 g) in DMF (10 ml) and the resultant mixture was stirred at ambient temperature for 15 minutes. 5,7-Difluoro-3,4-dihydroquinazolin-4-one (1 g) was added and the mixture was stirred at ambient temperature for 30 minutes. The mixture was poured into water (100 ml) and, with vigorous stirring, glacial acetic acid was added to acidify the mixture to pH5. The resultant solid was isolated, washed with water and with diethyl ether and dried under vacuum. There was thus obtained 5-(1-tert-butoxycarbonylpiperidin-4-yloxy)-7-fluoro-3,4-dihydroquinazolin-4-one (1.4 g); NMR Spectrum: (CDCl$_3$) 1.47 (s, 9H), 1.94 (m, 4H), 3.5–3.8 (m, 4H), 4.7 (m, 1H), 6.68 (m, 1H), 7.0 (m, 1H), 7.9 (s, 1H), 10.55 (br s, 1H); Mass Spectrum: M+H$^+$ 364.

A mixture of 5-(1-tert-butoxycarbonylpiperidin-4-yloxy)-7-fluoro-3,4-dihydroquinazolin-4-one (0.15 g), triphenylphosphine (0.216 g), carbon tetrachloride (0.12 ml) and 1,2-dichloroethane (5 ml) was stirred and heated to 70° C. for 1 hour. The mixture was evaporated and the residue was purified by column chromatography on silica using a 9:1 mixture of methylene chloride and ethyl acetate as eluent. There was thus obtained 5-(1-tert-butoxycarbonylpiperidin-4-yloxy) chloro-7-fluoroquinazoline (0.1 g); NMR Spectrum: (CDCl$_3$) 1.48 (s, 9H), 2.0 (m, 4H), 3.5–3.7 (m, 4H), 4.8 (m, 1H), 6.8 (m, 1H), 7.3 (m, 1H), 8.9 (s, 1H); Mass Spectrum: M+H$^+$ 382 and 384.

A mixture of the material so obtained, 6-chloro-2,3-methylenedioxyaniline (0.049 g), 5M hydrogen chloride in isopropanol (1 drop) and isopropanol (1 ml) was stirred and heated to 50° C. for 15 minutes and then to 80° C. for 45 minutes. The precipitate was isolated, washed in turn with isopropanol, ethyl acetate and diethyl ether and dried under vacuum. There was thus obtained 5-(1-tert-butoxycarbonylpiperidin-4-yloxy)-4-(6-chloro-2,3-methylenedioxyanilino)-7-fluoroquinazoline dihydrochloride (0.065 g); NMR Spectrum: (DMSOd$_6$) 1.4 (s, 9H), 1.8–2.0 (m, 2H), 2.0–2.15 (m, 2H), 3.05 (br s, 2H), 3.9 (d, 2H), 5.05 (m, 1H), 6.11 (s, 2H), 7.1 (d, 1H), 7.16 (d, 1H), 7.2 (m, 1H), 7.52 (d, 1H), 8.7 (s, 1H), 9.92 (br s, 1H); Mass Spectrum: M+H$^+$ 517 and 519.

EXAMPLE 32

4-(6-chloro-2,3-methylenedioxyanilino)-5-piperidin-4-yloxyquinazoline dihydrochloride Using an analogous procedure to that described in Example 31, 5-(1-tert-butoxycarbonylpiperidin-4-yloxy)-4-(6-chloro-2,3-methylenedioxyanilino)quinazoline dihydrochloride (0.14 g) was reacted with hydrogen chloride to give the title compound (0.113 g); NMR Spectrum: (DMSOd$_6$) 2.15–2.34 (m, 4H), 3.15 (m, 2H), 3.3 (m, 2H), 5.17 (m, 1H), 6.17 (s, 2H), 7.07 (d, 1H), 7.16 (d, 1H), 7.58 (m, 1H), 8.06 (m, 1H), 8.88 (s, 1H), 9.14 (br s, 1H), 9.32 (br s, 1H), 10.28 (s, 1H); Mass Spectrum: M+H$^+$ 399 and 401.

The 5-(1-tert-butoxycarbonylpiperidin-4-yloxy)-4-(6-chloro-2,3-methylenedioxyanilino)quinazoline dihydrochloride used as a starting material was prepared as follows using analogous procedures to those described in the portion of Example 31 that is concerned with the preparation of starting materials:—

Thus, tert-butyl 4-hydroxypiperidine-1-carboxylate (0.33 g) was reacted with 5-fluoro-3,4-dihydroquinazolin-4-one (0.18 g) to give 5-(1-tert-butoxycarbonylpiperidin-4-yloxy)-3,4-dihydroquinazolin-4-one (0.39 g); NMR Spectrum: (CDCl$_3$) 1.5 (s, 9H), 1.9–2.0 (m, 4H), 3.52 (m, 2H), 3.7 (m, 2H), 4.72 (m, 1H), 6.95 (d, 1H), 7.32 (d, 1H), 7.65 (m, 1H), 7.95 (s, 1H), 10.22 (br s, 1H); Mass Spectrum: M+H$^+$ 346;

5-(1-tert-butoxycarbonylpiperidin-4-yloxy)-3,4-dihydroquinazolin-4-one (0.31 g) was reacted with triphenylphosphine and carbon tetrachloride to give 5-(1-tert-butoxycarbonylpiperidin-4-yloxy)-4-chloroquinazoline (0.156 g); NMR Spectrum: (CDCl$_3$) 1.5 (s, 9H), 1.9–2.1 (m, 4H), 3.5–3.8 (m, 4H), 4.8 (m, 1H), 7.05 (d, 1H), 7.65 (d, 1H), 7.82 (m, 1H), 8.95 (s, 1H); Mass Spectrum: M+H$^+$ 364 and 366; and a portion (0.124 g) of the material so obtained and 6-chloro-2,3-methylenedioxyaniline (0.064 g) were reacted to give 5-(1-tert-butoxycarbonylpiperidin-4-yloxy)-4-(6-chloro-2,3-methylenedioxyanilino)quinazoline dihydrochloride (0.14 g); NMR Spectrum: (DMSOd$_6$) 1.4 (s, 9H), 1.85–2.0 (m, 2H), 2.1 (m, 2H), 2.95–3.2 (m, 2H), 3.92 (d, 2H), 5.1 (m, 1H), 6.15 (s, 2H), 7.08 (d, 1H), 7.15 (d, 1H), 7.55 (d, 1H), 7.6 (d, 1H), 8.05 (m, 1H), 8.86 (s, 1H), 10.35 (s, 1H); Mass Spectrum: M+H$^+$ 499 and 501.

EXAMPLE 33

4-(6-chloro-2,3-methylenedioxyanilino)-7-methoxy-5-piperidin-4-yloxyquinazoline

A mixture of 5-(1-tert-butoxycarbonylpiperidin-4-yloxy)-4-(6-chloro-2,3-methylenedioxyanilino)-7-methoxyquinazoline dihydrochloride (2.39 g), trifluoroacetic acid (10 ml) and methylene chloride (35 ml) was stirred at ambient temperature for 1.5 hours. The mixture was evaporated and the residue was partitioned between ethyl acetate and a 1N aqueous sodium hydroxide solution. The organic layer was washed with water and brine, dried over magnesium sulphate and evaporated. The residue was purified by column chromatography on silica using a 19:1 mixture of methylene chloride and methanol as eluent. There was thus obtained the title compound (1.44 g); NMR Spectrum: (CDCl$_3$) 1.8–2.0 (m, 2H), 2.15–2.3 (m, 2H), 2.75–2.9 (m, 2H), 3.1–3.2 (m, 2H), 3.9 (s, 3H), 4.65 (m, 1H), 6.0 (s, 2H), 6.46 (d, 1H), 6.72 (d, 1H), 6.8 (d, 1H), 6.91 (d, 1H), 8.5 (s, 1H), 9.21 (s, 1H); Mass Spectrum: M+H$^+$ 429 and 431.

The 5-(1-tert-butoxycarbonylpiperidin-4-yloxy)-4-(6-chloro-2,3-methylenedioxyanilino)-7-methoxyquinazoline dihydrochloride used as a starting material was prepared as follows:—

Di-tert-butyl azodicarboxylate (1.13 g) was added portionwise to a stirred mixture of 5-hydroxy-7-methoxy-3-pivaloyloxymethyl-3,4-dihydroquinazolin-4-one (1 g), tert-butyl 4-hydroxypiperidine-1-carboxylate (0.788 g), triphenylphosphine (1.28 g) and methylene chloride (15 ml) which had been cooled to 10° C. The mixture was allowed to warm to ambient temperature and was stirred for 1 hour. The mixture was evaporated and the residue was dissolved in methanol (25 ml). Sodium hydroxide (0.2 g) was added and the mixture was stirred at ambient temperature for 1 hour. The resultant mixture was evaporated and the residue was purified by column chromatography on silica using a 47:50:3 mixture of methylene chloride, ethyl acetate and methanol as eluent. There was thus obtained 5-(1-tert-butoxycarbonylpiperidin-4-yloxy)-7-methoxy-3,4-dihydroquinazolin-4-one (1.09 g); NMR Spectrum: (CDCl$_3$) 1.5 (s, 9H), 1.87–2.0 (m, 4H), 3.48–3.6 (m, 2H), 3.6–3.75 (m, 2H), 3.9 (s, 3H), 4.65 (m, 1H), 6.5 (d, 1H), 6.77 (d, 1H), 7.91 (s, 1), 10.7 (br s, 1H); Mass Spectrum: M+H$^+$ 376.

Using an analogous procedure to that described in the portion of Example 31 that is concerned with the preparation of starting materials, 5-(1-tert-butoxycarbonylpiperidin-4-yloxy)-7-methoxy-3,4-dihydroquinazolin-4-one (1 g) was reacted with triphenylphosphine and carbon tetrachloride to give 5-(1-tert-butoxycarbonylpiperidin-4-yloxy)-4-chloro-7-methoxyquinazoline (0.8 g); NMR Spectrum: (CDCl$_3$) 1.5 (s, 9H), 1.9–2.1 (m, 4H), 3.5–3.7 (m, 4H), 3.96 (s, 3H), 4.72 (m, 2H), 6.6 (d, 1H), 6.98 (d, 1H), 8.82 (s, 1H); Mass Spectrum: M+H$^+$ 394 and 396.

Using an analogous procedure to that also described in the portion of Example 31 that is concerned with the preparation of starting materials, 5-(1-tert-butoxycarbonylpiperidin-4-yloxy)-4-chloro-7-methoxyquinazoline (0.14 g) and 6-chloro-2,3-methylenedioxyaniline (0.064 g) were reacted to give 5-(1-tert-butoxycarbonylpiperidin-4-yloxy)-4-(6-chloro-2,3-methylenedioxyanilino)-7-methoxyquinazoline dihydrochloride (0.17 g); NMR Spectrum: (DMSOd$_6$) 1.42 (s, 9H), 1.8–2.0 (m, 2H), 2.0–2.15 (m, 2H), 3.0–3.2 (m, 2H), 3.85–3.95 (m, 2H), 3.99 (s, 3H), 5.1 (m, 1H), 6.96 (d, 1H), 7.05 (d, 1H), 7.12 (s, 1H), 7.15 (d, 1H), 8.78 (s, 1H), 10.1 (s, 1H); Mass Spectrum: M+H$^+$ 529 and 531.

EXAMPLE 34

4-(6-chloro-2,3-methylenedioxyanilino)-7-hydroxy-5-piperidin-4-yloxyquinazoline

A mixture of 7-benzyloxy-5-[N-(tert-butoxycarbonyl)piperidin-4-yloxy]-4-(6-chloro-2,3-methylenedioxyanilino) quinazoline dihydrochloride (2.3 g) and trifluoroacetic acid (28 ml) was stirred and heated to 80° C. for 6 hours. The mixture was evaporated and the residue was dissolved in water and the solution was basified to pH10 by the addition of 1N aqueous sodium hydroxide solution. The mixture was stirred at ambient temperature for 1 hour. The solid was isolated, washed with water and dried under vacuum. There was thus obtained the title compound (1.1 g); NMR Spectrum: (DMSOd$_6$) 1.6–1.8 (m, 2H), 2.0–2.15 (m, 2H), 2.65–2.75 (m, 2H), 2.9–3.05 (m, 2H), 4.8 (m, 1H), 6.1 (s, 2H), 6.62 (s, 1H), 6.7 (s, 1H), 6.92 (d, 1H), 7.05 (d, 1H), 8.25 (s, 1H), 9.2 (s, 1H); Mass Spectrum: M+H$^+$ 415 and 417.

EXAMPLE 35

5-[N-(tert-butoxycarbonyl)piperidin-4-yloxy]-4-(6-chloro-2,3-methylenedioxyanilino)-7-hydroxyquinazoline A mixture of 4-(6-chloro-2,3-methylenedioxyanilino)-7-hydroxy-5-piperidin-4-yloxyquinazoline (1.4 g), di-tert-butyl dicarbonate (0.737 g) and DMF (14 ml) was stirred at ambient temperature for 2 hours. The mixture was evaporated and the residue was partitioned between ethyl acetate and water. The organic phase was washed with brine, dried over magnesium sulphate and evaporated. The residue was purified by column chromatography on silica using a 24:1 mixture of methylene chloride and methanol as eluent. There was thus obtained the title compound (1.2 g); NMR Spectrum: (CDCl$_3$) 1.5 (s, 9H), 1.7–1.9 (m, 2H), 2.0–2.15 (m, 2H), 3.0–3.15 (m, 2H), 3.8–3.95 (m, 2H), 4.6 (m, 1H), 6.02 (s, 2H), 6.55 (s, 1H), 6.72 (d, 1H), 6.98 (m, 2H), 8.4 (s, 1H), 9.4 (s, 1H); Mass Spectrum: M+H$^+$ 515 and 517.

EXAMPLE 36

4-(6-chloro-2,3-methylenedioxyanilino)-5-piperidin-4-yloxy-7-(2,2,2-trifluoroethoxy)quinazoline A mixture of 5-[N-(tert-butoxycarbonyl)piperidin-4-yloxy]-4-(6-chloro-2,3-methylenedioxyanilino)-7-hydroxyquinazoline (0.15 g), 2,2,2-trifluoroethyl 4-toluenesulphonate (0.089 g), potassium carbonate (0.1 g) and DMF (3 ml) was stirred and heated to 95° C. for 24 hours. The mixture was cooled to ambient temperature and partitioned between ethyl acetate and water. The organic solution was washed with 1N aqueous sodium hydroxide solution and with brine and dried over magnesium sulphate. The organic solution was filtered and a 6N solution of hydrogen chloride in diethyl ether (2 ml) was added. The mixture was stirred at ambient temperature for 16 hours. The mixture was evaporated. The residue was dissolved in methylene chloride (3 ml) and a saturated methanolic ammonia solution (1 ml) was added. The mixture was filtered and the filtrate was evaporated. The residue was purified by column chromatography on silica using a 19:1 mixture of methylene chloride and a saturated methanolic ammonia solution as eluent. There was thus obtained the title compound (0.061 g); NMR Spectrum: (CDCl$_3$) 1.85–2.0 (m, 2H), 2.3 (m, 2H), 2.8–2.95 (m, 2H), 3.1–3.3 (m, 2H), 4.5 (m, 2H), 4.72 (m, 1H), 6.08 (s, 2H), 6.6 (d, 1H), 6.75 (d, 1H), 6.82 (d, 1H), 7.0 (d, 1H), 8.58 (s, 1H), 9.32 (s, 1H); Mass Spectrum: M+H$^+$ 497 and 499.

EXAMPLE 37

4-(6-chloro-2,3-methylenedioxyanilino)-5-(N-methylpiperidin-4-yloxy)quinazoline

4-Hydroxy-1-methylpiperidine (0.049 g) was added to a stirred suspension of sodium hydride (60% dispersion in mineral oil, 0.043 g) in DMF (2 ml) and the mixture was stirred at ambient temperature for 5 minutes. The dihydrochloride salt of 4-(6-chloro-2,3-methylenedioxyanilino)-5-fluoroquinazoline was treated with a saturated methanolic ammonia solution to give the free base (0.1 g) which was added to the above-mentioned solution of the sodium salt of 4-hydroxy-1-methylpiperidine. The resultant mixture was stirred and heated to 50° C. for 30 minutes. The mixture was cooled to ambient temperature and partitioned between ethyl acetate and water. The organic layer was washed with water and with brine, dried over magnesium sulphate and evaporated. The residue was purified by column chromatography on silica using a 25:24:1 mixture of ethyl acetate, methylene chloride and a saturated methanolic ammonia solution as eluent. There was thus obtained 4-(6-chloro-2,3-methylenedioxyanilino)-5-(N-methylpiperidin-4-yloxy)quinazoline (0.054 g); NMR Spectrum: (CDCl$_3$) 1.95–2.1 (m, 2H), 2.1–2.25 (m, 2H), 2.3 (s, 3H), 2.3–2.4 (m, 2H), 2.7 (br s, 2H), 4.65 (m, 1H), 6.01 (s, 2H), 6.7 (d, 1H), 6.8 (d, 1H), 6.85 (d, 1H), 7.45 (d, 1H), 7.6 (m, 1H), 8.56 (s, 1H), 9.5 (br s, 1i); Mass Spectrum: M+H$^+$ 413 and 415.

The 4-(6-chloro-2,3-methylenedioxyanilino)-5-fluoroquinazoline dihydrochloride used as a starting material was prepared was prepared as follows using analogous procedures to those described in the portion of Example 31 that is concerned with the preparation of starting materials:—

Thus, 5-fluoro-3,4-dihydroquinazolin-4-one (2 g) was reacted with triphenylphosphine and carbon tetrachloride to give 5-fluoro-4-chloroquinazoline (1.34 g); NMR Spectrum: (CDCl$_3$) 7.4–7.5 (m, 1H), 7.9–8.0 (m, 2H), 9.1 (s, 1H); and a portion (0.4 g) of the material so obtained and 6-chloro-2,3-methylenedioxyaniline (0.413 g) were reacted to give 4-(6-chloro-2,3-methylenedioxyanilino)-5-fluoroquinazoline dihydrochloride (0.73 g); NMR Spectrum: (DMSOd$_6$) 6.18 (s, 2H), 7.05 (d, 1H), 7.12 (d, 1H), 7.7 (m, 1H), 7.85 (d, 1H), 8.12 (m, 1H), 8.87 (s, 1H); Mass Spectrum: M+H$^+$ 318 and 320.

EXAMPLE 38

4-(6-chloro-2,3-methylenedioxyanilino)-7-isopropoxy-5-(N-methylpiperidin-4-yloxy)quinazoline Sodium triacetoxyborohydride (0.087 g) was added portionwise to a stirred mixture of 4-(6-chloro-2,3-methylenedioxyanilino)-7-isopropoxy-5-piperidin-4-yloxyquinazoline (0.125 g), aqueous formaldehyde (13N, 0.042 ml), acetic acid (0.019 ml), methylene chloride (5 ml) and methanol (2 ml) and the resultant mixture was heated to reflux for 3 minutes. The mixture was evaporated and the residue was partitioned between ethyl acetate and 1N aqueous sodium hydroxide solution. The organic layer was washed with brine, dried over magnesium sulphate and evaporated to give the title compound (0.11 g); NMR Spectrum: (CDCl$_3$) 1.42 (d, 6H), 1.95–2.1 (m, 2H), 2.15–2.25 (m, 2H), 2.3 (s, 3H), 2.3–2.4 (m, 2H), 2.7–2.8 (m, 2H), 4.6 (m, 1H), 4.72 (m, 1H), 6.05 (s, 2H), 6.5 (d, 1H), 6.75 (d, 1H), 6.82 (d, 1H), 6.99 (d, 1H), 8.52 (s, 1H), 9.3 (s, 1H); Mass Spectrum: M+H$^+$ 471 and 473.

EXAMPLE 39

4-(6-chloro-2,3-methylenedioxyanilino)-5-piperidin-4-ylmethoxyquinazoline dihydrochloride Using an analogous procedure to that described in Example 37, N-(tert-butoxycarbonyl)piperidin-4-ylmethanol was reacted with 4-(6-chloro-2,3-methylenedioxyanilino)-5-fluoroquinazoline (0.1 g). The product so obtained was dissolved in a 2M solution of hydrogen chloride in diethyl ether (20 ml) and stirred at ambient temperature for 3 hours. The mixture was evaporated and the residue was triturated under diethyl ether. The solid so obtained was washed with diethyl ether and dried under vacuum. There was thus obtained the title compound (0.121 g); NMR Spectrum: (DMSOd$_6$) 1.5–1.6 (m, 2H), 1.9–2.0 (m, 2H), 2.3–2.4 (m, 1H), 2.8–2.9 (m, 2H), 3.3 (d, 2H), 4.42 (d, 2H), 6.15 (s, 2H), 7.07 (d, 1H), 7.15 (d, 1H), 7.53 (m, 2H), 8.06 (m, 1H), 8.87 (s, 1H), 10.57 (br s, 1H); Mass Spectrum: M+H$^+$ 413 and 415.

EXAMPLE 40

4-(6-chloro-2,3-methylenedioxyanilino)-5-(N-methylpiperidin-4-ylmethoxy)quinazoline dihydrochloride Using an analogous procedure to that described in Example 38, 4-(6-chloro-2,3-methylenedioxyanilino)-5-piperidin-4-ylmethoxyquinazoline (obtained from the dihydrochloride salt by trituration under a saturated methanolic ammonia solution) was reacted with aqueous formaldehyde and sodium triacetoxyborohydride. The reaction product, obtained as the free base, was triturated under a 2M solution of hydrogen chloride in diethyl ether. The resultant precipitate was isolated, washed with diethyl ether and dried under vacuum. There was thus obtained the title compound, a portion of which was converted to the free base by trituration under a saturated methanolic ammonia solution. The free base gave the following data: NMR Spectrum: (CDCl$_3$) 1.35–1.55 (m, 2H), 1.9–2.1 (m, 5H), 2.3 (s, 3H), 2.9 (d, 2H), 4.12 (d, 2H), 6.04 (s, 2H), 6.75 (d, 1H), 6.9 (d, 1H), 6.98 (d, 1H), 7.48 (d, 1H), 7.64 (m, 1H), 8.62 (s, 1H), 9.38 (s, 1H); Mass Spectrum: M+H$^+$ 427 and 429.

EXAMPLE 41

4-(6-chloro-2,3-methylenedioxyanilino)-7-(3-piperidinopropoxy)-5-tetrahydropyran-4-yloxyquinazoline A mixture of 7-(3-bromopropoxy)-4-(6-chloro-2,3-methylenedioxyanilino)-5-tetrahydropyran-4-yloxyquinazoline (0.536 g), piperidine (0.12 ml), potassium carbonate (0.4 g) and DMF (2 ml) was stirred at ambient temperature for 16 hours. The mixture was evaporated and the residue was triturated under methylene chloride. The mixture was filtered and the filtrate was purified by column chromatography on silica using initially a 1:1 mixture of ethyl acetate and methylene chloride and then a 10:9:1 mixture of ethyl acetate, methylene chloride and a saturated methanolic ammonia solution as eluent. There was thus obtained the title compound (0.53 g); NMR Spectrum: (CDCl$_3$) 1.4–1.5 (m, 2H), 1.55–1.7 (m, 4H), 1.9–2.1 (m, 4H), 2.2–2.3 (m, 2H), 2.4 (m, 4H), 2.5 (m, 2H), 3.6–3.7 (m, 2H), 4.0–4.1 (m, 2H), 4.15 (m, 2H), 4.8 (m, 1H), 6.08 (s, 2H), 6.52 (d, 1H), 6.75 (d, 1H), 6.85 (d, 1H), 7.0 (d, 1H), 8.55 (s, 1H), 9.35 (s, 1H); Mass Spectrum: M+H$^+$ 541 and 543.

The 7-(3-bromopropoxy)-4-(6-chloro-2,3-methylenedioxyanilino)-5-tetrahydropyran-4-yloxyquinazoline used as a starting material was prepared as follows:—

Di-tert-butyl azodicarboxylate (1.66 g) was added to a stirred mixture of 4-(6-chloro-2,3-methylenedioxyanilino)-7-hydroxy-5-tetrahydropyran-4-yloxyquinazoline (1.5 g), 3-bromopropan-1-ol (0.49 ml), triphenylphosphine (1.9 g) and methylene chloride (20 ml) and the mixture was stirred at ambient temperature for 1 hour. A second portion (1.66 g) of di-tert-butyl azodicarboxylate was added and the mixture was stirred at ambient temperature for 16 hours. The mixture was filtered and the filtrate was purified by column chromatography on silica using initially a 1:1 mixture of ethyl acetate and methylene chloride and then a 25:24:1 mixture of ethyl acetate, methylene chloride and methanol as eluent. The material so obtained was triturated under diethyl ether. The resultant solid was isolated, washed with diethyl ether and dried under vacuum to give the required starting material (0.536 g).

EXAMPLE 42

Using an analogous procedure to that described in Example 41, the appropriate haloalkoxy substituted quinazoline was reacted with the appropriate amine to give the compound described in Table VII.

TABLE VII

| No. & Note | $(R^1)_m$ | $Q^1$ | $(R^2)_n$ |
|---|---|---|---|
| [1] | 7-[3-(4-hydroxy-piperidin-1-yl)propoxy] | 4-tetrahydro-pyranyl | 6-chloro-2,3-methylenedioxy |

Note

[1] 4-Hydroxypiperidine was used as the amine. The product gave the following data: NMR Spectrum: (CDCl$_3$) 1.5–1.7 (m, 2H), 1.85–2.05 (m, 6H), 2.05–2.25 (m, 4H), 2.5 (m, 2H), 2.8 (m, 2H), 3.55–3.65 (m, 2H), 3.6 (m, 1H), 3.95–4.05 (m, 2H), 4.12 (m, 2H), 4.75 (m, 1H), 6.05 (s, 2H), 6.5 (s, 1H), 6.7 (d, 1H), 6.8 (d, 1H), 6.95 (d, 1H), 8.5 (s, 1H), 9.25 (s, 1H); Mass Spectrum: M+H$^+$ 557 and 559.

EXAMPLE 43

4-(6-chloro-2,3-methylenedioxyanilino)-7-piperidin-4-ylmethoxy-5-tetrahydropyran-4-yloxyquinazoline A mixture of 7-[N-(tert-butoxycarbonyl)piperidin-4-yl-methoxy]-4-(6-chloro-2,3-methylenedioxyanilino)-5-tet-rahydropyranyloxyquinazoline (0.25 g), trifluoroacetic acid (1 ml) and methylene chloride (1 ml) was stirred at ambient temperature for 1.5 hours. The mixture was evaporated and the residue was purified by column chromatography on silica using a 93:7 mixture of methylene chloride and a saturated methanolic ammonia solution as eluent. The material so obtained was partitioned between ethyl acetate and an aqueous ammonium hydroxide solution. The organic layer was dried over magnesium sulphate and evaporated. There was thus obtained the title compound (0.07 g); NMR Spectrum: (CDCl$_3$ and D$_2$O) 1.5–1.7 (m, 2H), 1.9–2.1 (m, 4H), 2.2–2.3 (m, 2H), 2.8 (m, 2H), 3.32 (d, 2H), 3.65 (m, 2H), 3.9–4.1 (m, 3H), 4.8 (m, 1H), 6.08 (s, 2H), 6.52 (br s, 1H), 6.72 (d, 1H), 6.8 (s, 1H), 6.98 (d, 1H), 8.5 (s, 1H); Mass Spectrum: M+H$^+$ 513 and 515.

EXAMPLE 44

4-(6-chloro-2,3-methylenedioxyanilino)-7-(N-methylpiperidin-4-ylmethoxy)-5-tetrahydropyran-4-yloxyquinazoline A mixture of 7-[N-(tert-butoxycarbonyl)piperidin-4-yl-methoxy]-4-(6-chloro-2,3-methylenedioxyanilino)-5-tet-rahydropyran-4-yloxyquinazoline (0.25 g), a concentrated aqueous formaldehyde solution (37%, 0.5 ml) and formic acid (5 ml) was stirred and heated to 100° C. for 2 hours. The mixture was cooled to ambient temperature and evaporated. The residue was purified by column chromatography on silica using a 24:1 mixture of methylene chloride and a saturated methanolic ammonia solution as eluent. The material so obtained was partitioned between methylene chloride and an aqueous ammonium hydroxide solution. The organic layer was dried over magnesium sulphate and evaporated. There was thus obtained the title compound (0.1 g); NMR Spectrum: (CDCl$_3$) 1.4–1.6 (m, 2H), 1.75–1.9 (m, 3H), 1.9–2.1 (m, 4H), 2.2–2.3 (m, 2H), 2.29 (s, 3H), 2.9 (d, 2H), 3.6–3.7 (m, 2H), 3.95 (d, 2H), 4.0–4.1 (m, 2H), 4.75 (m, 1H), 6.05 (s, 2H), 6.5 (d, 1H), 6.72 (d, 1H), 6.81 (d, 1H), 6.97 (d, 1H), 8.5 (s, 11, 9.26 (s, 1H); Mass Spectrum: M+H$^+$ 527 and 529.

EXAMPLE 45

4-(6-chloro-2,3-methylenedioxyanilino)-7-[(2R)-2,3-epoxypropoxy]-5-tetrahydropyran-4-yloxyquinazoline Caesium fluoride (0.46 g) and (2R)-(−)-glycidyl tosylate (0.275 g) were added in turn to a solution of 4-(6-chloro-2,3-methylenedioxyanilino)-7-fluoro-5-tetrahydropyran-4-yloxyquinazoline (0.416 g) in DMF (5 ml) and the reaction mixture was stirred and heated to 60° C. for 2 hours and to 70° C. for a further 1.5 hours. The mixture was evaporated and the residue was partitioned between ethyl acetate and a saturated aqueous sodium bicarbonate solution. The organic layer was washed with water and with brine, dried over magnesium sulphate and evaporated. The residue was purified by column chromatography on silica using a 49:1 mixture of methylene chloride and methanol as eluent. There was thus obtained the title compound (0.36 g); NMR Spectrum: (CDCl$_3$) 1.9–2.1 (m, 2H), 2.2–2.3 (m, 2H), 2.8 (m, 1H), 2.98 (m, 1H), 3.42 (m, 1H), 3.6–3.7 (m, 2H), 3.95–4.1 (m, 3H), 4.45 (m, 1H), 4.8 (m, 1H), 6.02 (s, 2H), 6.59 (m, 12H), 6.72 (d, 1H), 6.81 (d, 1H), 6.97 (d, 1H), 8.5 (s, 1H), 9.27 (s, 1H); Mass Spectrum: M+H$^+$ 472 and 474.

EXAMPLE 46

4-(6-chloro-2,3-methylenedioxyanilino)-7-[3-(4-cyanomethylpiperazin-1-yl)propoxy]-5-tetrahydro-pyran-4-yloxyquinazoline A mixture of 4-(6-chloro-2,3-methylenedioxyanilino)-7-(3-piperazin-1-ylpropoxy)-5-tetrahydropyran-4-ylox-yquinazoline (1.3 g), 2-chloroacetonitrile (0.167 ml), sodium iodide (0.036 g), potassium carbonate (0.331 g) and DMF (15 ml) was stirred at ambient temperature for 5 hours. The mixture was evaporated and the residue was partitioned between ethyl acetate and water. The organic phase was washed with brine, dried over magnesium sulphate and evaporated. The residue was purified by column chromatography on silica using a 10:9:1 mixture of ethyl acetate, methylene chloride and methanol as eluent. There was thus obtained the title compound (0.69 g); NMR Spectrum: (CDCl$_3$) 1.85–2.0 (m, 4H), 2.1 (m, 2H), 2.4–2.5 (m, 6H), 2.5–2.6 (m, 4H), 3.42 (s, 2H), 3.5–3.6 (m, 2H), 3.9–4.0 (m, 2H), 4.0–4.1 (m, 2H), 4.7 (m, 1H), 6.0 (s, 2H), 6.42 (s, 1H), 6.65 (d, 1H), 6.78 (d, 1H), 6.9 (d, 1H), 8.42 (s, 1H), 9.2 (s, 1H); Mass Spectrum: M+H$^+$ 581 and 583.

EXAMPLE 47

4-(6-chlorobenzofuran-7-ylamino)-7-(2-pyrrolidin-1-ylethoxy)-5-cyclopentyloxyquinazoline dihydrochloride Sodium hexamethyldisilazane (1M solution in THF; 0.55 ml) was added to a solution of 7-amino-6-chlorobenzofuran (0.093 g) in DMF (3 ml) which was cooled to 10° C. and the mixture was stirred at 10° C. for 5 minutes. A solution of 4-chloro-5-cyclopentyloxy-7-(2-pyrrolidin-1-ylethoxy) quinazoline (0.1 g) in DMF (8 ml) was added and the mixture was stirred at ambient temperature for 1 hour. The mixture was partitioned between ethyl acetate and water. The organic layer was evaporated and the residue was purified by column chromatography on silica using a 49:1 mixture of methylene chloride and methanol as eluent. The material so obtained was dissolved in diethyl ether and 6M hydrogen chloride in isopropanol (0.1 ml) was added. The mixture was stirred for 5 minutes and then evaporated. There was thus obtained the title compound as a dihydrochloride salt (0.095 g), a portion of which was converted into the free base using an analogous procedure to that described in Example 3. The free base gave the following characterising data: NMR Spectrum: (CDCl$_3$) 1.55–1.75 (m, 4H), 1.75–1.95 (m, 4H), 2.08 (m, 2H), 2.6–2.75 (m, 4H), 3.0 (m, 2H), 4.25 (m, 2H), 5.05 (m, 1H), 6.6 (d, 1H), 6.8 (d, 1H), 6.85 (d, 1H), 7.38 (d, 1H), 7.45 (d, 1H), 7.6 (d, 1H), 8.42 (s, 1H), 9.5 (s, 1H); Mass Spectrum: M+H$^+$ 493 and 495.

The 7-amino-6-chlorobenzofuran used as a starting material was prepared as follows:—

Sodium hydride (60% dispersion in mineral oil; 4.6 g) was added to a stirred solution of 6-chloroanthranilic acid (18 g) in DMF (100 ml) and the mixture was stirred at ambient temperature for 30 minutes. Ethyl iodide (10 ml) was added and the reaction mixture was stirred at ambient temperature for 2 days. The solvent was evaporated and the residue was partitioned between ethyl acetate and water. The organic phase was washed in turn with water and brine, dried over magnesium sulphate and evaporated. The residue was purified by column chromatography on silica using a 4:1 mixture of petroleum ether (b.p. 60–80° C.) and ethyl acetate as eluent. There was thus obtained ethyl 6-chloroanthranilate (15.8 g) as an oil; NMR Spectrum: (DMSOd$_6$) 1.3 (t, 3H), 4.3 (q, 2H), 5.7 (br s, 2H), 6.6 (d, 1H), 6.7 (d, 1H), 7.1 (t, 1H).

A solution of sodium nitrite (4.5 g) in water (100 ml) was added dropwise during 5 minutes to a stirred suspension of ethyl 6-chloroanthranilate (12.7 g) in a mixture of concentrated sulphuric acid (27.9 ml), water (38 ml) and ice (76 g). The reaction mixture was stirred at 0° C. for an additional 20 minutes and then heated to 120° C. for 1 hour. The resultant mixture was poured into a mixture of ice and water and the product was extracted with diethyl ether. The organic phase was washed in turn with water and brine, dried over magnesium sulphate and evaporated. The residue was purified by column chromatography on silica using a 4:1 mixture of petroleum ether (b.p. 60–80° C.) and methylene chloride as eluent. There was thus obtained ethyl 6-chloro-2-hydroxybenzoate (9.8 g); NMR Spectrum: (DMSOd$_6$) 1.3 (t, 3H), 4.3 (q, 2H), 6.9 (d, 1H), 6.95 (d, 1H), 7.25 (d, 1H), 10.45 (br s, 1H).

Allyl bromide (5.5 ml) was added to a stirred mixture of ethyl 6-chloro-2-hydroxybenzoate (9.8 g), 1,5,7-triazabicyclo[4,4,0]dec-5-ene (10.4 g) and acetonitrile (250 ml) and the reaction mixture was stirred at ambient temperature for 20 hours. The mixture was evaporated and the residue was purified by column chromatography on silica using a 17:3 mixture of petroleum ether (b.p. 60–80° C.) and diethyl ether as eluent. There was thus obtained ethyl 2-allyloxy-6-chlorobenzoate (10.3 g); NMR Spectrum: (DMSOd$_6$) 1.3 (t, 3H), 4.35 (q, 2H), 4.65 (d, 2H), 5.25 (d, 1H), 5.4 (d, 1H), 6.0 (m, 1H), 7.15 (m, 2H), 7.45 (t, 1H).

The material so obtained was heated to 230° C. for 1 hour. The reaction product was cooled to ambient temperature and purified by column chromatography on silica using a 4:1 mixture of petroleum ether (b.p. 60–80° C.) and methylene chloride as eluent. There was thus obtained ethyl 3-allyl-6-chloro-2-hydroxybenzoate (7.3 g); NMR Spectrum: (DMSOd$_6$) 1.3 (t, 3H), 3.3 (m, 2H), 4.35 (q, 2H), 5.05 (m, 2H), 5.95 (m, 1H), 6.95 (d, 1H), 7.15 (d, 1H), 9.7 (br S, 1H).

The material so obtained was dissolved in methanol and cooled to −78° C. Ozone was bubbled through the solution for 30 min. Dimethyl sulfide (5.4 ml) was added and the reaction mixture was allowed to warm to ambient temperature. The mixture was evaporated and the residue was partitioned between diethyl ether and water. The organic phase was washed in turn with water and brine, dried over magnesium sulphate and evaporated. The residue was purified by column chromatography on silica using a 1:1 mixture of petroleum ether (b.p. 60–80° C.) and methylene chloride and then a 9:1 mixture of methylene chloride and diethyl ether as eluent. There was thus obtained 2-(4-chloro-3-ethoxycarbonyl-2-hydroxyphenyl)acetaldehyde which was immediately suspended in 85% phosphoric acid (18 ml) and the mixture was heated to 100° C. for 1 hour. The mixture was cooled to ambient temperature and partitioned between diethyl ether and water. The organic phase was washed in turn with water and brine, dried over magnesium sulphate and evaporated. The residue was purified by column chromatography on silica using a 1:1 mixture of petroleum ether (b.p. 60–80° C.) and methylene chloride as eluent. There was thus obtained ethyl 6-chlorobenzofuran-7-carboxylate (5.9 g); NMR Spectrum: (DMSOd$_6$) 1.35 (t, 3H), 4.45 (q, 2H), 7.10 (d, 1H), 7.45 (d, 1H), 7.85 (d, 1H), 8.15 (d, 1H).

A mixture of the material so obtained, 35% aqueous potassium hydroxide solution (12.7 ml) and methanol (20 ml) was stirred and heated to reflux for 1 hour. The methanol was evaporated and the residue was diluted with water and acidified to pH1 by the addition of 6N aqueous hydrochloric acid. The resultant precipitate was isolated, washed with water and dried under vacuum over phosphorus pentoxide to give 6-chlorobenzofuran-7-carboxylic acid (4.6 g); NMR Spectrum: (DMSOd$_6$) 7.05 (d, 1H), 7.4 (d, 1H), 7.75 (d, 1H), 8.1 (d, 1H).

A mixture of a portion (1 g) of the material so obtained, diphenylphosphoryl azide (2.2 ml), triethylamine (1.4 ml) and tert-butanol (2.7 ml) was stirred and heated to reflux for 18 hours. The mixture was allowed to cool to ambient temperature, poured into water and extracted with ethyl acetate. The organic phase was washed in turn with water and brine, dried over magnesium sulphate and evaporated. The residue was purified by column chromatography on alumina using increasingly polar solvent mixtures starting with mixtures of petroleum ether and methylene chloride and ending with a 4:1 mixture of methylene chloride and ethyl acetate. There was thus obtained a mixture of 7-amino-6-chlorobenzofuran and tert-butyl 6-chlorobenzofuran-7-carbamate. A solution of the mixture so obtained in methylene chloride (15 ml) was cooled to 0° C. and trifluoroacetic acid (1.2 ml) was added. The resultant mixture was stirred for 1 hour. The mixture was evaporated and the residue was partitioned between ethyl acetate and a saturated aqueous sodium bicarbonate solution. The organic phase was dried over magnesium sulphate and evaporated. The residue was purified by column chromatography on silica using a 3:1 mixture of petroleum ether (b.p. 60–80° C.) and methylene chloride as eluent. There was thus obtained 7-amino-6-chlorobenzofuran (0.376 g); NMR Spectrum: (DMSOd$_6$) 5.5 (br s, 2H), 6.85 (m, 2H), 7.1 (d, 1H), 7.95 (d, 1H); Mass Spectrum: M+H$^+$ 167.

EXAMPLE 48

4-(3-chlorobenzofuran-7-ylamino)-7-(2-pyrrolidin-1-ylethoxy)-5-cyclopentyloxyquinazoline dihydrochloride Using an analogous procedure to that described in Example 47, 4-chloro-5-cyclopentyloxy-7-(2-pyrrolidin-1-ylethoxy)quinazoline (0.1 g) was reacted with 7-amino-3-chlorobenzofuran (0.051 g) to give the title compound, as a dihydrochloride salt (0.074 g), a portion of which was converted into the free base using an analogous procedure to that described in Example 3. The free base gave the following characterising data: NMR Spectrum: (CDCl$_3$) 1.7–1.8 (m, 2H), 1.8–2.0 (m, 6H), 2.1–2.3 (m, 4H), 2.7 (br s, 4H), 3.02 (m, 2H), 4.3 (t, 2H), 5.08 (m, 1H), 6.61 (d, 1H), 6.84 (d, 1H), 7.3–7.45 (m, 2H), 7.65 (s, 1H), 8.64 (s, 1H), 8.76 (d, 1H), 10.3 (s, 1H); Mass Spectrum: M+H$^+$ 493 and 495.

EXAMPLE 49

4-(2-chloro-5-methoxyanilino)-5-(4-methylpiperazin-1-yl)-7-(2-pyrrolidin-1-ylethoxy)quinazoline trihydrochloride Using an analogous procedure to that described in Example 5, 4chloro-5-(4-methylpiperazin-1-yl)-7-(2-pyrrolidin-1-ylethoxy)quinazoline (0.11 g) was reacted with 2-chloro-5-methoxyaniline hydrochloride (0.064 g) in the presence of a 6M solution of hydrogen chloride in isopropanol (0.05 ml) to give the title compound, as a trihydrochloride salt (0.092 g), a portion of which was converted into the free base using an analogous procedure to that described in Example 3. The free base gave the following characterising data: NMR Spectrum: (CDCl$_3$) 1.8–1.9 (m, 4H), 2.32 (s, 3H), 2.48 (m, 2H), 2.65 (br s, 4H), 2.82 (d, 2H), 2.98 (m, 4H), 3.2 (d, 2H), 3.82 (s, 3H), 4.25 (m, 2H), 6.65 (m, 1H), 6.95 (m, 1H), 7.3 (d, 1H), 8.02 (d, 1H), 8.52 (s, 1H); Mass Spectrum: M+H$^+$ 497 and 499.

The 4-chloro-5-(4-methylpiperazin-1-yl)-7-(2-pyrrolidin-1-ylethoxy)quinazoline used as a starting material was prepared as follows:—

A mixture of 5,7-difluoro-3,4-dihydroquinazolin-4-one (0.091 g), 1-methylpiperazine (0.1 g) and DMF (2 ml) was stirred and heated to 100° C. for 1 hour. The mixture was evaporated and the residue was purified by column chromatography using a 97:3 mixture of methylene chloride and a saturated methanolic ammonia solution as eluent. There was thus obtained 7-fluoro-5-(4-methylpiperazin-1-yl)-3,4-dihydroquinazolin-4-one (0.09 g); NMR Spectrum: (CDCl$_3$) 2.42 (s, 3H), 2.72 (br s, 4H), 3.2 (br s, 4H), 6.72 (m, 1H), 7.0 (m, 1H), 8.0 (s, 1H); Mass Spectrum: M+H$^+$ 263.

Sodium hydride (60% dispersion in mineral oil; 0.96 g) was added to a stirred solution of 1-(2-hydroxyethyl)pyrrolidine (1.4 ml) in DMF (20 ml) and the mixture was stirred at ambient temperature for 10 minutes. 7-Fluoro-5-(4-methylpiperazin-1-yl)-3,4-dihydroquinazolin-4-one (0.09 g) was added and the mixture was stirred and heated to 100° C. for 3 hours. The resultant mixture was evaporated and acetic acid (1.4 ml) and methylene chloride were added in turn to the residue. The mixture was filtered and the filtrate was poured onto a column of silica and eluted with a 19:1 mixture of methylene chloride and a saturated methanolic ammonia solution. The material so obtained as triturated under pentane, isolated, washed with pentane and dried under vacuum. There was thus obtained 5-(4-methylpiperazin-1-yl)-7-(2-pyrrolidin-1-ylethoxy)-3,4-dihydroquinazolin-4-one (0.74 g); NMR Spectrum: (CDCl$_3$) 1.7–1.9 (m, 4H), 2.4 (s, 3H), 2.6–2.8 (m, 8H), 2.92 (t, 2H), 3.15 (br s, 4H), 4.2 (t, 2H), 6.6 (d, 1H), 6.8 (d, 1H), 7.92 (s, 1H); Mass Spectrum: M+H$^+$ 358.

A mixture of a portion (0.65 g) of the material so obtained, phosphoryl chloride (0.252 ml), diisopropylethylamine (0.94 ml) and 1,2-dichloroethane (30 ml) was stirred and heated to 80° C. for 2 hours. The mixture was evaporated and the residue was purified by column chromatography on silica using a 24:1 mixture of methylene chloride and a saturated methanolic ammonia solution as eluent. There was thus obtained 4-chloro-5-(4-methylpiperazin-1-yl)-7-(2-pyrrolidin-1-ylethoxy)quinazoline (0.23 g); NMR Spectrum: (CDCl$_3$) 1.9–2.1 (br s, 4H), 2.5 (s, 3H), 2.65 (m, 2H), 2.85–3.1 (m, 10H), 3.32 (d, 2H), 4.4 (br s, 2H), 6.85 (d, 1H), 7.05 (d, 1H), 8.8 (s, 1H); Mass Spectrum: M+H$^+$ 376.

EXAMPLE 50

4-(6-chloro-2,3-methylenedioxyanilino)-5-(N-methylpiperidin-4-yloxy)-7-(2,2,2-trifluoroethoxy)quinazoline A mixture of 4-(6-chloro-2,3-methylenedioxyanilino)-7-hydroxy-5-(N-methylpiperidin-4-yloxy)quinazoline (0.1 g), 2,2,2-trifluoroethyl 4-toluenesulphonate (0.071 g), potassium carbonate (0.08 g) and DMF (2 ml) was stirred and heated to 95° C. for 24 hours. The mixture was cooled to ambient temperature and partitioned between ethyl acetate and water. The organic solution was washed with water and with brine, dried over magnesium sulphate and evaporated The residue was purified by column chromatography on silica using a 45:46:4 mixture of methylene chloride, ethyl acetate and methanol as eluent. There was thus obtained the title compound (0.058 g); NMR Spectrum: (CDCl$_3$) 1.95–2.1 (m, 2H), 2.1–2.3 (m, 2H), 2.32 (s, 3H), 2.3–2.45 (m, 2H), 2.75 (m, 2H), 4.48 (m, 2H), 4.64 (m, 1H), 6.05 (s, 2H), 6.6 (d, 1H), 6.74 (d, 1H), 6.78 (d, 1H), 6.97 (d, 1H), 8.5 (s, 1H), 9.28 (s, 1H); Mass Spectrum: M+H$^+$ 511 and 513.

The 4-(6-chloro-2,3-methylenedioxyanilino)-7-hydroxy-5-(N-methylpiperidin-4-yloxy)quinazoline used as a starting material was prepared as follows:—

A solution of di-tert-butyl azodicarboxylate (5.44 g) in methylene chloride (20 ml) was added dropwise to a stirred mixture of 7-benzyloxy-5-hydroxy-3-pivaloyloxymethyl-3,4-dihydroquinazolin-4-one (6 g) 4-hydroxy-N-methylpiperidine (2.17 g), triphenylphosphine (6.17 g) and methylene chloride (100 ml) that had been cooled to 0° C. The resultant mixture was stirred at ambient temperature for 1 hour. The mixture was evaporated and the residue was purified by column chromatography on silica using a 10:9:1 mixture of methylene chloride, ethyl acetate and a saturated methanolic ammonia solution as eluent. The material so obtained was dissolved in a saturated methanolic ammonia solution (240 ml) and stirred at ambient temperature for 16 hours. The mixture was evaporated and the residue was triturated under diethyl ether. The resultant solid was isolated, washed with diethyl ether and dried under vacuum. There was thus obtained 7-benzyloxy-5-(N-methylpiperidin-4-yloxy)-3,4-dihydroquinazolin-4-one (3.68 g); NMR Spectrum: (CDCl$_3$) 2.0 (m, 4H), 2.3 (s, 3H), 2.35 (m, 2H), 2.75 (m, 2H), 4.5 (m, 1H), 5.15 (s, 2H), 6.6 (d, 1H), 6.82 (d, 1H), 7.3–7.5 (m, 5H), 7.92 (s, 1H); Mass Spectrum: M+H$^+$ 366.

A mixture of the material so obtained, triphenylphosphine (8.65 g), carbon tetrachloride (10 ml) and 1,2-dichloroethane (100 ml) was stirred and heated to 70° C. for 2 hours. The mixture was evaporated and the 7-benzyloxy-4-chloro-5-(N-methylpiperidin-4-yloxy)quinazoline so obtained was dissolved in isopropanol (2 ml) and 6-chloro-2,3-methylenedioxyaniline (1.9 g) and a 5M hydrogen chloride solution in isopropanol (2.1 ml) were added in turn. The resultant mixture was stirred at 50° C. for 20 minutes and at 80° C. for 30 minutes. The mixture was evaporated and the residue was suspended in ethyl acetate and stirred for 1 hour at ambient temperature. The resultant solid was isolated, washed with ethyl acetate and with diethyl ether. The solid was dissolved in a 19:1 mixture of methylene chloride and a saturated methanolic ammonia solution and stirred at ambient temperature for 15 minutes. The mixture was filtered, the filtrate was evaporated and the residue was purified by column chromatography on silica using a 50:47:3 mixture of ethyl acetate, methylene chloride and methanol as eluent. There was thus obtained 7-benzyloxy-4-(6-chloro-2,3-methylenedioxyanilino)-5-(N-methylpiperidin-4-yloxy)quinazoline (4.2 g); NMR Spectrum: (CDCl$_3$) 2.0–2.1 (m, 2H), 2.2 (m, 2H), 2.3 (s, 3H), 2.25–2.35 (m, 2H), 2.75 (m, 2H), 4.6 (m, 1H), 5.2 (s, 2H), 6.1 (s, 2H), 6.6 (s, 1H), 6.75 (d, 1H), 6.95 (s, 1H), 7.0 (d, 1H), 7.32–7.52 (m, 5H), 8.52 (s, 1H), 9.3 (s, 1H); Mass Spectrum: M+H$^+$ 519 and 521.

A mixture of a portion (1.5 g) of the material so obtained and trifluoroacetic acid (15 ml) was stirred and heated to reflux for 6 hours. The mixture was evaporated and the residue was dissolved in water and basified to pH9 by the addition of solid sodium bicarbonate. The mixture was extracted with ethyl acetate and the organic layer was washed with brine, dried over magnesium sulphate and evaporated. The residue was purified by column chromatography on silica using a 10:9:2 mixture of ethyl acetate, methylene chloride and methanol as eluent. There was thus obtained 4-(6-chloro-2,3-methylenedioxyanilino)-7-hydroxy-5-(N-methylpiperidin-4-yloxy)quinazoline (0.8 g); NMR Spectrum: (CDCl$_3$) 1.9–2.05 (m, 2H), 2.05–2.15 (m, 2H), 2.2–2.3 (m, 2H), 2.28 (s, 3H), 2.7 (m, 2H), 4.5 (br s, 1H), 6.05 (s, 2H), 6.5 (d, 1H), 6.7 (d, 1H), 6.85 (d, 1H), 6.95 (d, 1H), 8.4 (s, 1H), 9.35 (s, 1H); Mass Spectrum M+H$^+$ 429 and 431.

EXAMPLE 51

4-(6-chloro-2,3-methylenedioxyanilino)-7-ethoxy-5-(N-methylpiperidin-4-yloxy)quinazoline A solution of di-tert-butyl azodicarboxylate (0.26 g) in methylene chloride (1 ml) was added dropwise to a stirred mixture of 4-(6-chloro-2,3-methylenedioxyanilino)-7-hydroxy-5-(N-methylpiperidin-4-yloxy)quinazoline (0.12 g), ethanol (0.019 g), triphenylphosphine (0.15 g) and methylene chloride (2 ml) and the resultant mixture was stirred at ambient temperature for 1 hour. A 2M solution of hydrogen chloride in diethyl ether (3 ml) was added and the mixture was stirred at ambient temperature for 1.5 hours. Diethyl ether (1 ml) was added and the precipitate was isolated and dried under vacuum. The solid so obtained was dissolved in a 9:1 mixture of methylene chloride and a saturated methanolic ammonia solution. The mixture was filtered and the filtrate was evaporated. The residue was triturated under pentane and the resultant solid was isolated and dried under vacuum. There was thus obtained the title compound (0.092 g); NMR Spectrum: (CDCl$_3$) 1.5 (t, 3H), 1.95–2.1 (m, 2H), 2.15–2.5 (m, 2H), 2.3 (s, 3H), 2.3–2.4 (m, 2H), 2.7 (br s, 2m), 4.15 (m, 2H), 4.6 (m, 1H), 6.05 (s, 2H), 6.5 (d, 1H), 6.7 (d, 1H), 6.8 (d, 1H), 6.95 (d, 1H), 8.5 (s, 1H), 9.25 (br s, 1H); Mass Spectrum: M+H$^+$ 457 and 459.

EXAMPLE 52

4-(6-chloro-2,3-methylenedioxyanilino)-7-(2-fluoroethoxy)-5-(N-methylpiperidin-4-yloxy)quinazoline Using an analogous procedure to that described in Example 51, 4-(6-chloro-2,3-methylenedioxyanilino)-7-hydroxy-5-(N-methylpiperidin-4-yloxy)quinazoline was reacted with 2-fluoroethanol to give the title compound; NMR Spectrum: (CDCl$_3$) 2.0–2.1 (m, 2H), 2.15–2.3 (m, 2H), 2.35 (s, 3H), 2.3–2.4 (m, 2H), 2.8 (br s, 2H), 4.32 (m, 1H), 4.4 (m, 1H), 4.65 (m, 1H), 4.8 (m, 1H), 4.9 (m, 1H), 6.05 (s, 2H), 6.6 (s, 1H), 6.75 (d, 1H), 6.85 (s, 1H), 7.0 (d, 1H), 8.55 (s, 1H), 9.3 (s, 1H); Mass Spectrum: M+H$^+$ 475 and 477.

EXAMPLE 53

4-(6chloro-2,3-methylenedioxyanilino)-7-isobutoxy-5-(N-methylpiperidin-4-yloxy)quinazoline Using an analogous procedure to that described in Example 51, 4-(6-chloro-2,3-methylenedioxyanilino)-7-hydroxy-5-(N-methylpiperidin-4-yloxy)quinazoline was reacted with isobutanol to give the title compound; NMR Spectrum: (CDCl$_3$) 1.05 (d, 6H), 1.95–2.05 (m, 2H), 2.08–2.28 (m, 3H), 2.3 (s, 3H), 2.3–2.4 (m, 2H), 2.7 (br s, 2H), 3.82 (d, 2H), 4.6 (m, 1H), 6.03 (s, 2H), 6.5 (s, 1H), 6.7 (d, 1H), 6.8 (s, 1H), 6.95 (d, 1H), 8.5 (s, 1H), 9.25 (s, 1H); Mass Spectrum: M+H$^+$ 485 and 487.

EXAMPLE 54

4-(2,3-methylenedioxyanilino)-5-(4-methylpiperazin-1-yl)-7-(2-pyrrolidin-1-ylethoxy)quinazoline trihydrochloride Using an analogous procedure to that described in Example 5, 4-chloro-5-(4-methylpiperazin-1-yl)-7-(2-pyrrolidin-1-ylethoxy)quinazoline (0.11 g) was reacted with 2,3-methylenedioxyaniline (0.045 g) in the presence of a 6M solution of hydrogen chloride in isopropanol to give the title compound, as a trihydrochloride salt (0.105 g), a portion of which was converted into the free base using an analogous procedure to that described in Example 3. The free base gave the following characterising data: NMR Spectrum: (CDCl$_3$) 1.78 (br s, 4H), 2.3 (s, 3H), 2.5 (m, 2H), 2.6 (br s, 4H), 2.8 (d, 2H), 2.95 (m, 4H), 3.08 (d, 2H), 4.18 (m, 2H), 5.98 (s, 2H), 6.6 (d, 1H), 6.86 (m, 1H), 6.94 (s, 1H), 8.06 (d, 1H), 8.5 (s, 1H), 11.8 (s, 1H); Mass Spectrum: M+H$^+$ 477.

EXAMPLE 55

4-(6chloro-2,3-methylenedioxyanilino)-5-morpholino-7-(2-pyrrolidin-1-ylethoxy)quinazoline A mixture of 4-chloro-5-morpholino-7-(2-pyrrolidin-1-ylethoxy)quinazoline (0.27 g), 6-chloro-2,3-methylenedioxyaniline (0.14 g) and isopropanol (4 ml) was stirred and heated to 80° C. for 1 hour. The mixture was evaporated and the residue was dissolved in a 49:1 mixture of methylene chloride and a saturated methanolic ammonia solution. The mixture was filtered and the filtrate was poured onto a column of silica and eluted with a 97:3 mixture of methylene chloride and a saturated methanolic ammonia solution. The material so obtained was triturated under diethyl ether. The resultant solid was isolated, washed with diethyl ether and dried under vacuum. There was thus obtained the title compound (0.035 g); NMR Spectrum: (CDCl$_3$) 1.85 (br s, 4H), 2.65 (br s, 4H), 3.0 (m, 2H), 3.08 (m, 2H), 3.18 (d, 2H), 3.82 (m, 2H), 4.05 (m, 2H), 4.25 (m, 2H), 6.05 (s, 2), 6.75 (d, 1H), 6.95–7.1 (m, 3H), 8.52 (s, 1H); Mass Spectrum: M+H$^+$ 498 and 500.

The 4-chloro-5-morpholino-7-(2-pyrrolidin-1-ylethoxy)quinazoline used as a starting material was prepared as follows:—

A mixture of 5,7-difluoro-3,4-dihydroquinazolin-4-one (0.91 g), morpholine (0.9 ml) and DMF (20 ml) was stirred and heated to 100° C. for 1 hour. The mixture was evaporated. A saturated methanolic ammonia solution (1 ml) was added to the residue and the mixture was stirred at ambient temperature for 5 minutes. The mixture was evaporated and the residue was triturated under water. The resultant solid was isolated, washed with water and with diethyl ether and dried under vacuum. There was thus obtained 7-fluoro-5-morpholino-3,4-dihydroquinazolin-4-one (0.85 g); NMR Spectrum: (DMSOd$_6$) 3.05 (br s, 4H), 3.8 (t, 4H), 6.8 (m, 1H), 6.92 (m, 1H), 8.02 (s, 1H); Mass Spectrum: M+H$^+$ 250.

Sodium hydride (60% dispersion in mineral oil, 0.5 g) was added to a stirred solution of 1-(2-hydroxyethyl)pyrrolidine (0.7 ml) in DMF (15 ml) which had been cooled to 5° C. The mixture was stirred for 10 minutes. 7-Fluoro-5-morpholino-3,4-dihydroquinazolinone-4-one (0.75 g) was added and the mixture was heated to 80° C. for 1 hour and then to 90° C. for 3 hours. The mixture was evaporated and the residue was dissolved in acetic acid (0.9 ml) and diluted with a mixture of methylene chloride and methanol. The resultant solution was poured onto a column of silica and eluted with a 47:3 mixture of methylene chloride and methanol as eluent. The material so obtained was triturated under diethyl ether and the resultant solid was isolated, washed with diethyl ether and dried under vacuum. There was thus obtained 5-morpholino-7-(2-pyrrolidin-1-ylethoxy)-3,4-dihydroquinazolin-4-one (0.5 g); NMR Spectrum: (DMSOd$_6$) 1.7 (br s, 4H), 2.8 (m, 2H), 3.02 (br s, 4H), 3.8 (m, 4H), 4.2 (m, 2H), 6.45 (d, 1H), 6.7 (d, 1H), 7.92 (s, 1H), 11.7 (br s, 1H); Mass Spectrum: M+H$^+$ 345.

A mixture of a portion (0.26 g) of the material so obtained, phosphoryl chloride (0.084 ml), diisopropylethylamine (0.34 ml) and 1,2-dichloroethane (5 ml) was stirred and heated to 80° C. for 3 hours. The mixture was evaporated to give 4-chloro-5-morpholino-7-(2-pyrrolidin-1-ylethoxy)quinazoline which was used without further purification.

EXAMPLE 56

4-(6-chloro-2,3-methylenedioxyanilino)-5-phenoxyquinazoline monohydrochloride A mixture of 4-(6-chloro-2,3-methylenedioxyanilino)-5-fluoroquinazoline (0.213 g), phenol (0.45 g), potassium carbonate (0.828 g) and DMF (3 ml) was stirred and heated to 90° C. for 30 hours. The mixture was evaporated and the residue was partitioned between ethyl acetate and a 2N aqueous sodium hydroxide solution. The organic layer was washed with brine, dried over magnesium sulphate and evaporated. The residue was purified by column chromatography on silica using a 99:1 mixture of methylene chloride and methanol as eluent. The material so obtained was dissolved in diethyl ether and a 6M solution of hydrogen chloride in diethyl ether (1 equivalent) was added. The resultant solid was isolated, washed with diethyl ether and dried under vacuum. There was thus obtained the title compound (0.05 g); NMR Spectrum: (DMSOd$_6$ and CF$_3$CO$_2$D) 6.18 (s, 2H), 6.95 (d, 1H), 7.05 (d, 1H), 7.1 (d, 1H), 7.35 (d, 1H), 7.42 (m, 1H), 7.52–7.62 (m, 3H), 8.0 (m, 1H), 9.0 (s, 1H); Mass Spectrum: M+H$^+$ 392 and 394.

EXAMPLE 57

Pharmaceutical Compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (f) | Injection II | (10 mg/ml) |
|---|---|---|
| | Compound X | 1.0% w/v |
| | Sodium phosphate BP | 3.6% w/v |
| | 0.1 M Sodium hydroxide solution | 15.0% v/v |
| | Water for injection to 100% | |

| (g) | Injection III | (1 mg/ml, buffered to pH6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

| (l) | Ointment | ml |
|---|---|---|
| | Compound X | 40 mg |
| | Ethanol | 300 μl |
| | Water | 300 μl |
| | 1-Dodecylazacycloheptan-2-one | 50 μl |
| | Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

The invention claimed is:

1. A method for the treatment of an autoimmune disease or medical condition selected from transplant rejection and rheumatoid arthritis in a warm-blooded animal in need thereof which comprises administering to said animal an effective amount of a quinazoline derivative of the Formula I

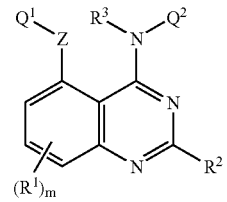

wherein:

m is 1 and the $R^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the $Q^1$-Z- group is selected from tetrahydropyran-4-yloxy, N-methylpyrrolidin-3-yloxy, 4-piperidinyloxy, N-methylpiperidin-4-yloxy, cyclopentyloxy and cyclohexyloxy;

each of $R^2$ and $R^3$ is hydrogen; and $Q^2$ is an aryl group of formula Ia

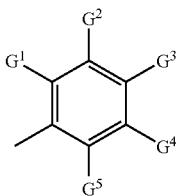

wherein G¹ is selected from chloro, bromo, trifluoromethyl, methyl, methoxy and pyrrolidin-1-yl, G² is hydrogen, G³ is selected from hydrogen and chloro, G⁴ is methoxy, and G⁵ is hydrogen,
or G¹ and G² together form a group of formula:—
—CH=CH—CH=C(Cl)—, —O—CH=C(Cl)— or —O—CH₂—O—, each of G³ and G⁴ is hydrogen, and G⁵ is hydrogen or chloro;
or a pharmaceutically-acceptable acid-addition salt thereof.

2. The method as claimed in claim 1 wherein:
m is 1 and
the R¹ group is located at the 7-position and is selected from methoxy, benzyloxy, 2-pyrrolidin-1-ylethoxy, 3-pyrrolidin-1-ylpropoxy, 2-pipendinoethoxy, 3-pipendinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;
the Q¹-Z- group is selected from tetrahydropyran-4-yloxy, 4-piperidinyloxy, N-methylpiperidin-4-yloxy, cyclopentyloxy and cyclohexyloxy;
each of R² and R³ is hydrogen; and
Q² is an aryl group of formula Ia

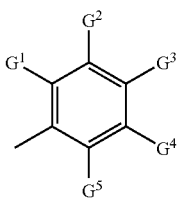

wherein G¹ and G² together form a group of formula:—
—O—CH₂—O—, each of G³ and G⁴ is hydrogen, and G⁵ is chloro;
or a pharmaceutically-acceptable acid-addition salt thereof.

3. The method as claimed in claim 1 wherein the quinazoline derivative of the Formula I selected from:—
4-(2-bromo-5-methoxyanilino)-7-methoxy-5-(N-methylpiperidin-4-yloxy)quinazoline,
4-(2-chloro-5-methoxyanilino)-7-methoxy-5-(N-methylpiperidin-4-yloxy)quinazoline,
4-(2-chloro-5-methoxyanilino)-7-[3-(4-methylpiperazin-1-yl)propoxy]-5-tetrahydropyran-4-yloxyquinazoline,
4-(2-chloro-5-methoxyanilino)-7-(3-morpholinopropoxy)-5-tetrahydropyran-4-yloxyquinazoline,
4-(5-chloronaphth-1-ylamino)-7-methoxy-5-(N-methylpiperidin-4-yloxy)quinazoline,
4-(3-chlorobenzofuran-7-ylamino)-7-methoxy-5-(N-methylpiperidin-4-yloxy)quinazoline,
7-benzyloxy-4-(2-bromo-5-methoxyanilino)-5-piperidin-4-yloxyquinazoline,
4-(2-bromo-5-methoxyanilino)-7-(3-methylsulphonylpropoxy)-5-piperidin-4-yloxyquinazoline,
4-(2,4-dichloro-5-methoxyanilino)-7-methoxy-5-(N-methylpiperidin-4-yloxy)quinazoline,
4-(2,5-dimethoxyanilino)-7-methoxy-5-(N-methylpiperidin-4-yloxy)quinazoline,
4-(2,4-dichloro-5-methoxyanilino)-7-(2-pyrrolidin-1-ylethoxy)-5-tetrahydropyran-4-yloxyquinazoline,
4-(2,4-dichloro-5-methoxyanilino)-7-(2-piperidinoethoxy)-5-tetrahydropyran-4-yloxyquinazoline,
4-(2,4-dichloro-5-methoxyanilino)-7-(2-morpholinoethoxy)-5-tetrahydropyran-4-yloxyquinazoline,
4-(2,4-dichloro-5-methoxyanilino)-7-[2-(4-methylpiperazin-1-yl)ethoxy]-5-tetrahydropyran-4-yloxyquinazoline,
4-(2-bromo-5-methoxyanilino)-7-(2-pyrrolidin-1-ylethoxy)-5-tetrahydropyran-4-yloxyquinazoline,
4-(2-bromo-5-methoxyanilino)-7-(2-piperidinoethoxy)-5-tetrahydropyran-4-yloxyquinazoline,
4-(2-bromo-5-methoxyanilino)-7-[2-(4-methylpiperazin-1-yl)ethoxy]-5-tetrahydropyran-4-yloxyquinazoline,
4-(2-bromo-5-methoxyanilino)-7-{2-[(2S)-2-(N,N-dimethylcarbamoyl)pyrrolidin-1-yl]ethoxy}-5-tetrahydropyran-4-yloxyquinazoline,
4-(2-bromo-5-methoxyanilino)-7-{2-[(2S)-2-(N-methylcarbamoyl)pyrrolidin-1-yl]ethoxy}-5-tetrahydropyran-4-yloxyquinazoline,
4-(2-bromo-5-methoxyanilino)-7-(4-pyridylmethoxy)-5-tetrahydropyran-4-yloxyquinazoline,
4-(5-methoxy-2-pyrrolidin-1-ylanilino)-7-[3-(4-methylpiperazin-1-yl)propoxy]-5-tetrahydropyran-4-yloxyquinazoline,
4-(2-bromo-5-methoxyanilino)-5-cyclopentyloxy-7-(2-pyrrolidin-1-ylethoxy)quinazoline,
4-(6-chloro-2,3-methylenedioxyanilino)-5-cyclopentyloxy-7-(2-pyrrolidin-1-ylethoxy)quinazoline,
4-(6-chloro-2,3-methylenedioxyanilino)-5-piperidin-4-yloxyquinazoline,
4-(6-chloro-2,3-methylenedioxyanilino)-7-methoxy-5-piperidin-4-yloxyquinazoline,
4-(6-chloro-2,3-methylenedioxyanilino)-7-methoxy-5-N-methylpiperidin-4-yloxy)quinazoline,
4-(6-chloro-2,3-methylenedioxyanilino)-7-(2-pyrrolidin-1-ylethoxy)-5-tetrahydropyran-4-yloxyquinazoline,
4-(6-chloro-2,3-methylenedioxyanilino)-7-(3-pyrrolidin-1-ylpropoxy)-5-tetrahydropyran-4-yloxyquinazoline,
4-(6-chloro-2,3-methylenedioxyanilino)-7-[3-(4-methylpiperazin-1-yl)propoxy]-5-tetrahydropyran-4-yloxyquinazoline,
4-(6-chloro-2,3-methylenedioxyanilino)-7-[2-(4-methylpiperazin-1-yl)ethoxy]-5-tetrahydropyran-4-yloxyquinazoline,
4-(6-chloro-2,3-methylenedioxyanilino)-7-(2-piperidinoethoxy)-5-tetrahydropyran-4-yloxyquinazoline; and
4-(6-chloro-2,3-methylenedioxyanilino)-7-[2-(4-pyridyloxy)ethoxy]-5-tetrahydropyran-4-yloxyquinazoline;
or a pharmaceutically-acceptable acid-addition salt thereof.

4. The method as claimed in claim 1 wherein the quinazoline derivative of the Formula I selected from:—
4-(2-chloro-5-methoxyanilino)-7-[3-(4-methylpiperazin-1-yl)propoxy]-5-tetrahydropyran-4-yloxyquinazoline, 4-(2-chloro-5-methoxyanilino)-7-(3-morpholinopropoxy)-5-tetrahydropyran-4-yloxyquinazoline,
4-(2,4-dichloro-5-methoxyanilino)-7-(2-pyrrolidin-1-ylethoxy)-5-tetrahydropyran-4-yloxyquinazoline, and
4-(6-chloro-2,3-methylenedioxyanilino)-7-(2-pyrrolidin-1-ylethoxy)-5-tetrahydropyran-4-yloxyquinazoline, or a pharmaceutically-acceptable acid-addition salt thereof.

5. The method as claimed in claim 1 wherein:

m is 1 and the $R^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the $Q^1$-Z- group is tetrahydropyran-4-yloxy;

each of $R^2$ and $R^3$ is hydrogen; and $Q^2$ is an aryl group of formula Ia

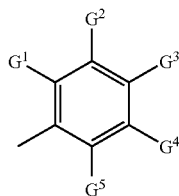

Ia wherein $G^1$ is selected from chloro, bromo, trifluoromethyl, methyl, methoxy and pyrrolidin-1-yl, $G^2$ is hydrogen, $G^3$ is selected from hydrogen and chloro, $G^4$ is methoxy, and $G^5$ is hydrogen, or $G^1$ and $G^2$ together form a group of formula:—
—O—CH=C(Cl)— or —O—CH$_2$—O—, each of $G^3$ and $G^4$ is hydrogen, and $G^5$ is hydrogen or chloro;

or a pharmaceutically-acceptable acid-addition salt thereof.

6. The method as claimed in claim 1 wherein:

m is 1 and the $R^1$ group is located at the 7-position and is selected from methoxy, benzyloxy, 2-pyrrolidin-1-ylethoxy, 3-pyrrolidin-1-ylpropoxy, 2-piperidinoethoxy, 3-piperidinopropoxy, 2-morpholinoethoxy, 3-morpholinopropoxy, 2-(4-methylpiperazin-1-yl)ethoxy, 3-(4-methylpiperazin-1-yl)propoxy, 2-[(2S)-2-(N-methylcarbamoyl)pyrrolidin-1-yl]ethoxy, 2-[(2S)-2-(N,N-dimethylcarbamoyl)pyrrolidin-1-yl]ethoxy, 3-methylsulphonylpropoxy, 2-(4-pyridyloxy)ethoxy, 2-pyridylmethoxy, 3-pyridylmethoxy and 4-pyridylmethoxy;

the $Q^1$-Z- group is tetrahydropyran-4-yloxy;

each of $R^2$ and $R^3$ is hydrogen; and $Q^2$ is an aryl group of formula Ia

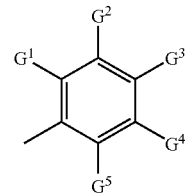

Ia wherein $G^1$ and $G^2$ together form a group of formula:—
—O—CH$_2$—O—, each of $G^3$ and $G^4$ is hydrogen, and $G^5$ is chloro;

or a pharmaceutically-acceptable acid-addition salt thereof.

7. The method as claimed in claim 1 wherein quinazoline derivative of the Formula I is selected from:

4-(2-chloro-5-methoxyanilino)-7-[3-(4-methylpiperazin-1-yl)propoxy]-5-tetrahydropyran-4-yloxyquinazoline,
4-(2-chloro-5-methoxyanilino)-7-(3-morpholinopropoxy)-5-tetrahydropyran-4-yloxyquinazoline,
4-(2,4-dichloro-5-methoxyanilino)-7-(2-pyrrolidin-1-ylethoxy)-5-tetrahydropyran-4-yloxyquinazoline,
4-(2,4-dichloro-5-methoxyanilino)-7-(2-piperidinoethoxy)-5-tetrahydropyran-4-yloxyquinazoline,
4-(2,4-dichloro-5-methoxyanilino)-7-(2-morpholinoethoxy)-5-tetrahydropyran-4-yloxyquinazoline,
4-(2,4-dichloro-5-methoxyanilino)-7-[2-(4-methylpiperazin-1-yl)ethoxy]-5-tetrahydropyran-4-yloxyquinazoline,
4-(2-bromo-5-methoxyanilino)-7-(2-pyrrolidin-1-ylethoxy)-5-tetrahydropyran-4-yloxyquinazoline,
4-(2-bromo-5-methoxyanilino)-7-(2-piperidinoethoxy)-5-tetrahydropyran-4-yloxyquinazoline,
4-(2-bromo-5-methoxyanilino)-7-[2-(4-methylpiperazin-1-yl)ethoxy]-5-tetrahydropyran-4-yloxyquinazoline,
4-(2-bromo-5-methoxyanilino)-7-{2-[(2S)-2-(N,N-dimethylcarbamoyl)pyrrolidin-1-yl]ethoxy}-5-tetrahydropyran-4-yloxyquinazoline,
4-(2-bromo-5-methoxyanilino)-7-{2-[(2S)-2-(N-methylcarbamoyl)pyrrolidin-1-yl]ethoxy}-5-tetrahydropyran-4-yloxyquinazoline,
4-(2-bromo-5-methoxyanilino)-7-(4-pyridylmethoxy)-5-tetrahydropyran-4-yloxyquinazoline,
4-(5-methoxy-2-pyrrolidin-1-ylanilino)-7-[3-(4-methylpiperazin-1-yl)propoxy]-5-tetrahydropyran-4-yloxyquinazoline,
4-(6-chloro-2,3-methylenedioxyanilino)-7-(2-pyrrolidin-1-ylethoxy)-5-tetrahydropyran-4-yloxyquinazoline,
4-(6-chloro-2,3-methylenedioxyanilino)-7-(3-pyrrolidin-1-ylpropoxy)-5-tetrahydropyran-4-yloxyquinazoline,
4-(6-chloro-2,3-methylenedioxyanilino)-7-[3-(4-methylpiperazin-1-yl)propoxy]-5-tetrahydropyran-4-yloxyquinazoline,
4-(6-chloro-2,3-methylenedioxyanilino)-7-[2-(4-methylpiperazin-1-yl)ethoxy]-5-tetrahydropyran-4-yloxyquinazoline,
4-(6-chloro-2,3-methylenedioxyanilino)-7-(2-piperidinoethoxy)-5-tetrahydropyran-4-yloxyquinazoline; and
4-(6-chloro-2,3-methylenedioxyanilino)-7-[2-(4-pyridyloxy)ethoxy]-5-tetrahydropyran-4-yloxyquinazoline;

or a pharmaceutically-acceptable acid-addition salt thereof.

8. The method as claimed in claim 1 wherein the quinazoline derivative of the Formula I is:

4-(6-chloro-2,3-methylenedioxyanilino)-7-[2-(4-methylpiperazin-1-yl)ethoxy]-5-tetrahydropyran-4-yloxyquinazoline, or a pharmaceutically-acceptable acid-addition salt thereof.

9. The method of claim 1 for the treatment of transplant rejection.

10. The method of claim 1 for treating or preventing acute rejection of a transplanted organ.

11. The method of claim 1 for the treatment of rheumatoid arthritis.

* * * * *